United States Patent
Ykema et al.

(10) Patent No.: US 12,018,269 B2
(45) Date of Patent: *Jun. 25, 2024

(54) TOMATO PLANT RESISTANT TO TOMATO BROWN RUGOSE FRUIT VIRUS

(71) Applicant: Enza Zaden Beheer B.V., Enkhuizen (NL)

(72) Inventors: Marieke Ykema, Harlingen (NL); Cornelis Walter Verweij, Enkhuizen (NL); Sergio De La Fuente Van Bentem, Amsterdam (NL); Frederic Michel Pierre Perefarres, Roquetas de Mar (ES)

(73) Assignee: Enza Zaden Beheer B.V., Enkhuizen (NL)

( * ) Notice: Subject to any disclaimer, the term of this patent is extended or adjusted under 35 U.S.C. 154(b) by 226 days.

This patent is subject to a terminal disclaimer.

(21) Appl. No.: 17/491,393

(22) Filed: Sep. 30, 2021

(65) Prior Publication Data

US 2022/0220499 A1    Jul. 14, 2022

Related U.S. Application Data

(63) Continuation of application No. 17/196,655, filed on Mar. 9, 2021, now Pat. No. 11,168,336, which is a continuation of application No. PCT/EP2019/084272, filed on Dec. 9, 2019.

(30) Foreign Application Priority Data

Jan. 14, 2019    (WO) ............... PCT/EP2019/050830

(51) Int. Cl.
*C12N 15/82*    (2006.01)
*C07K 14/08*    (2006.01)

(52) U.S. Cl.
CPC .......... *C12N 15/8283* (2013.01); *C07K 14/08* (2013.01)

(58) Field of Classification Search
None
See application file for complete search history.

(56) References Cited

U.S. PATENT DOCUMENTS

| | | | | |
|---|---|---|---|---|
| 7,148,397 | B2 * | 12/2006 | Osumi ............... | C12N 15/8282 536/23.6 |
| 11,168,336 | B2 | 11/2021 | Ykema et al. | |
| 2008/0016593 | A1 | 1/2008 | Gal-On et al. | |
| 2016/0100538 | A1 | 4/2016 | Arden et al. | |
| 2018/0208628 | A1 | 7/2018 | Geraats et al. | |
| 2021/0238627 | A1 | 8/2021 | Ykema et al. | |

FOREIGN PATENT DOCUMENTS

| | | |
|---|---|---|
| JP | 2021/505165 A | 2/2021 |
| JP | 2021/516548 A | 7/2021 |
| WO | WO-2004020594 A2 | 3/2004 |
| WO | WO-2018219941 A1 | 12/2018 |
| WO | WO-2019/162952 A1 | 8/2019 |
| WO | WO-2020018783 A1 | 1/2020 |
| WO | WO-2020147921 A1 | 7/2020 |
| WO | WO-2020148021 A1 | 7/2020 |

OTHER PUBLICATIONS

Amended claims, filed Feb. 21, 2022, during prosecution of EP Application No. 19880924.6, 4 pages.
"Call for submission of new research proposals for 2016," State of Israel Ministry of Agriculture and Rural Development. Partial English translation included (pp. 1, 2, beginning of p. 3, p. 8 section 4, and pp. 13 and 14 regarding section 4 item 1). 29 pages.
Alignment of genomic sequence of sample 2015-406 with SEQ ID No. 1 of EP3325502. 5 pages.
Alishiri et al., (2013). "Prevalence of Tobacco mosaic virus in Iran and Evolutionary Analyses of the Coat Protein Gene," Plant Pathol. J., 29(3):260-273.
Alliance Seeds, "Tomato—Candela F1," Product sheet of Candela. Available at <https://allianceseeds.co.za/wp-content/uploads/2018/03/tech-sheet-TOMATO-CANDELA-F1.pdf>, 1 page.
Approval of the Research Grant entitled « Coping with Tm-2 resistance-breaking Tobamo viruses in tomatoes» including the allocation of funds, and allocating the grant No. 20-10-0070. Dated Oct. 6, 2015. Partial English translation included (first page). 3 pages.
Arens et al., (2010). "Development and evaluation of robust molecular markers linked to disease resistance in tomato for distinctness, uniformity and stability testing," Theor Appl Genet, 120:655-664.
Bolger et al., (2014). "The genome of the stress-tolerant wild tomato species *Solanum pennellii*," Nat Genet., 46(9):1034-1038, 6 pages.
Confirmation of Research Commencement for the plan N° 2611159 18 / 20-10-0070. State of Israel Ministry of Agriculture and Rural Development. Dated Feb. 11, 2017. English translation included. 2 pages.
Cover page of Volcani Center internal grant. State of Israel Ministry of Agriculture and Rural Development. Dated Dec. 28, 2016. Partial English translation included (first page). 5 pages.

(Continued)

*Primary Examiner* — Anne Kubelik
(74) *Attorney, Agent, or Firm* — Foley Hoag LLP; Brendan T. Jones; David E. Shore

(57) ABSTRACT

The present invention relates to a tomato, *Solanum lycopersicum*, plant that is resistant to *Tobamovirus*, wherein the plant comprises one or more genomic sequences conferring *Tobamovirus* resistance. More specifically the invention relates to a tomato plant that is resistant to Tomato Brown Rugose Fruit Virus (TBRFV). The present invention further relates to a genomic sequence or locus providing resistance to *Tobamovirus*. In addition, the present invention relates to methods for proving a tomato plant that is resistant to *Tobamovirus*.

6 Claims, 6 Drawing Sheets

Figure 1:
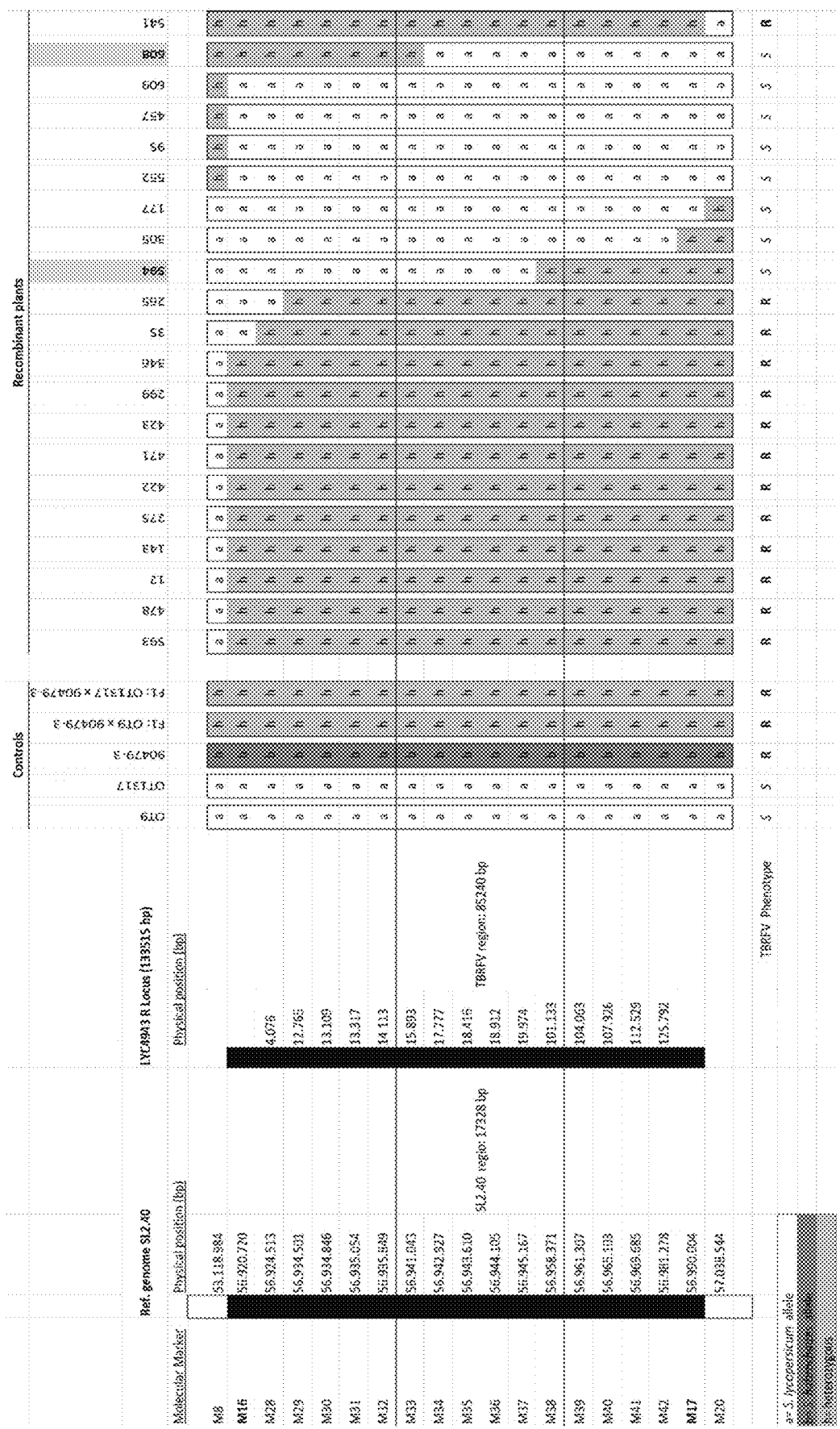
Figure 2:
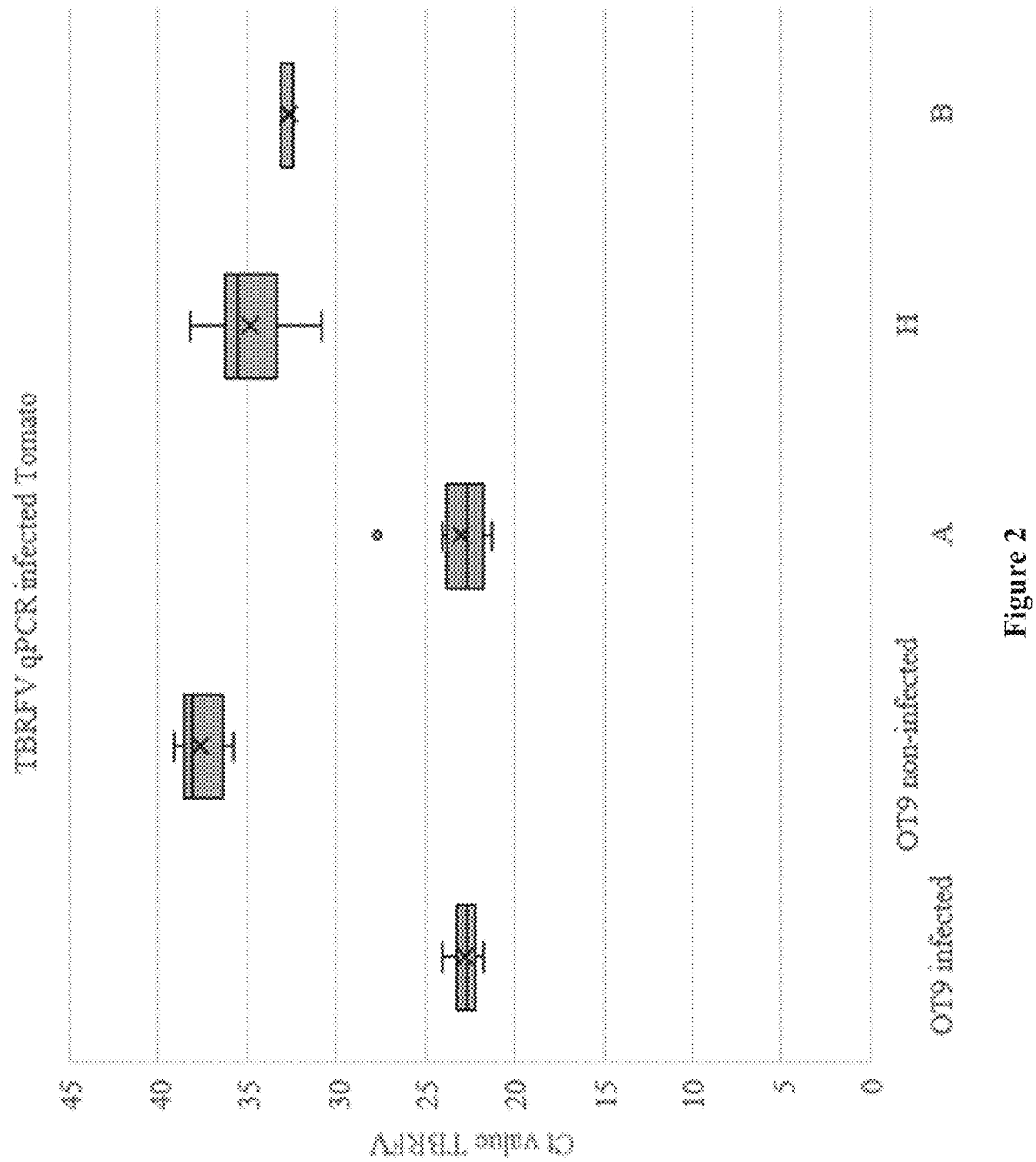
Figure 3:
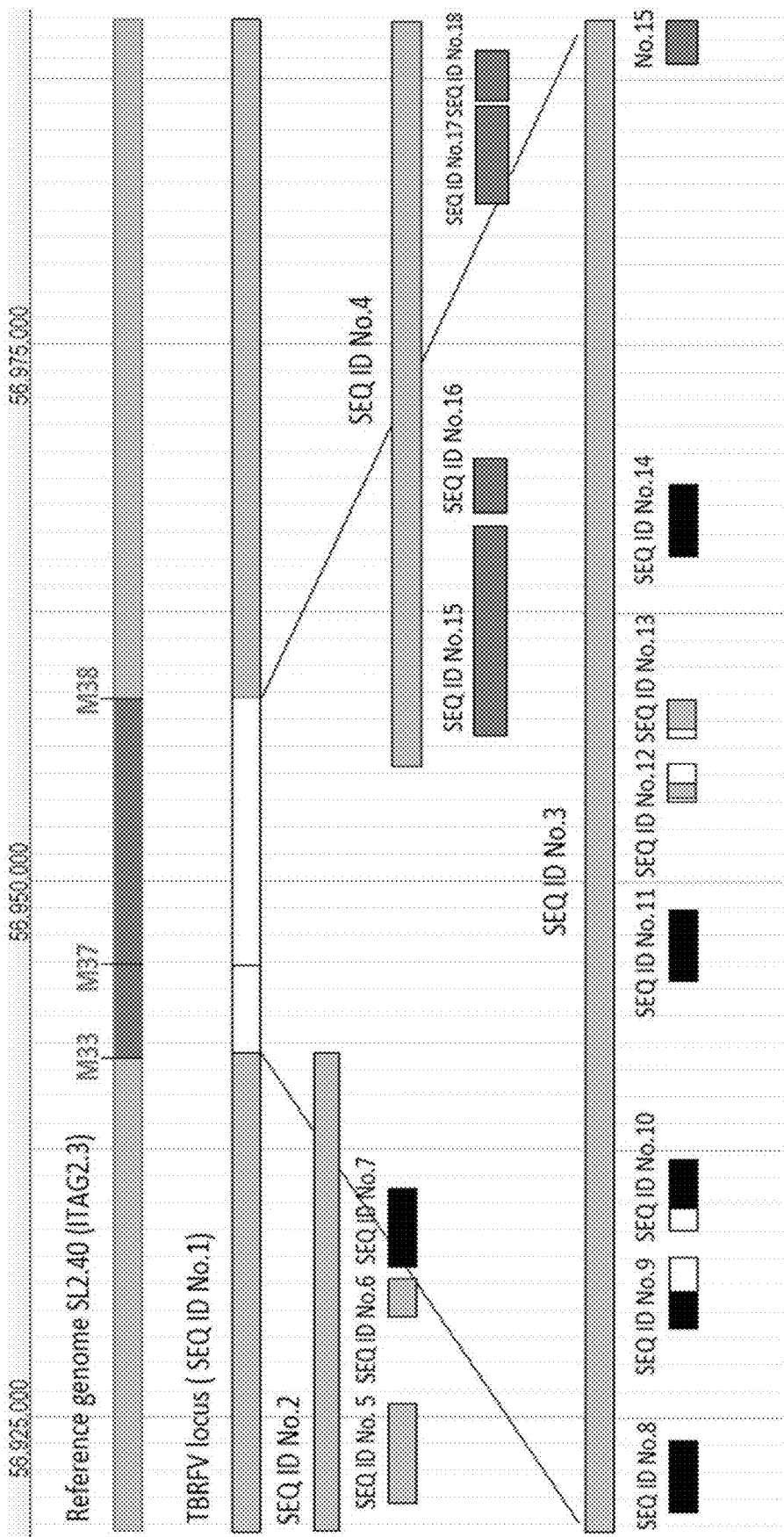

Specification includes a Sequence Listing.

(56) References Cited

OTHER PUBLICATIONS

Declaration and CV of Abdullah Ahmad Sa'sa, employee of Rijk Zwaan Export B.V., a subsidiary of the opponent. Dated Mar. 16, 2021. 4 pages.
Declaration and CV of Daniel Ludeking, employee of Rijk Zwaan Breeding B.V., a subsidiary of the opponent. Dated Mar. 16, 2021. 6 pages.
Declaration and CV of Hamzeh Zuhdi Habboub, employee of Rijk Zwaan Export B.V., a subsidiary of the opponent. Dated Mar. 16, 2021. 3 pages.
Declaration and CV of Robert John Dekker, University of Amsterdam. Dated Mar. 2021. 7 pages.
Declaration of Jochem Altena, dated Jul. 30, 2032, submitted in Opposition proceedings for EP3325502. 1 page.
Dombrovsky Declaration, Annex A (CV of Dombrovsky), and Annex B (list of exhibits), dated Mar. 2021, filed in Opposition against EP3325502. 7 pages.
Email confirmation that sequencing of the virus was finished, dated Jul. 8, 2015, from University of Amsterdam to Enza Zaden. 1 page.
Email from Enza Zaden on sequencing of AE50 isolate from Saudi Arabia in Jun. 2015. 1 page.
Email string from Enza Zaden on virus availability from Jan. to Jun. 2015. 4 pages.
Fedex Airway bill 1, dated May 10, 2015 (Annex 1 to D7). 1 page.
Fedex Airway bill 2, dated Jul. 9, 2015 (Annex 2 to D7). 1 page.
Fraiture et al., (2019). "MinION sequencing technology to characterize unauthorized GM petunia plants circulating on the European Union market," Scientific reports, 9(1):7141, 8 pages.
Ganz et al., (2014). "Coping with Tomato Tobamoviruses," The Ministry of Agriculture and Rural Development. English translation included. 8 pages.
Ganz et al., (2015). "TMV and ToMV Tomato Viruses Alert," The Ministry of Agriculture and Rural Development. English translation included. 8 pages.
GenBank Accession No. AP009297.1, Asamizu E et al., "Solanum lycopersicum genomic DNA, chromosome 8, clone: C08SLe0082C24, complete sequence," Dec. 11, 2006, 28 pages.
GenBank deposit: KT383474, "Tomato brown rugose fruit virus isolate Tom1-Jo, complete genome," Available at <https://www.ncbi.nlm.nih.gov/nuccore/KT383474>, 3 pages.
GenBank deposit: KX619418, "Tomato brown rugose fruit virus-Israeli isolate TBRFV-IL, complete genome," Available at <https://www.ncbi.nlm.nih.gov/nuccore/KX619418>, 3 pages.
Huang et al., (2012). "Virus-induced gene silencing and its application in plant functional genomics," Sci China Life Sci., 55(2):99-108.
Hudcovicova et al., (2015). "Molecular Selection of Tomato and Pepper Breeding Lines Possessing Resistance Alleles Against Tobamoviruses," Agriculture (Polnohospodarstvo), 61(1):33-37.
International Committee on Taxonomy of Viruses (ICTV), "Genus: *Tobamovirus*," Available at <https://talk.ictvonline.org/ictv-reports/ictv_online_report/positive-sense-rna-viruses/w/virgaviridae/672/genus-tobamovirus>, 6 pages.
Invitation to National Conference on Edible Tomatoes on Jun. 30, 2015, for Gantz S, Katari L, Ilani S, Avraham I, Ziger I, dated before Jun. 2015. English translation included. 2 pages.
Kadirvel et al., (2012). "Mapping of QTLs in tomato line FLA456 associated with resistance to a virus causing tomato yellow leaf curl disease," Euphytica, 190(2):297-308.
Lanfermeijer et al., (2005). "The products of the broken Tm-2 and the durable Tm-22 resistance genes from tomato differ in four amino acids," Journal of Experimental Botany, 56:2925-2933.
Lapidot Declaration, Annex A (CV of Moshe Lapidot), and Annex B (list of exhibits), dated Mar. 2021, filed in Opposition against EP3325502. 6 pages.
Lapidot, M. Request of a Research Grant: Temporary ID code 0781-003, "Coping with Tm-2 resistance-breaking Tobamo viruses in the Tomato (Hebrew title)/New solutions for new resistance-breaking tobamoviruses in tomato (English title)," dated May 18, 2015. English translation included. 6 pages.
Letschert et al., (2002). "Detection and differentiation of serologically cross-reacting tobamoviruses of economical importance by RT-PCR and RT-PCR-RFLP," J Viral Methods, 106(1): 1-10.
Li et al., (2013). "Complete Genome Sequence of a New Tobamovirus Naturally Infecting Tomatoes in Mexico," Genome Announcements, 1(5):1-2.
Li et al., (2018). "Linkage between the I-3 gene for resistance to Fusarium wilt race 3 and increased sensitivity to bacterial spot in tomato," Theoretical and Applied Genetics, 131:145-155.
Luria et al., (2018). "A local strain of Paprika mild mottle virus breaks L(3) resistance in peppers and is accelerated in Tomato brown rugose fruit virus-infected Tm-2(2)-resistant tomatoes," Virus Genes, DOI: 10.1007/s11262-018-1539-2, 10 pages.
Luria et al., (2017). "A New Israeli Tobamovirus Isolate Infects Tomato Plants Harboring Tm-22 Resistance Genes", PLOS One, 12(1):e0170429, 19 pages.
Maayan et al., (2018). "Using genomic analysis to identify tomato Tm-2 resistance-breaking mutations and their underlying evolutionary path in a new and emerging tobamovirus", Archives of Virology, 163(7):1863-1875, 13 pages.
Moreira et al., (2003). "Characterization of a new Tomato mosaic virus strain isolated from tomato in the State of Sao Paulo, Brazil," Fitopatol. bras., 28(6):602-607. English abstract only.
Moya et al., (2004). "The population genetics and evolutionary epidemiology of RNA viruses," Nature Reviews, 2:279-288.
Notice of opposition by Enza Zaden Beheer B.V., filed in relation to EP3325502, dated Mar. 16, 2021. 29 pages.
Notice of opposition by Rijk Zwaan Zaadteelt & Zaadhandel B.V., filed in relation to EP3325502, dated Mar. 17, 2021. 33 pages.
Notice of opposition by Syngenta Crop Protection AG, filed in relation to EP3325502, dated Mar. 15, 2021. 17 pages.
Notice of opposition by Vilmorin & Cie, filed in relation to EP3325502, dated Mar. 16, 2021. 35 pages.
Oosumi et al., (2009). "Gene Rpi-bt1 from Solanum bulbocastanum Confers Resistance to Late Blight in Transgenic Potatoes," Am. J. Potato Res., 86(6):456-465.
Panthee et al., (2013). "Novel molecular marker associated with Tm2a gene conferring resistance to tomato mosaic virus in tomato," Plant Breeding, 132:413-416.
Partial transcript of genomic sequence of Tobacco mosaic virus strain Ohio V, NCBI sequence database, published Jan. 10, 2012. 1 page.
Partial transcript of sequence of Israel virus 01, NCBI sequence database. 1 page.
Partial transcript of sequence of Jordan virus 03, NCBI sequence database. 1 page.
Rast, A. Th. B., (1975). Thesis titled "Variability of tobacco mosaic virus in relation to control of tomato mosaic in glasshouse tomato crops by resistance breeding and cross protection," Institute of Phytopathological Research, Wageningen, 88 pages.
Reply of the patent proprietor to the notice(s) of opposition, filed on Aug. 9, 2021 in Opposition proceedings for EP3325502. 86 pages.
Report on sequencing new ToMV virus, Jul. 2015, "Identification of viruses by small RNA sequencing," University of Amsterdam. 5 pages.
Run report of sequencing project performed by University of Amsterdam on new virus isolate, dated Jul. 7, 2015. 5 pages.
Salem et al., (2015). "A new tobamovirus infecting tomato crops in Jordan", Archives of Virology, 161(2):503-506, 4 pages.
Screenshot of Enza Zaden database transcript, showing the dates of receipt of virus isolated from Jordan and Saudi Arabia, 1 page.
Screenshot of the FASTA file created on Jul. 13, 2015 by the University of Amsterdam, on the virus genome sequence. 1 page.
Sequence alignment of KT383474 against SEQ ID No. 1 of EP3325502 using NCBI Blast, 5 pages.
Sequence alignment of KT383474 and KX619418 against SEQ ID No. 1 of EP3325502, 14 pages.
Sequence alignment of KX619418 against SEQ ID No. 1 of EP3325502 using NCBI Blast, 6 pages.
Sequence alignments of KX619418 and KT383474 against MS838349 (SEQ ID No. 1 of WO2017/012951) using NCBI Blast, 14 pages.

(56) References Cited

OTHER PUBLICATIONS

Shi et al., (2011). "Molecular Markers for Tm-2 Alleles of Tomato Mosaic Virus Resistance in Tomato", American Journal of Plant Sciences, 2(2):180-189.

Song et al., (2003). "Gene RB cloned from Solanum bulbocastanum confers broad spectrum resistance to potato late blight," PNAS USA, 100(16):9128-9133.

Tiwari et al., (available in NCBI database, Nov. 28, 2019). "Whole genome sequencing of Interspecific potato hybrid MSH/14-112," Crop Improvement, ICAR-Central Potato Research Institute, 5 pages. (Relevant portion of sequence only).

Turina et al., (2016). "First report of Tomato mottle mosaic virus in tomato crops in Israel," New Disease Reports 33, 1. <http://dx.doi.org/10.5197/j.2044-0588.2016.033.001>, 1 page.

Upov, (2011). Guidelines for the conduct of tests for distinctness, uniformity and stability: Tomato. TG/44/11. 71 pages.

Upov, Technical Committee (2015). Partial revision of the test guidelines for sweet pepper, hot pepper, paprika, chili (Document TG/76/8). TC/51/30. 25 pages.

UPS Airway bill 3, dated Jul. 7, 2015 (Annex 3 to D7). 1 page.

Van der Vossen E et al., (2003). "An ancient R gene from the wild potato species *Solanum bulbocastanum* confers broad-spectrum resistance to Phytophthora infestans in cultivated potato and tomato," The Plant Journal, 36(6):867-882.

Van Esse et al., (2020). "Genetic modification to improve disease resistance in crops," New Phytologist, 225:70-86.

Van Lieshout N et al., (2020). "Solyntus, the new highly contiguous reference genome for potato (*Solanum tuberosum*)," G3: Genes, Genomes, Genetics, 10(10):3489-3495.

Vegetables Bulletin—Field and Vegetables No. 285. Oct. 2015. The Vegetable Growers Organization. Partial English translation included (p. 1; p. 9 partially, pp. 10-11, 26 and 27 completely). 51 pages.

Vosman et al., (2006). "Minutes of first project meeting: Development and evaluation of molecular markers linked to disease resistance genes for tomato DUS testing (option 1a)," Available at <https://cpvo.europa.eu/sites/default/files/documents/techreports/Apendices_final_report_CPVO_tomato_project.pdf>, 4 pages.

Weber et al., (1998). "Tm-22 Resistance in Tomato Requires Recognition of the Carboxy Terminus of the Movement Protein of Tomato Mosaic Virus". MPMI, 11(6):498-503.

Workman R et al., (2018). "High Molecular Weight DNA Extraction from Recalcitrant Plant Species for Third Generation Sequencing," Nature, Protocol Exchange, 15 pages. (Preliminary version of a manuscript).

International Search Report and Written Opinion for International Application No. PCT/EP2019/050830 dated Jun. 27, 2019.

International Search Report and Written Opinion for International Application No. PCT/EP2019/084272 dated Jun. 19, 2020.

Sequence: AP009297.1 "Solanum lycopersicum genomic DNA, chromosome 8, clone: C08SLe0082C24." European Nucleotide Archive, Dec. 13, 2006.

\* cited by examiner

| Chromosome 8_SL2.40 | | | LYC4943 R Locus (133516 bp) | | Controls | | | Recombinant plants | | |
|---|---|---|---|---|---|---|---|---|---|---|
| Molecular Marker | Physical position (bp) | | Physical position (bp) | | O19 | 90479-3 | BC2: O19 × 90479-3 | 15321-02 | 15321-03 | 15321-07 |
| M33 | 56.941.043 | | | | a | h | h | h | h | a |
| M34 | 56.942.927 | | 15.893 | | a | h | h | a | h | h |
| M35 | 56.943.610 | | 17.777 | | a | h | h | a | h | h |
| M36 | 56.944.105 | | 18.416 | | a | h | h | a | h | h |
| M37 | 56.945.167 | SL2.40 regio: 17.328 bp | 18.912 | | a | h | h | a | h | h |
| M-SEQ 10 | | | 19.974 | | . | + | + | . | + | + |
| M-SEQ 11_1 | | | 36.480 | TBRFV region: 85.240 bp | , | + | + | , | + | + |
| M-SEQ 11_2 | | | 48.748 | | , | + | + | , | + | + |
| M-SEQ 14 | | | 52.303 | | , | + | + | , | + | + |
| M38 | 56.958.371 | | 77.410 | | , | + | + | , | , | , |
|  |  | | 101.133 | | a | h | h | a | a | h |
| TBRFV Phenotype | | | | | S | R | R | S | S | R |
| TBRFV ELISA (absorption at 405nm) | | | | | 1527 | | | 1109 | 1547 | 893 |
| TBRFV qPCR (Ct value) | | | | | 22,6 | | | 23,4 | 22,4 | 36,6 | a = S. lycopersicum allele
h = heterozygous
+ = S. habrochaites allele present
- = S. habrochaites allele absent

Figure 4

TOMATO PLANT RESISTANT TO TOMATO BROWN RUGOSE FRUIT VIRUS

CROSS REFERENCE TO RELATED APPLICATIONS

This application is a continuation application of U.S. application Ser. No. 17/196,655, filed on Mar. 9, 2021, which is a continuation application of International Application No. PCT/EP2019/084272, filed Dec. 9, 2019, which claims priority to International Application No. PCT/EP2019/050830, filed Jan. 14, 2019, each of which is incorporated herein by reference in their entirety.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 701802018402SEQLIST.TXT, date recorded: Sep. 13, 2021, size: 442,703 bytes).

DESCRIPTION

The present invention relates to a plant of the *S. lycopersicum* species that is resistant to *Tobamovirus*, wherein the plant comprises one or more genomic sequences. More specifically the invention relates to tomato plants (*S. lycopersicum*) that are resistant to Tomato Brown Rugose Fruit Virus (TBRFV). The present invention further relates to a genomic sequence or locus providing resistance to *Tobamovirus*. Furthermore the present invention relates to methods for providing a *S. lycopersicum* plant that is resistant to *Tobamovirus*.

*Tobamovirus* is a genus in the virus family Virgaviridae that infects plants, including plants of the Solanaceae family, such as tobacco, potato, tomato, and eggplant and are among the most serious threats to vegetable crops in the world. *Tobamoviruses* are particularly a problem in tomato crops grown in protected environments and are transmitted over long distances through external seed contamination, and mechanically from plant to plant through common culture practices through workers' hands, clothes, tools, and are capable to preserve infectivity in seeds and contaminated soil. Furthermore, common weeds, often asymptomatic when infected by the virus comprise a cryptic reservoir between growth cycles.

*Tobamovirus* infections can have disastrous effects in crops when they become contaminated. Prevention of infection, by, for example, raising seedlings in a virus free environment is generally costly and/or unfriendly to the environment. In addition, these methods do not always provide satisfactory results.

*Tobamoviruses* are non-enveloped, with helical rod geometries, and helical symmetry. Viral particles are rod-shaped and have a diameter of around 18 nm, and a length of 300 to 310 nm. Their positive-sense single stranded RNA genomes are linear and non-segmented, and around 6.3 to 6.5 kb in length. There are over 35+ virus species in this genus including Tomato Mosaic Virus (ToMV) or Tobacco Mosaic Virus (TMV), Tomato Mild Mottle Virus (ToMMV), and the recently newly discovered Tomato Brown Rugose Fruit Virus (TBRFV).

In tomato, naming of the four strains of *Tobamovirus* (more specifically ToMV) currently recognized (Tm-0, Tm-1, Tm-2 and Tm-$2^2$) is based on the introgressed resistance (R) genes Tm1, Tm2 and Tm$2^2$ from related wild species. The Tm1 gene was introgressed from *Solanum habrochaites* and is incompletely dominant. The Tm2 and Tm$2^2$ genes were introgressed from *Solanum peruvianum* and confer dominant complete resistance to ToMV. However new strains of *Tobamovirus* have emerged as resistance is overcome and recently resistance-breaking *Tobamovirus* species have been reported in commercial fields in Mexico, Jordan, and Israel.

In the end of 2014 and beginning of 2015 an outbreak of a new disease infecting tomatoes occurred in Israel and Jordan. Symptomatic plants showed a mosaic pattern on leaves accompanied occasionally by narrowing of leaves and yellow spotted fruit. Research showed that this new disease was a new *Tobamovirus*, called TBRFV. TBRFV infection is associated with necrotic lesions on leaves and tomato plants show mild foliar symptoms at the end of the season but strong brown rugose symptoms on fruits, making the fruit unsuitable for consumption. Furthermore, regarding to other members of the Solanaceae family, it seems that the TBRFV is capable to infect pepper plants as well, e.g. when planted on contaminated soil from a previous growth cycle of infected tomato plants in high temperatures above 30° C.

In the battle against *Tobamovirus*, resistance was introduced in tomatoes by introgression of the R genes Tm2 and Tm$2^2$, resulting in resistance to ToMV. However, these R-genes do not provide resistance to the new TBRFV, since different domains in the viral proteins comprised of different protein structure and a new resistance mechanism and/or resistant genes are required for a different resistance mechanism. Furthermore, it is highly likely that over time resistance will be broken, since the virus will adapt and evolve, resulting in viral breakthrough. Therefore, new resistance genes need to be identified and/or combined to provide resistant crops, especially against the new TBRFV.

Considering the above, there is a need in the art for TBRFV resistant tomato plants, more specifically TBRFV resistant *S. lycopersicum*. In addition, there is a need in the art to provide methods and means for providing TBRFV resistant *S. lycopersicum* plants.

It is an object of the present invention, amongst other objects, to address the above need in the art. The object of present invention, amongst other objects, is met by the present invention as outlined in the appended claims.

Specifically, the above object, amongst other objects, is met, according to a first aspect, by the present invention by a plant of the *S. lycopersicum* species that is resistant to *Tobamovirus*, wherein the plant comprises a TBRFV resistance gene that encodes for a TBRFV resistance protein, wherein the protein has at least 90%, preferably at least 95%, more preferably at least 98%, even more preferably at least 99%, most preferably 100% amino acid sequence identity with SEQ ID No.116. It is predicted that the TBRFV resistance gene encodes for a NBS-LRR resistance protein.

According to a preferred embodiment, the present invention relates to the plant, wherein the TBRFV resistance gene comprises a coding sequence that has at least 90%, preferably at least 95%, more preferably at least 98%, even more preferably at least 99%, most preferably 100% nucleotide sequence identity with SEQ ID No.115.

According to another preferred embodiment, the present invention relates to the plant, wherein the plant comprises one or more genomic sequences selected from the group consisting of SEQ ID No.1, SEQ ID No.2 SEQ ID No.3, SEQ ID No.4, SEQ ID No.5, SEQ ID No.6, SEQ ID No.7, SEQ ID No.8, SEQ ID No.9, SEQ ID No.10, SEQ ID No.11, SEQ ID No.12, SEQ ID No.13, SEQ ID No.14, SEQ ID No.15, SEQ ID No.16, SEQ ID No.17 and SEQ ID No.18, or having at least 95% sequence identity with any of said SEQ ID No's. The genomic sequences encode for one or more genes or genetic elements that provide resistance to *Tobamovirus*. Sequences have been examined on gene homology using public database of the National Center for Biotechnology Information (NCBI). Six genomic sequences have homology with sequences that encode for NBS-LRR resistance proteins (SEQ ID No.7, 8, 9, 10, 11 and 14). Four genomic sequences have homology with LRR receptor-like serine/threonine-protein kinase (SEQ ID No. 5, 6, 12 and 13).

Pathogen recognition by plants takes place via two relevant groups of host receptors involving two main types of proteins, namely Receptor-like kinases or proteins (RLK or RLP) and nucleotide-binding site leucine-rich repeat proteins (NBS-LRR resistance proteins). The first group are pattern recognition receptors (PRR) specializing in the recognition of pathogen associated molecular patterns (PAMPS). RLPs or RLKs are attached to the cell membrane and are extracellular immune receptors. Plant RLKs are involved in plant-pathogen interaction and defence responses and plant receptor kinases (PRKs) can be defined as proteins that contain an extracellular domain, a single-pass transmembrane domain and a cytoplasmic serine/threonine (Ser/Thr) protein kinase domain. Plant LRR-RLKs (leucine rich-repeat receptor-like kinase) possess a functional cytoplasmic kinase domain, and all of the plant LRR-RLKs analysed to date possess Ser/Thr kinase activity. The resistance to pathogens provided by these receptors is called PAMP-triggered immunity (PTI). The other group mainly comprises intracellular receptors called resistance proteins (R proteins). The majority of disease resistance genes in plants encode nucleotide-binding site leucine-rich repeat proteins, also known as NBS-LRR proteins. These proteins are characterized by nucleotide-binding site (NBS) and leucine-rich repeat (LRR) domains as well as variable amino- and carboxy-terminal domains and are involved in the detection of diverse pathogens, including bacteria, viruses, fungi, nematodes, insects and oomycetes. The majority of the identified genomic sequences that provide *Tobamovirus* resistance comprise multiple LRR domains. It is thought that these domains determine effector recognition and therefore disease susceptibility/resistance.

Pathogens develop counter strategies to overcome PTI through modifying or changing PAMPs or MAMPs. Then, plants will develop a way to recognize these effectors and trigger a faster and stronger secondary defence response known as effector-triggered immunity (ETI). ETI is mediated by R proteins and accompanied by localized cell death around the site of infection. The presence of these newly identified resistance gene and/or genomic regions encoding NBS-LRR proteins and/or plant receptor kinases will decrease the chances of the pathogen overcoming the resistance, or when combined with other resistance genes, disease resistance may even be further improved.

According to a preferred embodiment, the present invention relates to the plant, wherein the plant comprises the genomic sequence represented by SEQ ID No.3. The genomic sequence SEQ ID No. 3 comprises multiple sequences that have homology with sequences that encode for NBS-LRR resistance proteins and LRR receptor-like serine/threonine-protein kinase.

According to yet another preferred embodiment, the present invention relates to the plant, wherein the plant comprises SEQ ID No.8, SEQ ID No.9, SEQ ID No.10 and SEQ ID No.11.

According to the present invention, *Tobamovirus* resistance of the plant may be affected by one or more genomic sequences encoding a NBS-LRR protein selected from the group of SEQ ID No.8, No.9, No.10, No.11 and No.14, for example a combination of SEQ ID No.8 and SEQ ID No. 9, or SEQ ID No.8 and SEQ ID No.10, SEQ ID No.8 and SEQ ID No. 11, SEQ ID No. 9 and SEQ ID No. 10, SEQ ID No.9 and SEQ ID No.11, SEQ ID No.10 and SEQ ID No. 11. Furthermore or alternatively, the resistance may affected by one or more genomic sequences encoding a LRR receptor-like serine/threonine-protein kinase selected from the group of SEQ ID No. 12, SEQ ID No.13, or SEQ ID No.12 and SEQ ID No.13.

According to yet another preferred embodiment, the present invention relates to the plant, wherein the plant comprises the genomic sequences of SEQ ID No.8, SEQ ID No.11 and SEQ ID No.14.

According to a preferred embodiment, the present invention relates to the plant, wherein the plant comprises SEQ ID No.8, SEQ ID No.9, SEQ ID No.10, SEQ ID No.11, SEQ ID No.12, SEQ ID No.13 and SEQ ID No.14.

According to another preferred embodiment, the present invention relates to the plant, wherein the plant is resistant to *Tobamovirus* strains Tm-0, Tm-1 and Tm-2. In tomato, four strains of *Tobamovirus* have been identified; Tm-0, Tm-1, Tm-2 and Tm-$2^2$.

According to yet another preferred embodiment, the present invention relates to the plant, wherein the plant is resistant to Tomato Brown Rugose Fruit Virus (TBRFV).

According to yet another preferred embodiment, the present invention relates to the plant, wherein the TBRFV is virus isolate AE050.

According to yet another preferred embodiment, the present invention relates to the plant, wherein the plant is a tomato plant (*Solanum lycopersicum*).

According to yet another preferred embodiment, the present invention relates to the plant, wherein the one or more genomic sequences and/or TBRFV resistance gene is heterozygously or homozygously present in the genome of said plant. From the experimental data it can be concluded that the resistance is dominant and that the TBRFV resistance gene and/or genomic sequence must be at least heterozygously present in the genome of the plant to provide resistance against the *Tobamovirus*.

The present invention, according to a second aspect, relates to plants, plant parts, tissues, cells, and/or seeds derived from the plant of the present invention.

The present invention, according to a further aspect, relates to a resistance gene (TBRFV resistance gene) for providing resistance to a *Tobamovirus* in a *S. lycopersicum* plant, wherein said resistance gene is represented by a coding sequence having at least 90% nucleotide sequence identity with SEQ ID No.115.

The present invention, according to a further aspect, relates to a genomic sequence for providing resistance to a *Tobamovirus* in a *S. lycopersicum* plant, wherein the genomic sequence is selected from the group consisting of SEQ ID No.5, SEQ ID No.6, SEQ ID No.7, SEQ ID No.8, SEQ ID No.9, SEQ ID No.10, SEQ ID No.11, SEQ ID No.12, SEQ ID No.13, SEQ ID No.14, SEQ ID No.15, SEQ ID No.16, SEQ ID No.17 and SEQ ID No.18, or having at least 95% sequence identity with any of said SEQ ID No's. Preferably the genomic sequence is SEQ ID No.8, SEQ ID No.11 or SEQ ID No.14.

The present invention, according to a further aspect, relates to a resistance locus for providing resistance to a *Tobamovirus* in a *S. lycopersicum* plant, wherein the locus is represented by SEQ ID No.1, SEQ ID No.2, SEQ ID No.3 or SEQ ID No.4, preferably SEQ ID No.3.

According to a preferred embodiment of present invention, the resistance gene, genomic sequence or resistance locus provides resistance to a TBRFV.

Figure 5:
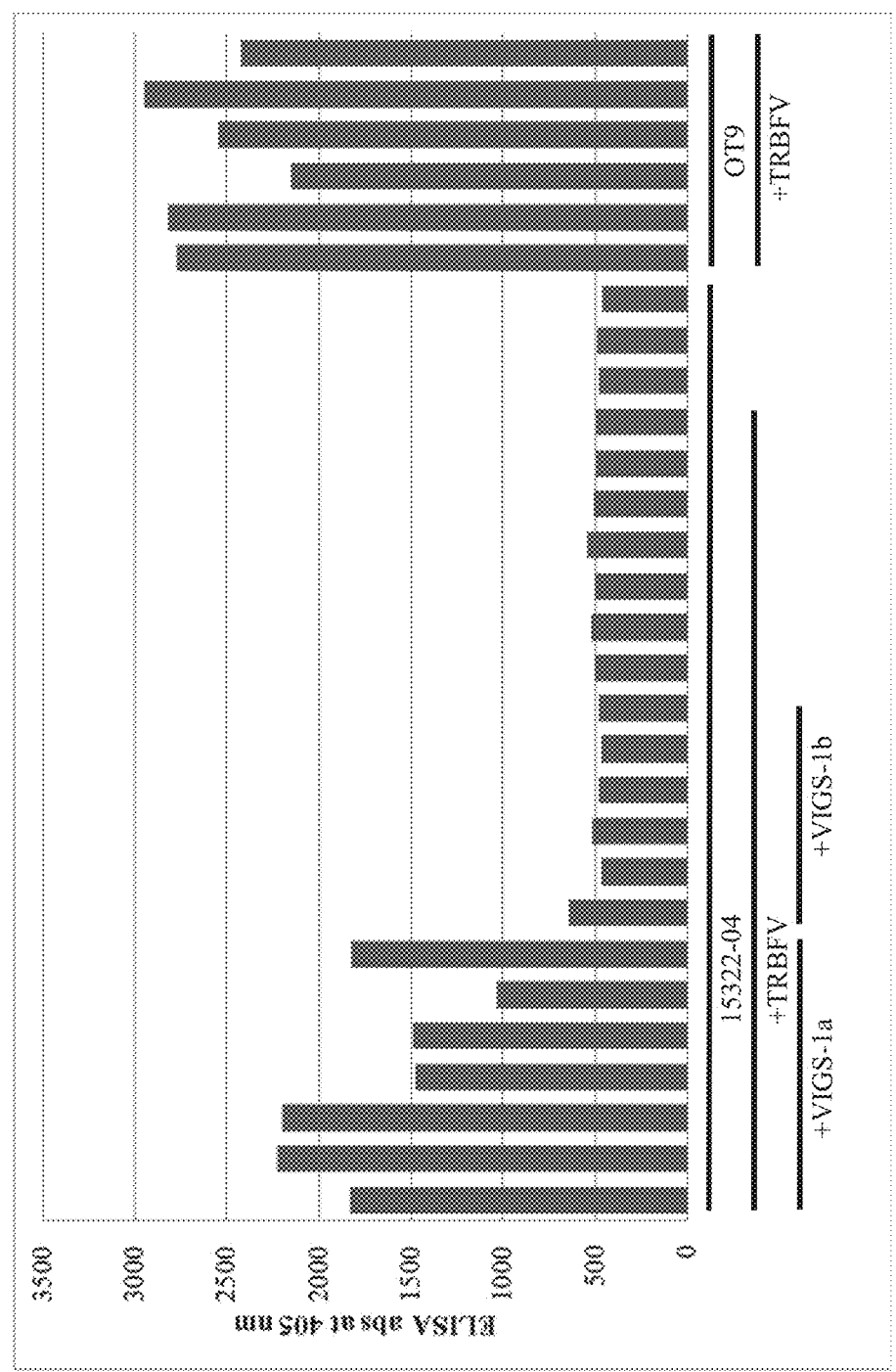

The present invention, according to a further aspect, relates to a method for providing a plant of the *S. lycopersicum* species that is resistant to *Tobamovirus*, wherein the method comprises the steps of;
  a) selecting a *S. habrochaites* plant that is resistant to *Tobamovirus*, wherein said selection comprises establishing the presence of the resistance gene genomic sequence or resistance locus of present invention,
  b) transferring the identified genomic sequence or locus of step a) into a *S. lycopersicum* plant thereby conferring *Tobamovirus* resistance to said *S. lycopersicum* plant.

Transferring can be done by crossing the selected *S. habrochaites* plant with a *S. lycopersicum*. Subsequently, a *Tobamovirus* resistant *S. lycopersicum* plant can be selected.

According to another preferred embodiment, the present invention relates to the method, wherein after step b) a first *S. lycopersicum* plant is selected that is resistant to *Tobamovirus* and is crossed with a second *S. lycopersicum* plant that is not resistant to *Tobamovirus*, and subsequently selecting *S. lycopersicum* plants that are resistant to *Tobamovirus*.

According to a preferred embodiment, the present invention relates to the method, wherein in step a) establishing the presence of the resistance gene (TBRFV resistance gene), resistance conferring genomic sequence or the resistance locus in a *S. habrochaites* plant is performed by one or more markers selected from the group consisting of SEQ ID No: 83, SEQ ID No: 84, SEQ ID No: 85, SEQ ID No: 86, SEQ ID No: 87, SEQ ID No: 88, SEQ ID No: 89, SEQ ID No: 90, SEQ ID No: 91, SEQ ID No: 92, SEQ ID No: 93, and SEQ ID No: 94, SEQ ID No. 105, SEQ ID No. 106, SEQ ID No. 107, SEQ ID No. 108, SEQ ID No. 109, SEQ ID No. 110, SEQ ID No. 111, and SEQ ID No. 112, preferably SEQ ID No. 105, SEQ ID No. 106, SEQ ID No. 107, SEQ ID No. 108, SEQ ID No. 109, SEQ ID No. 110, SEQ ID No. 111, and SEQ ID No. 112.

The present invention, according to a further aspect, relates to a use of a marker for establishing the presence of the TBRFV resistance gene, the TBRFV resistance conferring genomic sequence or the resistance locus in a *S. lycopersicum* plant, wherein the marker is one or more markers selected from the group consisting of SEQ ID No: 83, SEQ ID No: 84, SEQ ID No: 85, SEQ ID No: 86, SEQ ID No: 87, SEQ ID No: 88, SEQ ID No: 89, SEQ ID No: 90, SEQ ID No: 91, SEQ ID No: 92, SEQ ID No: 93, and SEQ ID No: 94, SEQ ID No. 105, SEQ ID No. 106, SEQ ID No. 107, SEQ ID No. 108, SEQ ID No. 109, SEQ ID No. 110, SEQ ID No. 111, and SEQ ID No. 112, preferably SEQ ID No. 105, SEQ ID No. 106, SEQ ID No. 107, SEQ ID No. 108, SEQ ID No. 109, SEQ ID No. 110, SEQ ID No. 111, and SEQ ID No. 112.

The present invention will be further detailed in the following examples and figures wherein:

FIG. 1: Shows an overview of the mapping of the locus providing resistance against *Tobamovirus*, more specifically TRBFV in *S. lycopersicum*. F1 plants were created by crossing *S. habrochaites* line 90479-3 that was selected for resistance phenotype with *S. lycopersicum* lines OT9 and OT1317 to create two populations for mapping. Over 700 plants were tested on TRBFV resistance and several recombinant plants (21 plants) were selected and the results of the disease test were combined with the marker data. Several molecular markers (M1 to M42) have been used to determine the position and size of the genomic sequence providing resistance to TRBFV. A clear segregation was observed between resistant (R) and susceptible plants (S). The results indicated that a genomic region located between markers M16 and M17 was providing the TRBFV resistance; the corresponding locus (named LYC4943 R Locus) is 133.515 bp in length and comprises several putative genes. Based on further fine mapping, the size and location of the genomic sequence that was harbouring the TBRFV resistance was determined to be between markers M33 and M38 and was approximately 68.000 bp larger compared to the SL2.40 reference genome of *S. lycopersicum* (85.240 bp vs. 17.328 bp, respectively). It is therefore most likely that one or more genes that are located within this region, indicated as "TBRFV region", are providing the TBRFV resistance.

FIG. 2: Shows the results of a qPCR for the detection of TBRFV in infected and uninfected tomato plants (*S. lycopersicum*) of the present invention and plants that do not comprise the TBRFV resistance locus. Low Ct values (i.e. below 30) indicate the high presence of viral RNA present in the samples. OT9 is a tomato plant that does not comprise the TBRFV resistance locus. The control sample (OT9 uninfected) showed a Ct value of between 35 and 40 cycles and the infected control sample (OT9 infected) showed a Ct value of between 20 and 25. Plants that show a Ct value above 30 cycles, preferably around 35 cycles were considered resistant, whereas plants that show a Ct value below 30 were considered susceptible. Tomato plants comprising the TBRFV resistance locus, homozygous (B) or heterozygous (H) have a Ct value above 30 cycles and were considered as being resistant. Furthermore, the results showed that the resistance is dominant Plants that did not comprise the TBRFV resistance locus (A and OT9 infected) showed a Ct value of between 20 and 25, indicating that the plant was susceptible to TBRFV infection.

FIG. 3: Shows a schematic overview of the genomic sequences SEQ ID No.1 to SEQ ID No.18 of the present invention that encode for one or more genes or genetic elements that provide resistance to *Tobamovirus*.

FIG. 4: Shows an overview of a further mapping of the locus providing resistance against *Tobamovirus* in addition to FIG. 1. A further recombinant selection has been performed by further genotyping plants with M33 and M38 to identify recombinant plants in the identified TBRFV region and further limit this TBRFV region. Recombinant plants have been further genotyped with markers (M-SEQ 10, M-SEQ 11-1, M-SEQ 11-2, and M-SEQ 14) covering the TBRFV locus and were specifically designed to eliminate candidate regions in the TBRFV locus, i.e. the genomic sequences SEQ ID No.1 to SEQ ID No.18 of present invention that encode for one or more genes or genetic elements that provide resistance to *Tobamovirus*. Recombinant plants 15321-02, 15321-03 and 15321-07 were screened for resistance by inoculation with TBRFV isolate AE50. Based on these recombinant plants in combination with phenotyping, ELISA and qPCR data for the determination of TBRFV infection, it was concluded that the gene conferring resistance is part of genomic SEQ ID No 14. Plants 15321-02 and 15321-03 do not comprise SEQ ID No 14 and were shown to be susceptible to TBRFV, with high ELISA scores and low qPCR ct-values that correspond to the values obtained with the susceptible control line OT9, indicating virus infection. Plant 15321-07 comprises the SEQ ID No 14 and was shown to be resistant to TBRFV, with low ELISA scores and high qPCR ct-values.

FIG. 5: Shows the TBRFV infection by ELISA in a homozygous TBRFV resistant line (15322-04) as well as a susceptible control line (OT9). Plants were infected with TBRFV (+TRBFV) and infiltrated with construct VIGS-01a that specifically targets the TRBFV resistance gene or with construct VIGS-01b which targets a different region within the identified TRBFV region. ELISA reading was done by measurement of absorption at 405 nm. Control plants OT9 infected by TBRFV resulted in absorption levels of 2000 abs or higher, whereas the resistant plant lines infected with TRBFV resulted in absorption levels of approximately 500 abs. In cases where the TRBFV resistance gene was silenced by VIGS-01a in the resistant plant lines, absorption levels of between 1500 and 2250 abs were measured, indicating viral infection. Silencing by VIGS-01b in the resistant plant lines, resulted in similar absorption levels as was observed in the infected resistant plant lines that were not silenced by VIGS.

Figure 6:
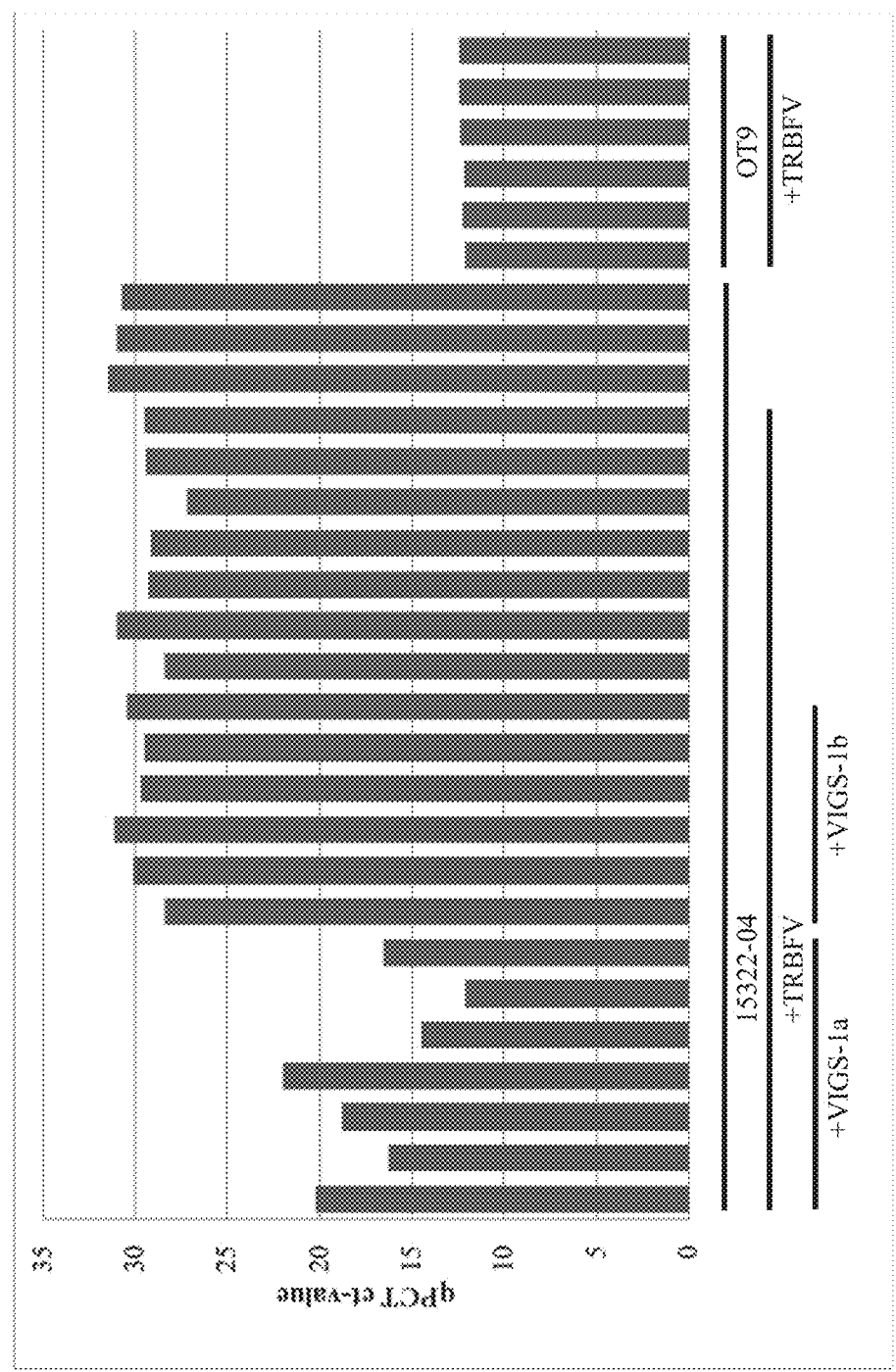

FIG. 6: Shows the TBRFV infection by qPCR in a homozygous TBRFV resistant line (15322-04) as well as a susceptible control line (OT9). Plants were infected with TBRFV (+TRBFV) and infiltrated with construct VIGS-01a that specifically targets the TRBFV resistance gene or with construct VIGS-01b which targets a different region within the identified TRBFV region. The infected control sample showed a Ct value of approximately 12 or 13. The resistant plant lines infected with TRBFV showed a Ct value of approximately 30, indicating TBRFV resistance. In cases where the TRBFV resistance gene was silenced by VIGS-01a in the resistant plant lines, Ct values were observed to drop to between approximately 12 to 20, higher than the infected control cells, and clearly indicating viral infection. Silencing by VIGS-01b in the resistant plant lines, resulted in similar Ct levels (Ct value of ~30) as was observed in the infected resistant plant lines that were not silenced by VIGS.

EXAMPLES

Inoculation of a Tomato Plant with TBRFV

The TBRFV isolate AE050 (Origin: Saudi Arabia) was used to perform the disease assays. As plant material, the Line OT9, which is a plant line susceptible for TBRFV, was used for virus maintenance. Symptomatic leaves received from the original samples were used for sap-mechanical inoculation on the Line OT9. The virus was maintained on systemically infected tomato plants OT9 by monthly sap-mechanical inoculation on new 3 weeks-old seedlings.

The tomato plants of the species of *Solanum pennellii, S. peruvianum, S. chilense, S. habrochaites, S. pimpinellifolium, S. neorickii, S. corneliomulleri, S. chmielewskii, S. cheesmaniae, S. galapagense* have been screened (~800 out of 912 wild *Solanum* accessions in total). Twelve plants of each accession were infected with TBRFV isolate AE050.

Seeds were sown in vermiculite, seedlings were transplanted in rockwool blocks and inoculated at 4 weeks after sowing. As starting material symptomatic leaves from infected-OT9 were collected and ground in a mortar and pestle in chilled demi water with carborundum (1 gr/100 mL). The oldest leaf from 3 weeks-old seedlings of each test plant was mechanically inoculated with AE050 by gently rubbing the leaf once with one finger.

The plants were phenotyped by visual scoring of the plants and the leaves. Plants were scored for visual symptoms at regular time intervals. Symptoms were visually assessed at 2, 4 and 6 weeks after inoculation, and ELISA tests on remaining plants were done from 6 weeks onwards, with 1 month intervals. More than 50% of the plants showed already symptoms at 2 weeks after inoculation.

Visual scoring was performed on a weekly basis. Plants were scored for visual symptoms. The presence of yellowing, mosaic pattern on leaves, leaf deformation (narrowing, mottling) was recorded on a weekly basis at the plant level. First symptoms were typically observed 12-14 days post-inoculation. Plants were categorized as "resistant" when no such symptoms on leaves were observed. Plants displaying any of the symptoms on leaves were categorized as "susceptible". Leaf samples were collected from asymptomatic plants (i.e. resistant) to test for the presence of virus by ELISA.

The screening allowed the selection of several candidates for resistance breeding, with the best candidate being LYC4943, a *S. habrochaites* accession from Peru. LYC4943 was symptomless and tested virus-free by ELISA for more than 15 weeks after inoculation.

Determination of TBRFV Infection by ELISA

Infection was determined by ELISA. One apical leaf (fully expanded) of every plant was collected. Leaves were crushed using a Type R302 D63N-472 machine (VECTOR Aandrijftechniek B.V., Rotterdam, The Netherlands) and sap was collected by adding 2 mL of PBS-Tween buffer. 100 μL of the extract was used for ELISA with antibodies against ToMV (supplier Prime Diagnostics, Wageningen, The Netherlands). ELISA reading was done by measurement of absorption at 405 nm with a FLUOstar Galaxy apparatus. Plants that gave absorption values more than 1.5 times of the clean control plants were considered infected (susceptible).

Bioassays and Mapping of TBRFV Resistance Genomic Sequence

The original LYC4943 (*S. habrochaites*) seed lot was segregating for the resistance. Nine different F1 families were sown for bioassay in order to identify the F1 families which were completely resistant (resistance is fixed) and which would be used for further backcrosses. Four F1 families germinated and were tested in bioassay. F1 plants created with LYC4943 plant 3 (90479-3) were selected for resistance phenotype to create two populations for mapping, choosing the *S. lycopersicum* lines OT9 and OT1317 as backcross lines. Markers M1 to M42 (respectively SEQ ID No. 19 to SEQ ID No.102) that have been used in the mapping are listed in Table 1.

298 plants (OT9×90479-3)×OT9) and 484 plants (OT1317×90479-3)=total of 782 plants were inoculated with the TBRVF isolate AE050. Two to three weeks after inoculation the TBRFV symptoms were present and phenotyping by eye was done. A clear segregation was observed between resistant (R) and susceptible plants (S) and resistant phenotypes could be linked with marker M1 (see Table 1) located on chromosome 8 at 2673609 bp on the reference genome SL2.40 (*S. lycopersicum*). 92 plants have been genotyped with 26 markers in order to flank the QTL (M2 to M27, see Table 1). Based on these results the resistance could be mapped between 53118984 bp and 57038544 bp on the reference genome SL2.40 (between M8 & M20, See Table 1 and FIG. 1).

TABLE 1

| Primer name | Primer sequence | Pos. SL2.40 | Pos. on Locus | SEQ ID No. |
|---|---|---|---|---|
| M1_F | GGTACAACAATTGACCAAGG | 2672994 | | 19 |
| M1_R | GCTAATTAAAAAGGAACATCAGC | | | 20 |
| M2_F | GCTATGGCGGAGAAGTCAAG | 18124 | | 21 |
| M2_R | AGTCACCTCCATAGTAGACC | | | 22 |
| M3_F | GGATCCAAGTTGTGTTCGAAC | 881036 | | 23 |
| M3_R | CTTCTCATCAATGTATGTGATTTC | | | 24 |
| M4_F | TGTATAACACCTGGTGCTCC | 15384575 | | 25 |
| M4_R | CCATTTTCTGTTACAAAATTTCAG | | | 26 |
| M5_F | GCTTCCCAATTTATGCTGAAG | 47887679 | | 27 |
| M5_R | GAGCCTCCCACTATAGTAATC | | | 28 |
| M6_F | AGAATTATCATTTGCAGGATCG | 50957946 | | 29 |
| M6_R | CTATGGTTCGCATGTCATGC | | | 30 |
| M7_F | CACAACGGCAATATACCTTGC | 53082561 | | 31 |
| M7_R | TGGAAGTATTAGAAAGGTCCAG | | | 32 |
| M8_F | CCATTGAGAATAACTACTGTAC | 53118984 | | 33 |
| M8_R | CCACAGGATGACTAACTTGG | | | 34 |
| M9_F | TGCAGTATTGATCGCATCTTCTA | 53452252 | | 35 |
| M9_R | GTTTGTTGCTGCCCTCAAA | | | 36 |
| M10_F | TGATCAAGAATTTTGTTTTAGCATAGA | 55664335 | | 37 |
| M10_R | TAAAGCATCAATTTTGCATTGTCT | | | 38 |
| M11_F | TCGAAGACTAACAAAGTCCTTGTAGA | 55720872 | | 39 |
| M11_R | GACACTCCGGCAGTTCCTT | | | 40 |
| M12_F | TTCTTATGTGAAAAATTGGGTGG | 55776574 | | 41 |
| M12_R | ACTACGCAGTCCCACAGCTT | | | 42 |
| M13_F | TTGTTTGGTGGATCCATGTG | 56448988 | | 43 |
| M13_R | AGGGAAAGGGCAAGGATG | | | 44 |
| M14_F | GATCTACCAATGGCTATTCATC | 56781521 | | 45 |
| M14_R | GCAAAACTTAACCGGTCTAAG | | | 46 |
| M15_F | TCTCGATGGTTGATAATTTGTTC | 56874054 | | 47 |
| M15_R | GGAATCGATTAACACTGGTTC | | | 48 |
| M16_F | CATCTTATTGAAGCTCTGCTG | 56920720 | | 49 |
| M16_R | CAAACAGTCCCTATTCAACAC | | | 50 |
| M17_F | GGTCTTGCGCTAATCAAAAG | 56990004 | | 51 |
| M17_R | GCGTTGTGGTGAAAGTTTTATC | | | 52 |
| M18_F | CTTGTTTGGATGGTTGTCAC | 57003163 | | 53 |
| M18_R | CAACAAAAAATATACAATCCGTCC | | | 54 |
| M19_F | GAGATAGAAGGAAACTTACCG | 57024614 | | 55 |
| M19_R | CAATTATCCCCTCAGTTCTG | | | 56 |
| M20_F | TATGCCTGTCCCTGAAAAGG | 57038544 | | 57 |

TABLE 1-continued

| Primer name | Primer sequence | Pos. SL2.40 | Pos. on Locus | SEQ ID No. |
|---|---|---|---|---|
| M20_R | AGGGTCTTGGATCAAATCTTGA | | | 58 |
| M21_F | TGTGGACTTGGAGTGGTATC | 57427631 | | 59 |
| M21_R | GTAGAAAGGGTAGGCATGTTC | | | 60 |
| M22_F | TACCAAAGCAAACACTGCCAC | 57441418 | | 61 |
| M22_R | AGCCACGAGATATATATTGGAG | | | 62 |
| M23_F | GATAAGACCGCCAATAACTAG | 60844273 | | 63 |
| M23_R | GTGATCTCCATGAGCAAATG | | | 64 |
| M24_F | TGAGTTGAGATGCTGTTCTAG | 61412883 | | 65 |
| M24_R | AGTCCACCAAGACTTAAAGAG | | | 66 |
| M25_F | GTCTGCCTTCTCTTGCATGC | 62277547 | | 67 |
| M25_R | GTTGCTCCAGACAGAATAAGC | | | 68 |
| M26_F | CATCGAAGAGATGTGTAGGG | 62418391 | | 69 |
| M26_R | TGCAGTTGAAGTAGACTTCAG | | | 70 |
| M27_F | TCAACGTTAGTGGTGATGCTAG | 62783214 | | 71 |
| M27_R | CAATTGCAGAAAGTGAAGCTG | | | 72 |
| M28_F | GTGGATTCAGTTAAACCAGAAC | 56924513 | 4076 | 73 |
| M28_R | GACATGTGGAACTTGACAAAAC | | | 74 |
| M29_F | GCGAGAGAAAAGATTCTCTAC | 56934501 | 12765 | 75 |
| M29_R | CATTCTTCACTCTCTCAAGATG | | | 76 |
| M30_F | CGTTTGGTGATCTGCCTTGTCTT | 56934846 | 13109 | 77 |
| M30_R | TCTTCTTGTAGGGAATCCAGAATC | | | 78 |
| M31_F | GTGTCCTGTGCTTGTTATTCC | 56935054 | 13317 | 79 |
| M31_R | CCTCAAACCTATTGCATCTGACA | | | 80 |
| M32_F | CGGCTCAGCGAGGAAGTGCAG | 56935849 | 14113 | 81 |
| M32_R | CGTTGACTGTTTTTCTTTATG | | | 82 |
| M33_F | GTAAGCTCCTTCATGTCAGC | 56941043 | 15893 | 83 |
| M33_R | CAAGTATTGTCTGCCGAGTAAC | | | 84 |
| M34_F | GCGTACAGACATATTTATGCAAC | 56942927 | 17777 | 85 |
| M34_R | GAACAGCTAAAAGTAAGAGCAC | | | 86 |
| M35_F | GTTCATGTGTGTTTATGGACC | 56943610 | 18416 | 87 |
| M35_R | CTTCACTAAATAAATAAGTGGTAG | | | 88 |
| M36_F | TATGGATTTGTGTCTCAGAAGA | 56944105 | 18912 | 89 |
| M36_R | TGTGGTCACCAAGTGGGTTTC | | | 90 |
| M37_F | GTCTTCCAGAGCAGTTATGCAAG | 56945167 | 19974 | 91 |
| M37_R | TGAGACTGCTAAGTTGACTTGTTTG | | | 92 |
| M38_F | GTACACCAAATCACAGACATCG | 56958371 | 101133 | 93 |
| M38_R | CCCAATTTGGTTTGTGTTGGAC | | | 94 |
| M39_F | GAAATTCCTTGCCTCCTCTC | 56961307 | 104063 | 95 |

TABLE 1-continued

| Primer name | Primer sequence | Pos. SL2.40 | Pos. on Locus | SEQ ID No. |
|---|---|---|---|---|
| M39_R | GTGGAAGCCATAGTGTACAAG | | | 96 |
| M40_F | CATATTATACAGTGAAAGCTTTG | 56965103 | 107926 | 97 |
| M40_R | GAATTGCAGTTCACTTGCTTC | | | 98 |
| M41_F | CCACAAAGCTAAAAAGGGATTG | 56969685 | 112529 | 99 |
| M41_R | TCCATGTGAGTTTTGTGTGTG | | | 100 |
| M42_F | GCCACATAAATTACATATAGCTG | 56981278 | 125792 | 101 |
| M42_R | GAACTATTCAACAAGCATAATAC | | | 102 |
| M-SEQ 10_F | GTCTTACAATAGTAAAATGCGCAG | | 36480 | 105 |
| M-SEQ 10_R | GCGGTTCGTTGATATTCCAAC | | | 106 |
| M-SEQ 11_1F | AGCGAAAGCGGAAGGAGTAC | | 48748 | 107 |
| M-SEQ 11_1R | TGTGGTGAGTAAGCAATGAATC | | | 108 |
| M-SEQ 11_2F | GTGTATAATTCGCCAGAATATACGG | | 52303 | 109 |
| M-SEQ 11_2R | CGTTTAGATAATTGTATATTACACATATG | | | 110 |
| M-SEQ 14_F | CAAATTATTACTTATGTTGTGATTTG | | 77410 | 111 |
| M-SEQ 14_R | ATTAAGCCATGATACACAAATTAC | | | 112 |

The whole population of 782 plants have been genotyped with the flanking markers M8 & M20 in order to find the recombinant plants for further fine mapping. This resulted in 21 recombinant plants (See FIG. 1). These 21 recombinant plants have been selected and genotyped with 11 markers M9 to M19 in order to further fine map the region (Table 1). The resistance could be fine mapped between 56920720 and 56990004 (marker M16 and M17) on the reference genome SL2.40.

Sequencing the resistant LYC4943 region using Oxford Nanopore sequencing technology resulted in a locus of 133.515 bp. The 21 recombinant plants have been genotyped with extra markers in this specific locus (M28 to M42) of LYC4943. Based on the recombinant plants, plants 594 and 608, it was determined that the resistant region was located between positions 56941043 and 56958371, based on the reference genome SL2.40, corresponding with positions between 15.893 and 101.133 on the LYC4943 locus (between M33 and M38, see FIG. 1).

Based on the fine mapping, the size and location of the genomic sequence that was harbouring the TBRFV resistance was determined to be between markers M33 and M38 and was approximately 68.000 bp larger compared to the SL2.40 reference genome of S. lycopersicum (85.240 bp vs. 17.328 bp, respectively). It is therefore highly likely that one or more genes are located within this region, indicated in FIG. 1 as "TBRFV region", providing the TBRFV resistance and is indicated as SEQ ID No.3 in this application. Based on the reference genome SL2.40 and in silico prediction analysis (ITAG 2.3), at least one gene is located in the fine mapped region that encodes for a CC-NBS-LRR resistance protein. Blasting the fine mapped TBRFV region against the database of National Center for Biotechnology Information (NCBI), resulted in seven genomic fragments of which five have homology with NBS-LRR resistance proteins (SEQ ID No.8, No.9, No.10, No.11 and No.14) and two have homology with LRR receptor-like serine/threonine-protein kinases (SEQ ID No.12 and SEQ ID No.13).

Next, further fine mapping was performed and a recombinant selection has been performed by genotyping 668 BC2 plants ((OT9×90479-3)×OT9×OT9) with M33 and M38 in order to identify recombinant plants in the TBRFV region, which resulted in three plants 15321-02, 15321-03 and 15321-07 (see FIG. 4). These three plants were tested for resistance by inoculation with TBRFV isolate AE50. Approximately three weeks after TBRFV inoculation the plants were phenotyped by observation, and ELISA and qPCR was performed to monitor virus infection. The recombinant plants have been genotyped with markers (M-SEQ 10, M-SEQ 11-1, M-SEQ 11-2, and M-SEQ 14, respectively SEQ ID No. 105 to SEQ ID No. 112) covering the TBRFV locus and were specifically designed to eliminate candidate genes in the TBRFV locus. This approach provided insight into which of the candidate genomic sequences SEQ ID No.1 to SEQ ID No.18 of present invention specifically provides resistance to TBRFV. Based on the recombinant plants and phenotyping by disease tests, ELISA and qPCR, we concluded that the gene conferring resistance is encoded by genomic sequence of SEQ ID No 14, more specifically the coding DNA sequence of SEQ ID No. 115 encoding the protein of SEQ ID No. 116.

Validation Tm0, Tm1 & Tm2 Strain Resistance in Plant Comprising the TBRFV Resistance Locus A tomato plant of the present invention (S. lycopersicum) comprising the TBRFV resistance locus (SEQ ID No. 1) was tested for resistance against the Tm0, 1 and 2 strains. The presence of the TBRFV resistance locus was determined by markers M16, M17 and M33. It was furthermore confirmed that the plant does not contain the $Tm2^2$ gene (is a known gene that provides resistance against Tm0, 1 and 2 strains).

In some case the plant did contain the Tm1 resistance gene. As a control, plants were selected that did not contain the TBRFV resistance locus.

Eight plants (See Table 2, 1 to 8) of which six plants comprise the TBRFV resistance locus (heterozygous), and two plants (7 and 8) do not have the TBRFV resistance locus have been inoculated with the Tm0 isolate. Eight plants (See Table 2, 9 to 16) of which six plants comprise the TBRFV resistance locus (heterozygous), and two plants (15 and 16) do not have the TBRFV resistance locus, have been inoculated with the Tm-1 isolate. Eight plants (See Table 2, 17 to 28) of which four plants comprise the TBRFV resistance locus (two homozygous 17, 18 +two heterozygous 19, 20), and four plants not have the TBRFV resistance locus have been inoculated with the Tm2 isolate. As control the susceptible cultivated tomato line OT95 was also inoculated with all three strains.

First symptoms were typically observed after 12-14 days post-inoculation. Plants were categorized as Resistant (R) when no mosaic pattern symptoms on leaves were observed; plants displaying any of the symptoms on leaves were categorized as Susceptible (S). The phenotype of every single plant has been compared with the TBRFV genotype. Results are summarized in Table 2 below.

TABLE 2

| Plant | Isolate | Phenotype | M16 | M33 | M17 | Tm2 | Tm1 |
|---|---|---|---|---|---|---|---|
| 1 | Tm0 | R | h | h | h | a | a |
| 2 | Tm0 | R | h | h | h | a | a |
| 3 | Tm0 | R | h | h | h | a | a |
| 4 | Tm0 | R | h | h | h | a | h |
| 5 | Tm0 | R | h | h | h | a | h |
| 6 | Tm0 | R | h | h | h | a | h |
| 7 | Tm0 | R | a | a | a | a | h |
| 8 | Tm0 | R | a | a | a | a | h |
| OT95 | Tm0 | S | a | a | a | a | a |
| OT95 | Tm0 | S | a | a | a | a | a |
| 9 | Tm1 | R | h | h | h | a | a |
| 10 | Tm1 | R | h | h | h | a | a |
| 11 | Tm1 | R | h | h | h | a | a |
| 12 | Tm1 | R | h | h | h | a | a |
| 13 | Tm1 | R | h | h | h | a | h |
| 14 | Tm1 | R | h | h | h | a | h |
| 15 | Tm1 | S | a | a | a | a | a |
| 16 | Tm1 | S | a | a | a | a | h |
| OT95 | Tm1 | S | a | a | a | a | a |
| OT95 | Tm1 | S | a | a | a | a | a |
| 17 | Tm2 | R | b | b | b | a | a |
| 18 | Tm2 | R | b | b | b | a | a |
| 19 | Tm2 | R | h | h | h | a | a |
| 20 | Tm2 | R | h | h | h | a | a |
| 21 | Tm2 | S | a | a | a | a | a |
| 22 | Tm2 | S | a | a | a | a | a |
| 23 | Tm2 | S | a | a | a | a | a |
| 24 | Tm2 | S | a | a | a | a | a |
| OT95 | Tm2 | S | a | a | a | a | a |
| OT95 | Tm2 | S | a | a | a | a | a |

R = resistant,
S = susceptible,
a = no resistance locus present,
h = heterozygous,
b = homozygous Result Tm0

All plants that contained the TBRFV resistance locus were resistant. Plants 7 and 8 did not contain the TBRFV resistance locus but were also resistant. A reason that could explain the results is that the Tm1 gene is causing the resistance to ToMV isolate Tm-0. In addition, plant 1, 2 and 3, did not contain the Tm1 gene, but did contain the TBRFV resistance locus, showed to be resistant.

Result Tm1

The resistant phenotypes are linked with the TBRFV genotypes, providing resistance against ToMV isolate Tm-1.

Result Tm2

The resistant phenotypes (hetero-, homozygous) are linked with the TBRFV genotypes, providing resistance against ToMV isolate Tm-2.

Determination of TBRFV Infection in Tomato (*S. lycopersicum*) by qPCR

Tomato plants comprising the TBRFV resistance locus (heterozygous or homozygous) and plants not containing this region have been selected for TBRFV bioassay using markers (M16 and M17). Plants were infected with TBRFV and the susceptible tomato line OT9 has been included as control (OT9 non-infected and infected).

After 3 weeks of inoculation, one leaf from the top of the plant of every single plant was collected in a 2 ml tube which contain a 6.35 mm metal bullet. The tube was frozen in liquid nitrogen. The tubes were shaken with high speed to pulverize the plant material. After spin down the tube, the standard RNA extraction using Macherey-Nagel™ NucleoSpin™ RNA Plant was carried out. RNA concentration was measured using DropSense 96 (Trinean) and was diluted to a concentration of 100 ng/μl. 900 ng have been used for cDNA synthesis using M-MLV Reverse Transcriptase (Invitrogen). 10 ng cDNA was used for Real-time PCR using LC green as Intercalating dye. Two primer combinations for amplifying the TBRFV strain were used, see Table 3 (SEQ ID No.103 and SEQ ID No.104, respectively).

TABLE 3

| qPCR primer name | Sequence |
|---|---|
| TBRFV-3 Fw | ACCGTTCAACGGCAATTTAGC |
| TBRFV-3 Rev | CCTATACACCTTAAAACCACTG |

The more viral RNA present in the samples the lower the Ct value in the qPCR, since less PCR cycles are required to amplify the cDNA (of the viral RNA) and pick up a signal. The control sample (OT9 uninfected) showed a Ct value of between 35 and 40 cycles and the infected control sample (OT9 infected) showed a Ct value between 20 and 25. Therefore plants that show a Ct value above 30 cycles, preferably around 35 cycles were considered resistant, whereas plants that show a Ct value below 30 were considered susceptible (see FIG. 2).

Tomato plants comprising the TBRFV resistance locus, homozygous (B) or heterozygous (H) all have a Ct value above 30 cycles and can be considered as resistant. The results are showing that the resistance is dominant. Plants that did not comprise the TBRFV resistance locus (A) showed a Ct value of between 20 and 25, indicating that the plant was susceptible to TBRFV infection.

Sequencing of Genomic Sequence of Resistant Tomato Plant

Genomic DNA was isolated from a resistant plant (*S. lycopersicum*) of the present invention, i.e. comprising the TBRFV resistance locus, according to the protocol as published on 27 Apr. 2018 in Nature, Protocol Exchange (2018), Rachael Workman et al,. "*High Molecular Weight DNA Extraction from Recalcitrant Plant Species for Third Generation Sequencing*". The sequencing libraries were prepared using the PCR free, no multiplex, DNA Ligation Sequencing Kit-Promethion (SQK-LSK109). The isolation procedure resulted in high quality sequencing libraries to be used in the Oxford Nanopore system for sequencing (ONT sequencing). Promethion Flowcell Packs (3000 pore/flowcell) version R9.4.1. were used for sequencing.

Furthermore, to further resolve the TBRFV locus and identify the gene providing the TBRFV resistance, we performed ONT sequencing on a resistant line (LYC4943). Sequencing of the entire transcript isoforms of the resistant LYC4943 line was done using the Iso-Seq analysis application (Pacific Biosciences of California, PacBio). This resulted in only one candidate resistance transcript/gene located in region between markers M33 and M38, more specifically the TBRFV resistance gene of SEQ ID No. 115. This transcript was predicted to encode for a CC-NBS-LRR resistant protein of SEQ ID No. 116.

Gene Validation Using VIGS

To confirm that the TBRFV resistance gene (SEQ ID No 115) was indeed the gene conferring resistance to TBRFV, a Virus Induced Gene Silencing (VIGS) analysis was performed. Tobacco rattle virus (TRV)-derived VIGS vectors have been abundantly described to study gene function in plants such as *Arabidopsis thaliana, Nicotiana benthamiana, Lycopersicon esculentum* and other plants (see for example Huang C, Qian Y, Li Z, Zhou X.: Virus-induced gene silencing and its application in plant functional genomics. Sci China Life Sci. 2012; 55(2):99-108).

As such, two VIGS constructs were developed (Table 4), one construct VIGS-01a to specifically target SEQ ID No 115 and a control construct VIGS-01b that targets SEQ ID No. 7, i.e. a sequence also located within the previously identified TBRFV locus.

TABLE 4

| VIGS construct | Sequence |
|---|---|
| VIGS-01a (SEQ ID No. 113) | GGAAGATTTTAATGAAAAGAGGTTGATAAAGAAAATT GTAGAATCTATTGAAGAAAAGTCACTTGGTGACATGG ACTTGGCTCCACTTCAAAAGAAGCTTCAGGACTTGCT GAATGGAAAAAAATATTTGCTTGTCTTAGATGATGTT TGGAATGAAGATCAAGATAAGTGGGCTAAGTTAAGAC AAGTCTTGAAGGCTGGAGCAAGTGGTGCTTATGTTCT AACCACTACC |
| VIGS-01b (SEQ ID No. 114) | AGAAGATTTTGATGAGAAGAAGTTGATAAAGGCAATT GTTGAATCTATCGAAGGAAACCCACTTGGTGACCACA TGGATTTGGCTCCACTTCAAAAGAAGCTTCAGGACAT |

TABLE 4-continued

| VIGS construct | Sequence |
|---|---|
| | GTTGAATGGAAAGAGATACTTTCTCGTTTTGGATGAT GTTTGGAATGAAAATCAAGAAAAGTGGGATAAGATAA AAGCAGTCTTAGAGGTTGGAGCACGAGGTGCTTCTGT TCTAACCACCACT |

The VIGS fragments were synthesized (IDT, gBlocks) and subsequently cloned into a TRV vector. The DNA sequences were confirmed by Sanger sequencing. The vector contained all sequences encoding for proteins that are required for a functional TRV particles including the target sequences. The VIGS vectors including the VIGS-01a and VIGS-01b constructs were transformed into *Agrobacterium tumefaciens* strain GV3101 and used in VIGS experiments to reduce endogenous mRNA levels in tomato plants used in this experiment. A homozygous TBRFV resistant line (15322-04) as well as a susceptible control line (OT9) were used in the VIGS experiment, in which plants were *Agrobacterium* infiltrated at seedling stage (cotyledons) followed by TBRFV isolate E50 inoculation three weeks after *Agrobacterium* infiltration. Two weeks after TBRFV inoculation the individual plants were phenotyped by ELISA and qPCR and this revealed that susceptibility was found in resistant plants infiltrated with construct VIGS-01a whereas no susceptibility had been detected in resistant plants infiltrated using construct VIGS-01b. Results of the ELISA and qPCR are shown in FIGS. 5 and 6, and results have been summarized in Table 5.

TABLE 5

| Plants | # plants | VIGS-construct | TBRFV infection | # S plants | # R plants |
|---|---|---|---|---|---|
| R line 15322-04 | 7 | VIGS-01a | Yes | 7 | 0 |
| R line 15322-04 | 6 | VIGS-01b | Yes | 0 | 6 |
| R line 15322-04 | 10 | No | Yes | 0 | 10 |
| S line OT9 | 6 | No | Yes | 6 | 0 |

In the OT9 line all plants were susceptible, as expected. The R line which was shown earlier to be fully resistant became susceptible to TBRFV in cases where the suspected TBRFV resistance gene was silenced using the VIGS-01a construct designed to specifically target this gene, whereas silencing using the VIGS-01b construct (control construct) did not result in any susceptibility of the plants tested. Based on these results it can be concluded that gene SEQ ID No 115 is the conferring resistance to TBRFV.

The invention claimed is:

1. A *Tobamovirus* resistant *Solanum lycopersicum* plant part, wherein the plant part comprises a Tomato Brown Rugose Fruit Virus (TBRFV) resistance gene encoding a TBRFV resistance protein comprising polypeptide sequence SEQ ID NO: 116, wherein the plant part is not a whole *Solanum lycopersicum* plant.

2. A plant part of claim 1, wherein said plant part comprises nucleotide sequence SEQ ID NO: 115.

3. The plant part of claim 1 or 2, wherein said plant part is a leaf, a fruit, a tissue, a cell, or a portion thereof.

4. The plant part of claim 3, wherein said plant part is a fruit.

5. A *Solanum lycopersicum* seed comprising a Tomato Brown Rugose Fruit Virus (TBRFV) resistance gene encoding a TBRFV resistance protein comprising polypeptide sequence SEQ ID NO: 116.

6. The seed of claim 5, wherein the seed comprises nucleotide sequence SEQ ID NO: 115.

* * * * *

SEQUENCE LISTING

<160> NUMBER OF SEQ ID NOS: 116

<210> SEQ ID NO 1
<211> LENGTH: 133515
<212> TYPE: DNA
<213> ORGANISM: Solanum habrochaites
<220> FEATURE:
<223> OTHER INFORMATION: TBRFV resistance locus

<400> SEQUENCE: 1
tctgtggttt gatgctttca aatcacagca atcctctgta taattatggt ttatatttta    60
ggggttttca gtttacaaag tcatttatc cttccaatca ccaaaagtat tatcttggct    120
ctagtgacta gtaacaagtt agttttgtgt tatgtggaaa tttacaacag atcaccttca    180

```
tactgaggag ggagatgatc attttgtcgt ggctcggccc gtctgtcttt tagccaaatg    240
ctgcgggaga gagtgggatt ataacagtaa gtattttgtg ttttaatact gcttctatca    300
gctaatgttt catagaaatg acagtgtgaa tgaaattgca aattttgtgt ggtaaatagt    360
ttcaggctcc aatctagtga tcattttttc tgggtaatca gttaacaaga tctctttaag    420
cattcaaatt tatgtatggt aggtaagtgc acatcatgtt aggaccgaaa ataagcgggt    480
gtaaatgcgg aagctagcaa agcaaacctc gaaagatcac gagtaagaag ataacgagaa    540
atataccaaa agacacaaag atttaacgtg gttcggtcaa ttgacctacg tccacaaagg    600
agatgagcaa tccactataa atatgagagt acaaaatata gagagaaaca acctcaacca    660
attcactcgg aatacatggg aggttcacac aagtgataac gtatcaagct tgtgacccac    720
aaattctccc tctaaccaaa actctcaaaa ctctttaaga ctacattgtg aatgctgatt    780
aagttagaag gaacatgtct ctatttatag agtcctaaac tttttcatac tagaaaaaag    840
attagtcaat tcaaaacctt ttcctaaaag gaaaacctat ttatggtaag aaatcagggc    900
aaataaaacc caacacatca tggtttgaac cgtactacat aagaaaagtt ctagtattta    960
aattgagaag gatagagggg aggggcctat ccttaaatct gttaaagttt tacgtactag   1020
cccaactatt tgtgcgcgtg aagaaaagat gtgacagctc cactatagat ttcagcacta   1080
ccatttagtt tgttacaaca ttttgctgaa attgagttag gatcttcttg agtcgcagag   1140
taatatcttc catgcgaatt ctctcttcag gcaaatcatt tgtacattca agagctaatt   1200
ccatgattga tttgaagcat ctatctttag aagtaaaatt ttcttcgttc agtgaaaata   1260
gattaatgtc cactacatcc accaatcggt ctggtaatga ttggcatatc catcttttca   1320
aggtgaagtc tccaacgaat agatcatcca cagggctctt tcttgtaaaa gtctccatta   1380
acaatatacc aaagctataa acatctcccg aagttgatac tttgccttca gacccatact   1440
ctacaaaaaa aataaatcac gccatcatta atgaaaataa ttaacaacat ttaaaatcct   1500
caagtgaact tgataataac atttacctgg tgccatgtag ccgatagtac ccaaagtctt   1560
ggtatgtgct attagcgtct cagatgtaag aagtttggat atcccaaaat cactcacttt   1620
tgccaccata tcttcatcca aaagtatgtt acttggtttc aaatcacaat ggacgactac   1680
aaacaaatgt cctccatgta aatactccac agcagaagcc acatcaatca tcacctttag   1740
tctttgagtt atatccaaaa ctttgtcagt agagtgaagc caacattcga ggttttcatt   1800
aggcatgtac tctagcacca acactttata atcgaaattt gcacaactac ttatcacctt   1860
aacaggtttt ctgtgtcgaa tgctacctaa aacttgacat tccacctcga aacttctaaa   1920
tgcaagttgc agttctgtat tgaataacctt tatcgccaca accattccat ctgctagtgt   1980 cccttatac accaaaccaa ggctccccct tccaatcaag tttgcttcat caagttgtt    2040 tgtcccttga gaaatatcat agtacgaaat cctcttatgt acctgaccaa atgtatcaac   2100
tagaggaagt tccgtactcc ttttcggca tttcagaaac caaatgataa aaatggttgt   2160
gactacaatt cctgaggaaa ctgatgcaag aacagaagtt aggactctgt tctttctttt   2220
tctttcaaga cttgtcactc tgcattgcat cacatggaag cgtgatgatc cacataatgc   2280
agggttaccc atgaatgatt cagctgtaaa atttacgaat ggccctccat ctggaatttc   2340
acccatgagc ccattgaacg agacattgaa atgcatgaga tgttcaagat tcctcaagga   2400
cttggggatc atgcctgata gattgttgct agatagatcc aaatattcca acgaaaccaa   2460
atcttcaaat acttcaggta tggaaccatc taacatattc tttgacaatg aaaggctaac   2520
```

```
caagctttgt agttggccaa tcgtgctagg aatctgacca gagaactgat taccatgtaa    2580
atgtaatatc cgcaaactcc ttaaattccc catttctact gcaagagacc cattcagcaa    2640
attggaggcc aaagtgagaa ttgaaatatc tttgttcctc caaaaagttg atggaatatg    2700
ggaaattagt gcattggaat ctaagtagag ttctcttaaa gatgaaagat ttccaaaaca    2760
atttggtaat tcaccagtaa gttgattttt ccccaagata atttggtaca agttttccat    2820
gttacacaag ctagttggta taattccatc taaattgttt ttctctaggc taaatctttt    2880
caacttcctc aagttcccca aatctggagg aatagatcct ataagtttat tgtctcccaa    2940
gcttaaccac tccaggttcc taaagttact gatgttaggt ggtattttc ctgtgatacc    3000 attttgaagg gcaatgaaat attcaaggga aaaggaccag tttcctgaac ctaaagatgt    3060
tggaagactt ccattaaatt ggttacctcc tatttgaacg ttttcatat acttgcaatt    3120 agataatgaa gtcaggaaac ttaactcgcc tgtagattga tcattcgtca attggtttat    3180
ttgcaagttg atgaattgta gctgttgtag cttttccaaga ttcataggta caggtccact    3240
aaacagattg cggccaaaat caagctggat aagcatggtg gaattcacaa tggaggtagg    3300
aatcagcccg gtgaactggt tatccccaag gtaaaggcct tcaaggtttg gaagagtatg    3360
gcctatgttt gagggaagtg ttcctgaaag ctcatttgct acaaatgaaa tcttttttag    3420
tccagaaatg ttgtacaaac gccttggaac ttcacccgat aatctgtttg gaccaagata    3480
cacttctttc aaatttacaa gatgttcaaa ctcctgagga attccaccat ataaactgtt    3540
gtcacctagg tctatcatct ctagatttga caaatttcca attgatggtg gaagaattcc    3600
caccaaattg ttccgtcgta gacttaatct tcgaattgct gataggttat cgatttcact    3660
tggtatatgt cctgtaaaat atatgtcgaa ttgtgtggtt actacactga aatgtccaat    3720
actgtataac agctttatag tcactaagtt actataaata acagaaactg ttagttgtat    3780
gccttttaaa tagttcagca atcctcacaa actgttttga tgtccttttg aagatgggac    3840
taaatggatc aacatggata attaggattc atatagcaga cacaaactag aattgagcca    3900
atgtagtagt tactgttgtt gtttgaaaat gaagaacaaa gagctatacc aacattttt    3960 gctactaccc tttgaaatgc aaatactaat ttccttataaa tgagttgaag agcaagtttt    4020
taaatatcaa agatctctag tgctacaagg tgagaagtcc agcaataaag ttaggtggat    4080
tcagttaaac cagaacatta taaatacctg ttatgttatt ccatccaaga aatagatgtt    4140
gaagttttgt caagttccac atgtctctag gcaagtttcc tgtaatagga tattacgata    4200
agttatatgt acctctcacg gcctatgatt gtttaactaa aaaattgttg caatctttgt    4260
tgtcaatatg aaccaaaagt agcagagaaa gaagttggtt ccgttttttt ttacctgtga    4320
agtggttata tgacaaggac aaatatatta gctctttgca tttgtctaaa ttgcttggta    4380
gttggccaga gagttgattt cttgctattt gtaatccctc cagccgcgga agattatggc    4440
aaatgtcatt cggcaaagtc ccagatagtg cattataaat caaattgatg accttcaaag    4500
aagagacatt gaagatagac gaaggaacag atccaaagag atcattttca gaaagatcca    4560
acaactcgag ccttctcagt aatccaagac tttctggaat ttgacctgtg agattattca    4620
ttgacaagga caagtgcttc agcctcctca aatagccgag ttcatcaggg atttcaccgt    4680
tgatgctgtt gttgccaatg tccaagaaac taagaaagga gaggttccca atatctgtcg    4740
cgattgaacc tcttagtctg agaccattga ggtctagtga tgtcactctt tgatgccttt    4800
tactgcaaga tatgcctatc caattgcaaa cgtgagtccc ctttgtccag ttttcgaca    4860 acattccatt tggatctgaa gttatatgag ctttgaaagc taaaagagca gcctcatcag    4920
```

```
ttgaaatgtt cgatgcatta gtattcgaga ggtacgttaa caaaactagc aatcctataa    4980
tcatagccac ggaaaccgtt ttgtgcaact tctcttgcag ctatttgtgg gggaaattta    5040
taagtgcctg attttttatt tttcaagtga cattaatata tatttctata attaaaggca    5100
ataaagaatc atgtattagc actggaatat atagaatcta gagttcaatg tcaatgatca    5160
acatatatac gtaatatgtt ttgagacatt ttttttttaaa ttgaatgttg ctgaacttga    5220
ctgcaattca ttgctgaagg gaaatcattg gttgtgggat tctgtagtga tagtaaaata    5280
atttacttgg atttataagc cttgtatatt cattattcaa gaatattaaa gactaaaatc    5340
atgatataat gtcatcattc gaatgtatat agcctccgct gaatagatgt ttgacaaaag    5400
aacgtgaagt gttacggtca aattagtgaa tctaacgtgt aatgttggat ttacgtgaat    5460
tcaatagctt ttattcctat cttttatata tattaagtaa tttattaaaa atctaaaatt    5520
atcgtatatt actatcttgc agtctgtgtg agaatactat tttgataatc gtcaaataat    5580
tatctataaa tttcaaatct tgaatcacac ttatttaata ggaggaaatg gtaaaaagga    5640
agtgaggttg acaagatctc aagactcttt cttaattttg atgaaatgtt gtaaaaactt    5700
gaattagtag attgcatggc atcactatac acgtgtcagt ctagtgttta gagaaattta    5760
atcaaagaat ataagttata atatatatta tccatgagaa tcttgagaaa gattttctgt    5820
atctgtctga tgaaatagaa attggagttt cccaattcta tattacttgg cttattctaa    5880
cttctagtgc agaatctgca gatggtcaat attctttgaa tatataatag caaatttgat    5940
tattagtttc attttttaaac tattgatagt tttaaaaata tttattattt aactaattaa    6000
atttaaatat atcctcgatc ttgcaatatg agagaaatac atctctaaat tctttccttt    6060
tcaacatttc tttcgttttt ctaattaaaa gcctcatact tatacaagag tttgaaacca    6120
cttgatatgt cacgtgacaa aaagaattg tatctaagtt tggctactca tgtagagaag    6180
tattttaaaa gcggtcaata tctcaaaaga gaaacaaata aattatgtat ctacaaatta    6240
taaaaaaagg agtctaccttt attgggaaa gtcatatgca attcatgtat gctttcctaa    6300
ttggggatac aaagtcaatc ttgttaaacc cctaaactat tacaatcatt ttaagaatta    6360
tatatatatg tactatttga gtgttgacaa aagccttaaa ttatcataaa actcatatta    6420
aaatatctct tagagtaata tgacatgtca tgtgaatatt atgtttgaca aactcaatt    6480 caaagagttc aaagtggtta tacacgtagg ttttagaaaa attctaaact cactgttttg    6540
tgactttcat acctaaaatt gttaggtgtt tatataacca cccctgaatt ataccatgaa    6600
attattgtgc caggtggcct aatttgaaat ttaatagggc tgaattaaga ttttttgaagt    6660 caattaaaga aaatattttt ttaatttatc ctgaataagc ttgctatttg aggggtttga    6720
gaaatatcgg tagggcggta catgggctaa taaaattgat taaaaatata atatgatatt    6780
aaatttaaaa ttaaagagaa tccaaactca aaacaattag gttaatattt ctatttagct    6840 atttatctttt gttatcttga aaaaaactta ataaatatta taaagataat tttatttgtg    6900
gatttgatta acaagtagta acattaacat catgtaatat tgttttgtgg atatttttcg    6960
ataatatttt ttaaattata atttataatt taatttaata attataaaaa aataaaaaaa    7020
aagtgggcca cggcaagttc tgtagctctc acgtacttat gggttggacc gacccatttt    7080
ctgacccata caaaaatga gctagcctag cttaacccat aaaatatcaa aacatgtatg    7140
gattagccca ggatgagata tgttagccca tattgacagc tctattccca catcaacaag    7200
gtatttaata tgtcaacttg aaaagaaaag atattccaaa attaatctgc ttatactcta    7260
```

```
tcaattccat atctcactta gtgaaatttc gcagaatata tcgttgaata tattgttgtt    7320
gtcgttgtcc tctcccatca ttctaaattt aaagaacatg caatgtaaga ggtaatttag    7380
aaaacttagt tcggccgtag aagaaggatc atctgtaaat ttattcctct gcaagttgat    7440
gctctgttgg aaatttatta ctacaagata gattggttaa tttgaccgta aaacagttga    7500
cattcttttg tcaaggatct attctgggga ggttatagat atacatttga ataatgacat    7560
tgtcaagtaa attatttaac tgtcaataca gaattccaca accaatggtt tatttccctt    7620
tagcaatgaa ttgcagtcaa gttcagctag caatatacga ttaaaagttg tttcaaatca    7680
ttggtattaa ttagataagt attgactcaa ttacaagtat acacacagta tatatagaat    7740
ggcgtttgaa acgaaaaaca taggcacaaa tagcagctaa agaagttgaa caaatccaaa    7800
tggttgcgaa gactattatt atagcatgcc tagttttgtt agcatgcctc tcagttacta    7860
atgcatcaaa cattacaact gatgaggctt ctcttttagc tttcaaagct catataactt    7920
cagatcccaa tgaatgttg tcgaaaaact ggacaaaagg aactcacatt tgcaattgga    7980
taggcatatc ttgcagtaaa aagcatcaaa gagtgacatc attagtcctc aaaggtttaa    8040
ataaatgcac caaacttgaa gttctgtcct tgtcttataa caaattcact ggtaattaac    8100
taacttgtaa acttttcatt tactaatttc ttcttgaatt aatcatcatt tttgtgtgtg    8160
tctgtcattt tataattgat aggaaattta ccaagagaca tgtggaacat gtcaaaggtt    8220
caagaactgt ttattggatg gaataacttt acaggtacgt gattcttgta tgtattaaat    8280
cttgaatact cttcacgaag ttcctaattt cactagatat agtcaatttg tgcattgtct    8340
agtaacaaac aaagattaat atatgttgtg gagaacattt tcgaaagaca ctctatgtct    8400
gatctttagc atgataacca tgtacttatt ttcaaaatga atttgcagga aatataccaa    8460
atgaaatgaa cctaccatct atttgcagga aagttaacaa agcttgagca tctcaactat    8520
ctgaaagtct cttacaatga gttatcaggt gaaataccag atggagggcc ttttggtaat    8580
tttcacagct gaatcattca tcggcaacga agagttatgt ggaccgccta gattccaagt    8640
caaggtgtgt gaaatccaga caacgtgac aagaagaaac aggaagaaaa cagtactaaa    8700
atttgttctt ggaccagttg cagctggagg tttagtcata ggggttttag gcatgatatg    8760
gttgttgaat tatcggagac gtaacaacca acttattcct ttaactgatt ggtatgatca    8820
gttatcacac aaaaggtttt cttactatga acttgttcga gggactaaca actttgacga    8880
atcaaatttg attggaaagg gaagccttgg tatggtttat aaggggacat ttacaaatgg    8940
gaccatagct gctgtaaagg ttttcaatgc acaactgcaa gatgcattca agaggtttga    9000
tttggagtgt aaggttttgc gtaacactcg aaataggaat cttgttaagg tgataagtag    9060
ttgtgcaaat cttgattta aggcattggt gtttgagtac atgcctaatg gagatcttga    9120
ttattggctt tactcacaca acaatttctt ggatttaaac aagaggctga aaattatgtt    9180
tgatgtggct tgtgtcgtag agtatctaca ccaaggccat tcacttgtag tggtccattg    9240
cgacttgaac atacttttgg atgaagacat ggttgccaga gtaagtgatt ttggtatatc    9300
caaactcttg accgcgtatg atccagtggc attgacaaag actttaggca ccattggcta    9360
cacggcagca ggtactgatc aaacttttat ttactaatta ctttcttcaa cttgtattcg    9420
atatgcatat atgatgtatt tcattttaat ggcagagtag ggatagtgtc aactatgggg    9480
gatgtttaca gctacggcat tttattgatg gaaaccttca caagaaagaa accagtagat    9540
gatgagtttg ttggagacct tacattgaag agatgggtcg cggaatcata tcctcataga    9600
gtcattgtta tgaaataaaa acgaatacac gctgaacgtc acttatgagt catttatcta    9660
```

```
atatgatcca ttaacaattg attaatgtaa cgcaaggaag aagaaaacaa tttgcattgt   9720
tatgaatgaa tgtgtttgta ctacaatata tacagtactg acaagtccag caaactttct   9780
aaccaactta ttctaaccaa ctctactcat tattaattta gctcacttaa tcaagaaatt   9840
aaacttaaca actaactacc attactcatt caactgatca cggaacatca acacattttg   9900
ttgatttctt tcacacacac cctctgcttc gaaaacccct cttttttaaca tgtaagcgac   9960 aatatctttt ttttaggaga gtgttcaaca ttgagcataa aaataataaa atagagaaca  10020
aaaaagatga gtataaaata aataataata taagatcgat tttaccgatt gtcaattttg  10080
tgtatggact aaagaaataa cagcttcaca tatctaatat taaatgtaat actgaatttc  10140
acatatggtc agaggtgaat ccacctgcac ccgatatatt ctttttttaaa aaaattatat  10200 gtatatatat agattgttga taagacggta atatatttaa ttgtgcactc ttataacgaa  10260
caaatgattt gacttgtcca ttggaaaaac gaaaagtgtc acataaattg agacatgggg  10320
agtaacattt ctttcttaaa ttttttcgtgt gaagtcaaac taattcatat aaaatgagac  10380
ggaaggagta ctgtttaata ttaattgcat atggtagtaa atttgataga catggtcccg  10440
tgggagtgtg tgttatttcc attgaataat tgagtttgta attgttacaa gtccattcta  10500
atttccaaca ccttacttca tttcaaaaat atactctatg gctgaagctt tccttcaaat  10560
tatgttagag aatctgactt gtttcatcca agggaacttg gattgattct tggttttaag  10620
gatgagttca aaaagcttca agcacgtttt actacaatcc aagctgtggt acaagatgct  10680
cagttgaagc aattgaagga caaggcaatt gaaaattggt tgcagaaact caatggtgct  10740
gcatatgaag ctgatgacat cttggacgaa tgtaaaactg aggcaccaat tatacagaag  10800
aagaataaat atgggtgtta tcatccaaac gttatcactt tccgtcacaa gattgggaaa  10860
cggatgaaaa agattatgga gaaactagat gcaattgcag cggaacgaat taagtttcat  10920
ttggatgaaa ggactataga gagacaagtt gctatacgcc aaacaggtaa atattttctct  10980 aaataacagc tttatatcat caaattcatg tgtgttttgg ggattttgtc taagtagata  11040
agtggttcaa aatctattat ctaaatctgt ttggtgaagt ctttaacata tatataaatc  11100
catagcttac tcatatgccc caaagtctaa atgacaggat aaagccagag ttgttttaga  11160
ttttataaat taacaaagat aataatgtaa attcaaaata gtgcatttgt tttatatttg  11220
aaatatgtct gctgcttctg atcaagctga tcattgtctt ttgcaaaatt cttctttgtt  11280 tttttttgctg actcttaccg atcttggacc aggttttgtt ttaaatgaac cacaagttta  11340
tggaagagac aaagataagg atgagatagt gaaaatcctg ataaacaatg cccaaacact  11400
ttcagtcctc ccaatacttg gtatgggggg actaggaaag acgacccttg cccaaatggt  11460
cttcaatgat cagagagtaa ttgagcacttt ccatcccaaa atatggatttt gtgtctcgga  11520 agatttaatg aaaagaggtt gataaaggaa attgtagaat ctattgaaga aaagtcactt  11580
ggtgacatgg acttggctcc acttcaaaag aagcttcggg acttgttgaa tggaaaagaa  11640
tacttgcttg tcttggatga tgtttggaat gaagatcaag ataagtgggc taagttaaga  11700
caagtcttga aggttggagc aagtggtgct tctgttctaa ccactactcg tcttgaaaag  11760
gttggatcaa ttatggcaac attgcaacca tatgaattgt caaactttttc tcaagaagat  11820 tgttggttgt tgttcatgca acgtgcattt gggcactaag aagaaataaa tcttaatctt  11880
gtggctatcg gaaggtgat tgtgagaaaa tgtggtggtg tgcctctagc agctaaaaact  11940 cttggaggta ttttgcgctt caagagagaa gaaagacagt gggaacatgt gagagatagt  12000
```

```
gagatttgga aattgcctca agaagaaagt tctattctgc ctgccctgag acttagttac   12060
catcaccttc cacttgattt gagacaatgc ttttcatatt gtgcagtatt cccaaaggat   12120
accaaaatgg aaaaggaaaa tctaatctct ctgtggatgg cacatggttt tcttttatca   12180
aaaggaaact tggagctaga ggatgtaggt aatgaagtat ggaatgaatt atacttgagg   12240 tctttttttcc aagagattga agttaaatat gatcgaactt atttcaagat gcatgatctc   12300
attcatgatt tggcaacatc tctatttttca gcaagcacat caagcagcaa tatccgagaa   12360
ataaatgtag aaggttacct acatatgatg tcgattggtt tcgcaaaagt ggtgtcttct   12420
tactctcctc ctcacttgca aaagtttgtc tcattgaggg ttcttaatct aagttccatg   12480
ggacttaagc agttaccgtc ctccattgga gatctagtac atttaagata cttgaacctc   12540
tctctcaata acatgcgtac tcttccaaag cagttatgca agcttcaaaa tctgcagact   12600
cttaatgtag agtattgctg gtcactttgt tgtttgccaa agaaacaag  taaacttggt   12660 agtctccgaa atctcttact tgatggttgc gatggattgg attctatgcc accaaggata   12720
ggatctttga catgccttaa gactctaagt ttctttgtta ttggcgagag aaaagattct   12780
ctacttggtg aattacgaaa cctgaatttg tatgggtcag ttgaaatcac gcatcttgag   12840
agagtgaaga atgatagggga tgcaaaagaa gccaatttat ctgcaaaaga aaatctgcat   12900
tctttaagca tgagatggaa aaaaccacat agatatgaat cagaagaagt tgaagtgctt   12960
gaatccctca aaccacaccc taatttgact tctttactaa tcactggctt cagaggattc   13020
cgtcttccaa agtggatgaa tcactcagtt ttgaaaaatg ttgtctctat gcaattaga    13080 ggttgtgaaa actgctcatg cttaccaccg tttggtgatc tgccttgtct tgaaagtcta   13140
gagttaggag atgggtctgc ggaactgaag tatgttgaag attctggatt ccctacaaga   13200
agaaggtttc catctctgag aaaacttatt atagtcaatt ttgataatct gaaaggattg   13260
ttgaaagagg caggagaaga gcaattcccc gtgcttgaag agatgacaat tagctggtgt   13320
cctgtgcttg ttattccgac cctttcttct gtcaagaaat tggtagtttta tcggaacatg   13380 tcagatgcaa taggtttgag gtccatatat aatcttaggg ctcttacttc cctcaacatt   13440
agccataact tgacagctac ttcgctccca gaagagatgt tcaaaagcct tgcaaatctc   13500
aaatacttgg aaatctcttt catcttcaat ctcaaagagc tgccaaacag cctggctagt   13560
ctcaatgctt tgaagcatct gaaaattgaa tattgtgacg cactcgagag tctccccgag   13620
gaaggggtga aggttaac ttcactcaca gaattatcca taacaaattg taagaggcta     13680
aaatgtttac cggagggatt gcagcaccta acaaatttat cagttaggga atgtccaaca   13740
ctggccaagc ggtgtgagaa gggaatagga caagactggt acaaaattgc tcacattcct   13800
catctgctta ttactaatga gatgtaattt tctgattttt cttttggaaa caaatcaact   13860
atttgtaacc aattcgtatt ggacttttga gccctgcatt tgttcgaata cgcctttcaa   13920
cctgtatatc agtgtataac aaatgtatac aatatgtata ctgctgctca atctgcaga    13980 tttgattttc cagcaacaca tttgctgatt cttccgacct gtaaattaat ttccagcagc   14040 tcatttttttt gtgttcaacc tgtacgccag ttgtgagggt ctaagacttg aggaggagt    14100 ttgagccttt acggctcagc gaggaagtgc agggatacgg gcgaaatccg ttaggactca   14160
tggcgaatgc acgtgaaacg gatcaaaagg aaacataaag aaaaacagtc aacgatgaaa   14220
acaattctgc atttatacgc ataactaagg caatgtaaat caaattgaag aatgggcagc   14280
caagataaat gaaagcaaat aaagccacaa tgcatgtttt aaaatactat aaccctgcca   14340
tgctgcatag acacacattt atattcaaga ttcaagtcat aacaaaatat aatttgaaag   14400
```

-continued

| | | | | | |
|---|---|---|---|---|---|
| tttaaagctc | tggatatcag | cttactacag | ttcaatcttc | ttacttaaaa | aagatgctaa | 14460 |
| aaaaaaacaa | aattcaactc | ttccaggcaa | ctaacaatat | caaacctaca | aactaacata | 14520 |
| tgagcaaaaa | aaaatcattg | aaataaaggc | atacaaatac | taaaatgaca | accactagtt | 14580 |
| catgaaaaac | aaaatggagc | aggcaataaa | taataaacaa | gataatagat | aaatatgtct | 14640 |
| tttaattttta | ttttattttta | tatttgtatc | cttcaaattt | gaatgtacac | ataatttgat | 14700 |
| attttaacttt | gtatataatt | gaacaagtac | atagttaagt | catatgtagc | ataaatatat | 14760 |
| atatatatat | atatatatat | gaaacaccac | ctatgacaca | atttccatga | agcatgtaca | 14820 |
| cttttatttg | ttcatttcaa | tactgagttt | aagtattttta | ctttgtttca | tattatagtt | 14880 |
| gaacaccata | aatataaaat | aatatcaaat | ttaaaaaata | tatttatgta | ttatgcttta | 14940 |
| aaaaatatttt | tttaaaaatc | tagtaattgc | cccaccataa | aagagatgcc | cattatacgc | 15000 |
| cgaaagaatg | tttaaaatca | aaagcaactg | ttagttattg | gattgaaaaa | taaaaccaaa | 15060 |
| tactccaatt | gagagacatg | gcggcccat | ggtggaataa | ttattacaac | acaccttcca | 15120 |
| taattaaagt | ttgaccttac | acctagagac | aatcaaattt | tggatttggg | tcttattttta | 15180 |
| ctagttaaca | tttcagataa | tcacttaatt | ttaaataatt | tatttcgata | gtcattcaac | 15240 |
| tttgaattat | tctgttagaa | agtcattcaa | ttctattttta | aagtcaaaag | tcactaatat | 15300 |
| ttgagttgtt | ggtttaaaag | gtcattcaac | tctctttata | attcaaaagt | aacataatta | 15360 |
| ttttttgttt | cacttaaaag | acatccgatc | aacttaaata | ttttttcata | aaatcttatt | 15420 |
| tttatgttaa | actattcttt | ttaaaaataa | taagatattt | attttagaaa | aagggaaaat | 15480 |
| atgttaaaaa | gttagttatt | ccaaaaaaga | agaaagaagt | tggaattgaa | aagaaataat | 15540 |
| ataaaaaccg | cagcacagtg | ccttttttct | tattactttt | tatttaaaag | atagttataa | 15600 |
| agaaatatta | tacttcaaca | aaatttaata | aaataattaa | aagcagctta | taattttatt | 15660 |
| ttatttttgt | attcagtcaa | atttaataaa | aaatttcatt | ttaaaataat | tgtctgactt | 15720 |
| tctaagtaaa | attagttgag | taattttttag | gttataaaac | aaaattgagt | gactttcgaa | 15780 |
| gttaactcaa | atctgagtga | ctttctaagt | gaattattcg | aagttgagtg | aatattaact | 15840 |
| ccttatacaa | gttcgaggaa | gatattgaaa | aagattgtac | atatgggggtt | cgtaagctcc | 15900 |
| ttcatgtcag | cttataaaag | gcttcacaca | agtatatata | gcgggtaaaa | ttttattttg | 15960 |
| tgagaggtag | aaatgttact | cggcagacaa | tacttgtatg | acatgcttaa | agcttcatttt | 16020 |
| ttttctctttt | cacctatttc | tatcttcttc | ttctctcttt | ttttctccgt | gcttcataaa | 16080 |
| atttttatttt | attttttcatc | aaaaacttga | tacttaatat | attttattga | atgaaaattg | 16140 |
| atttaataat | ttttattttttc | aaatgttaaa | atcaagacaa | atcaattaag | ttgatttttt | 16200 |
| tcattacttt | attttttttttc | cttgcgattt | gttttttgtg | gacttctcga | aaatatataa | 16260 |
| taatataaaa | ttatcctctg | aaaaaattat | gcattacgaa | gaatttaatc | attactaaga | 16320 |
| aatttgataa | aaaattccca | atgatttttac | tatattctta | caaaaattaa | agatttaagg | 16380 |
| ctgatatatt | aaagatgtct | tgttaatatt | ttatttaaat | aaaataatca | attaaattac | 16440 |
| gagttattttt | gaacatgaaa | aaacactttc | aatttttatct | aaataaaaat | ataaattaaa | 16500 |
| ttacaaagta | aaaagaataa | ttattataaa | gagaaacaca | tgagtactca | caaagagaac | 16560 |
| aaaaaaaata | tttataataa | ttttttttagc | ttcagagaag | gttatacgta | taatcaaaat | 16620 |
| tattacggat | catttattaa | taaaataata | aaataaaaat | tctcctaaaa | aattaatgta | 16680 |
| tgatcttttt | ataagcaaac | acaaaaatta | tttaattaca | ctatattaaa | tttctttaat | 16740 |

```
ctcactaaaa aactatttttt tctcgtttca tttactttaa gttttccttg aataaataat    16800
ataaaaataa aatagttaaa cattgtggct aattttttt aaaaaaaca caaagacta        16860 caaaggagaa caagagaatg agaaacaaaa gtttacggga aaagagtctg atataccct      16920 taactttgtc atttggagct aatatatccc tcgttataaa agtggctcat atatgccctt     16980
accgttatac aaacggctca tatataccc tgtcgttata aaatgactca catatacct       17040 taatttgtgg aagttaaaaa ttagttttaa atttatattt aatacttcta attttaaaa      17100 aaaattattt agaggtatat atgattcttc tatcaaagtt caaggtatat tttaattttt     17160
ttttcataca taaactattt ttgacttctt ttattataat tatttgagtt tcttattctt     17220 atttttatttt tttttctttc attccttagt ttaaagagag agaaaatta aactattttt     17280 tttgtatgta ttgtaattta atttcgtatt caagaaaaa aatttagtca tctacaataa      17340
gttttacaag aatattagtg aaaaatata taaatttgat tatcaaaata ataattataa      17400
attagtcatt gaaaaaaaa gtcaaaaaaa aatgttttg agaattaaat ttattcatat       17460
gagattatat tttatagaaa aaataataaa aatttagatt aaaattatat ttttttcatt    17520
ccgttagatt aaagggatat ctcgagccat ttgtttacaa gtagggtata tatatgctac     17580
tttcatgtta ggtatatcag ctctaaataa caaaattgat gggtatatca gaccctttc     17640 tcaagtttaa attaatgtga aaagttttta agtgtgggtc ccatgttgta catttaaaat     17700
tctcatacaa cagacaaaag gttagctttt cacaaaataa aattttttccc atgtgaaact    17760 caaaataaaa taattgcgta cagacatatt tatgcaacac aacattaatt tatttattta    17820
cccattcaat aagtaaagga ataattataa agctttgtgc tcttactttt agctgttcat    17880
atttcattcc aacatcgatc ttatagattt attgctaatt cacaacaatt ccagcaatct    17940
acatggctga agctttcctt caaattttgt tgaaaatttt gacttcttc atacaagagg     18000 aacttggatt gtttttggt tttaagaacg agtttgaaaa tcttaaaagc acgtttacta     18060
cgatccaagc tgtgcttgaa gatgctcagg agaagcaact gaaggacaag ccactagaaa     18120
attggttgca gaaactcaat attgctgcat atgaagttga tgacatcttg gatgaatgtc     18180
aaactgaggc agcaagactc aaagagacta aatatgggag ttatcatcca aaggctatcg     18240
cttccgttta caagattggg aaaaggatga agagataat ggagagacta gatgcaattg      18300
ctgcagaacg aagcaagtt catttggaaa aaggactac agagagagaa gctgctagac      18360
gagaaacagg tgctcatctt taattagttt atattcattt ttttgcgatt atcaagttca     18420
tgtgtgttta tggacccaag ggactttttt ctaatctaat gtttgtctca agtctaaaca    18480
gatttgtaat tctaccactt atttatttag tgaagttctt aaacatatat acatggtgta     18540
agccagctca gataaatcca tagtcagttg tttcggactg aacttaactt ggatgtcaat    18600
ttttcaaagt caatcatgtt ttcaactcct cccctgatt ctcatctctt tgtagtgcaa     18660
aaatcttctc tctgttttc gctaaacata ttctcgtgtg aacatatatt gcttgaaaca     18720
ggttttgttt taactgaacc agaaccttat ggaagagaca aagaagaaga tgagatagtg     18780 aaatcctga taaacaatgc ccaacaactt tcggtcctcc caatacttgg tatgggggg     18840 ctaggaaaat cgactcttgc ccagatggtc ttcaatgatc agagagtaac tgaccatttc    18900
catcccaaaa tatggatttg tgtctcagaa gattttgatg agaagaagtt gataaaggca    18960
attgttgaat ctatcgaagg aaacccactt ggtgaccaca tggatttggc tccacttcaa    19020
aagaagcttc aggacatgtt gaatggaaag agatactttc tcgttttgga tgatgtttgg    19080
aatgaaaatc aagaaaagtg ggataagata aaagcagtct tagaggttgg agcacgaggt    19140
```

```
gcttctgttc taaccaccac tcgtcttaaa aggttggatc aattatggga actttgcaac    19200
catatgaatt gtcaaatctg tctcaagaag attgttggtt gttgttcatg aaacgtgcat    19260
ttgagaacca agaaaaaaat aaatcctaac cttgtggcta tcggaaagga gattgtcaaa    19320
aaaagtggtg gtgtgcctct agccgccaag actcttggag gtcttttgcg cttcgtggat    19380
caagaaagag aatgggaaca tgtgagagat aatgagattt ggaatctgcc tcaagatgaa    19440
agttctattc tgcctgccct gagacttagt tatcatcatc ttccagttga tttgacacaa    19500
agttttgcat attgtgcagt attcccaaag gacacggtaa tggaaaaagg aaatctaatc    19560
tctctctgga tggcacacgg ttttcttttta tcgaaaggaa acttggagct agaggatgta   19620
ggtaatcaag tatggaatga attatattta aggtcttttt tccaagagat tgaagttaaa    19680
gatggtaaaa cttatttcaa gatgcatgat ctcatccatg atttggcaac atctctattt    19740
tcggcaagag catcaagcaa caatatccgt gaaataaatg taaaacggaa cccacatatg    19800
atgtcgattg gttttgcaaa agtggtgtct tcttactctc cttctcactt gcaaaagttt    19860
gtgtcgttga gggtgcttaa tctaagtgaa ttaagactta agcatttacc gtcttccatt    19920
ggagatctag tacatttaag atacttgaac ctctaccgca ataacatgcg tagtcttcca    19980
aagcagttat gcaagcttca aaatctacag actcttgatc tacagtattg cgccttactt    20040
tcgtgtttgc caaatcaaac aagtcaactt agcagtgtca gaaatctttt acttcatggt    20100
tgctataaat tgaattctat gccaccaagg ataggatctt tgacatgcct taacactctt    20160
ggttgctttg ctgtgggaag gaagaaaagt tgtcaacttg gtgaattacg aaacttgaat    20220
ctctatggct caattcaaat cacacatctt gagagactga agaatgatag ggatgtaaaa    20280
gaagccaatt tatctgcaaa agaaaatctg cattctttaa gcatgacttg gaaaggacca    20340
catagatatg aattagaaga agttgaagtg cttgaagccc tcaaaccaca ctccaatgtg    20400
acttgcttaa caatccatgg cttcagagga atccgtttcc cagagtggat gaatcactca    20460
gttttgaaaa atgttgtctc tattgatatc cggggttgcg aaaactgctc gtgcttacca    20520 cccttggtg agctgccttg tctaaaaagt cttaagttac aggacgggtc tgcggaaatg    20580
gagcatgttg attctggatt ccctacaaga aggaggtttc catctctgag aaatcttatt    20640
atagtcaatt ttgataatct gaaaggattg ctgaaagagg caggagaaga gcaattcccc    20700
gtgcttgaag agatggatat ttggtggttc cctgtgtttg ttattccgac cctttcttct    20760
gtcaagaaat tgttagttca ttggaacatg tcagatgcaa taggtttgag ttccatatca    20820
aatctcaggg ctcttacttc actccacatt agaactaact tcatagctac ttcgctccca    20880
gaagagatgt tcaaaagcct tgcaaatctc aaatacttga aaatctcttt cttctacaat    20940
ctcaaagagc tgccaaacag cctggctagt ctcaatgctt tgaagcatct ggagatgaat    21000
tgttgtccca aactggagag tctccccgag gaaggggtga aggtttaac ttcactcaca    21060 cagttatcca ttcatactg tgagatgcta aaatgtttac cagagggatt gcagcaactc    21120
acaaatttat caattaagaa ttgtccaaca ctggccaaga ggtgtgagaa gggaatagga    21180
caagactggt acaaaattgc tcacattcct catctgctta ttactaatga gatgtaattt    21240
tctgattttc ttttggaaac aaatcaacta tttgtaaaat ctatttgtat tatacttgat    21300
ttttcttggt tatgtaacaa taaatatttg aaaattttca tataaaaata gttacatttc    21360
tatatgtata attcgccaga ataatacata tatatgtata atatacaatt atttaaccga    21420
tatacatata taattcacct ctctcccact ctctgtcctc tctcactcgc ctctctcctc    21480
```

```
cctctctcaa tttcgctttc catatataca aatacaatta tctaaaagat atatatatat   21540
atatgcaatt catctctctc ccactctttg cttcacttga caactatgac atttaacatt   21600
ggacaagcac aaattgacac ttaaaaactg gttacagaaa ctcaacgctg ctgcgtataa   21660
agttgatgac ttattgaatg aatgagaata cgaggcagca agactaaagc agtctcgact   21720
aggacggtat catccaaagg ctatcaatac aaactcagtt gtttagacca cgaaaagact   21780
gtgaattcaa tacaggagta gttaacgatt actctaattc tatgtcacag aaagtaattt   21840
cataagcgag aaaatcctct agcatttttc catttctctt tatggcgtgc aaatatcgtt   21900
atctattttc tgctgtctcc tagctaatta tcttgaatgt acgtaacact ctctatttat   21960
ttccaagaga ttgaactaaa atctggtaaa acttatgatc tctgttttca gcaaacacat   22020
caagcagcaa tatctgcgaa attaaacaca tatgatgatg tcttcttact caccgagtta   22080
ttagttatgc taaaatgttt acccgaggga ttgcagcacc taacaaatct cacaattttt   22140
ttttattagt gaaagcatag ttatcaaaat aaaaacaaaa aatgagcaat atttatacaa   22200
cagacaaaaa aaagaatgat ttttcatatt ctttgcttat gttaccgatt cataacccat   22260
ataaaaacaa atttcaatca cccattaaac caaaaatgat taaacaaaaa aaatcttcta   22320
gatatctaac taatgaataa taacatattc agtgtagtcc cacaagtgga atctgggtta   22380
actatccaac taatcataga tcaaaattgc agtgaaaggt attttattag accacttcca   22440
atctcaacta tttcaacaca aaacttatat tcaatctttg atggataata gaccatctat   22500
ttttaattcc cttttctcac caacaaattg aaatgtcagt gatgtttctg agcaacaaaa   22560
agtactttaa gatgatattc taaatgtgca caatttcatg ctccaacaat cgaccaatta   22620
gattaaaaaa tatactcatt gagtatttct tctgtcacat ggtcaatacc atagaaaatg   22680
aaaaatataa tcacaatttta acaacataac tattgagatg gaatatgttt catctagtta   22740
aaaaaaattt acttgagaat gttgtttgtg agcattacac taatagacgt cagatgattt   22800
tcggatggtg gtcaaatgac acttgttact ggttcaagca gagtaatggg atgtgaaatt   22860
gcccttcaat cgtagaaaat ggaatatata aagcaaagtt acacaattta atcgtactct   22920
tgaaacttat ctctctataa tccatgtttg ctataaacaa taatattgtc ttacacatat   22980
tcaacaatta catatcctat ttaaactaat atacgaaata tattcaataa aaagtgcatg   23040
cagacgattt ttctacaata aagactccag gtttagagtg tttagcgact cctgataaag   23100
acaatgagat tatagtaaac aggagaaaca gagcagctct tcataaataa agaggaggaa   23160
aaaatctacc gattgatgca cgtaaaagag taaatgtgag actaatgaca ataacctgtt   23220
gttggagaga tttatataga tgagtatttg aaaagtttac gatcaaatga acttgagcgt   23280
cagaaaagtt gtcgcttgag cagtaactgt tatagtgatc aatgaggcat ttttttggaga   23340 attaaattag gtctcaaact atgagcaaat ttaatttata ataaattaat acttattaaa   23400
actgtagggt taaaacggta aatcaagttt atgattaaac tcttcccact tataataata   23460
taagattaaa aataatcata aaatagaatg gtgcattggt atcaaacaag aaatatgtga   23520
aactaattaa gagaatatag tctctaaggg tatgaatata tcgatgaatg cttgattgaa   23580
aaataataat aaatgtatat aagtctttaa tgaaataaca aaggcacgag ataaatttat   23640
tagaaatata aatctacata ttctaggtat tacaaaaaag atcctaaaat atgtagcaaa   23700
caaatgactt attcttctat aaagcacgta accatcgaag tttaatgtta atacgataag   23760
attgccttga gaatgcattt acttgtgata agtccacggg tctacgtata agtatagttt   23820
attgtattct tataaaataa tagtaaaaat aatagtctct ttttatttca aatttaattt   23880
```

```
ttaataaaca gaaaataaat taataaaata agacaaaaaa caataataat attatagaca    23940
tgtttatgat gagtacgtat aatttgaagg ggaaaactac aaattcaaac tcaagagaaa    24000
ataataaagg tttggaataa aatatctaag atacggaaag attaaaatgt gttctctaac    24060
taaaatcttc atcttcatga ataattaaca tgaaaataga ggatccacca aaaattaaat    24120
aggagaagga aagagactta ttagaaaaat gatgaattat aaaatctaaa agcctatatg    24180
tgaaaataag agaacaagaa tattgcataa aaaaaaatta tagctacgaa aaatactatg    24240
tgtgatttta aagataaaat ctattttatt gttacatgta tcatatttat tgttgaaatt    24300 tcaccttta aaaaatgaaa aacaagctaa gaaaaaaaaa gtaaaagag gaaaatgaac       24360 aaataaaaga ttaatagaga aagggaaaa ataccaatga atatcctgat tgaaactgca     24420
ttatataaat cttcggatca atccatttac cttgaatttc aagaacactg caaattcgat    24480
cataaattaa tctaaaaaga ggcatgttta tgataaaagg ggggaaaaca gtgttagaag    24540
aaaacaataa agaaatagtg ttagaagttt gaaatcttca tgtttcaaaa agaacaaat     24600 taatcttcaa tgtcaagtaa aatctcaaga tctctagtaa agaaaattta ttttatact     24660 acaaacaaat taatggcatt ttaaacatat aaagaaatat gaggatcaac atattataga   24720
ttaactacaa gttttcatgt ccttaaaaga taacttatca accacaaaca aaagtaaatt    24780
gaagggcaag agatgaagaa gtcttcagtt tgttaactta attggtgttt ctatcttcca    24840
tgtcttttga aatgtgtatg aagatgaaat gtttcaagta cttgaagatg aaatatagtt    24900
tcttacttgg atgcttaaca atgttattac ttcaaaaaga acctgaaaaa aatcattatt    24960
cacttggttg cttaactatt ctattacttc aaaagattta ttactttcaa ttggctttc    25020 acttacccta ttcatggtga ttaatatgta agtttcatgc aatgtctttt caattatcct    25080
aattattgta attgaaatgt gaatttattt ttcagataat taaaatatta tgttttttt     25140 catataataa tgttcaagaa taaattggta attcaacttt aagctaaagg gcttcccact    25200
tataataata tgatatgata tgatgattat tagatgtaat tttctgattt ttcttttgga   25260
aacaaatcaa ctatttgtaa catctatttg tattatactt gattttctt gggtctgtaa     25320 aaataaatat ttgaattttt tcatattaag attcataatt agtcttatag cttaactgta    25380
agaaagaaat tacaaattaa atttgacaaa taattaagct acttaaataa cttaattgtt    25440
caatataaaa ttttaaggat tgcctaaact tagaaaaaaa aaacaattaa atttagttat    25500
atggttgcaa tgtgtaatca aatagtaata aatatgtggc tgtttgtaca gctacaatat    25560
gacatgagat aattaaaata tatgtgtctt taagctctcc tcttttttgtt tgttttgagg   25620 aaaatctgtt gtattttgat gtgtataatt ggttaattat acactctttt agaaacaaat    25680
agtgttgaat ctacaataac atgtgaatac atagatttga taaaatataa aatcgtaaat    25740
agattagacc atctttttta ttgacagagg tgaaagacaa agcaaccca caagaaaaga     25800 taggtatgaa actagctagc agttttatga acaattaata taaaatataa aacacttttt    25860 atttttactca acaattaatt tataagctat ttttatttta aaacacttaa aataagttaa   25920
ttcgaacatg tactataaat caaaacaaat aaggaaaaaa aggaaaagct aaaggtgtgt    25980
ttggtatgaa ggaaaatgtt ttcctaaaaa ataaatagat tttggattta ttttctcatg    26040
tttgattggt aagtagaaaa tattttcctg tgtttgattt atgaatgaaa ttaattttg     26100 gggggtgggg gtgggtgggg gctggtaggg gtggatagggg ggctggccgg gtggaggagg   26160
gtaggagttt aaaaataaaa atttgaagtt gaaaatattt taaaaagcaa aattaattt     26220
```

```
tggggagggt gaggtttagg ggctggtcgg tggtgggtgg acggggtca aggatcgagt    26280 gaaaaaataa attttaaaat tgaaatatatt tttattaata ttgatatttt cctaaatttt   26340
tgaagggaag tcattttcct taattttag gaaaatgagt tgatttgaaa aatattttct    26400 aaaacttta ttccaaccaa acatgaaaaa attgaaaat attttccaga aaatgttttt     26460
cttcatacca aacacactca aaagagact cttttaatca agtattattg ctaaaaaaaa    26520
aagagacaaa gaataataat ttaccccata aatttcgcaa atcaatctat aaagattga    26580 gggtgagata ttgataagat aaacaatca aaataataga taaatatgtc ttttagttta    26640
atttaatttt atatttatat tccttaattt agaatggaca cataatttga tatcttaact   26700
tgtatataat taaacaagta tgtatatata tatatatata tatatatata tatatatata   26760
tatatatata tatatatata taaacacca cctatgacac aatttccatg aaggatgtgc    26820
acgtttattt tattgattct atacaagttt aagtatacgc ttattcatac tatagttgaa    26880
taatataaat ataaaataat atcaaattta aaagatatat ttatatatta tcttaaacaa    26940
atatgtttta aaaaaaata aaatctagta actacccac cataaaagtg atgcccttat     27000
acgccgaaag aacgtttaaa atcaaaagca actgttagtg ttattggatt gaaaaataaa   27060
accgaatact ccaattaaga gacatggcgg ccccatggtg gaataattat tacaacacac   27120
cttccataat taaagtttga ccttatacct aatgacaatc aaattttgag ttcggatcct   27180
atttcatgag ttaatatctc atataatcac ttaattttaa ataattcatt tagtatgtta   27240
ttcaagttta aattgttcac ttaaaaagtc attcaactct attttataag taaaaaatca   27300
ctaatatttg agttgttcat ttagaaagtc attcaactct ctttataatt caaagtaac    27360 tcaattattt ttgtttcact taaaaagtca cccgatccca acttaaatat ttttttttca   27420
taaaatctta tttttatgtt aaactattct tttaaaaaaa aaataagata tttatttag    27480 aaaagggaa aacatgttaa aaagttagtt attccaaaaa agaagaaaga agttggaatt   27540
gaaaagaaat aatataaaaa aaaaacgcag gacagtgcct tttttttctta ttactttta   27600 tttaaagat aggtataaag aaatattata cttcaacaaa atataataaa taattaaaat   27660
aagcagctta taatttttatt ttatttttgt attcagccaa atttaattaa aaaatcattt   27720
aaaaataatt gaatgacttc ttaagtaaaa ttagttgagt aattttaag ttataaaata   27780 aaattgagtg actttcaaag tgaactcaaa gctgagtaac tttctaagtg aactattcga   27840
aattgagtga acatctgaga tattaacacc ttattttata cgtgaaacaa tttaaactat   27900
attacaaaag ttggaggaag atattgaaga aagattgtac atatgttcgt aagctccttt    27960
atgtcagctt ataaaaggct taacacaagt atatatagcg ggtaaaattt tattttgtga   28020
gaggtacaaa tgttacttag cagacaatat ttgtatgaca ttctctcagc ttttgccaag   28080
tggagtttgg gtctcactta cagaaaatgt gcttaaagct tcattttttt ctcttcacc    28140 tatttctatc ttcttcttct ctctttttttt ctccgttctt cataaatttt attttattttt  28200 ctgtcaacaa acatcgatac ttaatatatt ttattgaatg aaaattgatt taataatttt   28260
tatttttcaa atgttaaat caagacaaat caattaagtc gatttttcat tactttttt    28320 ttccttgcga tttgtttttt gtggacttct cgaaaatata taataatata aaattatcct   28380
ctgaaaaaat tatgcattac gaagaattta atcattacta agaaatatga taaattattt   28440
ccttacaaaa aaattaaaga tttaaggctg atatattaaa gatgtcttgt taatatctga   28500
tttaaataaa ataatcaatt aaaattacgag ttattttgaa cataaaaaaa cactttcagt   28560
attatctaaa taaaaatata agttaaacta caaagtaaaa aaaaataatt attataaaga   28620
```

```
gaaacacatg agtactcaca aagagaacaa aaaaaatatt tataatgatt tttttagctt   28680
tagataaggt tatacatata accaaaatta ttacggacca tttgttaatg aaataataaa   28740
atataaagat tctcctaata aattaatgta tgatcttttt taaacaaaca caaaaattag   28800
ttaattacac tatatttaat ttctttaatc tcactaaaaa aactattttt tctcatcaca   28860
tttactttaa atttttcctta aataaataat ataaaaataa aatagttaaa cattgtggct   28920 aattttttt tttttttaca aaaaaacaca aaagactaca aaggagaaca agagaatgag   28980
aaacgaaagt ttaaagggaa aaagtctga tatacttctc aacttttca tttggagctg   29040 atatatttct cgttataaaa gtgactcata tatgccctta tcgttataca aacgactcat   29100
atatctgagt catttgttta caagtaaggt atcactttct taaaaaagca atgatatcat   29160
ctctaaaacg acaaagattg aggggtatat cgatcctttt tcaaagttta aatgaatgag   29220
aaaaagtttt aagtgtgggt cccatgttgt acatttaaaa ttctcataaa ctgacagaag   29280
gttagctttt cacaaagtaa aattttttccc atgtgaaact caaaataaaa taattgcgta   29340
cagacatgtt tatgcaacac aacattaatt tatttattta cccattcaat aagtgaagga   29400
ataattataa tgctttgtgc tcttactttt agctgttcat atttcattcc aacatcgatc   29460
ttatagattt attgttaatt cacaacactt ccagcaatct acatggctga tgctttcctt   29520
caaattttgt tgacttcttt catacaagag gaacttggat tgaaaatcta aaaagcacgt   29580
ttactacgat ccaagctgtg cttgaagatg ctcaggagaa gcaactgaag gacaagccaa   29640
tagaaaattg gttgcacaaa ctcaatgttg ctgcatatga agttgatgac atcttagatg   29700
aatgtcaaac tggaattttt aaccaaatta agtcattata taaaataatt taccaaagta   29760 aaatatttt ctaaagttt acaaaactaa tataaacgta tttcatggta acgttttagg   29820
gtatatttta ttttttaaaa actaatgact ttaggttgat atcgttcttt gtaagtaacg   29880
ttttactcct aaaacgttat tttcaataac attttactct taaaacgtta ctcatagtaa   29940
cgttttactc ctaaaacgtt attttcaata acatttact cctaaaacgt tactatgagt   30000
aacgttttag gagtaaaacg ttactgtgag taacgtatat caatctgacg ccatcaactt   30060
ttaaaaaata aaatatatcc taaaacgtta ctgtggaata cgtttatact agttttgtaa   30120
aattttagaa aaacatatta ttttggtgaa tgactttata taatgactta gtttggttaa   30180
aacctcgtca aactgaggca gcaagactca atcagactaa atatgggagt tatcatccta   30240
aggctatcac tttccgttac aagattggga aaaggatgaa agagataatg aagaaactag   30300
atgcaattgc tgcagaacga agcaagtttc atttggaaaa aaggactaca gagagagaag   30360
cttctagacg agaaacaggt gctcatctta aatatattag tattaattac aacaatttaa   30420
ttagtttata ttcatttttt tgctattatc aagttcatgt gtgtttatgg acccaaggga   30480
cttttttcta atctaatgtt tgtctcaagt ctaaacagat ttgtaattct accacttatt   30540
tatttactga agttcttaaa catatataca tggtgtaagc cagctcagat aaatccatag   30600
tcagttgttt cggactgaat ttaacttgga tgtcaatttt tcaaagtcaa tcatgttttc   30660
aactcctccc cctgattctc atctctttgt agtgcaaaaa tcttctctct gttttcgct   30720 aaacatattc tcgtgtgaac atatattgct tgaaacaggt tttgtttaa ctgaaccaga   30780 accttatgga agagacaaag aggaagatga gatagtgaaa atcttgataa acaatgccca   30840
acaactttcg gtcctcccaa tacttggtat gggagggcta ggaaattcga cgcttgccca   30900
gatggtcttc aataatcaga gagtaactga ccatttcaat cccaaaatat ggatttgtgt   30960
```

```
ctcagaagat tttgatgaga agaagttgat aaaggcaatt gttgaatcta tcgaaggaaa    31020
gtcagttggt gaaaacatgg atttggctcc acttcaaaag aaggcattgt gtcgatttga    31080
gataatacga gaaaaatata catgcgaaaa acaagacaac agatttcgtg gttcaccaat    31140
aaattggctc gtccacggga agagggcggg ttttattatg gaggcaaaaa ccaattctga    31200
gaatagggtt tgccatagcg tctatatata gtgtaaacta agcccctaac aggcttgggc    31260
ccaaaatata aattgaatga taattaaggg cccaattcaa ggcattcaac aaatctccac    31320
cttgacttga attctccaag cagattcttg ggcgcactat gatagtgcca ggcctccccc    31380
ctcttcctcg ggttgccctt gagtataatt acttgacacg atgttgagca agtcaaacga    31440
gtgttgaaac ttgctcacgt ggagccaagc tttgtgaaca tatcagcggg attatcaaca    31500
gttctacttt cttcaccttg attctcttct cacttctcgg gaaaatgata cctccgtcaa    31560
tatgcttggt tctctcatga tggacttgat ccttggctag acaaattgcg ctcaaaagct    31620
gtcaatacac acgtgctttg agtcatgatc gagaccaaga tcactaacca gccccttca    31680 accaaatccc ttcttttgca gcctctgtca aggccatgta ctccgcttcc gtagtagaca    31740
aagtcccatg taggttgcaa agttgccttc aatgacgcgg atcctcaagg gtaaacactt    31800
gagtcatccg atcttcttgt gtcaacatct ccaaagatag tctgaatcag aatagccaat    31860
aaccaagcac tgagtatcac ctccataaat gggaccagcg tcggatgtac ctctaaggca    31920
ccgaaaaatt ctcttctgac tgccaatgtt ctctccacgt tgtcccatga atgctcacta    31980
cactaatttg catgtactaa atctggcctt atacagacca tagcatacat caaacttcct    32040
cagcactggc ataagggact cgtgacatat actccttctc ttcttctgac tgtggagccg    32100
aacatggcga gtgggatgga taaaggcgtg gggtatcaat gggcttagat gaagacatgc    32160
caaacctagc caagaccttg aatgtaacct tctctgtgac aagaaaagtt tccttctctc    32220
tctgtctcta atgatctcca tccctaaaat cttcggctcc cggatccttc atctcaaact    32280
cagactaagt aaacccttga cttctgagat gtcatacttc ttctttgcag ctatcaatat    32340
atcatctaca taaagcacta gatagatgaa tgaatcatcc ttgagcctat tgtagtagac    32400
acaacaatca tatgagctcc gagtatagcc caacttcacc atatagctgt caaaccttt    32460 ataccacatc cttggagact gcttaagtcc atataaggac ttcttcaact tcaggacgtg    32520
attttccttc tggaacttgg aaaccatcct ttgagtcatg tatatctctt cctccaactc    32580
tccatgtaga aacgctgtct tcacatcaag ttattcaagc tccattctga tgtgtaacta    32640
tcgctagtaa cactcggatg gaagtatgtc tgaccactgg tgagaagatc tcattgtagt    32700
ccactccctc tctttggttg aaacctctgg caacaaccct ggctttatac ttgactcctt    32760
ctgctggtga tatcccttcc ttcttcttga aaacccattt gcaagtaata atctttctcc    32820
ccgaaggctg tatgaccaga tcccatgtct gattcttgtg tagggactcc atctcatctc    32880
ccatagcggc aaaccatttt tcagaatcag aacttaaaat ggcttctttg taagtagacg    32940
gctcagatgt atctacctct tcagcaacct gcagtgcata acccaccatg tcctcaaaac    33000
catacctcgt aggtggccga actccaaccc tccttggccg atcttgagct aaactctgat    33060
ggatatctga tggcatagat tctggaatat cagtttctgt ctgtggctct tgatcctcct    33120
cttcaggttc tttcaaatcg ctctcgttct gaatgacttg aaactccacc tgtttatcaa    33180
gactcccagt ttctgacgta gttgtaggct tcacaatggt tctaagcaga gaactttcat    33240
caaagacaac gttcctgctc ataataaccc tcttttctgg agccggatta cgaaaccttt    33300
cactccatct catgccccaa atactccttt ttggctcttg gtttctaact taccttcact    33360
```

```
gacgtgatag taagccgtac aaccaaaagc tttcagattt gaataatcgg cagcttttcg  33420
accacatctc cataggtgtt ttgcactgtg gctgtatgtg gtcccttgat tatcagtagc  33480
aaagctgtac taaccgcttc ttgagaatct tctatcccca gcattgaaag catgcacctt  33540
gctctctcca gaagtgtttg attcatccgc tcggctacac cgttctcttg tggtgtattt  33600
ctaagcacat gcgatgtcgg gcaatccttc atccttacga attgatcaaa ttcagaccaa  33660
cagaattcca gcccattatc agttcgcaac ctcttgatct tcttccctgt ttgattttcc  33720
atcaaaattt tccactcctt gaacttctgg aaagcttcac ttttatgctt catcatgtac  33780
acccaagtca tccttgagta gtcatcaatc atggacacaa aaaatgggcg acctcccaaa  33840
gactcaacac ggcatggacc ccaacaatca gaatggatat aatcaagtgt gccttttgtt  33900 cttttgaatgg cctttggaaa cttgttgcga tgtagtttc caaagacaca atgttcacaa  33960
aactctaggc tcttaacctt atgaccagca agaagatcct cttttgatg aatttgcatc  34020 cctcttcac ccatatgacc aagtctattg ccataactta gtcatatcct tctggtgaaa  34080
ttctgacgat gcaacatggg ctgaacctgt aaccggaacc ttgtagaaaa tataaaagta  34140
ccacatgaca cctttcaaga atcaatttga acctttccag accccaagac tccatctttt  34200
cccgaccatt tgaatcccct gctgtcaaaa gactgagaga tatcagattt tcgtcatcaa  34260
tggaacgtgc tgaccctcgt tcaatgtgcc aaaactaaat cgtcgtgtcc ttatcttgat  34320
cagcctgtcc caaccacctt gcggtgaaac tgttggccat cgagatcttg cctcaaatct  34380
accactcata agtcgtgaac cactctccct aggacagatg tgataggatg ccccagaatc  34440
gagaacccac atatctgaat gatgagtgtg ctcatcgtca actagggcaa tatcttcttg  34500
aattggtgtc ttcttgacta gcaacagcag agaccactga ttgttttcga ttgcttcttc  34560
ttcttggaca atcaaatttc aatgtccctt ctccttgcag taattacaaa catcatccct  34620
ttgcaccttc gacatcggct tattttttctt tccgccgttt tccttcccttt tccgctcttg  34680 gtcagcaggc ccggaaggta taatgtcgta cttgtgccgt tagccttatg ccgtaattcc  34740
ctgctatgaa gggccgatct gacttcttcc agtgacacag tatctttccc aacaatgaac  34800
gattgaacaa aattctcaaa cgacattggg agagatacta acaatcaggc gacatcttca  34860
tcctcgatct tcacatcgat attcgcaatt ctaataacaa agtattcaat tgctctaagt  34920
gttccctgag ttgtaccttg accattcgta aaccgaatag gcgttgtttg aagcagcttg  34980
ttggttagag attttgtcat gtacaaactc tccgacttca accgagacca gacggtctct  35040
tcatccgaga ccctctgcgtg atgacgtcat ccgcgagaca caaagatgat cgtcagtgcg  35100
cctttcctcc ggaatctcca tctcgggagt aacgacggcg ttcttgtctt tcgacaacgg  35160
cgcccgtaaa accttgttgt ttcaacaaag cccgcatctt gatcgccata aaccaaactg  35220
gctattcctc caccgtgaat ttgtcgattt tcacgttcaa agcgtacatc tcaattctca  35280
agaacacccg attaaccgag aggctcgata ccaatttgtt gtgcgaatt tgagataata  35340 cgagaaaata taaacgcgaa aaacaagaca acagatttac gtggttcacc aataaattgg  35400
ctacgtccac gggaagaggg aacatttat atggaaggc aaaaaccgta attacgaata  35460
gggtttgcca taagcgtcta tatataacta aactaagccc ttaatgcttg gccaaaata  35520 tagaattgac agataattaa gggcccaatt caaggcattc aatgaagctt caagatatgt  35580
tgaatggaaa gagatacttt ctcgtttttgg atgatgtttg gaatgaaaat caagaaaagt  35640
gggataagat aaaagcagtc ttagaggttg gagcacgagg tgcttctgtt ctaaccacca  35700
```

-continued

| | |
|---|---|
| ctcgtcttaa aagggttgga tcaattatgg acactttgca accatatgaa ttgtcaaatc | 35760 |
| tgtctcaaga agattgttgg ttgttgtgca tttgagaacc aagaaaaaat aaatcctaac | 35820 |
| cttatggcta tcggaaagga gattgtcaaa aaaagtggtg gtgtgcctct agccgccaag | 35880 |
| actcttggag gtcttttgcg cttcgtggat caagaaagag aatgggaaca tgtgagagat | 35940 |
| aatgagattt ggaatctgcc tcaagatgaa agttctattc tgcctgtcct gagacatagt | 36000 |
| tatcatcatc ttccagttaa tttaacacaa agttttgcat attgtgcagt attcccaaag | 36060 |
| gacaaggtaa tggaaaaagg aaatttaata tctctctgga tggcacacgg ttttctttta | 36120 |
| tcgaaaggaa acttggagct ggaggatgta ggtaatcaag tatggaatga attatacttg | 36180 |
| aggtcttttt tccaagagat tgaagttaaa gatggtaaaa cttatttcaa gatgcatgat | 36240 |
| ctcatccatg atttggcaac atctctattt tcggcaagag catcaagcag caatatccga | 36300 |
| gaaataaacg tagaaggtta cccacatatg atgtcgattg gtttcggaaa agtggtgtct | 36360 |
| tcttactctc cttctcactt gcaaaagttt gtgtcgttga gggtgcttaa tctaagtgaa | 36420 |
| ttaagactta agcgtttacc atcttttggag atctagtaca tttaagatac ctggatttgt | 36480 |
| cttacaatag taaaatgcgc agtcttccaa agcagttatg caagcttcaa aatctgcaga | 36540 |
| ctcttgatct aaagtattgc tggtcactat gttgtttgcc aaaagaaaca agtaaacttg | 36600 |
| gtagtctccg aaatctttta cttgatgatt gcgatggatt gaattctatg ccagcaagat | 36660 |
| taggatcttt gacatgcctt aagactctaa gtagatttgc agtggggagg agaaaaagtt | 36720 |
| gtcaacttgg tgaattctga aacctgaatc tgtatgggtc aattgaaatc acgcatcttg | 36780 |
| agagagtgaa gaatgatagg gatgcaaaag aagccaattt atctgcaaaa gaaaatctgc | 36840 |
| attctttaag catgagttgg aatatcaacg aaccgcgtag atatgaatca gaagaagttg | 36900 |
| aagtgcttga agccctcaaa ccacactcca atgtgacttg tttaacaatc aaaggcttca | 36960 |
| gaggaatccg tctcccagag tggatgaatc actcagtttt gaaaaatgtt gtctctatta | 37020 |
| caattggagg ttgtgaaaac ttctcatgct taccactgtt tggtggtctg ccttgtctag | 37080 |
| aaagtctaga gttatggaat gggtctgcgg aattggagta tgttgaagat tctggattcc | 37140 |
| ctacaagaag aaggtttcca tctctgagaa aacttattat agtgaatttt gataatctga | 37200 |
| aaggattgct gaaagaggca ggagaagagc aattccccgt gcttgaagag atgaaaatta | 37260 |
| gctgttgtcc tgttttttgtt attcagaccc tttcttctgt gaagaaattg aatgcttatt | 37320 |
| ggcacaagtc agatgcaaca ggtttgagtt ccatatcaaa tcttagggct cttacttccc | 37380 |
| tcaacattag ccataactcc acagctactt tgctcccaga agagatgttc aaaagccttg | 37440 |
| caactctcaa atacttgaaa atctcttact tcgataatct caaagatctg ccaaacagcc | 37500 |
| tggctagtct caatgctttg aagcatctgg agattaattg ttgttatgta ctagagagtc | 37560 |
| tccccgagga agggtgaaa ggtttaactt cactcacaca gttatccatt gcatactgtg | 37620 |
| agatgctaaa atgtttatca gagggattgc agcaactcac aaatttatca attacgaatt | 37680 |
| gtccaacact ggccaagcga tgtgagaagg gaataggaca agactgatac aaaattgctc | 37740 |
| acattcctca tctgctgatt acatagtgtc atactaaatt aaatgattct tatagcaata | 37800 |
| ttattggttc aaccaacaaa actaaatctc taattatatt acttaattgc ttttagtttg | 37860 |
| ctacaattat cactcatgac taacattatg tatcaattac gtggtttgtc ttcaattttg | 37920 |
| tataattagt catgttttta tatgtataat tcgctagaat aatacagata tatgtataat | 37980 |
| atacaattat ttaactgata tacatatata attcacctct cttccactct ctgtcctctc | 38040 |
| tcacttgcct ctgtcctctg ccaatcgacg agatgagcct acgaaagatt tcaagttcag | 38100 |

```
actatgatga ctgacatcct cacttacgca acgaaatgga gttgatggag tagccagtgc    38160
ccttgagtca ttctcttcgg tatcgccttc tctcatcgtt aatggcgccg caaggcactc    38220
gactagcaag ttagacctta gttagggcga aagatttctt ggatggttca tttcagtctg    38280
aagtcgggtc aagtcatgga attgatgtga agttctctca atttcgcttt ccatatatac    38340
aaatatatat gtataacata caattatcta aatgatatat atatatatat atatatatat    38400
atatataagc aatttatctc tctcccactc tttgtttcac ctgacaacta tgacaactat    38460
gtttgttagg gctggaaggt ctaacttcac tcaccgagtt atttgttgaa catatgctaa    38520
aatgtttacc cgaggaattg caccacctaa caaacctcac aatttttttt ttataagtga    38580
aagcatagtt aaactctcaa atgtagatga taattaagct cttgaagatt attgctgaat    38640
taagtgaatt cgtcaagcta tatttgtaaa attcttatgg ccaaacaagt aatattgcaa    38700
caaattgtag aaggattatt atactcttaa cactaactaa aagattcttc caattctcaa    38760
agcaatttat attcctttcc aaccaaagag gttttccaaa tttgctttct agcaaaaaac    38820
aattttctgc acgataggaa tagatctcat atatactccc tccgtttcat tttatgtgaa    38880
gtagtttaac tgagtacgga atacaaaaat aaaagaaaga catttaaaat ttatggtcta    38940
aaatgaaggg aaaaaggtcg atatctcctc aactttgtca ttttagaaat gatatacctt    39000
gttatgaaag tggctcatat ataccctac ttgtaaacaa atggctcaca tatacctttt    39060
tcctctaacg ggaaatgaaa aataataatt ttcaatctaa attttttatt ttttttctaa    39120
aaaatataag tccatatgag taaatttaat tctcgtcaaa caatttttttt tttttttactt    39180 tttttttgtt tcaatgacta atttataatt attagtttga taatcaaatt tatttatgtt    39240
tcactaatat tcttgtaaaa cttattgtag atgaaaaaaa aaaaatttga atacgaaatt    39300
aaattacaat aaacacaaaa aaatagttta tttttttttt tctttaaact aaggaatgat    39360
agaaaaaaat aaaataagaa taagaaactc aaataattat aataaaagaa gttaaaaata    39420
atttatgtat gaaaaaaaaa ttaaatatac tttgaacttt tattgaagaa tcatatatac    39480
cactaaataa tttttttaaa attttttaag taataaatat aaatttaaaa ctaattattt    39540
aaaattttgt taaatgaagg gtatatttga acaattttgt aacggcaggg gtatatgtga    39600
gccgtttgta taacggtaag ggtatatacg agccacttt ataacgagag tatatcagat    39660
tcaaatgaca aagttgaggg gtatatcaaa cccttttccc ctaaaatgaa taataaaaaa    39720
ttgtgtgagt ataaatcatt tcattaagag taaatggaca atttaaaatt aaattgttac    39780
ttaatatagt aacgtatctt ttttgttttt gagtctgctt taaaaagaaa ataaaccata    39840
taaattggaa catagggagt atctacttac aaagtaaaag ttgtgtgtag aagattttgg    39900
catacaaatc aaatcatata tcatatcata tatcatcata tcatatatca catcatatca    39960
tatattagta aaagcatgaa taaaaaaagt tgaaagttga attacggttt tattccttct    40020
attaattaac ttgttataaa atatttaaat atttgatttt acaagtttaa ttaaaatgtt    40080
aaatgacttt tagacttcct acgattaatt tctaattaaa tatctaatttt attaatattt    40140 atcatttata atctatatgt atataataat tataattttt taaaataaaa gtctaattat    40200
aattttaatg acttttttaga cttcctaaca ctaattccta attaaatatc taattttatta    40260 atatttttat catctataat gttataataa gcatctttag aaggtttctc tgaaatactc    40320
tttaaaagaa tgcttggact atgccatcct aaggttgaaa ccagtaggca aagaaggtc    40380 gttatgggga gtaaacaaag ttgaggcgct gttagggtaa ccaattaaag aagaaagctg    40440
```

```
tagtagtgac taggcgagat gattattaaa tcattattat tacataataa gtaagtataa   40500
tttattaaga ggtcggaagg aataaaactt ttagcaaaaa tgaataagat gactacctac   40560
ctaattgatg atgatgatga atataagata ttattacttt atatattaaa aaatcttaat   40620
actgatcaag ttagcagtct caaaaatctt tttttacttc atggttgcca taaattgaat   40680
tctatgccac caagtatagg atctttgaca tgccttaaga ctctaggtca ctttgttgtg   40740
ggaaggaaga aaggttctca acttgatgaa ctacgaaacc taaatctcta tggatcaatt   40800
tcaatcacac aactagagag agtaaagaat gatagggatg caaaagaagc caatttatct   40860
gcaaaagcta atctgcattc tttaagcatg agttggaata tcaacgaacc gcgtagatat   40920
gaatcagaag aagttgaagt gcttgaagcc ctcaaaccac actccaatgt gacttgttta   40980
acaatcaaag gcttcagagg aatccgtctc ccagagtgga tgaatcactc agttttgaaa   41040
aatgttgtct ctattacaat tggaggttgt gaaaacttct catgcttacc actgtttggt   41100
ggtctgcctt gtctagaaag tctagagtta tggaatgggt ctgcggaatt ggagtatgtt   41160
gaagattctg gattccctac aagaagaagg tttccatctc tgagaaaact tattatagtg   41220
aattttgata atctgaaagg attgctgaaa gaggcaggag aagagcaatt ccccgtgctt   41280
gaagagatga aaattagctg ttgtcctgtt tttgttattc agacccttc ttctgtgaag   41340 aaattgaatg cttattggca caagtcagat gcaacaggtt tgagttccat atcaaatctt   41400
agggctctta cttccctcaa cattagccat aactccacag ctactttgct cccagaagag   41460
atgttcaaaa gccttgcaaa tctcaaatac ttggaaatct ctttcttcga taatctcaaa   41520
gagctgccaa acagcctggc tagtctcaat gctttgaagc atctgaagat tagttgttgt   41580
cccaaactgg agactctccc cgaggaaggg gtgaaaggtt taacttcact cacactgtta   41640
tccattacat actgtgagat gctaaaatgt ttaccagtgg gactgcagac actcacaaat   41700
ttatcaatta agaaatgtcc aacactggcc aagcgatgtg agaagggaat aggacaagac   41760
tggtacaaaa ttgctcacat tcctcatctg ctgattactg attagatgta attttctgat   41820
ttttcttttg gaaacaaatc aactatttgt aacatctatt tgtatgatac ttgatttttc   41880
ttggttatgt aacaataaat atttgaaatt tttcatatta aagattcaga atgagtttta   41940
tagctaactc tatattttca cagtttaata acgtaaaaat gtgatattta tatcaaatta   42000
ttacttatgt tgtcatttat caacatgttg gagatgattt tgacagttta ttaaagaatt   42060
tctaagtttt tattgtttgc acaagtaaca agccataaat taagtttcga gataaaagtg   42120
atttgtgtat catggcttaa ttagtcggaa tttcaagttt ttttctcaag ttatatatat   42180
gacaatttgt aaaaaataga tagtattgat tttgatttaa ttcaagcatt tttaaaaata   42240
taaacattat aatatgggag atacacacgc taaacgcgta cccagaaact agtatataaa   42300
gaatcatgac cgaaaaataa aatgaagttc tgtcaacaac tatctcgaca tctttgctga   42360
tatatatata tatctaacta gtgtacttat tcggacttga catggtataa aaagatatta   42420
aatatatttt taaataatta ataaatgata taataaaaag aaagaaatac aaattcagtt   42480
atgattctga taaaagggaa actaattttc tgattttct tttggaaaca aatcaactat   42540
ttgtattata cttgttaatg ttgcaattat tagtgaacag ttgtattttg gattatcact   42600
tacagcagat gtctaaaatg tgaataagat aatacttaga ataatttatg caatatactt   42660
ttgtttaaat acaagaaatt taaataaaga ttgctaaaga ttattatttt gaatgaaaga   42720
ttttgatttt gttactttgt cgcctatgta acatagtact gttgcaaaca tatacatatg   42780
tgttcatttt tcccccttgtg tttcatttta ttttctacaa ctcataaata ctaaaaagaa   42840
```

-continued

```
aacgttagga atgagtttta actagattta aattttaaca aaaacaacgt gattatattt    42900
cactaaattg acttaaatat atttatactt aaaaaaaaat tattaattta taatattaat    42960
gggaccatat atttatataa aaattttcta taaatatatt atcttatatc tcctctaaat    43020
tcatttcacg agaattaaaa ccatcctaac ggatgacgtt gccaaaaaga atagaaattt    43080
tctttgaaag cgtgttaagt ttttttaaa aaaagtaat ggtctcactt tgtatatatg      43140
aagaaaaaa aaacccaccc ctttcttctt cttcttcaaa cccccacccc cgcttttca     43200
aaacccacca gccccctta cctgcttgtc ttttcttcct catattcccg acgtcaccct     43260
atccccaacc caccccatcc tctttctcat ttttcgaact ctacattcaa agcacataaa    43320
taaaagaat cacatttaag attcatataa ttttttact ctttactttt gagatttgat      43380
ttttcttaaa aagttatgat tttttgaaa ataagaata gggcataaaa gaagatgagg      43440
ttttgtcaac caatctataa tgttaatggc tgggaatggt gattgaagca atggatagag    43500
aaagattttt ttttaaaaaa aaagagaag aaaatcact acaatcagta accgcaattg      43560
cagtaggctt acatcatgga gtatcccaat gagtctcttc actgttcaat cggccatcgg    43620
taaccgcatt acaatgggct ttgggtcacc cacccaattt cttataaata gaaagagaca    43680
tgagatttat gattgcacct agatcacata gtgatttggc aaagtgtaat aatacgaatg    43740
gtacatgaaa tagtgaaagc gccaggatct tccttcttct gcacaagagt tcttgtgaca    43800
atagcactac aatgctgcat tcagttatca tcctcaaaac ttaccgatct cttctttgta    43860
actatatcct tcatgaactt ggcataaccg gaccatttgc tccaaagctt ctatcaaagg    43920
gacattgatg gaaagttgct tcaacatagt gataaaatgt tggtatttac cattctcact    43980
attcttcacc aatctaaaag tggtggtggt ctaggaatgg ggaccacttt ctagggtatc    44040
tttgcttttt tcgccgcttt gtccaccaat tcaccactag tttccaccac ctcttcatct    44100
tttctcatct catcttctac cacagacgac ataggtgaat caatagtttg catacctcct    44160
caagtagtga ctgtcatgca atgtccatca tttttaggat ttgaatggaa ttactatgaa    44220
aagtgacagt tgtcgcgggt tctgatagtg aacaattgga ccatttataa ttcaagatgc    44280
ttaatcgaga ccgcatgtgc atccaccttt ttcccgatat tagccaaatc acctctcaat    44340
ttcttggcgt gctcatcact agcatcaaac cttctcatca tctttagcaa catatcttca    44400
acttgcgccg tactacctcc accatctcaa ggagcaactt tctgattttg aggtggaaca    44460
tagggcacac ttcaatcatt tctattacca tagttacccc ggttgaagtt gttatctcgg    44520
ttgtagtttc ttctcgaact tactggccct cttgttgtaa ttcccattct gcattttcaa    44580
tttaaaattg ttgataaaaa agacaaaaac ataaaaattg atatgaaaga gctttggtta    44640
agtaacaatc taattatcat agtgtcatat tcaattcaat gattcttata gcaatattgt    44700
tggttcaaca gtttaacttt actcgctgag ttttctattt atgatgttaa aatgtttacc    44760
gaagggttat tatacttgtt tttaatgttg taactattag gggtagatta tcactttatg    44820
aatgaatatt ttggcacatt ggaaaaacac caaatatagc gcgcaaaagc taaacaagga    44880
aattttcata tattggatat agtctttgtc atttccaaag gtctccaaca tagagatagt    44940
aattgagaga aaacttctat tgctattaaa tagaatctgc aattaaaaaa aaaataaatt    45000
attattatat tttatattat aagtgggaag atgcttagtc taaaggtgga ttaagaaaac    45060
gccttcaact tttttaatta tcattattat attatattat aaataataat taattatttt    45120
tctataagtg tgaaactatt aaagttgaat aaccttttaa ttctacaaga actcaccatt    45180
```

-continued

```
aagttgaatg acttttttaac tcttcaagaa atcactaata agtcttttta cacgtcgtct   45240
tataatgata atattgtaca tttgaatttg gtttagagag cataaatccc ttattatact   45300
atgtgttttc aagcatttct ttacatttag attttttta tttttttgcta taattcaagt   45360
tatattctta aattgatatt taagtgtttg atttctcaca tgaaaatata cagttaaaat   45420
tttgttttat gaactcatga tgtaatttt tctcaggtat aattttaatg tgattcttt   45480
gcagacaatt gactaaaatt tttagtagaa attgcaccaa tacaaataag gtatgcggca   45540
tgtctctcca acaattttac attttttgca tgattatttt ttaataaatt tgatatacat   45600
acgattattg tatttttaac tagattttaa taacttaatg catgtttttt tttataatag   45660
agcctccttg ataactttac aattacttat tgaaatttat ttttcttcaa tctcctagct   45720
tccgagataa aatgggtaac taatatttct ccctcaacaa catggagcaa aaaaaatcga   45780
gaaaatctat gaagaagaca tattctaaca aatggagtaa tttaatttaa tttaaaggag   45840
tacttaatag tcaaatatga atagtaaagt aagagaaaaa aaaataaaaa aattagaata   45900
tgacaagtat gaaagacaac catgaacaaa ttattggagt ttttttgttca tgctacaaag   45960
aacaataaag ttactatgtc atttgaatgt aatatgtaga caacatatat acttgttaca   46020
agtatatatg gtaattcaaa ttttggtaca aattgagcag gtgtgttatg tgtgtattgt   46080
tcctttctta gaaagtaac aaactaatat attgtagatt tcgacctaat aacataaaaa   46140
tgtaaattat ttatcacatt aaattttgtt gtccaaattt gacaagttat tggaatatct   46200
aattatttga catttacatt ttacaataaa gaagtcattt ttataggttg attgtccatt   46260
tatttcgttt atattttttt cgttaaatca tttttgaaaa ttttcaaact gtgattttaa   46320
tatattttt tagtttaatg taattttaat ataactccta caatatataa tattttttgtg   46380
ggactgacat gcaaaacacg tgtcttggac tagtctttca cataaagaca gacaactaag   46440
aagattgtat cgcggataaa cgctactgga atagccctat tatgaagagt gtttgtcaaa   46500
cagccaaatg actgtagttt tttcttttcc agaaatatga ctgaaggact atatcttgga   46560
tcgatcagag tgcatgaatc actcagtttt ggaaaataaa gttttgcttg ataaacacaa   46620
atttatctat tcacaccaca agcaatggta agtcatcata aaaaaaaaga gagagagaga   46680
aatttgttgt tagatcgaga aagattttga taattgacga atagacgaac aaatgaaaga   46740
aacaggttgc atgtacatgt tccttttcaaa ccaaatccga ctgggattgt caaccatgcg   46800
aattagaagt tataaagtaa tggaagggtt gcttttttcga cccgaacgaa gagtgcaaaa   46860
ggtttccttt cataaagaaa tcctaagcaa agtgggaagt gtaaacgaag taggtagcat   46920
aagcgagtag gaagtataac gacgtgaata aatttcaaat ctgaatggag tagatgatca   46980
gatatgtaaa acaagtacaa gatgaaaaag gttttgaaga gtccaaagtt tataaatagg   47040
gcaatatttt ctttggagaa aattgtgcac ttaaacagag agttacaagc aaaatacaat   47100
caaatagagg gagtttatat ttgagtgaat tctgattacg aactgcagcc aacacaagaa   47160
aacaagaatt gaagaactca ttcattggct tatgttttat agttcttaag tcaagttttt   47220
ttgtattgag ttttatcga gttgtatatt taaccctttc taaatccagt gaagtataaa   47280
ctggagtaga aatagagtct ttaagttaaa gacttggaaa cataaaccttt gggggatttt   47340
gttggagtct aggaattaga atcagttcta gtattgcaag agttggaatc cgaattcata   47400
acttgaagtg ggatcgacga tctagttggt tgttggtagg gccgactcaa caagattgag   47460
ggcctaaagt caaaccttaa agagggctcc aatattttt taattctttt taaaaaaaaa   47520
aaaaaaaaa ctaataatca tgtatatatt atttaaaatc tattttctag cttttctaga   47580
```

```
tgtgaagtca ttaattacta ttttctaatg gatttgtttt aataattctt tttcaattga    47640
taatatagct aatacattca atctcattgt tgatattaca tatataagat tttatcaatt    47700
taaattttaa aaaattcttt cggccgaaac aatagttctg gattgttaac tttattcgtt    47760
aagcaatata tgcattagga ttagaatcaa gtcttttat tagattgcgt atttccatta     47820
aatcattatc ttctacttgt attatttctc ttaataataa taactaaagc gagcatgtat    47880
acttactatg aatatcaaca acaacaaaag ttcaagaaaa attacaaaat aagttagtat    47940
aataaaactt ggcttgcgaa tttgataaat tgatataaca atactgaaat agtgtttcat    48000
ttcttcaata taatgactgt ttgtttaaac aagacactca aaaacaaatt ttattttttt    48060
taacatgtaa gcgacaataa cttttttta ggagagtgtt caacattgag cataaaagta    48120
ataaaataga gaataaaaaa gatgagtata agataaataa taatataaga tcgattttac    48180
ctattgtcaa ttttgtgtat cgactaaaga aataacagct tcacatatga atttgtattt    48240
taggctgctg taagtactaa aagatagtta ttcaaccagt agaagagatg aaggtggggg    48300
gcagctgttg gcaatcaata agggcatatt gagccaattt ttttcttctc tgaaaaactt    48360
tggcagagaa attaaggcta acgaaaaagtc tttgtgcagt tgtttcccaa aactttgtga   48420
attgtatttc aaaaaataca ttatttaata ctccaacaac tttgtgattc cactctagac    48480
taccatcaca tatctaatat taattataat agtgaatttc acatatggcc agaggcgaac    48540
ccacctgcac ccaatatatt tttaaaaaaa attcatatgt agattgttga taagacgcta    48600
taatatattt aattgtgcac tcttataatg aacaaatgat ttgacttgtt cattgaaaaa    48660
acaaaaagtg tcacataaat tgagacatga aaataatat ttctttta aattttcgt       48720 gtgaagtcaa actaattcat atataaagcg aaagcggaag gagtactgtt taatattaat    48780
tgcatatggt agtaaatttg atagacatgg tcccgtgggg tgtgtgttat ttccattgaa    48840
taattgagtt tgtaattgtt acaagtccat tctaatttcc aacaccttac ttcatttcaa    48900
aaatatagat tcattgctta ctcaccacat actcgatggc tgaagctttc cttcaaattc    48960
tgttagaaaa tttaacatct ttcatacaag gggaacttgg attgtttttt ggttttaagg    49020
acgaatttga aaatctgaaa agctcgttta ctacgatcca agctgtgctt gaagatgctc    49080
aggagaagca actgaaggac aagccactag aaaattggtt gcagaaactc aatgttgctg    49140
catatgaagt tgatgacatc ttggatgaat atcaaactga ggcagcaaga ctcaatcaga    49200
ctaaatatgg gagttatcat ccaaaggcta tcgctttccg ctacaagatt gggaaaagga    49260
tgaaagagat aatgaagaaa ctagatgcaa ttgctgcaga acgaagcaag tttcatttgg    49320
aaaaaaggac tacagagaga gaagctgcta gacgacaaac aggtgctcat cttaaatata    49380
ttagtcttag ttacaacaat ttaattagtt tatattcatt ttttggcgat tatcaagttc    49440
atctgtgttt atggactgaa cttaacttgg atgtcaattt ttcaaagtca atcatgtttt    49500
caactccccc ctgattctta tctctttgta gtgcaaaaat cttctctctg tttttcgcta    49560
aacatattct cgtgtgaaca tatgttgctt gaaacaggtt ttgttttaac tgaaccagaa    49620
ctttatggaa gagacaaaga ggaagatgag atagtgaaaa tcctgataaa caatgcccaa    49680
caactttcgg tcctcccaat acttggtatg gggggctag aaaatcgac gcttgcccag      49740 atggtcttca atgatcagag agtaactgac catttccatc ccaaaacgtg gatttgtgtc    49800
tcagaaggtt ttgatgagaa gaagttgata aaggcaattg ttgaatctat cgaagaaaac    49860
ccacttggtg acgacatgga tttggctcca cttcaaaaga agcttcagga taggttgaat    49920
```

```
ggaaagagat actttctcgt tttggatgat gtttggaatg aaaatcaaga aaagtgggat    49980
aagataaaag cagtcttaga ggttggagca cgaggtgctt ctgttctaac caccactcgt    50040
cttaaaaggg ttggatcaat tatgggaact ttgcaaccat atgaattgtc aaatctgtct    50100
caagaagatt gttggttgtt gttcatgaaa cgtgcatttg agaaccaaga aaaaataaat    50160
cctaaccttg tggctatcgg aaaggagatt gtcaaaaaaa gtggtggtgt gcctctagcc    50220
gccaaaactc ttggaggtct tttgcgcttc gtggatcaag aaagagaatg gaacatgtg     50280 agagataatg agatttggaa tctgcctcaa gatgaaagtt ttattctgcc tgccctgaga    50340
cttagttatc atcatcttcc agttgattta acacaaagtt ttgcatattg tgcagtattc    50400
ccaaaggata cggtaatgga aaaggaaat ctaatctgtc tctggatggc acacggtttt     50460
cttttatcga aaggaaactt agagctggag gatgtaggta atcaagtatg gaatgaatta    50520
tacttgaggt cttttttcca agagattgaa gttaagatg gtaaaactta tttcaagatg     50580
catgatctca tccatgattt ggcaacatct ctattttttgg caagagcatc aagcagcaat   50640
atccgagaaa taaacgtaga aggttaccca catatgatgt cgattggttt cgcaaaagtg    50700
gtgtcttctt actctccttc tcacttgcaa aagtttgtgt cgttgagggt gcttaatcta    50760
agtgaattaa gacttaagcg tttaccatct tccattggag atctagtaca tttaagatac    50820
ttgaacctct ctcgcaataa catgcgtagt cttccaaagc agttatgcaa gcttcaaaat    50880
ctacagactc ttgatctaca gtattgctgg tcactttgtt gtttgccaaa tcaaacaagt    50940
caagttagca gtctcagaaa tcttttactt catggttgcc ataaattgaa ttctatgcca    51000
ccaaggatag gatctttgac atgccttaag actcttggtt gctttgctgt gggaaggaag    51060
aaaagttgtc aacttggtga attacgaaac ctgaatctgt atggctcaat tcaaatcaca    51120
catcttgaga gagtgaagaa tgataggat gtaaagaag ccaatttatc tgcaaaagaa      51180
aatctgcatt ctttaatcat ggaatgggac gacgatgaac gtccacatag atatgaatca    51240
gaagaagttg aagtgcttga agctctcaaa ccacactcca atgtgacttg tttaaaaatc    51300
tatagattca gaggaatccg tctcccagag tggatgaatc actcagttt gaaaaatgtt     51360 gtctctatta gaattggagg ttgtgaaaac tgctcatgct taccaccgtt tggtgatttg    51420
ccttgtctag aaagtctaga gttatggagt gggtctgcgg aagtggagta tgttgaacat    51480
tctggattcc caacaagaag aaggtttcca tctctgagaa aacttattat agacaatttt    51540
gataatctga aaggattgct gaaagaggca ggagaagagc aattccccgt gcttgaagag    51600
ttgacaatta gttgttgtcc tgtgtttgtt attccgaccc tttcttctgt caagaaattg    51660
gtagtttatg ggaacatgtc agatgcaaca gttttttaggt ccatatataa tcttagggct   51720
cttacttccc tcaacattag ccttaactcc atagctactt cgctcccaga agagatgttc    51780
aaaagccttg caaatctcaa atacttggca atctctttct tcgacaatct caaagagctg    51840
ccaaacagcc tggctagtct caatgctttg aagcatctga aaattgaatc ttgttatgca    51900
ctcgagagtc tccccgagga agcggtgaaa ggtttaactt cactcacaca gttatccata    51960
gaatactgtg agatgctaaa atgtttaccg gaggaattgc agcaactcac aaatttatca    52020
attacgaatt gtccaacact ggccaagcga tgtgagaagg gaataggaca agactggtac    52080
aaaattgctc acattcctca tctgctgatt acatagtgtc atactaaatt aaataattct    52140
tatagcaata ttattggttc aaccaacaaa actaaatctc tagttatatt atttacttgc    52200
tcatcatagc tatagtttgc tataatcatc actcgcgatt aacattatgc atcaattacg    52260
cgggctgact tcgatttttgt ataattagtc acgttttat gtgtataatt cgccagaata    52320
```

```
tacggatata tgtataatat ataattattt aaccgatata catatataat tcacctctct   52380
cccactctat gtcatctctc actcgcctct ctcctccctc tcttaatttt gcttttcata   52440
tatacaaata catatgtgta atatacaatt atctaaacga tatatatata tgcaattcat   52500
ctctctcccg ctcttttgct tcacctgaca actatgacat ttaactttgg atatgcacat   52560
ttaaaaactg gttacagaaa ctcaatgttg ctgcgtataa agttgatgac ttattggatg   52620
aacgtgaata cgaggcagca agactaaagc agtctcgatt aggacgttat catccaaagg   52680
ctatcaaata cgaactcagt tgtttagacc acaaaaagac tgtgaattca atacaggagt   52740
agttaacgat ttagaagaga tctactctta acgctaacta aaagattatt ccaattctca   52800
aagaaaattt atattccttt ccaaccaaag aggttttcca aatttgcttt ctagtaattt   52860
tttttttttt ctgcacgata ggaatagatc tcatatactc cctccgtccc attttatgtg   52920
aagtagttta actcgtacgg aatacaaaaa tgaaagaaag acatttaaaa tttatggtct   52980
aaatgaataa taaaaaatcg tgtgactata aatcatttca ttaagagaaa atagacaatt   53040
taaaattaaa ttgttactta gtatagtaac gtgtcttttt ttttttaaac tgtctaaaaa   53100
agaaaataaa ttatataaat tggaacatag ggagtatcta cttacaaagt aaaagttatg   53160
tgtagaagat tttggcatac aaatcatatc atatatcatc atatcatata tcacatcata   53220
tcatcatata ttattataag catgaagttc aaaacttaaa agttgaatta ccattttagc   53280
cttatactaa attaaaatat tataaaataa ttaattaatt aaatattaaa tatgcttaaa   53340
ttgttaatta agttgattca cttattgtta aaataaatag gagaatgaat agttgtaaaa   53400
ataattaatt ataaagttat tacaaaaact tattagagaa acgtttcatt tctctatcga   53460
tcgattttag gtgtaatttt gtcataatgt gtattaatac cacacctcca ctatctcatc   53520
attaatatcc acaccttcat aatcttccac actctcaaga agttgatggc ataattatga   53580
gacttttgat tttactcaat gatgtcctat aaattgcggt atttgacaca acaatctata   53640
cactttgaag atatttaggt acagtttgga agaaattaaa aaaaatgtct atatttctat   53700 tgttttatc ctttagtata tatttaaatc acttttaaa ctgctcataa caccgattca     53760
ttaattttcc ttatcttcat ttgttgttta taggaaggaa atgtgtacaa attgttagat   53820
cttctaatgg agtttacaac gagagaaggg atgttcaagt cttccggagg ttgaaatcaa   53880
ttttaatttc aagtattata ttcatgcttt tagatgttta tatatatata tatatatata   53940
tatatatata tatatatata tatatattca aatgagtcaa catagactaa tatgagactt   54000
aaaggtcgga aaattggagt atcacaatta gtagtaaaac aaagtaagaa atctcaatta   54060
gatatatttt attattttt aagaaataat acactcatgg gtataagtgt gaagctccaa   54120
aatgcaaaaa gttgaattac tattgtatcc ctataatagt taattatttt taaatattag   54180
ttcatatgat attattaaat tatacttctt tgaaattaat aacataataa aaaccaaatt   54240
catctttgaa gtgcaaattt atcgtccttc attattgata atttgaatgc actaaaaact   54300
atttaatatc ccggaaggtg gaagagtgaa agtattcata attaatttct agataaaatt   54360
ttactagata aaaagtata catgcattgg aattaataat ttaaaaataa agaaataatg   54420
atttagcctt ttaagttacc tacttttatt atgctcttta aaccattgtt attattttt   54480 aaaaaaaaaa ctcatattaa ggtgttagct tgattagtct aaagatatca aaatgtcatt   54540
tcttggatca cttaatttgt aacgttttta tcttctatta gcgtgattct ccattttcct   54600
atattatata ttatactttc tcatgtaatc atgttatcta tatttatttt tttatataag   54660
```

```
tttgttatgc tcaatgtttt atttatcttt atttgaactc atctaaattg ttgaatattt    54720
caactactaa taaattttt aaatttgact tttttttat gaaaatacaa ttaagaaatg     54780
acgctaatat ttcatagtga tgatgcagta agtgaagcaa cacagattga actgtttcaa    54840
gtggtatcaa ttttcaggta ataaatcatt gttccttata tgcaattaat tatttttgtg    54900
taagttgata tgttcttaat aaaattttgg tttgattttt aaataaaaat tattttatag    54960
aagttgagac ggtacactta attggattat ccaaaaaaag aatcttttac acaaggacaa    55020
gaagaaagac ttctagctttt atcactgcat tcatgacaat caatggaata tcctacaaga   55080 caaaagttg atgtgattct gtacaagtga atccaactca ctaacaaaaa aattaaagaa     55140 agaaaaaat gaacatgaag agaataaaaa tgaagatgaa gagaatcaat ggtgtcttat     55200
aagttgatga accactgtaa cttcattatt ttttaaattt acgaggaaat gaattattga    55260
cgaaatttat gaaatgtaca tatataccctt tgggtcggta acaaatgtga ttgaaagtag   55320 tatttttca tgcataatag ctaattcttg atatatatat tgtttaaatt tattatttgt    55380
actacaaaca ttgtatgata tattttagga taagcgtaac gcatgcgacg tggaaactag    55440
tatattagta aaagcatgaa taaaaaagtt gaaagttgaa ttacgatttt attccttcta    55500
taattaactt gttataaaat atttaaatat ttgattgtac aagtttaatt aaaatgttaa    55560 atgacttta gacttcataa gattaattta taattaaata tctatttat taatatttat     55620 catttataat ctatatgtat ataataatta tattttttt taaataaaag tctaattaaa    55680
atattaatga cttttagact tcctaacact aatttctaat taaatatcta atttattaat   55740 attttttatca tctattatct ctctctatat aataatttta caaaaattaa caaaaaagt    55800 ctctacgtaa attttatac tttttttt attctcataa atttttccta aataacaaaa      55860
tttaataatt tgaaggatgc aaatctgcaa aatggagaca cacacatttg ataatgtcct    55920
cttaattatc attaaagaat gactctaact agcttcacaa atttaaattc attgatactt    55980
aattactcgg agaaaagtag atgaagactc ttaatttga tagtatatgg aaggagtcaa     56040
taaagtttcg tagatttatg caataatttt gtacttattt tttcatctac atatacatag    56100
tcttatgaga atgatgtcta cattgtattt tttcttaaat ctgtttcttt tgtcttttat    56160
ccccaattag acttcttaat ttaatttat acaaatgttt tattgtcata agtctttata    56220
cttattttgt aattgtagca ttttattgtt cattacaatt tgcatatata tatttccatg    56280
aaatattagt aattctatca tatctataaa aattcacatg aaatacacgt gcaaagcacg    56340
tgttcagaaa ctagttagga aaacaacaca aatatacatc tgaactatcg taaatgatat    56400
acagatacca tcatcatact tttgggacat tggtgtccat gtcgtcaaaa aaatagagca    56460
aatatattaa tggacatcac gtgtcagaat catatcaatt gatccaacat ttattaaatg    56520
tttgatcgaa gaatagattg tgtcacatgt ccctatttag tcatctgtta aaatgaatga    56580
catatgggtt gggccgacca ttttctgacc cacacaaaaa atgggctagc ccggtttaac    56640
ccgtaaaata tcaaaacatg tatggattag cccggataag gtgtgttagc catattgaca    56700
gctttatccc cacatcaaga aggtatttat atgtcaactt gaaaagaaaa aattttccaa    56760
atatgatctg cttatactct atcaattcca tatctcactt agtgaaattt cactgaatat    56820
attgttgttg ttggtgtcct ctcccatcat tataaattta agaacatgc aatgtaagac     56880 gtaatttaga aaacttggtt cgcccgtaga agaaggatca tctgtaaatt tattcctctg    56940
caagttgatg ctttgaatct gttggtacat ttcctctaaa catgttagat tggattgaat    57000
cttaagtcat catgtgttac tatctgaaag accaatattt aaatttattg ctcacaagta    57060
```

```
aaaattagaa ctaaaaatat acaaacatga agttcaacat atattataac ttaattcata    57120
aaagaaaaat tatttgcatg cataatattt gtttattcat ttcttagtgt acatatttta    57180
actttatcag cgtagtaatt tggtttgatt tgtttgtttg ttataatgta attacaagtg    57240
tacttagctt gtttgattac acaagtgtaa tcatataatt atactgaatt ttaaagataa    57300
aagttaatta tttgaaacaa aaaaattata ttaggcaaat aagagccttt ataaatgata    57360
ttcaattgaa tatttaagat atatagtgtc ttttaaaaaa tatgttattt aataaacata    57420
tgttcttaat taatattata aaaaaagcaa atgatttata tatttcaatg tagtatttt     57480 aaagtaaatt aatcataaaa attaaaaatg catgaacatc atgaaatgct tgtttcacaa    57540
aaaaattaat attataaata taatgtcata aaatcataga aaaataattg acaaaagaac    57600
taatttatca agtctaactt aaaaagaata ggttgcaatg gaatatcaag tcaatactcc    57660
taaaacaaat gaaattgaaa atataatata agttctaaat ttaaaataaa aaatttaaca    57720 taatacttt  atgtcaaatt tcaacataat atgattaaaa gaaaggaaa  atttaagtcc    57780 gtaactttgt tcaacaataa attctacttt aattcaaaaa ttagaatact aacaaaatta    57840
tactaataat ttttttagat attatgaaga attgcatgaa atcacatgaa gtaaaagtta    57900
aaaataagaa ggaaatgaaa tataaataat aaaggaaaac tttcatatat agccacttaa    57960
aaataattaa ttactctcca tagctatagt ttgataatta caatttgtag ctacatgtta    58020
tgtggaggag agagaggcga gcgtcacttg gagagagagg cgagagagag agggggaaaa    58080
gagtgggaga aaggtgaatt gtatatgtat attggctaga taattgtata ttatacatat    58140
gtaattgtat atatggcaag agagattgag agagggagga gagaggcgag tgagactgtg    58200
agagagagag agaggcgagc gagatcaaga gagggaggag agaggtgagc gagagagggc    58260
agagagtgag agggatgtga attgtatatg tatataattt tatataactg tatattatac    58320
atatacattt gtataaatgg caagcgagat tgggagaggg atgagagaga cgagcgagag    58380
agggcagaga gtgggagaga ggtgaattgt atatgtatat aggctaaaaa attgtatatt    58440
atacatattt atttgtatat cctggcaaat tatacatata taaacatgat aattatacaa    58500
acatgaagtc aacccacgta attaatgtat aatgttagtc gcgagtggta attataacaa    58560
actatagtta tgatgcataa ttaaaataat ataagtttgt ttattcgcat aattttttcct   58620 tttttaaatt cctccttcta ttcaacttgc attttttgtc aaatataatc atcgttaaaa    58680
attatttgat gttgaattaa caaacatcca tctttattat atcacatgtt gtgacatgca    58740
ccaaaacgat aaaaacgaca ccttcaaaat gatttttttt aaaataagcc tagttaattg    58800
atgtttaaca tataaataat caactaataa ggttaaaggc ttacacatac aaactaaaaa    58860
ttagatcaaa tgcactaaaa ataaataata tgaggaaaat ctgttttagg gattatagtg    58920
tcccccaacg accaagtctt atttttaatg gagcatcatt gattggtcta ttgacaaaga    58980
aaatttggaa attaatgatt ttgttttatc ctctggaaat ttattatgtt atcacaacta    59040
tttgttaatt tgaactgcat aaaagttttt gttcgaactt catatatgaa aattctaaac    59100
aagaattgga aacttgaaat gaatccaaca tttaaatcaa tagataatta ttgattgaat    59160
ttcttaatac gtatatatac aaaagatctg aataaaagct attgaataca ttacatgtta    59220
tattggttaa tttgaccgta aaacagttga cattcttttg tcaagcatct attctgggga    59280
ggttatatat atatacattt gaataatgac gttatactat agcctaaaac tacataaaaa    59340
atgtcaagta aattatttaa ctgtcaatac agaattccac aaccaatagt ttatttccct    59400
```

```
ttagcaatga attgcagtca agttcagcta gcaatataca attaaaagat gtttcaaatc  59460
attggtatta attagataag tattgactca attacaagta tacacacagt atatatagat  59520
ggcgtttgaa aacgaaaaca taggcacaaa tagcagctaa agaagttgaa caaatcaaaa  59580
tggttgcgaa gactattatt atagcatgcc tagttttgtt aacatgcctc tcagttacta  59640
atgcatcgaa cattacaact gatgaggcac aaatgactat atctagtgaa attaacatgc  59700
agatgaatag gcatatcttg cagtaaaaag catcaaagag tgacatcatt agtcctcaat  59760
agctttggat ttagaggttc aatcgcgaca gatattggga atctctcctt ccttaacttt  59820
ttggacattg gaaacaacag tttccatggc caaatacctg atgaaatagg gcgtttgagg  59880
cgtttaaaat acatgtattt gcagatgaat aatctcgctg gtcaaatccc agaaagcctt  59940
ggatttctca caaggcttca agttcttcat ctttctgaaa atcgtctatt tggaaatgtt  60000
ccagcttcca ttttcagcgt gtcttcttta aaggacattg atttgtctca gaattacgag  60060
ttaactggga gttaccaaa tgagatatgc actaatcttc cagtgttgga atatatatcc  60120
ctgcaagata atcaatttgt aggtgaactt cctaaaggtt taaataaatg ctccaaactt  60180
gaagttctgt ccttgtctta taacaaattc actggtaatt aactaacttg taaactttc  60240
atttactaat ttcttcttga attaatcatc attttgtgt gtgtctgtga ttttataatt  60300
gataggaaac ttaccaagag acatgtggaa catgtcaaag gttcaagaac tttttattgg  60360
atggaataac ttaacaggta cgtgattctg tatgtattaa atcttgaata ctcttcacga  60420
agttcctaat ttcactagat atagccaatt tgtgcattgt ctagtaataa acaaagatta  60480
atatattttg tggagaacat tttcgaaaga cactctatgt atgatcttta gcatgataac  60540
catatactta ttttcaaaat gaatttgcag gaaatatacc aaatgaaatg aacctaccat  60600
ctatttgcag gaaagttaac aaagcttgag catcttgttg ggttatgggt cttttcccct  60660
tcctatttgg ataactaaaa gcccaatttg gaccaatcca ttttgccta taagcccatt  60720
cttatgaggc aaatataaac tgattttagg gtctgatttt cagaacatat agagagttct  60780
tcagcagcca aaaagagaga aagagagatt ttcgcaggca aaattcagat ctaatagaca  60840
acttcaaatt gcgattcccg cttcttttct tatccgattg agttgatttt tggacagcat  60900
attgtcttca tctcaatctt tgattagaaa ctgacagagt tggatttggt ggcctgcgac  60960
tttcagtttt gcttttgtcg tgagcgaagc tgcaaaattg gtgattttgc tcctttaatt  61020
ttctagattt ggtgcaatct tattttgttg ttgctcgttg tttggcactt gttttgtggc  61080
caatttggga gaacaatatt gtaactcttg gtgattatag tggagctttt ggtccgtggt  61140
ttttactctt cacatgaagg gttttcaacg taaatcttgg tgtcttatgt gattggtttc  61200
acattgtctt gttatatttg tttggttgaa ttggaatcgc cttactatca tattgcttgt  61260
ggttgtttgt cttctcttgg ttcaaatcga aaagggaaa gtatagactt ggatattctt  61320
ccgttatctg tcgtcagcat tcttggtagt gtcttgtctt tcccaacaaa gtggtatcag  61380
agcattgggt attgttgatt gtcgttttga atgatggaga caaatatgag caaaatggtg  61440
tttttaaatg gtagtaacta tcatatttgg aaaggcaaga tgaaagatct tctatttgtc  61500
aagaagatgc atttacctgt gtttgttct aataagccta agtctttgaa tgatgaagaa  61560
tgggaatttg agcatcatgc aggtttggct atattataca atgggttgaa gataatgtta  61620
ttagaaatca gtattgtgaa tgagacatgc caaaagtttg tggacaagtc gagacacttt  61680
atgcttcaag attgtgtaac aactgctcct attgaacaat taatgaatat cgtataaaga  61740
gggcactcct atttctgatc atattaatga ttttagggg ttcttgaccg gctgtccgaa  61800
```

```
atgggtgtaa agtttgatga tgagatacag ggactttggc ttcttaatac cgccagatct   61860
tgggaaactc ttcagtttct ttgaccaatc tgctcccaaa gggtgttgta accatcggaa   61920
tatactaaaa gtagtgtctt gaatgaagaa ataagaagaa gatctgacct catcttcaga   61980
cttctacact ccgatgtttt tccactgaag ataggggga aaacaagtcg gtaggaggaa    62040
tgatagaggt aaaagtgtat gtcaaagtct aagtctaaca caagaatatt acatgtgact   62100
attgccacaa gaatgggcat atcatgaaat attgttacaa gcctgagaga tatgagacaa   62160
caaaaaagag aaggcgataa tgaaaatcgt gttgttgttg ttgctaatga tcttcttct    62220 tttttcttg atgcaaatgc cattaatctt gttcgtgatg agtctagctg gtttgtggat    62280
tcgggtgcta cttctcatgt catgccaaag aaggaattct atttcttata ctccggggta   62340
attttgaaac gttgaaatgg gcaataatca tgaagttgaa gttattggca ttgggacagt   62400
ttgtttggaa aataacaatg gttcaaaact agttctcaat aatgtcaagc atactccgga   62460
tgttcgcttg aatttgattt acgtaggata tcttgatgat gaggttatgt aaacacatt    62520 tggtgttggc tagtggaagc ttactagagg tttgatggtt gtggcccgtg gtgacaagtt   62580
gtctaacttt gtatgtattt ggggctccgt ttcgagagac tcaagaattt ggtagagaat   62640
gatacttatc gaagttatgg catgtaaaat ttgagtcata tgagcgagaa gaggattgat   62700
agtttggcta agaaaaattt gctttctgga gtgaaacaag caagttgaa gaaatgtgtt    62760 cattgcttag ccggtaaaca taagagtttt cttttgaaat catccgcctt caagaaagct   62820
tgatttgctt ggagttggta cattcccgat tttgtggtcc ttttaaggta agatcccata   62880
gtggtgcaat tttactttgt gactttttat tgatgatcat tctcgcaaac tcggggtatt   62940
tcctttgaag tccaaggatc aagtacttga tgtgttcaag agttttcagg ccttggttga   63000
aagacaaaca ggaagacatt gaaatgcatc cgctcgaata atggtggtga gtatattggt   63060
cctttttgat agatattgaa gagagcgggg tattaggcac gaaaactcct ccaaaactcg   63120
cggttaaatg gtttagcaag gaggatgggc agaactctag ttgagaggct tagatgtatg   63180
ctctcggatg ctaatttgcc attcctttag gcggaagcac ttaatctgcc gcttatgtta   63240
tcgatttatc tcctttgttg ctttagatag atggtgatgt cacagcggag tttgggtggt   63300
aagaatgttt cttatgatca tcttagagtc tttgggtgta aagcctttgt acatgtttct   63360
aaggatgaaa ggtcaaagtt ggatgttaaa actaggcgag gtatcttcat tggttatagt   63420
caagatgaat ttggctatcg tttctatgat ctgttgagaa gaaacttgtt agaagccatg   63480
atgttgagtt ctttgaagac caaacaattg aagattttga caaagtgac aaggctgatt    63540 ttcgagtagt gagagcttag ttgatgttga tccggttcct ttgactattg ccgaagaaaa   63600
tcttcttaat gaagaaaatc aagttgataa tgaagatggt gatcatgttc taatgaccgg   63660
catgatgttg tttatgctcc caagaagatg atgtggttgt ccaacaacca attatagatg   63720
ctccggagag ttctctcgca cgatctagta gagaattcct tcatctcgtg attctcctaa   63780
tgagtatgta cttgacttac ggggagaacc cagagtcttg atgaggccat ggaaagtgaa   63840 gaaaagaaa ggtggtttga tgctatggaa gatgagatta aatccttgca tgataatcat    63900
acctttgatt tgttgttacc taaactgaaa aactttttga aaaaaggtgg gttttttcgg   63960
gtgaaacatg aagatggtaa tccggttcca ccagacaaag ctagattagt tgtcaaggga   64020
tttaatcaga aaagggagtt gattttgatg aaatattctc tccgattgtg aagatatcat   64080
ccattcggtg tggttctagg tcagctgcaa gtctagattt agaggttgag caaatggatg   64140
```

-continued

```
ttaaaaaccg ctttcctcca tggtgactta gactaagaaa tttatatgga gcaaccggaa   64200
ggttttgaag tcaaggtaaa agagaattat gtttgcaaat taaagaagag cttgtatggt   64260
ttgaaacaag ctcccgtgca aagggtaca gtgaagtttg gtttttatg agtcaaaggg     64320
gcttcaagaa gacttcttaa ccattgtgtt ttgtgcaaag ttctctgatg gtgactttta   64380
ttgttgcggt tgctttatgt tgatgacacg cttgttgtcg ggtcataata cttgcagtag   64440
gatcaagttg aagcaaggag tcgaggcaag tcttttttgca tgaaagactt agaccaaaga  64500
aggcagattc ttggcatgca gattgcccgt gatagaaaaa gccaagaaat tggtattatc   64560
acaagagaaa gtacattttt aaagtacttc aagcagattc aaagatggac aaagctaagg   64620
ttgtcaagac accttagcta tgccttcaaa ttgaaagcat ggaaatgctg tcctttctag   64680
cgatgatgga aaggaagata tgaagaaagt tccttatgct tcaaattggt agtttgatgt   64740
atgcgatggt ttgtacaaga ccgatattgc tcacgctgtt gagttgttaa gcgggtttct   64800
ttctaatcca ggaagagaac attggaatct ttgtgaagtg ggttatgaga tatctcatgg   64860
cacttctagt ccgagtttgt ttttggcagg aagcctatt ttttgatttt atcttgatta    64920
ggacatggtt ggtgatgttg atactcgcaa gtctacttgg tgcttggtta cttttagggg   64980
agtattgtct tggcaatcta gattgcaaaa tgtgttactc tatctctact atggaaggct   65040
tattcttttc gtgaagcttg taaagaattg ctttggatga agagattatt aagaacttgg   65100
tttgtgctca aagaggtatg tactttattg tgaccggtca aagtgctata catcttggca   65160
agaattctac gttccatggt cggttaaaca cattgatgtg agataccatt tgattcgaga   65220
tgtattggat tctaagttgc ttgagcttga aaaagattca tacaaatgac aatggttccg   65280
atatgatgac taaagctttg ccaagaggaa gtttgaagat tgttgcatgg tcgtggggac   65340
gggcggtcct ccacatagtc gtgagggaga attgttgggt tatgggtctt ttttccttct   65400
atgtggataa ataaaagccc aatttggacc aacctatttt tgcctataag cccattctta   65460
tgaggcaaat ataaactgat tttagggtct gattttcaga acatatagag agttcttcag   65520
cagccaaaaa gagagaaaga gagattttcg caggcaaaat tcaaatctaa tagccaactt   65580
caaattgcga ttcccgcttc gtttcttatc cgattgagtt gattttttgga cagcatattg   65640
tattcatctc aatatttgat taggaactga cagagttgga tttggtggcc tgcagcttca   65700
gttttattgt gaggaattag ctgcaaaatt ggtgattttg ctccttttaat tttctagatt  65760
tggtgcaatc ttattttgtt ttgttgctca ttgtttggca cttgttttgg ccaattttgg   65820
agaacaatat tgtaactctt ggtgattata gtggagcttt tggtcccgtg gttttactct   65880
tcacatcgaa gggttttcca cgtaaatcgt ggtgtcttgt gtgattggtt tcatattgtc   65940
tcgttatatt tgtttggttg aattacctgc tgccttagta tcatattgct tgtggttgtt   66000
tgtcttctct tggttcaaat cgaaaaaggg aaagtataga cttgggtatt cttccgctgt   66060
tatcctgtca ggcattcttg gtagtgcctt gtctttccca acacatctca actatctgaa   66120
tgtctcttac aatgagttat caggtgaaat accagatgga gggccttttg gtaatttca    66180
cagctgaatc attcatcggc aatgaagagt tatgtggacc gcctagattc caagtcaaga   66240
tttgtgaaat ccgaacaacg tgacaagaag aaacaggaaa aaacaagact aaaatttgtt   66300
cttggaccag tgcagctgga ggtttagtca tggggtttta ggcatgatat ggttgttgaa   66360
ttatcggaga cgtaacaacc aacttattcc tttaactgat tagtatgatc ggttatcaca   66420
caaaagtttt tcttactatg aacttgtttg agggactaac aacttgact ttaatcaaat    66480
ttgattggaa agggaagcct tggtatggtt tataagggga catttacaaa tgggactata   66540
```

```
gccaactgta aaggttttca atgctggcgc aagatgcatt caagaggttt gatttggagt   66600
gtaaggtttt gcgtaacacc gaaataggaa tcttgttggg tgataagtag ttgttcaaat   66660 cttgattttta aggcattggt gtttgagtac atgcctaatg gagatcttaa ttattggctt   66720
tactcacaca acaatttctt ggatttaaac aaaatttgaa aattatgttt gatgtggctt   66780
tgtgtcagag agtatctaca ccaaggccat tcaaaacata gtggtccatc atgacttgaa   66840 catactttttg gatgaagaca tggttgccga gtaagtgatt ttggtatatt caaactcttg   66900
accgccagat gatccaaagg gcattgacaa agactttagg caccattatc ctggcactgt   66960
gcccgatcaa attttatttt actaattact ttcttcaact tgtattcgat atgcatatat   67020
gatgtatttc attttaatgg tagagtacgg gtcagaaggg atagtgtcaa ctatggggga   67080
tgtttacagc tacggcattt tatttatgga aaccttcata agaaagaaat gatagatgat   67140
gagtttgttg gagaccttac attgaagaga tgggtcatgg aatcatatcc tcatagagtc   67200
attgttatga aataaaaacg aatacaagtt gaacgtcaat tatgagtcat ttatctaata   67260
tgatccatta acaattgatt aatgtaacgc aggaagaaga aaacaatttg cattgttatg   67320
aatgaatgtg tttgtactac aatatataca aagatcgaca agtctagcaa actttctaac   67380
caacttattc taaccaactc tactcattat tcatttagct cacttaatca agaaattaga   67440
cctaacaact aactaccatt aactcattca actgattgtt gggttatagg tcttttttccc   67500 ttcctatgtg gataaataaa agcccaattt ggaccaaccc atttttgccc ataggcccat   67560
tcttatgagg caaatataag cctatttagg gtcttatttt cagacaaaac agatcagttt   67620
ttcagcagcc aaaaagagag aaagagagat tttcgcaggc aaaaatttag atctaatagc   67680
taacttcaaa ttgcgatttt cacttcgttt cttatccgat tgagctgatt tttggacagc   67740
atattgtctt catctaaata tttgactagg aactgacaga gttggatttg gtggcctgta   67800
gcttcagttt tgctgtcgtg aacagtagct gcgaaattgg tgattttgct ccctttaatt   67860
ctctagattt ggtgcaatct tattttgttg ttgctcattg tttggcactt gttttgtggc   67920
caattttgga gaacaatatt gtaactcttt ggtgattata gtggagctgt tggtccgtgg   67980 ttttttactct tcacatcaag agttttccac gaaatcttgg tgtctttgtg attggtttca   68040
cattgtcttg ttatatttgt ttggttaaat tacttgccgc cttactatca tattgcttgt   68100
ggttgtttgt cttctcttgg ttcaaatcga aagagaagt atagacttgg atattcttca   68160
tttgttatcc cgtcgagcat catttgttat tgccttgtct tttcccaaca agtggtatg   68220 tcaggagcat tggttattgt tgattgtcgt tttgaatgat ggaggcaaat atgagcaaaa   68280
tggtgtgttt aaatggtagt aactatcata tttggaaagg caagatgaaa gatctttatt   68340
tgtcgaagat gaatttacat gtttgcttct aataagccta agtctttgaa tgatgaagaa   68400
ttggaatttg agcatcctgg gtttcggcta tattagacaa tgggttgaag ataatgttag   68460
aaatcatatt gtgaatgaaa cacatgccaa agtttgtggg acaagctcga gacacttttat   68520 cttgaagacg gcaacaaaca agttgttcta ttgaaacaat taatgaatat cggtataaag   68580
agggcactct atttctacga tcatattaat gattttcagg gtgttcttga ccagcctgtc   68640
cggaatgggt gtaaagtttg atgatgagat cacagggggac tttggcttct taatactcat   68700
ccggactctt gggaaacttc ttctagtttc tttgactaat tgctcccggt ggtgttgtaa   68760
ccatggaata tactaagagt ggtgtcttga atgaagaaaa tgagaagaag atcttgcctc   68820
atcttcttaa acttcactcc gatgtttttgg ttcttgaaga tggggagaaa caagtcagta   68880
```

```
gatcgaatga tagaggtaaa agtagaagca agtcaaagtc taaatacaag aatattactt    68940
gtgactattg ccacaagaat gggcatatca tgaaatattg ttacaagcac aagagatatg    69000
agacaacaaa acaagagaag gcgataatga aaatcgtggt tgctgttgtt gctaatgatg    69060
atcttctttt ttcttgtgat gcaaatgcca ttaatcttgt tcatgatgag tctatttggt    69120
ttgtggattc ggtgctactt ctcatgtcac gccaagaag gaattatttt cttcttatac     69180
tccgggtaat tttgaaacgt tgaaaatggg caataatcat gaagttgaag ttattggcat    69240
tgggacgttt tgtttggaaa gtaacaatgg ttcaaaacta gttctcaata atgtcaagca    69300
cacccaaatg ttcgcttgaa tttgatttcc gtgggatatc ttgacgatga gggttatgtt    69360
aatacacttg gtgttggcgg tggaagctca ctagaggttt gatggttgtg gcccgtggtg    69420
acaagttgtc taacttgtat gtatttaggg gctccatatc cggagactcc aagaatttgg    69480
tggagaatga tacttcatcg agttatggca tgaaggtcga gtcatagaga aggggattga    69540
tagtttggct aagaaaaatt ttcttctctgg attgaaacaa gcaaagttga agaaatgtgt    69600
tcattgctta gcgggtaaat agaaaagagt tttttttag tcatccgcct tcaagaaagc     69660
ttgatttctt tggagttggt acattccgat tttgtgtggt cctttaaggt aagatctcat    69720
ggtggtgcac tttactttgt gacttttatt gatgatcatt ctcgcaaact ctaggtattt    69780
cctttgaagt ccaatgatca agtacttgat gtgttcaaga gttttcgtgc cttggtttaa    69840
agacaagcag tggaagacat tgaaatgcat ccattaagat aatggtggtg agtatattgg    69900
tccttttgat agatatttgc agagcggggt attaggcatg aaaaacctcc aaagactccc    69960
tcggttaaat ggtttagaag cagaggatga gcgagaactc tagttgagag ggttagatgt    70020
atgcttttag atgttgtcgt cgattccttt tgggcggaag cacttaacat cgctgcttat    70080
gttatcaatt tatctccgtt gctttagatg gtgatgtcct cgatgtagtt tggatcgtaa    70140
gaatgttttt acatcatctt gtagtctttg ggtgtaaagc ctttgtacat gttcctaagg    70200
atgaaaggtc aaagttggat gttaaaacta ggcaaagata tcttcattgg atatggtcaa    70260
gatgaatttg gctatcgctt tctatgatcc cgttgagaag aaaacttgtt agaagtcgtg    70320
gatgttatgt tcttttgaag accaaacaat tgaagatttt gacaaactga caaggctgat    70380
tttgagagta gtgagagctt agttgatgtt gatccggttc ctttgactat caacttggga    70440
agaaaatttt cataatgatg aaaatcaagt tgataatgaa gatggtgatc atgttcagta    70500
atgacctatg acgatgacgc tttttgatgc tcgatgcaga agatgacggg ttgtccaaca    70560
accaattata gattctccga gagttctctc agacgcatct agtagagaga gatttcttca    70620
tctcgttatt ctcccaatga gtatgtactc ttggtgacgg ggagaacccg agagtcttat    70680
gaagccatgg aaagtgaaga aaagaaagg tggtttgatg ctatgaagaa tgagattaaa     70740
tccttgcatg ataatcatac ctttgatttg gttaagttac ctaaaagcgt aaaaagcttt    70800
gaaaaaaaag ggttttttt gttgaaacat gaagatggta atcaagttcc acggtataaa     70860
agtagttgtc aagggattta atcggaaaag ggagttgatt ttgatgagat attctctccg    70920
ggttgtgaag atgtcatcca ttcgtgtggt tctaggcttg gtacgcaagt ctagatttaa    70980
gttgagcaaa tggatgttaa accgcttccc atggtgactt agatgaagaa atttatatgg    71040
agcaaccgga aggttttgaa gtcaagggta aagagaatta tgtttgcaaa ttgaagaaga    71100
gcttgtacgg gtttggaaac aagctcccaa agcaaattgg tacagaagtt ttggttcttt    71160
atgctgggga aaggcttcaa gaagacttct tcagaccatt gtgttttttgt gcaaaagttc    71220 tctgatggtg actttattat tgtgttgctt ttatgttgat gacatgcttg ttgttgggtc    71280
```

```
ataatacttg cggggattca gaagttgaag caagagttga gtaagtcttt ctttatgaaa    71340
gacttaggac caaagaagac agattcttgg catgcagatt gtccgtgtga tagaaaggct    71400
aaaaattggt attatcacaa gagaagtaca ttcagaaagt acttccacag tattcaagat    71460
ggacaaagct aaaggttgtc agtgacacac ttttagctat gcacttcaaa ttgagcacta    71520
gcttaggtgt ccttctagtg acagatgaga aggaagatat gaagaaagtt cttatgccta    71580
gctgggttgg tagtttgatg tcacgatggt tttgtacaag accggatgtt gctccatatt    71640
tggggttatt aaccgttttc ttttctaatc gggaagagag aacattggaa tctttgtagt    71700
gggttatgag atatctttgt ggcacttcta gtaaagtttg tgttttagtg cagaagccta    71760
ttctttgtgg ttatccggat tcggacatgg ctggtgatgt tgatactacg caagtctact    71820
tgatgcttaa ttcttttttg tggggagctg tgtcttggca atctaggttg caaaatgtgt    71880
tgctctatct actctctgct ggaggcttat tctttatcgt tgaagcttgt aaaattactt    71940
tggatgaaag attaacacgg gaacttggtt gtgctcaaga gaggtatgtg ctttattgtg    72000
gtcaaaagtg ctatacatct tggcaagaat tccacgttca atagtcggtc taaacacgtt    72060
gatgtgagat accattggat tcgagatgtg ttggattcta agttgcttga gcttgaaaag    72120
attcatacaa atgacaatgg ttacgatatg atgactaaag ctttgccaag agggaagttt    72180
caagattgtt gcatggtgct tgggatggcg ggcctccaca tagtcgtgag gggggagaat    72240
tgttgggtta taggtctttt ttccttccta tgtgataata aaaagcccaa tttgaccaac    72300
ccatttttgc tcatagccca ttcttatgag gcaaatataa gccttattta ggatcttatt    72360
tcggaaaatg acagttagtt ttttggtgag ccaaaataga gaaagagaga ttttcgcagg    72420
caaaaattca gatctaataa ccaactttaa attgtgattc ccgcttcgtt tcttatccga    72480
ttgagctgat ttttggtcag aatattgtct tcatctcaat ctttgactag gaaccgacag    72540
agttggattt ggtggttcgg taacttcagt tttctttgcg aatgagcgat ggctaaattg    72600
gtgattttgc tcctttaatt ctctagattt ggtgcaatct ttttgttgtt gtcgttgttt    72660
gacacttgtt ttgtggccaa ttttggagaa caatattgta actcttggtg attactggtg    72720
ggagcttttg gtcctgtggt ttttttactct tcacatcggg ccgattttcc gtaaatcttg    72780
atgtcttgtg tgattggttt cacattgtct tgttatattt gtttggttga attcttgctg    72840
ccttactatc atattgcttg tggttgtttc ttctcttggt tcaaatcaaa aggaagtata    72900
cttgggtatt cttccatcgt tatcctgtcg aggcattctt atttgtgcct tgtctttcct    72960
aacactgatc acggaacatc aacacatttt gttgatttct ttcacacaca cctcctcaaa    73020
aaaccctctt ttttaacatg taagcgacaa tatcttttt aggagagtgt tcaacattga    73080
gcataaaaat aataaaatag agaacaaaaa aagatgagta taaataata aataataata    73140 taagatcgat tttaccgatt gtcaattttg tgtatgaact aaagaaataa cagcttcaca    73200
tatgaatttg tattttaggc tgctgtaagt actaaaaata gttattcaac cagtagaaga    73260
gatgaaggtg ggggccagct gttggcaatc aataagggaa agaaaagaca aggaatattg    73320
agccaatttt ttttcttctg tggaaaactt tggcagagaa attaaggcta acgaaaagtc    73380
tttgtgcaat gaccccatgg gcatgtgcag ttgtttccca caactttgtg aattatattc    73440 caaaaatac aaattcatta tttaatactc caacaacttt ttgattccac tctagactac    73500
catcacatat ctaatattaa atgtaatact gaatttcaca tatggtcaga ggcgaatcca    73560
tcagcacctg atatattctt ttttaaaaa aattatatct atatatacag attgttgata    73620
```

```
agacggtaat atatttaatt gtgcactctt ataacgaaca aatgatttga cttgtccatt   73680
ggaaaaacaa aaagtgtcac ataaattgag acatggcgaa taatatttct ttcctaaatt   73740
tttcgtgtga agtcaaatta attcatataa aattagacga aaggagtaat gtttaatagt   73800
aattgcatat ggtagtaaat ttgatagacg tggtcccgtg ggagtgtgtg ttatttccat   73860
tgaataattg agtttgtaat tgttacaagt ccattctaat ttccaacacc ttacttcatt   73920
tcaaaaatat actctatggc tgaagctttc cttcaaatta tgttagagaa tctgacttgt   73980
ttcatccaag gggaacttgg attgattctt ggttttaagg atgagttcga aaagcttcaa   74040
agcacgttta ctacaatcca agctgtggta caagatgctc agttgaagca attgaaggac   74100
aaggcaattg aaaattggtt gcagaaactc aatggtgctg catatgaagc tgatgacatc   74160
ttggacgaat gtaaaactga ggcaccaatt atacagaaga agaataaata tgggtgttat   74220
catccaaacg ttatcacttt ccgtcgcaag attgggaaaa ggatgaaaaa gattatggag   74280
aaactagatg caattgcagc ggaacgaatt aagtttcatt tggatgaaag gactatagag   74340
agacaagttg ctacacgcca aacaggtaaa tattttttcta aataacagct ttatatcatc   74400
aaattcatgt gtgttttggg gattttgtct aagtagataa gtggttcaaa atctattatc   74460
taaatctgtt tggtgaagtc tttaacatat atataaatcc atagcttact catatgcccc   74520
aaagtctaaa tgacaggata aagccagagt tgttttagat cttataaatt aacaatgata   74580
ataatgtgaa ttcaaaatag tgcatttgtt ttatatttga aatatgtctg ctgcttctga   74640
tcaagctgat cattgtcttt tgcaaaattc ttctttgttt tttttgctga ctcttaccga   74700
tcttggacca ggttttgttt taaatgaacc acaagtttat ggaagagaca aagataagga   74760
tgagatagtg aaaatcctga taaacaatgc ccaaacactt tcagtcctcc caatacttgg   74820 tatggggga ctaggaaaga cgacccttgc ccaaatggtc ttcaatgatc agagagtaat   74880
tgaacatttc catcccaaaa tatggatttg tgtctcggaa gattttaatg aaaagaggtt   74940 gataagaaa attgtagaat ctattgaaga aaagtcactt ggtgacatgg acttggctcc   75000
acttcaaaag aagcttcagg acttgctgaa tggaaaaaaa tatttgcttg tcttagatga   75060
tgtttggaat gaagatcaag ataagtgggc taagttaaga caagtcttga aggctggagc   75120
aagtggtgct tatgttctaa ccactacccg tcttgaaaag gttggatcaa tcatggggac   75180
attgcaacca tatgaattgt caaatttgtc tcaagaagat tgttggttgt tgttcatgca   75240
atgtgcattt gggcaccaag aagaaatgaa tcttaatcta gtggctatcg gaaaggtgat   75300
tgtgaaaaaa tgtggtggtg tgcctctagc agctaaaact cttggaggta ttttgcgctt   75360
caagagagaa gaaagacagt gggaacatgt gagagatagt gagatttgga atttacctca   75420
agatgaaagt tctattctgc ctgccctgag acttagttac catcaccttc cacttgattt   75480
gagacaatgc ttttcatatt gtgcagtatt cccaaaggat accaaaatgg aaaaggaaaa   75540
tctaatctct ctctggatgg cacatggttt tcttttatca aaaggaaact tggagctaga   75600
ggatgtaggt aatgaagtat ggaatgaatt atacttgagg tctttttttcc aagagattga   75660 agttcaatat gatcgaactt atttcaagat gcatgatctc attcatgatt tggcaacatc   75720 tctatttttca gcaagcacat caagcagcaa tatccgagaa ataaatgtag aaggttacct   75780
acatatgatg tcgattggtt ttataaaagt ggtgtcttct tactctcctc ctcacttgca   75840
aaagtttgtc tcattgaggg ttcttaatct aagttccatg ggacttaagc agttaccgtc   75900
ctccattgga gatctagtac atttaagata cttgaacctc tctctcaata acatgcgtac   75960
tcttccaaag cagttatgca agcttcaaaa tctgcagact cttaatgtag agtattgctg   76020
```

```
gtcactttgt tgttttccaa aagaaacaag taaacttggt agtctccgaa atctcttact   76080
tgatggttgc gatggattgg attctatgcc accaaggata ggatctttga catgccttaa   76140
gactctaagt ttatttgtta ttattagaga aaagattctc tacttggtga attacttaaa   76200
cctgaatctg tatgggtcaa ttgaaatcac gatcttgaga gagtgaagaa tgatagggat   76260
gcaaaagaag ccaatttatc tgcaaaaaag aaaatctgca ttctttaagc atgagatggg   76320
aaggaccaca tagatatgaa tcagaagaag ttgaagtgct tgaatccctc aaaccacact   76380
ccaatgtgac ttgtttaaca atcactggct tcagaggaat ccgtctccca gagtggatga   76440
atcactcagt tttgaaaaat gttgtctcta ttgcaattag aggttgtgaa aactgctcat   76500
gcttaccacc gtttggtgat ctgccttgtc tagaaagtct agagttacgg agtgggtctg   76560
cggaagtgga gtatgttgaa gattctggat tcccaacaag aagaaggttt ccatctatga   76620
gaaaacttac tatagaaaat tttgataatc tgaaaggatt gctgaaagag gcaggagaag   76680
agcaattccc cgtgcttgaa gagttgacaa ttagatgttg tcctgtgttt gttattccga   76740
ccctttcttc tgtcaagaaa ttggtagttc atgggaacaa gtcagatgca atagttttga   76800
ggtccatata taatcttagg gctcttactt ccctcaacat tagccataac ttcacagcta   76860
cttcgctccc agaagagatg ttcaaaagcc ttgcaaatct caaatacttg gaaatcgctt   76920
tcatctccaa tctcaaagag ctgccaaaca gcctggctag tctcaatgct ttgaagcatc   76980
tgtttattaa ttgttgtttt gcactagaga gtctccccga ggaagcggtg aaaggtttaa   77040
cttcactcac acagttatcc ataacatact gtaagaggct aaaatgttta ccagagggat   77100
tgcagcaact aacaaattta tcagttaggt attgtccaac actggccaag cgatgtgaga   77160
agggaatagg acaagactgg tacaaaattg ctcacattcc tcatctgctg attactgatt   77220
agatgtaatt ttctgatttt tcttttggaa acaaatcaac tatttataac atctatttgt   77280
attatacttg atttttcttg attatgtaac aataaatatt tgaaattttt catattaaag   77340
attcagaatg agttttacag ctaactctat attctcacag tttaataacg taaatatgat   77400
atttatatca aattattact tatgttgtga tttgatttat caacatgttg gagatgattt   77460
tgacagttta ttaaagaatt tctaagtttt tattgtttgc acaagtaaca agccataaat   77520
taagtttcga gataaaagta atttgtgtat catggcttaa ttagtcggaa tttcaagttt   77580
tttctcaagt tatatatatg gcaatttgta aaaaatagat agtattcatt ttgatttaat   77640
tcaagtattt ttaaaaatat atacaaataa tatgggggat acacacgcta aacgcgtacc   77700
caaaaattag tatataaaga ataatgacga aaaaataaaa tgaagttcta tcaccaacta   77760
tctctacatc ttttgctgat atatatatat atatatatat atatatatat atatatatat   77820
atatatatat atatatatat atatatatat atatatatat atatatatat atatatatat   77880
atatatatat atatatatat atatatatat ctaactagtg tacttattcg gacttgacat   77940
ggtataaaaa gatattaaat atattttaaa taattaataa atgatataat aaaaagagaa   78000
atacaaaata agttatgatt ctgataaaag gaaacttaca taaatgtgtt ataataaaaa   78060
aatatttacc atttatagct ataatttttt ttttcactcg atcacttttta attaatttat   78120 aatacaagtt taatatatat tacaaagaac aatttattat tcacatacaa tacaagtttt   78180
aatgatggat tttatcacac attttaatac acttataata taatgttact attttttacc   78240
aaacaaacac aatatatttc aaaaacaatt ataattcaaa tatattgcat aaataattca   78300
cttttaataa atattacaga tttatcacaa tattgctata aatgataata aacaaaagta   78360
```

```
tcgctaaaat cagtaattat tttttaacat atattaattc atgtaattttt tcttattatc    78420 tattcagaaa aattgcttaa aaaatctcat ttgacatttt caatttaaaa ttgttgataa    78480
aaaagacaaa aacataaaaa ttgatatgaa agagctttgg ttaagtagca atctaattac    78540
atagtggcat actaaattaa atgattctta tagcaatatt attggttcaa ccaacaaaac    78600
taaatctcta gttatattac ttaattgctc atcatagcta tagtttgtta taatcatcac    78660
tcgcggttaa cattatgcat caattacgtg ggctgacttc gattttgtat aattagtcat    78720
gtttttatat gtactagatt ctgagaacat gccttgcacg tttgtccttt attattatta    78780 acttttata tactaaaaag ttaagtaatt aaaagatgc ttaaataaac aataatagtt      78840
taaccattta tcttttattc gctaaataat aactaatata atatgaagaa cattaaatag    78900
atgataatat ctaccttagt aattggttct taaaaagcat attaaaaatt taattctcaa    78960
agtgttttta cataaatagt ggagaatgac tcttcacatt gagcttttaa ttttaaaaaa    79020
ttatgtgtat gagaaataat taacattcaa taattaggta gaataatatc acattatcat    79080
aaataaaata atatctctaa gtcaaaagta gacattctag tttggaaaat aattactact    79140
aactatttat gggtccagct ccaatcaata atctatagat gggagtttga caattttttca   79200 gctatagtta aaattttaca tcaacaataa ataacttatt atcacagtag atagacgttt    79260
gatgcataaa agttataaat gctaaaagat tttgtcaatg tagtacatat gcaaacttat    79320
gataaaaaca cttggtatat tacgaaacac acttgaagcc attaccatga ttaacatatc    79380
aattattttt atcattatat cacatatacg tcttcttttt aaccttaaaa gtattgtaca    79440
catgatttat gaagagaaaa gaatagtact cctttttca tgtaacgacc tgtttagtcg      79500
ttttgagcag cagaatttat ttctggaaaa actgtctgag tcaacggaac ccacgacgga    79560
ccgtcatggg cacgacggac cgtcgatggt gtctcattcc aaaacactta gaattttgaa    79620
atttgggtct gaaatcgact ctccaacttc gtgcttgaga tggccggggc gaacaagtaa    79680
gtggagccgc acggctgcac cgtcacaaat cttccatggg gaagtgatcc gaatgtgtgg    79740
atttggcggg gagatgccgt ccacgatcca cgacgggacg tcactgttgc gcgtaatccc    79800
ggtgggtcgg atttctgtta agtgatttaa ggggcgtttt ggactattcc tgctttaatt    79860
ataaagttag tgggttaatg ttaataagtt taattacttg ggggttaaaa gaggtaaccct    79920 tgagttaatt agtgggttat tattgacatc tttatactta attatattct aattagggta    79980
aaagaaagag ggtttgaata agaaacaata gaaagaacaa tgagagggaa agagaaacga    80040
gaaagagaga aacgaacgaa gaggaaaaca caagctttgg gaaaattgct ttcttgatca    80100
aaattcttcg gtggaggtag gttattgttt ttatactatt cgtagtaaac tcttaatagc    80160
gaatgatatg tgttgggttg tattgtaaag tcttctatat gcttaattgt atgcttgtat    80220
aaatgtgatt atataattgt gataaaataa gcaagataaa gctattgaat cccaaatctt    80280
gaaaacccct tgttaatgat gatgccttgg tataaaagaa ggcttgatga actaaagtaa    80340
tgatattgat gatgtcttgg tataaaagaa ggcttgatga actaaagtaa tggggttgat    80400
gatgccttgg tataaaagaa ggattgatga attaatagaa tgagattagt ggagcgggtg    80460
tcacgaaccg acacatagta ttagggggac cgggtgtcac gaaccgacac gtagtattag    80520
ggggaccgag tgtcacgaac cgacacatag aattagggga tcggtgtca cgaaccgaca     80580 cgtagaatta ggggatcggg tgtcacgaac ccacatgtat aattggggat cgggtgtccg    80640
aaccgacacg tggaattag gagatcgtg tcacgtgcgg acaaatagta gtaggggcgg     80700
gtgtcacata ccaaaccaag aggaataaag ataatgaatc ttgaaagatg ttaatatact    80760
```

```
caatctaatg aacctaatcc caaataggta tggtattgag gcttgagtct catgtgaact    80820
tggcggtgct tattaatgat tatagtactt gttgttgtta cacatattga gtattgtagt    80880
tgatttatga tattatcagt atatcttttg ttttctattt tgagttggcc gatgatacct    80940
acctcgatgc ccgtgtttta tcttgaccct acttgtattt gttttctttg ttatttgtgt    81000
agtgtagcaa gcgtaccgtc gtcttcaact cattgccaac tctgtgatct tcattacacc    81060
ggattttagg gtgagctaat gcttctagct tggactggat cttcttcctc atgtcttgat    81120
gccttgaagt tccggcatgg actagatttt gtttatttta gcttctttag aatactctta    81180
gtttagtaat ttgatcatag atgttcttgt ggtgatgacg ggattttggg gaatactagt    81240
tgttgaattt tagaagttat tgaattggtt ttattaatga gtttaagtct tcatattact    81300
tctgttgata ttatattgaa atgttggggt ttagattggt tggttcgcta acataggatg    81360
gtaagtgtgg gtgcgttggc tcggttttgg gtcgtgacaa acttggtatc gagcattagg    81420
ttcgttggtc tcatcacaca agagaaccag tctagtagag tcttaaggag cgtaggggggg   81480 gccttttact tttctttgag aggctataag actttaggaa attttccttt cttttctttt    81540
tctttattac ttggatccaa ttggtatcta ggtgatacaa attggtaatc gaccatcttc    81600
actctatttt tcgcaaatgg ttagaacaaa agcgacgact aacaacagca ccgatagcgc    81660
gggcggagcg aggtgcgtcc cgggcgtgct ggggagtaca tggctgggaa ggcggctgac    81720
agaggccgtg gtgaaattag gtggggagac gtctacaggg acaaacacc gccccatagt     81780 actgggcggt gactcactcc acccggtagg tggtaagaga gggtgaggaa ggaggcccgg    81840
caagtgcgag gagatgagga actaccgctg acctacccgg agatgataaa tcaggttctg    81900
cttaccttag taggttgctc tgatcaaggt caaacacctc gatgtttctg ctgcttctct    81960
cgggttttgg aaatacgacg ggcaaaatct gtttcacgca tggatatgcc attggaagcg    82020
aaactatttc ctcgtttgac tacggggcct atgatgacaa gcggtgacaa agatgaacca    82080
agaagggatt gaaattgaaa cctccgtctt caagggtgct aaccgggatg cctacgattt    82140
tccgtcgatt gtcatgagtt accaagataa aatgggcata gtggaacgat tcggtgttga    82200 gttttttggac ttatcagttt caaaggaacg ccaaatgcgc ggcggtcaca tgttgagtgt    82260
caaccaacgg aggaaccacc tatgacttgg ccattctcta gcttatttat ggaagtatat    82320
cccctgacct tgagggatag gaggagatga gtttttttggc ttagagcaag tagaacgacg    82380
gtcacttcat atgaaggcta agtttcgtgc attatctagg tatgtcactt tgcgcccggg    82440
ttcacaagaa gcggattcaa accgttttgt gaaaggggtt gaggtcagtt ttcagcccctt   82500 ttgtagcggt ggcaaaatga aatccttcca gaaagtggta gacttctgtg atagaggtgg    82560
aggagtaaag taggatgact tcaccatggc atcgacatca aaaaggtttg aaaagggaga    82620
ggtttaatgg ttcttacact acagggcgag agttcgagga ttttcggtgg gccgttgtct    82680
gctcaggagg ctgtggtggg gtccgctacc ggaccgtgac atttctgcgg gagtagggtc    82740
attccagacc tcaatcattc tcacaaatac tatactgggc tccagagaat gttatggatg    82800
tgggaggctg gaccataatg ggaagttatg acgaggtccc atgggccagg ccagctaggt    82860
ggggtggtgg taggagaggc agttgataag gaggccagtg gccaggtaat gggtgagtcc    82920
tgaaggcagc caggagtgag gacaagtgaa ctacaacctt accacatggt gagggcagcc    82980
gaggcagcag gcaaattagt aggggctacg gctgtgcagc ctcgcagtct ggcggggaca    83040
tcagatgttg ttatcaccgg taatcttttg gtttgtgatt gcatggctac gtcattatcg    83100
```

-continued

```
gatcctgatc cacatttcat atgtatcttc ctatttgtta ctggtgtaat ttacattgtg   83160
aattgcttga catgctattt gtgtttctac tccgttggtg agtcatgata gttgaaaagg   83220
tatataggtc ttgtccgtga cttttgtggg gagcacactc atgtagattt ggttatttta   83280
gaaatggttg atttctgatg taattacggg tatgacttgc tttccaaatt ttgcaatctt   83340
agattgtaat gctaaaagcg taacgttggc caagccaggg acatccagat tagtaatggg   83400
agtgtgacta cacttccgct ccagataaat atcatatcct ttttcgtgct aagagaatgg   83460
ttagtaaagg gtgtttagcc ttcttggcac ctcagtgatg atactaagta ccttcgagtg   83520
agcctggggt ttcggtagtt cgtgagtttt agacgtgttc cctcgcacct tctccggtat   83580
gccaccgacg aggatattga cttttgcatt gatttgggcc gagtactcat tcccatttcc   83640
cccccttata gaatggctca aacgagttaa ggagttaaaa gcccaacttc aaaaactgtt   83700
aggggaagag ctttattagg ccgagtgcat ccccttaggg tgctttgttt ttgtttgtga   83760
agaagaagat gggagtcttc ggatgtgcat agattactgg caactaaata aagtaactgt   83820
taagaacagg taccctcttc cctcgcattg atgacttgac cgatcgattt ctaaggtgct   83880
atgtcttctc taagattgac ttgagatggt tatcatcaat tgaaaatcca ggcgtgagat   83940
atgccaaggc ccttttcgaa gacgtatggg gcattatgaa ttcttggtaa tgtccttugg   84000
actaacaaaa tgcccctgct actttctgcg agcttgatga gcattttta agccatatct   84060 atggatctct ttagatcgta tttattgatg atatcttgat atactcaaga gaagaagga   84120 acatgaggag catttgagag ttgtgttgga aatgttgagg agaaaaagct ttatgccaaa   84180
ttctccaagt atgagttttg gctagattga ttgtccttct tgaggcaacg tagtttctaa   84240
gggaggagtg atgtagatcc ttctaagatc aagtagttag aagaattggg taagacctac   84300
taatatgtcg taaataagaa gctttgttgg tttaaccatt ctaccgtcga tttgtcaagg   84360
gattctcttc cattgcttcc caattcgaac ttaactaagc agaatgttcc atttgtatgg   84420
tcggatgaat gtgaggaaat cttttcgtaa actcaagacct tgtttgactt caccgcacct   84480
atccttacct ttccaaagag agagggtaag aacttcattg tgtattgtga tgcatcatat   84540
tctggttcgc aaaaaaaaaa aaaaaagtgc taatgcaaga gaagaacgta attgtgtatg   84600
cttcgaggca attaaaggtg catgaacgta attatccaac ccacgtattt ggagttggtc   84660
atggatagtt tttgcattaa acaatggaga cactatctat atgggggggtt aagtgaagtc   84720 tatcacggat catcgtagcc tacagtatgt ctttaccgga aagatttgaa tttgagacgg   84780
agggaggtgg atgaactaa tgcgaaggat tatgatgttt accatcttgt atcacccaga   84840
aaggctaatc ttgtggcggt ataggtagaa aaagcaggag catggtagtt tagctcactt   84900
gcaagcttct aggcgcccat tggcctagag aggtgagact acggctaata actttatgag   84960
attggaagta aaaaatgaga agggagtgat tttttggcgg tgtggaggcg tagatattct   85020
tttcttgaca agatcaaagg aaaaacagtt tttaatgatg agaaattgat ccgaattagg   85080
gatatggtgt tatgagggag agtctaaaaa agcaacaatc gatgaggaag gtgttttgag   85140
aatcaaggga agggtgatgt gtaccctgcg ttgatgactt gatcaacact attatgagag   85200
gctcatagtt caaggtattt tatacacctg gtgcaaccaa gatgtatcgt gacctaaagc   85260 aacactttg gtggagtaga atggtagcga cattgttgat tttgttgcca aatgtccaaa   85320
ttgtcaacaa gtaaagtatg aacaccggag gcaggaggaa cactttcaga gaatgcccat   85380
tctgaatgga aatgggagaa attgcaatgg atttcgtggt tggtcttcca aagacaatgg   85440
gtaaatgact ctatttgggt gattgttgat aggttaacta agtctgctca tttcattcgt   85500
```

```
caaggtgact tacaatgctg agaaattagc caaactttac atccagtaga ttgttaggtt    85560
catggagttc cactctccat catatcggat aaattaccag tttactttaa gttttggaga    85620
acattgcatg cggaattagg tactaggttg aaccttagtg cgcatttcac ccctcgagac    85680
gatggagatg atcggcgagc gattcaagtg ttggaggata tgccgtgcat gtgtgataga    85740
atttggtggc catgggatag cttcttaccc ttagcggagt tttcatacaa taatagctat    85800
cactcaagta ttgacatggc cccatttgaa gcattgtatg gtaggagata taggtctccc    85860
attgggtggt ttgatgcatt tgaggttaga ccttgggggt cttgaccttt tgaggttatt    85920
agaggcggtg aaatctattc agaaaagctt ttaagcggta aagtaggcaa aaataatgtc    85980
cggatcgaag gttagagact taaggtttat ggagggtgag caagtcttct ttgaaggttt    86040
tcgccaaaga aaggggtgat gcggtttggt aaagaggtaa gctaagccca aggtatattg    86100
gaccatttga agtacttagc gaataggga ggtggcttat gaattagcct tgcctcgggg    86160
ttgtcagagt gcatccggta tttcatgtgt ctatgttgaa aagttaccat ggggatggaa    86220
acacatcatc gttgggattg atctggcttt gatgagaatt tgtcccataa gtatgagcct    86280
ttgtgccatt ctagatagag aaattcgcaa gttaagatca agtgagattg catccatcaa    86340
agttcaatgg aagaatcgac ccgattgaag aggccacttg gggagaagga agtcgatgtg    86400
caaagaaaga tacccacaac ctacttacgt attcgtgtac tcccgctttt ttttttggcg    86460
tgatcgttcg aggacgaacg atgggtaaat tggtatctat tgtaacgact gcttagtcgc    86520
ttttgagtat tgattttatt tccccgaaaa actgaagtca tcggaaccca cgacggaccg    86580
tcacgggcac acgacggacc gagggtgtct cattccaaaa cacttagaat tctggaattt    86640
gggtaccgaa tcgactctct cgaacttcgt aacgatggcg acggaccgtc gtgagcggcg    86700
gaccgtcaca catcttccat aggaattgag tctacgaact tctgtgtgac ggcggcggag    86760
acggaccgtc gcagtacccg tcactgcaat cccgtaatcc cagctggccg gtcacattaa    86820
gtgatttaag gggcgttttg gactattccc tttaattata agttagtgg gttaatgtta    86880 ataagtctaa ttactgaggg ttaaaaagag gtaaccttga gttaatttgg gttattattg    86940
acatctttat acttaattat attctaatta gggtaaaaga aagagggttt gaataagaaa    87000
caatagaaaa gagcgagagg aagagaatga gaaagagaga aaacaagcga gcgaaaaaac    87060
acaagatttg aaattgcttt ttgcttgatc aaaattcttg attggaggta ggttattgtt    87120
tttatactat tattagtaaa ctcttaatag cgaatgatat gtgttgggtt gtattgtaaa    87180
gtcttctata tgcttaattg tatgcttgta tgaatgtgat tatataattg tgataaaata    87240
agcaagataa agctattgaa tcccaaatct tgaaacccc ttgttaatga tgatgccttg    87300
gtataaaaga aggcttgatg aactaaagta atgagattga tgatgccttg gtataaaaaa    87360
agggttgatg atgccttggt ataaagaag gattgatgaa ttaatagaat gagattagtg    87420
gagcgggtgt cacgaaccga cacgtagtat taggggacc gggtgtcacg aaccgacacg    87480
tagtattagg gggaccgggt gtcatgaacc gacacataga attaggggat cggtgtcac    87540 gaaccgacac gtgggaattg gggggatcgg gtgtcacgaa ccggccacgt ataattgggg    87600
gatcgggtgt caccgaaccg agccgcgtag aattagggga tcgagtgtc acgcatcgac    87660 cacatagtag taggggagcg ggtgtcgtcg caccgacaca agaggaataa agataatgaa    87720
tcttgaaaga tgttaatata ctcaatctaa tgaacctaat cccaaatgag tatggtattg    87780
aggcttgagt ccgcatgtgt gaacttggcg gtacttatta atgattatag tacttgttgt    87840
```

```
tgttacatgt tgagtattgt agttgattta tgatattatc tgatatatat actattttct    87900
attttgagtt ggccgatgat acctactcag tacccgtgtt ttgtactgac ccctacttgt    87960
atttgttttc tttgttattt gtggagtgta gcaaacgtac cgtcgtcttc aactcaaccg    88020
caactctagc cagtcttcat tacaccggat tttagggtga gctaatgctt ctagcttgga    88080
ctggatcttc ttcctcatgt cttgatgcct tgaagttccg gcatggacta gattttgttt    88140
attttagctt cttagaatac tcttagttta gtaatttgat catagatgtt cttgtggtga    88200
tgacttccag attttgggga atattagttg ttgaatttta gaagctattg aattggtttt    88260
tattaatgag tttatgtctt ccgcattact tctgttgata ttatattgaa atgttaaggt    88320
ttagattggt tggttcgctc acataggagg gtaagtgtgg gtgccagtcg cggctcggtt    88380
ttgggtcgtg acatttcata acattactct ttgaataatt aatataaatt gagcaatata    88440 aactttttcaa aatgacttat tctagatata tgatcaattt gaggaatgaa tgttccaaca    88500 aacatatat agactaataa gatcaataaa ttatacatat aaacgaaaag tttaaataaa    88560
aatcaaccct caaaatcaca tatatactac atagaatatg attcattctt tatctccaat    88620
taggtgggtc attttttattt tagttccatat atatatgtgt gtgtgtgtgt gtgtgcgtgt    88680
gtgtgtgtgt gtggcgtctt ggcgtcttgg cgtgtcttgg tgtgttaatg tgcgtgtgcg    88740
tgtgtgtgtg tgtgtatgaa tttcatcagt aattaagata catagtagaa catgaattgt    88800
atattactat tttcttcatg taggatacaa aatattctaa taaaaaaatc taagaaagta    88860
catcaacata tataaaaagg aaatatataa tacttaggac ggacaaaagg agcggataaa    88920
aacaaaaaat aattactaca catacaaaat gatttgcaaa gttcattttt gcatgataat    88980
ctctcatcct cttcttgtca tatacatgaa gatcatgcta gataatttat agaagtagct    89040
atgatgacct ttgaatagat aattaatttg cattaaatta gttcaatggt tttagtccat    89100
atcaaatttg tttaatggaa aaaattttca aatactcctg attttcacaa tagagtaatt    89160
aattattaat gtgaatttga tacatgcatc aatctaaatg agttatttat caaaaataaa    89220
atgaaataga gtagactaaa aataataaaa tagctaatga attctaaaac ttttaaataa    89280
caaaaattaa agaaagaaat agttctagtt tataagaata gtggaacttc ctcaataact    89340
aacaaaaaca taaacaaatc tatatctttt ttattgcata tgttatgaac aattacattc    89400
atcaacaatt atccatcaat aattatacat tagaataaca aagcatatgc atcaacaaaa    89460
agtaattgtg ttgaacaatg tgtcaagtgt aattacatcc accataatt attcataaac    89520 aattatacat cggaataact aagtgtgcat taatataaag tgattttgaa gataattttt    89580
tggtatttat agttacaagt ttggaattgt aaaagtcatt taaaaattaa tgatatacat    89640
aacgtttatg agaattagat tgtttaaagt tgagcatatg taaagtttct tactaaaatc    89700
taaatgtgtc atattaagat gtatggtaat tcaaaggaca ttttttgttct ttaatgttaa    89760 ttgatatttt gaatataatt tatcatcttt ttgttatgaa atacttcatc tcttgaactc    89820
tattttagaa taaaagacaa attaaacatt tctttaatta tttctaccta gaaacataat    89880
ggattaatac catataagta ttatttaagt aatatttat taattattc tttaataata    89940 tttaaattag taaagggta gaatcataat cctattttaa agttaagatc ttctcactta    90000
taataaaata ataataattt acggactagc cccgcttgtt tacctatatt agtcaataca    90060
tttttaaaaa aaagtataaa tattattaat aatattgttt tatgtttaaa aattaaaagg    90120
agtatatact ccttaaaatg agtaaaagaa tctatgagat ttttttatcca aatacttttt    90180 ttttctagat agaataaatg aaataataag ttctaaattt aatcaataaa aacataaagt    90240
```

```
tgcagaatat aaaaatattt agcaatactg tttttcttct tcaacgctac ctcgtctttc   90300
gttattaggg gtatttattt acaaacatga aatcacacca tgattttatt ttcatacaag   90360
tagtaaatca tttataaatt ctaaaaaaac acattaaata taatgcatgc taattttttg   90420
tagatttaat tatgagaaaa aactaattac atcaattatt caattctctt atccaataac   90480
ctagagtgtt cactacatga taatcaactt gttataacaa acataatctt taaaagaaga   90540
tttgtacatc agacatgtaa atgaaaaatt ttcttttctt ttttcactgc cattattcaa   90600
gaaaaagtag tcaatttacc ttccttcaac cgaaaaattg aatgtaacaa ataatgaact   90660
aagtaaaaat atgcaacatt gaaatgaaaa ataatactta ccaaacaaca aataaatgtc   90720
catgacgcct ttaaccttct tgaagaatgc atcgaatgca ctgaaatgat taaattctaa   90780
ttcagatact atattctcca agatttaccg tcaataaatt aacaaaacaa catacatatt   90840
ttttctcaca caagtaggtt tgttttacct catgaacgtt gagcagacta tttgtccaaa   90900
tgaaaaactc tctagaatta tttatcaccct gtttgcgttg aaaacataaa ttttcgatga   90960
aaagaataaa acaaaacatg taatattagt tctatctata tacatatatg cctaaaattt   91020
attgatcaaa agaaacatga aaattttgaa gaagaatttt tgagataaat caattcacat   91080
gctattgtca tgagaagaca tcaaaataat gtattttgtt ggaaaaatca tgtatataat   91140
tttatcaatg gaactcttca aattctttaa cttaaaatta aataaaagat gttttgaaat   91200
gtttgaactt catttgtttg aatgactatt tatctttcat tatatcttta ttactttaaa   91260
gtttattatc taattattta ttaaaaatac ttttacattt taaaaaatag aaaaaattta   91320
agtgaatggt aaaatggtaa tttaactttg aggttaggag cttcccactt ataataatat   91380
atgatgataa ttcgccagaa taatacagat atatgtataa tatacaatta tttaaccgat   91440
atcatatctg attcctctct tccactctct ctcctctctc acccgcctct ctcctcccac   91500
tctcaatttt cctttccata tatacaaata catatgtata atatacaatt atctaaacga   91560
tatatatata tatatgcaat tcatctctct ctcactcttt gcttcacttg acaactatga   91620
cacttaactt tggatatgca caaattgaca tttaaaaact ggttacagag aaacttaatg   91680
ctgttgcgta taaagttgat gacttattgg atgaacttga atatgaggca gcaagactct   91740 gttttttcagc aaaacacatca agcagcaata tctgagaaat taaacacata tgatgatgtc   91800
ttcttactca ccgagttatt agttatgcta aaatgtttac ccgagggatt gcagcaccta   91860
acaaatctca caatttttttt tgataagtga aagcatagtt aaactctcaa atgtagatga   91920
taattaagct cttgaagatt atcgctgaat taagtgaatt cgttattagt ttcaaaatgt   91980
ttagcctcct tgggacctga cgaatgattt aaatttcaaa cacaaggtca agctatattt   92040
gtaaaattct tatggccaaa caagtcatac tgcaacaaat tgtaaaagga ttattatact   92100
ccaaaagtaa agatttagaa gagatctact cttaacacta actaaaagat tattccaatt   92160
ctcaaagcaa atttatattc ctttccaacc aaagaggttt tccaaatttg ctttctagta   92220
attttttttt tctgcacgat aggaatagat ctcatatact ccctccgttc catattatgt   92280
ggtgtagttt aattcaatac ggaatataaa aatgaaagaa agactttaa aatttatagt   92340 ctaaaatgaa taataaaaaa ttgtatgact ataaatcatt tcattaagag taaatgtaca   92400
atttaaaata aaattgttac ttaatatagt aacgtgtctt tttttttgga aactgcctaa   92460
aaaaaaaaaa atagtcatat aaattgaaca cagggagtat ctacttacaa agtaaaagtt   92520
gtgtgtagaa gattttggca tataaatcat atcatatatc atcatatcat atattagtaa   92580
```

```
aagcatgaat taaaaaagt caaaaagtta aattacgatt ttatcccttc tattaattaa    92640
cttgttataa aatatttaaa tatttgattg tacaagttta attaaaatgt taaatgaatt    92700
ttaaacttcc taatattaat ttctaattaa atatctaatt tattaatatt tatcatttat    92760
aatccatatg tatataataa ttataatttt ttaataaaag tctaatcaaa atattaatga    92820
cttttagact tcctaacact aattcctaat taaatatcta atttattaat atttttatca    92880
tctataatct ctctatatat aataatttta caaaaattaa taaaaagtct ctacgtaaat    92940
ttttatactt ttcttattct cataactttt accctaaata acaaaattta ataattttaa    93000
gggtgcaaat cttcaaaatg gagacacaca cattgataat gtcctcttaa ttattattaa    93060
agaatgactc tagcttcaca aatttaaatt cattaatgct taattactta gagaaaagta    93120
gatgaagact cttaattttg atagtatatg gaaggattgt gtactaattt tgtacttatt    93180
ttttcatcta catatacata gtcttataaa aatgatgtct acattgtatt ttttcttaat    93240
ctgtttcttt ttgtcttttt cccccaatta gacttcttaa tttagttttc tacaaatgtt    93300
ttattgtcgt aagtctcttt acttattttg taattgtagc attttattat tcattataat    93360
ttgcatatat gtatttccat gaaatattag taattctatc atatctataa aaattcacat    93420
gaaatacacg tgctcagaaa ctagtaagga aaacaacaca aatatacatc cgaactatcg    93480
taaaaatgat atgcagatac catcctcata cttttgggac attgctgtcc attacgtcaa    93540
aaaaatatag catatatatt aacggacatc acgtgtcata atcatatcaa ttgatccaac    93600
atttaataaa tattcgatcg acgaatagat tgtgtcacat gtccctattt agtcatatgt    93660
taaagtgaat gacatatatg ctctagtttt gaaactttct tgtaaaattt aagtatatgc    93720
cctaaatttt taacaatatt ttgctacatt ttacgttttt tccattcacg tattttctta    93780
tttactaaac aagtttctat cgtcctcaga gtatttcctt aattagcact aaatgttgtg    93840
atgtttttct tcaactaagt ttcattgaag gattgagatt aaacctattt cggtatccac    93900
gatctttgaa tgaatcgcca aactctatct atgaatttaa tagcaaaagc tcagatttg    93960 ttccaaattg agatataata tttctataaa gaaatttaaa ttaatgatgt gatataatga    94020
taatgaattc agttttttaca ttagaaagac tctattttc tctcttactt cacaacaatg    94080
caagaattct taaagaccta aaaatggggt aggggtgggg gaagggggcc aacaacaaca    94140
agattctaaa ttcttgaata tttttaacta aaaaattaat tcttttccca atggattcaa    94200
attgaaaagg aaaactacaa cttttgtgatt atcgcgcttt caaaatgttg aatagattgt    94260
cttcaggtgt gagaagaatg agagtgagat ggagaaccat acgaataaag aaattctcaa    94320
gtacgattcc aatggaagga attgaactac ctattttgat cggagataac aagtcattcg    94380
atagagagat tttgaaactg catatgtttc ctaaatgaaa gttatatatt agctagatag    94440
ggatatagat gggttgaatt ctcaaaatct aagaataatt ttggatatgt ctaaagtgat    94500
tggaaagtga atatatttag gacaaattac atgattcgat atacttcact attatatata    94560
ttatttttac atatactttt aaaacactag tttctggaca cgtgcattga acgtgtatct    94620
caaatatatg aaatagatat ttttgaaatt gtaagacaat tctaaaatat ggttgtgatg    94680
tttagttatg tatgagagca atttaataaa atatgtatga gacttttta atttgtttcc    94740 catttggtgt tccgctagct aattcaaatt catgtgtgac attccacttt gaggatactt    94800
cctataaagt ctttccatca tcaagaattg aattcaaaag attgaattta gaacgaacga    94860
atatttatca atcaatcaac ttatttgatg aaaacatata tgaatttcag tttgcacata    94920
ttataaaagg gcaaacttca tatttcaagg gtactaccta taggtctttt ccattatcaa    94980
```

```
gaattgaatt caaaagattg aatttagaac gaacgaatat ttatcaatca accaacatat   95040
tcgatgaaat atatatgaat ttcggtctgc acatatttta aaagggcaaa cttcaaaatt   95100
tatcgtatat gccccaaatt tttaacaata ttttgctagt ttttagtttt ttccattcac   95160
gcattttctt atttactaaa caagttccta tcgtcctcag ggtattttct taattcagca   95220
ctaaatgttg cgatgtttct cttcaacaaa gttttcattg aaggactgag attaaaccta   95280
tttgggtatc catgatcttt gaatgaatcg ccaaactcca tctaagaatt taatagcaaa   95340
agctcagatt ttgttcaaaa ttgagatata acatttctat atagaaattt aaatcaatga   95400
tgtgatataa tgataaatat gaattcagtt tttacattag aaggattctt tttttctctc   95460
ttatttcaca acaatgctag aattcataaa aacctaaaaa tgggaatatt atcatattat   95520
aattaaaagt aaaactctat tttagaaata gtggactaaa catctaaact aataattcaa   95580
tggcctacgt tgatgtaagt tacgttattt tagcaaaatt aagaagaaat tccttcattt   95640
gagggtagaa tcataaaaat aaaaaatgaa aaaatacata tgaaatatct taccgcaatc   95700
atgtgccctc tttgtatttt tcattactat tgtctctccc cccaacttga tcaattactt   95760
tttttaggaa aaataatcca cgatgaatgt attcgtcaat tttcactgat tatgtgaaca   95820
caaattatta agttctctct tgaatgaaaa caaaaaaaaa agaaattatt taaagaatca   95880
aaaaaaatta aacgtaaatc cccttgcact atttagagaa attttctatg tgaagcatat   95940
ttcacaatta attgcacatt tctctgttct cttcttctct tcttgaataa aaagtcaata   96000
cctaaattcc catgataaga gtatcaaaga aacatattac tggattaggg atgaatcatt   96060
tatgaaattg tgaagtgatt ttagatactc acagaaaaaa aatcaccaag aatttataag   96120
gagtggatga ttgtgattta tgatcgaaaa aagatgaagg ttaaaattgt tgtgactatt   96180
aatacgaaat atgtcttctt taacaaataa agtttatttt aatttttaaat gatacaaata   96240 atattgaagt atgtacatga tgaaaatcgt aagaagaaat acaagtatga ttgatgaata   96300
agttgctata atttattcac cgattctttc ttatgtagta cctcgagttt ggttgaattt   96360
cgaacttgat caatagttgc aaacaacact tgagatattt taagaagaag aaatataaaa   96420
atgtgaagaa acacttcaat ttatagctaa caaattgtgt tatgaatatg tgttaattgt   96480 gtcttttag taaagctaca acccttcgaa aaaggcattg ctcatgagaa agtcacaata   96540
ctgagaaaaa gttacaactt atcaaaaaag acacaatgct ttcgaaaact caaaaccttt   96600
tgaaaaaatc acaacccttc tgaaaagtca caactcaccg aaaatgtcac aactgtcaat   96660 ttcaacccctt caaaaagtta caattcatag caaaaattca caaaccgttt aatgaaaaaa   96720
aactatctat atttaatata atataagtaa ataaaataaa aataaattaa ttgtgtattt   96780 tttttaatt ggggatatta tagtaattta acattcattt tgggagttca tgcttttag   96840 gtagtgctag tttcgagcac gtgttttgca cgtgtgatcc atgtgaattt tatagatatg   96900
ttagaatgac taaaaattaa tggcaatata tatgtaaatt gtaatgaaaa ataaaatgta   96960
acaattacaa atctagtata aagacttacg gcaataaaac attcatagaa aactaaatta   97020
agaagtctat agagagaaaa aaagacaaaa agaaacagat ttaagaaaaa tacaatgtag   97080
acattattct tataagactg ataaatatat agctgaaaga ataagtataa aattagtaca   97140
tataactctc tgagttcttc aactcctttc atatcctatc aaaattcaag agtcttcttc   97200
atctacttta acaatagaat aaaattaata gcctaataat cttggtaggg gtttcatgag   97260
ataaaaagtt gaattttata gatagagtag aaggaatatc aaaagatatc tttaagttta   97320
```

```
agtttagata tttggaagtt atgaatatga aaagattaga gttatgaatg ttgagagtaa    97380
aaaagttgaa taagtaatta taaaataata ataaataagt aaataatatg aaaaagaaaa    97440
ttaaaggtag caaaccatgt agaaagaaca actaaagttc ttatcacgta attaatttta    97500
atttaaattt gttaagctag agtcattctt taataataat caagaggaca ttatcaatgt    97560
gtgtctccat tttgcagatt tgcaccttt aaattactaa atttcgttat ttatcataaa    97620
gaataatact ttatccacat aaattatatt attcatgaga ggggttaagg aaagttatga    97680
gaagaggaaa agtatagcaa tttaggtata gactttttaa tttattttt ttttataat    97740 tattatatac atatagatta tatgataatt attaataaat tagatattta attaggaatt    97800
aatcttagaa agtctaaaag tcattaagat tttaattaaa taaacaatca aatatttaaa    97860
tattttataa catttaattt atagaagaga taaaaccgta attcaacttt caactttttt    97920
tgttcttgct tttagtaata ctagcaatta taacaaactc atcagcatca actcgacctg    97980
tatatttcat aatcaataat gtcttgtaaa tattcatcga tgtgtcgaaa caaagccccc    98040
cacgtataat acaatcatct tctaattaat tgagctcaag cactttgatg aaaaatcgaa    98100
tggcaggatt ccacaagtaa atatgcttgt ttataccaat cagtataaaa ctatgactgt    98160
taggttgtgg agcctgatta atatttgatg tattatttat tctctgtaac taatatact    98220 ctgaattatt aatatatacc ccaccgccgt ggaagtttac ccacgggggt gttaccacga    98280
aatattggtt tctctctttc tagatctctc tagatctctc atctctctca aaagtttttg    98340
tgttcttcat tcatcaagtg tgtgtggatt cgatcctaac aacgacaaga acctaaaatc    98400
atacaagttg ggggaaaagc tcattatcat gacttagagg ataggtgagt tcttccacaa    98460
tgagttgttg gtttatttat tgaaagcaag ggttagagtt ctacgttgca ttgacaattg    98520
ctcctccttc tcgacgttga tttgagagat gaataaaatt tggacttgaa attcaagaat    98580
gtcatgatcg tgaaacacac ttgaatcgta atagagattt cacagataaa attgaaagaa    98640
ttatcataat ggtttcattg ggtagataca ccatcttgac aagtagtaga ttttctgggt    98700
aattttaatt ctcgtatttc tgatatagac atatgctcac aaattgacgt gaaaccgcat    98760
gcgaaattta ggaacttatg caggtgtttg ggcgcagttt tgactgtcta ttgttgttcc    98820
ctaattaaat atacaccttc tctgtttcaa cttttccaaca gttttgtgct aaagtatttg    98880
ttgttgcatt tatttattca aacttaattt gttccaaaat atcatcagag tacaaactaa    98940
aggattcaac atgccttgag tacattttat actgtcaatg gcaatgctac agcaattaag    99000
caccagtaca tgaagcaacc gtttattggt tgagatttga gtgtcagtgt cattcctttt    99060
ccattctttg ttttttggtag taactatgat attgccattg tttataactt caatgatctg    99120
ctgatattgt ggagcatgca aaactaaaag ctatcgagta aaagtgatca taatgtgcta    99180
gttcatataa gaccatctaa aagctatcaa ttaaaactta tcgcagtgtg ctaggaagtt    99240
aagggtgtac atatatttgc aattggcagc aaaacagagc aaaagcaaag cattaagatc    99300
agaaaaagta gattaacctt aacaaatcga gctcgcctat tgtcccctac agcaaagtta    99360
aacacctgca gtgtttaaaa accacaaaca acatttaaca aaagtgaatg attaaaagta    99420 aaaaagaaa aaatcgagaa agataaaaaa gaacagaaga cggcataaac tacaatatat    99480
gttttccatc acaggttatt catatcatcc cccataaaac tttctacttg agcactacca    99540
agaaactatt gaggatgtgg gaccttggga tggttagtca aaatgagctt ctattatatc    99600
cttctgtgtc cttctattaa agctctcctc ttccttgttta ttttgtggag tcccaatttt    99660
ggcgtggcca attccatgat gccaaattgg taacaaatac ttgaaagagt gatgactcaa    99720
```

```
gagagatggt gaagaaagta gacatagttc aacgaattga agtcatattc gagaacaata   99780
ttatccagat agttcaatga agtcatttat tcaaaattca taagcaaata ttaatgtgga   99840
aaagttctat tcatttccaa attgaacaaa agaagcaaac aatagataag gtctccaaca   99900
tggagataat aattgagagt aaaaacttct attgctatta aatagaatct gcaattaaaa   99960
aaaaaattac atagatacaa tatggaactt caatatgtac aacttggaaa ccctttcaat  100020
gcttgaggtc tcagttttta ccacattcag atacaaaaat gtagtaacaa tggcaattgt  100080
gcgcgattct aaaatggcaa aaaaataatg ccaacttaac tatggaaatt atgtacagat  100140
ataactaact ataaaactta aatcgtacag tggcatatca acagagcctt cttaggctct  100200
gctgctatca tcaaaaaaag cttttgactg attctggcag ttcatggagt agtataagct  100260
tcggacgatt tgaactgatt cacacagcat gtaactgatt taaaaattca gttttactct  100320
atcagagtca ccaactcctt tcttcccaga agaactagca gccgcttgtt ccttcaaagc  100380
ttccttctcc agtttcttct tttcagcatc agctgcttgt tcattctcat cacgtgatt  100440 tttaaacatc ttcatgaaca ccaccaaaat ttgtgtcact gcatccagaa agtaaggaaa  100500
tgaaaactga caaagttcgt cacaaacatt gtccggttaa agagttggtg aggaaaaatc  100560
tgttgaagca attctcacac cagttaaaac aagatctcaa ggacaaacgc aattcgagaa  100620
atctagccga tggctatatg cactcaacaa aagctacaaa ggccataaat gttgcatccc  100680
ataatcttca cataaagata gacaactaaa aagcatcact gataaacgct actggaatat  100740
ctatattacc aagactgttt gaacgactgt agttttttct tttccagatg actgataagt  100800
gataatacag caagaaaata acgtatgtat ctctaacctt gctcaaaggg gcatcgagct  100860
ggatcttcgc caaaatacag ggataggag tctgcactcc ttccctgcag atttacagga  100920
tagaaaaaca atcaataaac ttggcatggc ttatacatcc aggaggcttt aaaatatgac  100980
ataatggatg caagaaactc accacttcaa tataaagagt agtgagagac ttgacttcag  101040
cctcagcagt atcaaggaaa ttctttaaca cctgagaagg aatgcacgag tcacaaaccg  101100
catatttcag atgtttataa caaaattata tgtacaccaa atcacagaca tcgcaatcaa  101160
gtttgactgc atcaccagac tccactctaa aaccatgtcc aacacaaacc aaattgggag  101220
ttttcccagc gcaagccttt ttcacttgac cttgttaaga acacaaatgt catccatcca  101280 tggggacac ctatcactct tctaaaacag tggtacactg cttccttact ttgttttctc  101340
aaactatcta gaataaagct ttttgatagt aaatagggat ccttgtaatg tataatgaag  101400
gaaacctggg gaaagaggaa tccgcacaac gccgttcatt tcatatctgg cgtaagaaaa  101460
tctcgagaat ttgataatac atttagggt cgtttggtag agcgtattaa gaaaaatcat  101520
ggatgcatta gccttgttta ttgctagtac catgtttggt actcttttct aaactatgta  101580
caactagtgt tgcattagtt atacactatc gtttattaaa gtagattatg atatgaccttt  101640 caaagttaaa atttaaaact aaaaagaaac attatcttgg aagtacaagt aactcatttg  101700
gtttgtagga ataattcaca tgttaccatt ctctttctc accttctgaa atcctgaaga  101760
tattgtacca tcattgtcgg atgcagtaag ttccttgttca actttctcaa gacctttact  101820
cactgcttgc atttcttcag ccaaagactt cagttgaatc taaccatata atatgatgta  101880
aacaaacatt tcagttcacc aaaataccag tagtactgca aaggaagacc ataataaata  101940
gcaagggtac cttagaagca gcttccaagt gaagaagatc cttgtcaaaa tcaagcaact  102000
ctggcatttt ctcagcaagg agctgacaaa aaaacgaatt tacacatttg gcatcacatt  102060
```

-continued

```
gagaagtgca aacatatata tgccgaagag taaagactaa ggctggtcaa gccagctata 102120
gttgatagct aaaggctatc aactaaagtt cactgatggt tgggcaaaag aacagcataa 102180
acgtagaata ctgaaagtag aaaataaata caaaaacata tagttttcta cagaactcaa 102240
ccttctatat tacaggaacc tcatgggtgc accaaaaagc aataagggac aagaggctat 102300
tccttaactg tgcaaattac tctacacttt caaaagctct cctaattctc actctccaca 102360
aaacccacat aagtgcaaaa gcatacccttt cacgccttgt gtctcctcct tcatcttccg 102420
ccatttcagt tgagcaacat tacttataca gtgacgggca tcacccaaat ttaccaaacg 102480
aacaccacat ttcccaccat aaccgagaag ttatcgcaca atctagaaga cgattcgcgt 102540
cttcacctga ccccttaca cataaaacac cgcccaacat aagtagttct cctcttcatt 102600
cttttatcat ccatcaagat caccctctt gttcctaacc aagtgaaaaa acctaccttt 102660
ctcagtacct tagggatcca tatcaaaata tatggaaggc tatctttctt ctcattgatc 102720
aaaaatttgt ccaaagaaaa ggactttagc aaatttattc ttaggcggcc aaaatgaaac 102780
ttagattaca atgaaacctt aacaaagaca agaattcaat gaaacctaaa caagacaag 102840
gaccagacaa tagagtctag ctaaaaagaa tctgggcttg cttttcaat tcaaatctgt 102900
gagcgaggat tcctctttct cttctccaca aaaatttgaa gtggtttata acttacggag 102960
tatccgataa tctcttgcaa tcttgtataa gcctgtgcag atgaaataac ttgaacattt 103020
ccaggagtca atcgatttgc accagtcgac cagtgggagc gataattta agatataaac 103080
atcatataac cttccttta gcctattccc acttgagcgt acttcacagc tgatacgctc 103140
ataatacttg acgccccgaa ataatgaaca gggatagata tggagataca atttaagaaa 103200
atgaaccta ggcacttcaa tataagagaa gagagaagta gaacaaaata aagaacaatg 103260
caactgaaaa aatgttgaaa ataaagtgaa cgatataaga tggattagtt ttcagatttt 103320
catctttaag agctgctgac tctcaaaaat ctgctacacc gccttgccgc cgccttcttg 103380
tttgagtgct caacagaagc acctatacgc acttggactt tccttagggt gatttaatag 103440
atttttgtg tattttattt ccaattgttt catttggcaa gatactctaa gcttgaaatt 103500
tttaatttct atttagatag tcttgtatgc ctaattcat gtttgatctt ctatttcatt 103560
ttagagtatt ggagttgata ctggatctag ctatcaccga cctactgtcg tactagcgtc 103620
aagtgcagca cttagccaat aatccccaat aatagggct acacttagac aaagtatgaa 103680
tcaagaagtt gtaagtgtta gatgcatgtg tggcatttag ctatgtttaa cctcttttgc 103740
tggagtaatc tctcctttgt aaatgatatg gatcaatcaa cccaccaata gttctagtaa 103800
ttcctgaact actaagtgta ctaccaagca ttctaaagcc tcatgcatct tccttgattg 103860
tgtagaacat gccatactta tgtggtgagc cttgcttgtg cactatggct cccacttgtg 103920
catcaccatg cctcgtgcat gctacatcat cagaccatgc tcttgtgcta acactatcac 103980
cataccagcc cagccatgcc tccatgaaac agttcctaat tttctttgcg ttactactaa 104040
gacaacgaat cgtttgatct tgaaattcct tgcctcctct ctgttagcct ggtccatggc 104100
tttgttgcac ttgcgcatca tgccacactt atgtttgtga accgtgcttg tacactatgg 104160
cttccactag tgcttcttca ccatgcctca tgcatgcttc atcttagtag catcctcttg 104220
tgccaaaaca accacgccta ccagccatgc ctaacatgga actgttcccc aatttcttta 104280
actttctaat taaaacttaa acaaagaatc atttggtttt tgagtgttga aaccttgaaa 104340
gcgctcgcct cctctaaagt agccccttc atggttttag atgggttatg acatagacct 104400
caaatacact tggcactttt tcaatccaat catgagctac tcaacaatta ttactgagcc 104460
```

```
aaaactaatc tgattcaact tacgcttaag tcacctccaa ctcttcccaa ttcagagcta 104520
attgatcaat actaattaca taaaggtaaa aacagaaagg catcataatg cagtaattct 104580
accttgcaca gataatgcat caaggtcatt ttgttgtttc tcgcacgagt gtcagaaagc 104640
ttaagaagac tgtccaactt gaaccctaca gcagatcctg taacgtaatt acaaaacaaa 104700
gatgttagtc acgatgcctc cacccaacaa ctgattattt tcttatagag atatagatct 104760
tagaaaactg tacctcgtgc tgtaccctga ttcagtgcat tacccaatgt tagaatggtc 104820
tgcattatct gacgtaattt ggcagattct ttcacctact tgaccaggaa attcagttag 104880
agcctagtta aatcagaatg tgccaaatca aacttcataa ggtattaaaa atacctctct 104940
agtagcatca ttgattgtac tcaggttact tctcaagtcc ttcacctgaa caattcaaca 105000
tattatagtc aacagaaaat taatggcaga atccatagac attagatcac taagaagtac 105060
aagagaaaat acctgattag agaaagtgat agtaaatgaa acactcgta acttggactc 105120 aactcgtggg accttcatca gctccaggaa aaactgaaac gggtattact tatccggtta 105180
attacttata acttaaagga taggaaaact tgtacttccc cacatatatg gtcaaaatgg 105240
agaagacctg ctcacacttt ccaagcatcc ccttgtcccc attatagttc tggaaaatag 105300
aacataacca gtaagatcaa attgtgaaat caagaataac aattaaatat caaattgcaa 105360
gtatagactg tcaagaaact aacataacta agttcacaaa gagaggggga aatcaagcag 105420
aaacaagtat ggatctacat acacaaaaga ctaagatata tgcctatgtt tatacacatc 105480
cacacccacc gggaaaggaa gttcccagga aaaggtatct gcatgattag acattgaaac 105540
agacacatga gcatgcacgc acagcataga tgcaagtaca tactgtataa gcatgaaacc 105600
gccaaatggg tcattgactt atgggcatca acctacacag ctacttgcaa caaatggcac 105660
atcaacaaaa ctataggctc ctgctgttcc tacgactcac ttaactattc ttacgttaag 105720
tacaattgca gaatgtgaag gttccgactc ttgtttccaa atactatggg caaaaaactt 105780
caatatggag tattttctct aaacgggaaa agttaaaaga agaatcaaag caaacttcag 105840
aacatacctc taatattact tgtgaactca aaataaatga ctagacacac attataagca 105900
tattattgta acttaaactt tgccatgata ggcaagcaca gtaggatgag aaagagatta 105960
taccctcagt gtctccattt cttcttttgt tgggcaaaat tttatcagat tttcaacctg 106020
atcaatgtcc agagctgatg aatccaaagc caaaatagca ttctgtatga catgcataca 106080
aatataattt gtaagaaatc cgcggtaaat tttcctttgt aaacagaaat tttatttgca 106140
tttgcataat actggccgcg agttcaaata gcggacccca acttgtctgg aactgaggcg 106200
caactgttgt tataatatta gtaaaaagaa atccatggca aatatttcat tcatttcaat 106260
gtacctccat taaaactcaa aataaggaaa aagaacttc caaagaaacc atgcatgagc 106320
atcctaaaga aatgctcgtc agtcattaca cttattgaac acatgcatga atcagcatat 106380
tgatactgtg cattatgaaa catgattttg accaaaggcc aaaggataga atattttata 106440
caatttctat catgattcct ttgaatttca aaggaaaaat atccataaga gttcaatttt 106500
gaactcttca agttcggtga aattacatga tcttttcaac acaataaaat tatcaaaaat 106560
ataaaaaata agaaagtctt ttggataaat agttctacag ctacttccat agaaagctcc 106620
ttttctcctt gtacaaaata aaggtttctt tatccatttc attgaactcc ggctaaaaaa 106680
tatttctaat aacgatagtg tctgatccta cttgtgctcg tatcttgact aatttatagg 106740
gtacttgaca cctcctatca acataggtat ggggaactat gccctccaaa atgcaatcag 106800
```

```
atgaggaaaa ccaccaagtc ttagttttgg tcgctactag aaaaaccact tggccacact    106860
ctaaagtgct cattgaactc caccaatatg agaaaagcat aactaacttg aaactgaatt    106920
acaaggagaa ctgttatagg ttaatggcta acataaaaat agtcaaacta ccaaactcct    106980
ctgtgtatga cctaaatgtt atgtgtagtt aaccgattta tacgttcttc attcctttgt    107040
tgagaaaaaa tatagatagt taatcaatat attgtacttc tattaagcag aaacgaagat    107100
acttcaatt agagttcagt acataatata atcttttga tctagtaaaa agattatagc    107160
atgaagagtt caatacatac aagatacaac aatcttttcc ttttttttgt tgttgagaat    107220
ggacttttag tcaaacccat taagctgatt caataatttt gcagatctat ttgattcatc    107280
agatacatac ttctatagtt ttagcaaatg tacaagggga ttaaaaaaaa ctaaatact     107340
aaattgtaat cttttggaaa ataaagtcaa acaacatatg cattcaattg catatgtaat    107400
ttgttacttg atttcaattg ataaacacat caggattcgt taattttaat ggctgtttag    107460
tttgtgttac tttttaaatt attagcagct caatttccaa atatctgatt gtcctaaagc    107520
ccaagtaaag atcacataat ctaatagttt catctgataa acaataatag attattatca    107580
aaagacccac ctgttggcta gaagacataa attagtgcgc aatagataaa agtatcgaag    107640
ctcatagtag aaacgagaag acacaaaaag aactcacaag catatcaggc aggggaatct    107700
tgattttgt aagcatgatt tcacaattgt atgccctgcg caaatcaatc tggcaaaagc    107760
atatgttaag aaatcatccc ggtcttttaa cagttagacc aaaatgtaac acttccagtc    107820
tttcactata aataatggga gttgtgtaaa ataaacctca atcctcagg aagaaaaaga    107880
agccaacacc aatagactgt tcaccaacta ttccatagtg atctcatatt atacagtgaa    107940
agctttgaaa actatcagtt tctttctata gaagttttct atctctttcc caatttagca    108000
ctaacagata aattaagaag caagtgaact gcaattcatt catggtcaat ggccatcccc    108060
atgggacaca gtgcccatta tgagcacagc ctccgcaact ctttcattag atctagacat    108120
gtatcgcagc ctaataaaat tactctgttg catgaattta catctcaaag tattaacaca    108180
acttttaaga atttttcaaa ggcaaccatt attttttat atgattgact ccatccacta     108240
aaccctctgc ctaagacgcc caagagaggt ttcccccttt atcccttcgt taatcaaacc    108300
cccaacctta tggttggaga tgaaggacct taccctagga tatcactcca gtcaaagata    108360
attgtcttaa ctttcatgaa acagaaatgg tattacctac aggatggaga aggaggact    108420
tttccaccca agtttatgt aatcatccac atccaggctg aaaaaacata agttcttctc    108480
tataagggca tgcttgtttc gaaacgtcac ctatgttaaa cccatttaag cctttctatt    108540
tacttctttt cttccaccctt gttagccaca agataccaca aaaagtgctc tttaaaacct    108600
atctaatatt taattgtttt gttaaactag taaagaaagg agatacactc atcctacaac    108660
actcacttta ctacatgaaa gacttgctag ataatgccta ctggagaata acagttgtag    108720
agactggaaa caagataaag catatataac ttgccaattg cacttttct ggttgttga     108780
tttttgaacc acgtcggcct ccacctttgc tagtgccatc agtagctgaa gccaccgaaa    108840
acaaattctc aagctccgta atatcaattt caggtgctct gtcatgtaca ttaataaaat    108900
cttatcagaa ctaccataa cagacagata acaaataaaa gttgcagtac ccaacacaaa    108960
ctaggttaag ctcaaagggc tcagaactac tatatctgta atctattaag cattcgaagt    109020
tgaaaccatg agaatgatag tgcttatgac aacctgttaa ggggtttcac gagacacgag    109080
aaatagcgaa caatttagct ctgactatta acttgaaatg acacacaaag ttctcattgt    109140
aattttcat ccccaaaaat aaaatcttta tacctggaag tattttcctt gttttgcgta    109200
```

```
tcagcccata aactcccttg catagcccgt gtaactttcg accaatgtaa gggcttcaat    109260
gaagctttt  tcggaggaat tgaagtacct cctgtacctc gcccttttcc tagagcagtt    109320
gaacctacag aggctcttac acgtccggta gatggaggtg gtggcgctgg cacactaagg    109380
ccctttccac caggcggggg aggtggagtg ggtgtcaaac cccgcctagg gggtggtgga    109440
gcattaggag cctttggtgc tggtggaggt gctggtggag tggaaccttg cctaggaact    109500
cccaaaggag gtggaggagg tgcaggtggc cttgtagaat tgtttgacgg tggaggtggt    109560
ggcggtggag gtgccaacgg agtaggccta tttgatgaag aaggcggagg tggaggcggt    109620
ggtggtggag gtgccaacgg agttggccta tttgacgtag aggatggagg tggaggcggt    109680
ggtggtggag gtgccaacag agttggccta tttgacgtag aggatggagg tggaggtgga    109740
ggaggtggag gtggaggtgc caacgaagtt ggcctttttg acgtagaaga tggaggtgga    109800
ggtggaggcg gtggaggtgg aggtgccaac agagttggcc tatttgaagt agaggacgga    109860
ggtggaggtg gaggtggagg tggagcggga ggtggagggc ctttggaaag ggctgaaggg    109920
gtaagcgggg gaggtggaga aggcgggaa  gttacacaaa gcaagggtga acacttcaat    109980
gacatgaaag gggagggggag gggtggagga ggagctgata aattacagtt agatggaccc    110040
cgaggaggag gaggtggagg tggaggtgga ggcaaggcac ttctagaagt agaaaacgta    110100
gggacagatg gtggatgtgg aggagcagaa gagcataaaa ggctctgatt aggaagtggt    110160
ggaggtggtg gaggtggcgg aggtcctcta gaaaagctat caggggaagt tgaagaagta    110220
ggttgtcttg gcggtgaatg ttctctatgg ctaccaattg aaggtggtgg tggtggtggt    110280
ggtggaggtg gaggtggagg tgatctatta gaacttgcaa gtggtggaag cggacgagta    110340
cgttggacag aagaagggac accaattata ggaggaggtg gaggtggtgg aggaggcgga    110400
ggaggtaatg agacctcctt gctaggagaa ccaaacagag agggtggtga aggggagat     110460
ggagctgatg attgagtgac ttttatacta gaaatcacag aggcaggtga cggaggtggt    110520
gaaggtagcg gagaagaaga ggaagtcctt gtatcgcaaa tttgaactcc ctttaaacgt    110580
tcaggagaaa tggcagtatc caattgacag ttactttcag aaagagactg aacaggacca    110640
agatctgact ttgaaagctt catttgaccc tcagaaatct tgggatcaga agttccatca    110700
gaagctgaat cctgttcatc taaaaagttg acatctgttg tattagcata actaatacta    110760
ctagcttct  ctgagtccag aaaatccaaa ctgtcggcaa tgctcgatgc attatttct     110820
tcttcagaat caaatgggga tgaataccca ctcatcctac tttgcaaaat tgacaaatct    110880
ttcatatcat tcagcaccga tagctgttta acaaccaca  acgcagcatc atcaccagta    110940
tcaacccaat cagcaccact aaaaagttct tgtaccccttg aaaaggcttc aataggaagt    111000
ccaccagtct cctcaccatt gagagctgca gtgggagctt ttagtggaga tatgctctca    111060
acatcaccaa ataaaacctg caaagcagaa agtataagtt agaggagaaa tatgaagagc    111120
aaaggtgatc caataaaaca aaactaatca gacagtttgt aaataagtat tcacctcagc    111180
tcgaaagcct tttggatagc gtgccttttga atcccataga atatccaggt tatcgcagtt    111240
taacatcaaa atgttagagc gaataaaagc agtgttaaac acaatacgga acatcatgac    111300
ttccctttca ggatccaggt ctaagtggac acactccaaa actacatctc cttgcaccaa    111360
acactgaata tcaatcttga tgacatcact gtccttctgc aaaacaataa caatcatgtt    111420
gccacagagc agaattgaag aagacaacaa acaagatgca gtgatagcaa ttttcacct    111480
ggcgataatg tcgaaggctt ctacctttct tcggcatgga gtacaacata tgagttgaca    111540
```

```
atccatcctt gctgagaagg ttccttccaa aaatgcgcac aattggccta cacccttttt 111600
gattgtcaaa tcttggaatg gcacgaagaa tgaggcaatc cagagaaaga gcttgttcag 111660
gaggaggcca ctcgggagat atatttcttc ttgatatata ttgcaggtaa cgaagctgag 111720
aagggaatgg gttcaaaggt gacaacaatt gcgataaacc tttaggtgcc tcacgataaa 111780
ccatctcgag agttttctc tctccgcttt gtaactttct gaaaaccaag aaactggcga 111840
aaatgaaggc tagaagggc caaccacctc tctcacagtg taacaaaatt acattgttat 111900
gattttgaag agagagccaa ctctcacaga tacatagaaa atgatgtatc aatgacaatg 111960
gcagtacagg acagccttca tattgtcttg ggtaatccat tacagtcaca tcatactcgc 112020
ataaaatctc agcaaactgg ctccttttct cgccttctct gaaattgaaa gcaagaaagg 112080
aggaatctgg aaattcttca tgtagttcat ttatgatttc gtgcaagtaa agctgataaa 112140
ttccctcagg cagtacttca gtcgaaaaac aagaatcaaa aactgcagat attcaacata 112200
agataaaaag atgttgagaa aactacaatg cacttccaat gttcaataaa aaacacatta 112260
taaagtcaaa gctagttcct ttaccatata ctctatcatc aagttccagc aacccatctg 112320
ggggccttct atagaaaaat ctactcaaca gcgacataat actgagccaa tatatcacct 112380
aaatttacct gacatcaaag aaattcaaac ccatttcat tcctttggtg tcccaatatc 112440
aaagggtca gagaatcagc tcgtacaaat tcaagaaaat gtgaaattca taagaagaac 112500
tcaaaattaa tctcaaattc agaataccca caaagctaaa aagggattga actatatttc 112560
aggcgaaaaa attggaactt gacaccaaat aaactacaac aagactgaaa cacacacaaa 112620
actcacatgg aaaatatttg catataaaac accaaaaag gaaatctttg aactgaagca 112680
aaccgacaga agccgttgag gaaggattcg agatgtgagg tgaagaaccg acagtgttgc 112740
cagtaaagtt ttcacctgcg cttccgatt ttagtatgaa ttttttttt tttctgatta 112800
cggatttgaa ctctttggag ttcaaaattt tgggaacgaa aaaaagggg ctgatttttt 112860
attttaacat atggttgttt tcaatttttg aaattacaga accaacccaa tacttgtatg 112920
gataactttt agttagtgtt ttattttcga aaactctacg atgaaggatc gatcggaaat 112980
aatttttatt ttctactcat aattaggaat aagattataa tgtgaaatat tcaatgatga 113040
ttaatgaata gtgttatatt taattgatta ttattgactt gaataataat aaaaatataa 113100
attacaaata tatataaatt aaatacgaat gagtataata taactttctt aaaacaattg 113160
agtgcgatgg cttaatggtc aagatgaata tattgtactg gatgatcatg tctttgaatc 113220
cccatttata tcagggtcaa atacataaag agatttctaa acttgttggg ttttttttctt 113280
cacgtacttt aactacgtca ttttttctatt gaatcattga accatccaaa aatttattcc 113340
tttaagaaca ttgttggttt attttgatcg gctattctat tgtaaatgcc tttaattggg 113400
ttcgaattgt aatgattttg attgaaggaa tgaagacaac ccgttttagt ctcatttgtt 113460
ttttaacgtc ttcaaatgac ttaattaaaa tacaattatt ctcgaacatt tttactatca 113520
attggactaa tgatttctga aacaacatat atatcctcta tcaatccccc tcacaaatct 113580
ggtttcacat cagacaacag tgtttattta aatggaacaa attataggg tttaatgatt 113640
caataggaaa atgacgtagt taaagtacct gaggagaaaa aacacaagtt tagagatttg 113700
cttatgtatt tgaccttaaa tcagctatcc aacatgcact tttgagcttt ctatgggtgc 113760
gctaatactt gtgtgtcaac ttttttaaag atatatatga ataaatatat ataacatgat 113820
tttttttttg aaattaacag gtatacgtgc acctcattta tacatgttag gtctgtctct 113880
aaaatcagat ctacaaagtt acatcgggta tgttttttaat attattgtgg ttgtttgtaa 113940
```

```
taaatatttt aattagagtt gttcaaaatc aaatcgaaat tgataattcg aattggaaaa   114000
aaaagttatt gatttatcag tattgggtta ttgatttagc gatttagtta agggtctgat   114060
tttttttgtt atcgggttat cagtttgaag ttttttctcc cgatagtaaa ttaaataatt   114120
atatttatac cattttatgt ttgactcgaa gtttgctttc ctacttttat ttttggttat   114180
tcaatgtatc tgcttttgag taagatgtaa cttgtgaact gatgtgcata gtttatttgg   114240
tttgtcacct tgtttctaag tgattttaa tataaatttt tgtgtcaaat cttaaccagt    114300
taaactgata accaaatcga tagcgataaa aaatcgataa gccaatatgt taatagttct   114360
ataacgattt aacatctcta cacactatca accaataagc caatcaataa actttaaaac   114420
cgaatcgaac agaccgatac gcagagctaa ttctaatgac aataatcgat tgtggaatct   114480
atattaatgc atggctgcat tgaactctaa attgaagtat cttcttttct gcttaaatta   114540
cctccaaaag gtaccaatga taccaaaatt tccaggcttg gttgatgggc caaagtgacc   114600
atgtgatcgc cttattggg cttttagccc agttaaactt agggcccaat gacgcatatt    114660
ctatcagcaa caagaagtat tgttggtgac tagagaattt tagaatgtaa ttaaactatt   114720
tttggccaac aaaaaatata aatgatatac aatatttaat ataaaactag aaaaagttaa   114780
cattattcct caatgagtat gattcgaaat gcatagacga ggctatatac aaaaatagag   114840
gaagattgga tcgcctattt gaatctggtt tggtgttaga aattcgtaga taaatcgagt   114900
tgaaaaaaac gttgtgacac gtgttttacg tatgagagcc aaatgatatg gactttgatc   114960 aactttttcaa gatgtattt ttcgtcatat tgatattgag aaagattgca atttatagta    115020
ttgtcctcat tgttttagaa aaccaaaaga ttttaagttt gaagtataga attaatccaa   115080
tcaaatttag ttttgaaagt caattaaagt gactctcaaa aacgcaaatc atgataaat    115140 tttgaaataa attagggtgt ttttttttatt gttctatctc atttgtttga aatatagtat   115200
ttagaaatta cgcgaacatt ctaatcgtta ttcattgagt aatataccctg attataagac   115260 gattaatatt gagattgtga gacaaaagga agaaaatata aatttatagt actaaggaca   115320
agggcggacc cacaaggtgt caagtcgggt gctcgaaaca cccattaacc gttattgaaa   115380
tatgtatatc tatgttaaaa tcgatagcta tttgtataaa attaacatag agcacccaat   115440
gaataaatca tatagttggc ccaatggttc tagaatgggt acttaagact cttttaatgt   115500
tattgtacca aggttcgaat tccgccactg actaaggatc acgatggagt catggagatc   115560
attatttgga taatataaca agcaaatgca acttaaattc aaatttcttt tattcaatta   115620
caattaatta aattatgatt aaatcatttt ataagtggag atcattattt ggataatata   115680
acaagcaaat gcaacttaaa ttcaaatttc ttttattcaa ttacaattaa ttaaattatg   115740
attaaaaaat cattttataa gtaaaaatac ttctataaaa ggaaattta tccttaaaat    115800 tcaaatatta aacttcaaat taacaacaca tgcaaccttta tacaaaacaa atcaactagg   115860
atacctcccc caataattaa attggtggtc aataaaattg tactccataa ttatgaattg   115920
tagttggcaa taataaatat gcattgtatt gtcctcatcg actagtcaat ggaacattta   115980
tgaaaccaaa aaacatgaat caatgttctc tacttgcacc aaagttttta tgaatgagaa   116040
ataatattag atttgtccgt taaggatttc aaatgtttta aatattgtac ttggggtata   116100
aatgagcttt ttttatcag taaattttta tcgtatatct gatgattata gatctccatt    116160
ctcagaaaca tcacttgaaa atagttgtta ctccatccgc tcacccaatt ataacatcga   116220
tcttaataaa aatacataaa aatcatttag ttcaaatggt ttccctcact ttatatttt    116280
```

```
atcattttttt tctattacca attaattagt tttgttataa aatcgttgat ggtcaacaat    116340
tataactcta tcttgattgt catacgattg ttaagatgga gtttcagcga ggttaaaaat    116400
taactcgttg gtataattat gcattattta aattttattt gagatgattt tatagattaa    116460
tggtaattaa tttagtcttg aggagtaaaa taaaatcgtt ataggttttt gagtgttcct    116520
aacatcagaa tggtgacatc attatgaagt tataaagaca tataatataa tttaaactag    116580
gaaaaaagat aaatatcctt ttgaattatc gtaaatagta tgtaaatgct ctctgtcaat    116640
tttttgggac actgatgctc ctgtcgttca aaaactagaa ataatatata ctctttacac    116700
taacggacac acacgtgtca taatcttatt caccaattct acatttattg acggagaaga    116760
ttgcgccatg tgtttctatt tagtcttcct ttagagttaa cggcatataa actttagttt    116820 ttttttttaca gcaggaacat caatgtccca aaaatatgac aaagaatatt tccatatcat    116880
ttacgatagt ttgagatata ttttcccttt ttccatttaa actaatatgc aaaatacgat    116940
cctgctcctc tttatttctc ttctctccat tttccccaag tttccatttg gattaatgac    117000
acatgtcatg ggttaaaata aatggttaaa atttaatttt tcaaagtaaa cctctaaaca    117060
tgatttagtt aatatatata ttatatatca agtatcaaaa ttttttataat ttcacaatct    117120 tagcaaacat attatttttgt ccatattatt tatgtaaaaa gttttcttcc tataattttt    117180
ttttttcgta ggatctttttt tatttttttat tttataaat attttaattg taatcttttg    117240
ttaaaggtat attggtccgt gattaataaa ttacctagag ataatcaaat cattttgaca    117300 aactaattt aatttcataa taagattaag aatacggtga taccaagaca tacgatagat    117360
taattatagt tttcatactt ctattcagtt gcttattctt ctaattagat aaaaaaaaat    117420
ttatataaag ggaaaaaaaa gatcctacgt aaaaagaaat aataggaaga aaacttttttt    117480 tacctatatt tatggacaaa ataatatgtt cctaagattg tgagattata ataattttga    117540
tgcttgatat ataatatatt tattaactaa atctgtcacg acccaaacgg gtcgcgagtg    117600
gcacccacat ttactctcct atgtgagcga accaaccaat ctaatcccaa catttcaacc    117660
ataataaaca gaaataaag cgaaagactt aaaactcatt aacgaaatca attaataact    117720
tctaaaattt aatattcatc atccccaaaa tctggaagtc atcaccacaa gaacatctat    117780
cctcaaaata ctaaatctaa gaatgtctag aaaactaaaa taataaacag ctagtctatg    117840
ccgaaacttc aaggcatcaa gacacacgaa ggaagatccg tcaagctgct aaagcgttag    117900
ctcaccccga gatccgacgt gatgaagacc ggctagagtt acggttgagt tgaagacgat    117960
gatacgtttg tgcgactcca caaataacaa agaaaacaat tacaagtagg gtcaagataa    118020
aaaacagtaa tcgaaagtag tatcattgcc aactcaaaat agaaagcaat atatttcaga    118080
taatatcata aaatcaacta atattcttaa caggtgatag caacaagtat aaaactcatt    118140
tataacaaac caaccacatc catgaggact caagcctcca taccatactc tttagggaaa    118200
caagttcttt ggattgacta tattaacata tttcaagatt cattatcttt ctatctccgg    118260
tgtcggaacg tgacaccgat cctcatcata ctatctggtg ctctaacgtg acacccgatc    118320
catattctat cctgcgtggg aacgtggcac cgatcctcat tctatctcgg tgccgaatgt    118380
ggcaccgatc ctcattctat cccagtgccg aacgtgggca ctccgatcct cattctatca    118440
cggtgcggga acgtgacacc cgatcctcta ttactatccc ggtgctcaac gtgacacccg    118500
atcctctaat ctcattactt tagttcatca agccttcttt tataccaaga catcatcatt    118560
aacaaagtaa aatttaggat ttaagattca acagcctcat catgctagtt tcatcacaat    118620
tatatatata aactcatcat gctagtttca tcacagttat atatataaac tcatcatgca    118680
```

```
tacacacaat taagcatata gaagagttta caatactacc caaaacatat cattcgctat   118740
taagagttta ctatgaaata gcataaacca taacctacct ccaccgaaga atcgcgatcg   118800
acaagctatc ttcccaaagc tgcgttcttc ctctctctct ttgttctttc tattttcctt   118860
attcaaaccc cctttcttt taccctaatt agcatataat taagtataaa agatgataaa   118920 atacccact acttgtttcc aaggttatct cttttaaccc ccaagtaatt gaattattaa   118980
cattaaacca ctaactttat aattataagc aggaatagtc caaaacgtcc cttaaaatat   119040
ttaacagaaa tccgacccat tcggtcacgc gttttagacg gcccgtcgtg ctgcgacggt   119100
caaatctctt tgcttccgta caaagttcgg gagactcaat tcattaaaaa gtccagcggc   119160
ggcccgttat gctcggagac ggtcgccccg ccacccgtcg tgacgttcga tcgatctcgg   119220
tacccaaatt tttaaattct aagtgtttta gaacgagacc cctcgacggt ccggtcgtgc   119280
ccatgacggt ccatcgtggg atccgtcgac tcaccagctt tttccggaaa taaaaatcac   119340
gctaaaaacg actaaacagg tcgttacaaa atcatggtta aaggtttact ttgaaaaatt   119400
aaatcttaac tatttatttt aacctataac atgtgtcatt aatccaaata gaaacttgaa   119460
aaaaatgaag agaaagagaa atggagagga gccgaatccc gcaaagtaga aatatatttg   119520 accccctgcta ttaactatta aaacgttctt gtttcatttt gaacttgcaa atatctgtgg   119580
tacactacaa atttaagggt tataatatct attaataaac ctaattagta agggctaatg   119640
agactttaaa cacaataggc aaatgacagg taagccctca gattttgatt ctcctatatc   119700
acacatgacg ttgtcagagg tcaaaactgt cattatatgt ccaaaatacg tgagtatgat   119760
tttttagcag caagaaacca aaaaaaaaaa aagagataca gattttggca atttatacct   119820
ttttgaattg aaatgattac acacctttt cacattgtca gtttatttc ttttggggt   119880 ctaaaagttt tggtttttga aaaaaaaaat atccgttgat ttaattttgg agtaatttaa   119940
gggggatgtt tggttatgaa aatataaaaa tattcatttt atttaaaaaa aattaaagtt   120000
gaagtttgaa ttgtgttggg ttatattttt tgtaaataat atgtataatt ggttatgttt   120060
ttgggtgact aaaagtattt actttagaaa agaagatatt tatgtcaaga aaataagtgt   120120
tgcttaagag tagaaaaata ttattttgac aaaaaaaatg cacttaaaaa cactttgaag   120180
aaatgcaatt aaacactaat tgtcgtgtaa gaggtcttta aaaattaatt ggtcaatgca   120240
ttatgatcac aaaagtattt ttaaaaaatt aaacctttac taaaataaat taattttaga   120300
aattcgacct aacaagtcat aaaaataaaa taaactttta cttatttaat gtttgaaggc   120360
cattaacaat tgaattaata ttgcttttc aataaagatt tgattttaac caaccctcaat   120420 taataccaat taaagtttaa ttttgtaaat tggattgaag ttgcacaaat gagtatattt   120480
agttatgtac taacatcttc catattaatt ctcctaaatc tttaggtaca tattttcctt   120540
ttccatattt ttaacgattt tactttctaa gttttaaact ttaactttt taaattaatt   120600 agttcaatct tcttcttctt ctttttttt tggagggaca taatttgatc gatctattaa   120660
tcataaaaca tgtctttttt tttgtccaat attatatgaa ttttatgaaa taaatttatt   120720
ttagaacttt ttaacgtatt ttgacttta gctttattca atccgccttc actgacaaaa   120780
attccaaata aaaataaagt gctaaagtat aatttatata ctctctctgt tttataaaga   120840
atggtctaat ttgacttgat acgatatttc tcctatttta taaagaatga tctaatttga   120900
tttgatacga aattaaatat acaaccctta catgccacgt ggaaagttat tgtcagaaaa   120960
aaaaaattat tcttttgat atggactata aaaaaaaggt cattccttt taaaacgagc   121020
```

```
agaataatat atatcccaaa actttattat tgagaaagca tctaaaattt gatatggcaa   121080
ttgcatgaat gtggagtaaa attattctaa tacaccagat atgatgccat gcagaaatga   121140
tgtggaaact atatatagca caattcccaa tgaaatttaa tgtactgtct cataactata   121200
tagtataggc tttcctctaa ctatacataa agttacccct aaaatatagg ctagctaccc   121260
ttctagcttt cccccaaatt ctaaattaga acaaaaaaat atttctacat cttttttacag  121320
tttttagtcc ctttcactct tgggggttat tggaggtaaa attatttata gtaatttaga   121380
attttatatg tataaattat aaaaacttat atttgtggca tctttggagg taaattatta   121440
atagtaattt agaatttat gcgtatgagt tataaaaact tatatcattc atataaggta    121500
gaagatataa taattaaatt ttatataata attatctgta ttactaatat ttgtataact   121560
ttaatcaatc attctttaat gagcaatttt cacatataac aaataaaaaa atcatatttt  121620
gtatgttata acaaagtttg cttaattaag gctccataaa gaacatagaa acatataatt   121680
cgctatacat atacggttga agcaaattgt ataaaacgaa gtgtataaaa caagaaagag   121740
aaagacatca agagaatcgt ataaaataa attgtattat tataagtgta tagaacgatt    121800
atatacaatt tgaatttgta taaaatgaga aatagagaaa gacaaaagag acttgacagg   121860
gaatatacaa ttgaatcgaa ttgtataaaa cgagaaaaga gaaattagat acaatttgaa   121920
aattgtataa aacgagaaag agagaaagac aaaagaaact ggtcagatga gtattttttat 121980
tgtataatta taagtgtata ggacgaaaat atatgtactt gtatgtgtat atacaatttt   122040
ctcacgcttt atacaaacat aaacacaatt tatacattta gcttctgttt gtataagtga   122100
gaaaggcgag ggtggtgagc gagatttggg agagtggcga gcgagatctg aagaggaga    122160
gagagggaa caaaaatata tgtattatac aatttctct gctttaaaca attagaaata    122220
atttttatat acttgtgttt gtataaaaaa taaggaagcg agtgagagat tagaggaaag   122280
tggcgagcga gataattggg agagaggcgc ctggcaattt ttcgcaaata tttgcgatgg   122340
agcacaatta tatcaaactc taactacatt tattttagat tattagtttg ctattatata   122400
taatttttctt tttttttaatt gtttagtact tgaaagttga gtaagtgttc taacccaaaa  122460
tgagttatat ttatacactg atactcctat ttaaagttta gtaatagtac ttatgtagac   122520
cattgtataa gttttttaact ggccaacaat ctatttcata caatatatttt ggacttacaa  122580
acactataga acttatcttt aagtattaaa gataattttt tatcacataa gcaggagcct   122640
ctatttgatc tatttcgctt taatataacg tgcaatatcc tatttgattt tcttatttac   122700
tttaattata gactcgagat ttgtaaaact tcttattttg aggataacta gtgtatcaat   122760
atcactttcc tatttaacctt atgtgacgcg acacataact tccatttaat gtactttctt   122820
ttagtcccgc tcatccaaaa atatttaaac tctttggtcg gtctccaaat ctcttatata   122880
tcattaattc aatagcatga ctcatcaata aaatattata tcatctacac ataacataca   122940
ttgtgatact tccactcgaa tatgtcatgt taattcatcg atcatcaaag caaataaaaa    123000
caaattgaga actaattcct agtgcatccc atctcgattg gtatcaaggt cttttttcttt  123060
aacagtcctt acttagatct tgactccatt atacatgcct ttaattactc taatatatat    123120
cgtaattata tttctagact ccaaacatct tcgtaaaacc tctctcataa tcaccatata    123180
aataaaagat aactcaaact tgacctatta agagttgatt ggttgaaatt ccatgttaaa    123240
gatctgaaaa aggccttata taaaaatggt cctttgtaca gtctgttgat tctgattcca    123300
aattgtttat gcctaaaaca aacatgatct aaatatttaa ttaaaaggtc tctaattcaa    123360
tcaagatcca ttttgtagtc aaaatatata ctattttggt ggaattttgg acataagaat    123420
```

```
taatgaaaaa tagtccatta tattttttc atagttaaac aacacactt atactacatg   123480 cctatttttt gctagtaatt tcgcctaaga attaaaatta aaagtgctaa ttaattaaga   123540
cattaagctg taaaaatatt taaatatgca aaggctaatc attaatgcaa aaacaatagg   123600
ctccccaacc gcactttcat atataaatag caagaaggaa ataataagta aaatggataa   123660
aaatatgata acgtctagat acacaaagac tatcttattt gaaaaaattg tttatataat   123720
agcaacctat tagtttaaat taaatgttat aaccatagtt tgatttaact gtaactctta   123780
ttaaattctt gttgttcaca tcccgttcac cactctcact cgtctctcca ctttatagaa   123840
acacaaatgt atacattgcg tttgtgtttg tataaagcaa aaaaaattgt atatacaaaa   123900
ataatgcata tattttcgtt cgatacactt atgattatga aaatacaatt tttccttgcc   123960
caatttcttt tgtctttcta tcttttcgt tttataaaca caattatac aattgattct    124020 tttgtatatg tataccgaaa catattatat aattttttt ttgtatataa gtaacgaa     124080 atatccatag caaacataaa gtttgctata aagcgtaatt aatgtaaact atagttataa   124140
cttacaaata taattttgt atttcttata tgtgaaagtt gctcttttt ttcaagtgtg    124200 tgaataaatt aatacttaaa gtatgtaatc acttttaatt gggaaaatgc ataagtatcc   124260
caacaaccta tgtccgaaat cacagagaca cacttatact atactaaggt cctattccc    124320 tatgaacttg ttttataaat aactttatac ccttttccgg ccttgatgcg ggagaggcat   124380
gagtgcaatt caatcttgtg gtgtattcgt ttgtagtgag tagggcctct ttctcgttga   124440
tctgacacta tcaaccacat aacttaaaaa aattgtcagc cacttgggg cccacaagag    124500 agtgtcacgt aggccgtaaa gggatagaaa gttatttata aaataagttt acatgggtaa   124560
tatgacctta gtatattatg agtgtatctc taaaatttcg gacatatgtt gaaggggtac   124620
ttaagcattt ctccctttta attatatgca ttaacctcta ttagttataa aaaaaaact    124680 tattttgaga ttgaagcata taatgaaatg caataacaca tattattcac atttttaaa    124740 cgttcaacat aattatatat cgtggatctt gctttcgaaa taactggaat cggcatgcta   124800
gtccgaaatt ctcgtggaag cttcattaga ggccacactc gtcggttagg atgacaacaa   124860
gatccactta tggccgagga actgggtgtt caagaagcac taagctggtt gaaggacact   124920
ttacggcaaa caacccagat agttatagag atggacaatc tttttggtta aacaagagat   124980
aaaaaaggtg caaaaactac tcttactttt atgttattat tcatgattgt aaagcattcg   125040
tgtgtgactt tacttctatt tctttgtctt tcgataaaag atgagcaaac cagtgtaccc   125100
atcagttagc tcaaattttg ggttttatga ctaatgctat aaagcggata atagatctcc   125160
atctttaatt caagatgtac tcaattttaa tttgatcaat aattaattaa aatgtttgat   125220
taaaaaaaaa aagaatgttc atcatactaa acctactttg taatgacata taaactaac    125280 tattttgatg aataatcaaa ctactcaact ttctttaaag gttttgaaga acaaaaatgt   125340
catattggct atttacactt catttagcta ataagaaatt gattttcctt tcttataatt   125400
ttttttgtgt ttttctttct cacctccatt ttttctgact tagagctcgt tttgattgat   125460 ttaaagaat agttttttaaa tcaaacttaa ataattttaa attaaaaaat aaaaagtaga   125520
aggagatcta cttttaattt taaacttatt ttaagtcatt tataatcttg tcaatcatat   125580
aaagtcaaaa ttctgactca aaaataagtt tgattaactc ttgagtcaat tcaaacaccc   125640
tcttagtttt aattgacatc tataacctct aattttaggt atgtacaaat aaatacttaa   125700
atttatataa aaattaaaca aattaatatt tgtgatatgt gacattgcat aagacaattt   125760
```

```
tatatcaacg tgatgtccta cctatattac gccacataaa ttacatatat attgatcttt    125820
caattttata tcgtttaaat tatacatata taccctatca aaaagtatt atgcttgttg     125880 aatagttcta acttgtaaca tccactttcc tctttccact tcaatcccaa aaacatttct    125940
tacaaatttg caaaaaacaa tgaaaaggac ttaattagca aaagagacca caaatgaaa    126000 gggtcacatg gggtgtgtta aaactcaagc ctaaaaagac tttgttttgt ttttgaatag    126060
atatatcact caaaaaccca aaaagcaaac cagtaaaagg tgaccccaaa agcttcccc    126120 acacacacac tgaagacaac tttccagtaa tggcggcaca tgaagaacaa caccaccatc    126180
atcaacaaca agaacaagag aaccccattt cctctttatc cttaaaaccc aacaataaac    126240
acttggagaa gattttctcc tcatatttgg gtctaagttt cgctgtcttt cttgggtctt    126300
taccaagaaa tgcagtttct ttggttggga gacttcagaa ccgtaacaag gagctaactt    126360
ttcagcttat tgatacagag gagcagttaa agcagctact tttcaggaga aaagaggatt    126420
caaaggcaaa tgcaagagtt gtggaaatct ttgcaagtca tagacatgcc tggcagcaag    126480
aagagaagag gttgttacag cagatcgatg agtgtgatga agaaattgct gagttaagag    126540
ggagagctga gcagtttgag acaatggaaa gtgagttgag ggctaatatt gaggacttga    126600
aaagggagat tagtgaaaga gatgaaatgt tgaactttat gagtagaagg ggttgtgaga    126660
tggagaatag tactagtgga gatggtggga gtgatggtgt tggagattgt tatgctgaaa    126720
tgggtttgag gtttgggaaa gttgggtat ctgaagggat ggatttgggg gtagggatgg      126780
aagagtgtta cttggctaat gggattccta atgctgaaca aatgagtggt gtttatggac    126840
agagtaatgg gtttaactca gaatacttga attctgcttc taagttttgg gctgaaaaag    126900
ctagtccttg gcaggtatga tccattcatt atttcttttt gggaactttt ttgttcttta    126960
tagttgttgt tatttggggt tttatagtga gtggtgtcat aatgtggtaa aaataaacgc    127020
aaaagtcctt tccaggatct tcatatgtag gaagaacttg gactaaagtt tgtcgcttta    127080
atgtttgtct tatatatggt ttttcatggt gaaacttatg aataaagttg cttcttttat    127140
ttaaccatgg gattgtactt taagtactac cacctgatat tctttctttt agtgtttatc    127200
tgtttgttca tcttgaggct gtggaatttg tttttgtatg tgatatctga tgaaacaaat    127260
gatccagagc aattgaggat gaacgaaatt aagtaataaa atgtttggct tatagggttc    127320
ttggtgaagt acaggccttt atgatctttc ttcacatacc tgaaaatttc acaggaatat    127380
ccacttctaa ttgtttctga taaagctgaa atgaaggtgt ttctccagga gtagttcagc    127440
gccaaattca aattgaattg tataatgatt acattctgag atgcttatta atgaaatatg    127500
tagtttagtg tgtactcagt gacctcctac ttgtcttgtg atttgtcttt attgttgaga    127560
ctcttgtctc tattatctaa aattttgaat ggtttgatct tcttagtggc tgctgaaagt    127620
tcaaactacc caggatatgg ttttctgttt actgaaagat aatactcacc tcaactgttc    127680 attttttaccc tatactggtg ttatggacca ctgcttgaaa accaggtcac cgttttgtac    127740
ttttcttctt tcaccgtttt cgtcctatta gaggtttgca attcttgctt caagaatggt    127800
cccctttggc tgaatacttt gcatgaaggt tggtttcctg gttatgaagg aagctcaaaa    127860
aaatgtattc gggtaactct agaaatccga atccgtttta aaacggaccg ttttgttggc    127920
atagaccact gtgcctctaa ataccaact aatgacatcc aattatatat ccccttttggt    127980 ttgggaagtt caattctggt taaaatggat ccgtatatca gcaaaggatg ggctgttatc    128040
agtcaacatc tagtccatct gttatatttc tgtttaagat tcatcaacct caatggaaag    128100
atgtcctctc cctttcttgt tgcaagctgt atcttgtcct tgtctgtctc tgtatcttat    128160
```

```
tttccaatta caatgttatc tttggtaatt cgttacacat ccttgaaata aagcaaatgc   128220
ctccatgaaa cttgaactcc ccgcggcctc taatccaggc actaatcttt cccgttcaaa   128280
aggatcactg gaacattttc ctatacttgg tggatgtgtc aaagtttgga ctaggtagag   128340
atcacacatt caatttatgg ctgtgttttt tgtcttttat cattttttgtc tttttatatt   128400 atatagaaaa gaagatctgg attttcttac ccttggtaca gtcacccttt tcatttattt   128460
ggaaccagag ggaactggag catttcacta tgttgtcttc aactttaata gaaaggctaa   128520
agaaaacaca caaccttaaa aataaaccta aattgcctaa ctattagttg atctatgcct   128580
tgtgagctgg ttaaggatta gtcatattta caatggttag agcaaaaaga gaaataaaca   128640
tctagatcac aatgcttata ttctagtttc aagcttgaat ggtaggagaa atgaggttct   128700
tttgactctt attcagcttc ttccttctat gtgagatgtc ctacctatct tagtaaaacc   128760
agcttggtat ttaggatgct attgggtctt aagaaaatgt gttttcttca tgcaggatat   128820
gcagtatgat tctggcgatt cacttcacca tttaaagcat tttgtagcaa ggtaaacatt   128880
ctgtgattag ttagacagat gcttagatgt ttgcattttg atgttgaatc aactaactag   128940
ggtgagccct tttgctttct cagacgggag gccccttgga agatagatgg tgaatcaaca   129000
ggagtctcct ccaaactaaa gttacttgag caggagctac tgaatttgga aaaaattggg   129060
aagactgatt tatctaaggt accatcatca acgcggaagc aagtgaagag ataccaagct   129120
ctagctggca agattgatga tttatgcaga agaatggtaa ttactgcatc tctgcaagct   129180
tattggttat aactttagta tatggatttc aaagcttgtt acatgcatgc ttaggttttct   129240 ctaagaatgg acaatagtct tgattacatc tgctaactca aatatttaga tgttgggtta   129300
tactcttagc ttgcacgact aggccttaca attagctttt tacctaacac aaacatacat   129360
ctgataatga tctccctccc tcttagcagc aggccagtga tccttgcgaa tcaaacctga   129420
gtcctgagtt ccggacccaa agacagaccg agttttttgct tgaagcattt cgacttcagc   129480
agcgtgcatc tgaaactgca cagaagctga tggtactaca aactgacagt ggaaaaagtt   129540
attacgggga cgaatttgaa gggcaagccc aactagccac taaacgatcc tttgactcca   129600
tccggaacaa cttaaaagaa atccaacgga atttagagat atggcttgcc agaattattg   129660
gggatctgga gggaatcctt tctcgagatg gtgcttctcg tgtaagggat tattacatat   129720
ctagatatcc ttttgttcaa tagttatgtc ttaacatgct cagtaaaatc atgattgaaa   129780
aaatgatgta taggtccttc ctgttatgtt aacaagatag ctccagctga atgaacaata   129840
tgaggttgat aagtccattt atgcacataa atctgcttca cagaagcaaa ctattaatgc   129900
taactagtac tttaaagagt gaagatttttt gacagaatta ttgctggatg tcactgttcc   129960
tgatctggat gcttgtcatt tactagtttt acttggtccc ggtctttctg gattaaaaag   130020
ttgaaaggat ggtgtggccc tttgcaactg gataaatgtc atgtctacac aaatctggca   130080
aacattaaat atttgtggac caagtttaca gccccatttg atttgaaatc agattgattt   130140
taagttgata tttgttttga tttggattct taagctgtat tgattattct taagcttagc   130200
aaatgagcaa atcatatttt catgaataag atatcaaaat attctaggaa gttgaattaa   130260
caagttatat agcttcatgt tactttttttt ataaataaat atttgtaatt atatgttatt   130320
ataaactttc aaatatgttc aataaaccaa acaacagtaa tactttcttt tgataaaagt   130380
tattcgcttg gtacaaacaa tttcttccgc tagattttct ttttttaaatt ttaaaattat   130440 gggtcttttc ttgtaaaaat taggtttctt tttctcacct aacctagtcg tggacatgag   130500
```

```
ttcataagtt gaataatctc taactaaaag gatagtcaag gatgtgccac cgtcgaacaa   130560
gaaggatagt taaggacact ctcaagcaaa ggccagtagc atgtactcta aatttagtca   130620
aagttccaat acaagctttt tgagcgccac tgtgactttg ataggtggaa aaataattaa   130680
aatttatctt taatatataa tactcccttc attttaccac aatacctatt aattgatgta   130740
atggcctgag gttataactt ttaaccatct ctgttctatt tatgtcaaga agtgcaatca   130800
ggttttgaac caagtagcta atcactcaat ataaagaaac caaattcaaa cttttttagg   130860
ggtttattat agaaggttca gacatactta tagcagtaat ttttttttcct agccaggaaa   130920 aggcatacac ctgctgttac actaaaatca aacaagccac ataatccaat tccaataaca   130980
atttaacaac atagatagat gagccttatg ctgaagcagc accttcttcc agcaactgtt   131040
tcaccttggt gatgtagtcg ttcatggctt catcggtgga ttttcctgtc atagatgcat   131100
gcagtgcaat tagttgtgtt tctcatacaa ccaagagaaa ggaagtcaat ctgaacactg   131160
ttgttagatc acatacctcc aacagccttc catgcatccc actttgctct gtctctcatg   131220
ttgaaaatgc caggacggcc tgcccataag aaagggcgta agaacaaagt gtagctagtt   131280
tgagacagca tgtacatatg cataagacat ttcaagcatt atactcactt gtgttgacac   131340
tgccaacggt ggcttgcttg taaagtccgt aagaataag cttgttctca ttggtggtac   131400
tctcaggcaa tgtcttagct ttctcagcat gtgcttcaaa ttcctcctga aacccaaata   131460
gttcagtaaa aaggtgtggt agctgaagtt acaaagataa atttccaggt atactttctt   131520
agtgataaaa taaggatgag aatccaactt aatagttgag atcgaaacta tttgtgaatt   131580
aagagggaac tgaacttatg gaaatctaaa atacaaattg agtgttcctt cattgggtaa   131640
atgaaaagtt tgcagttcag gatatcaaat atgtacgaat tcattgatgg actttagcac   131700
aagtgtacgt ttagcctagc ggtgaaaagg gttcattcta tttagccaac ccgagttcaa   131760
ttctcgcttt atttattttt ataacttgaa tccgcttcgt gaaaatccta ggtccgccac   131820
tggttagtga aagagtattt gcaagaatgt tagacaagaa aagcacaaca atacattcct   131880
caacattgta agagattctg ctggccaaca ttttgctttg acaatgttaa gacgcaaatt   131940
ttagacacat gtgttaatca tacaattctc caacctttttc ctcttctaga aatgcttcta   132000
tttacagatc acagtgaagc accaaaaaca tcctcagata atgtattatg acctcttcag   132060
tttgtttact ggtttgccct gtttgttacc ctacgattca accattacca ctcagtagcc   132120
tacatacttg tggtaacagg aatccttta gtgcgaggcg attggccaac caacaatttt   132180
tgtagtcact taaaaatagg tcagactaaa ttacatccac tataggttat gaacagcaga   132240
gaaatttcaa agacaggctg aacacaaagt gcacatttcc ttcaactttt ccccttcccc   132300
aataaaagaa atatggaagg gtgatgatag gttttttgacc aggaaacaaa aactagtctt   132360
ggactaggca atacaggata ggaaagagaa agaagcgggc gctatctcat attcaatttt   132420
tgctagacta tttacacaga agttggccaa tgtagcacca tataaatttg agaaagagcc   132480
atttgttcac tactaacatt ttgatggccc taactgcaca tgaactaata gtaatctgat   132540
tctaacatct cgttccctgg gtttagtcat cgacttaagc ttcaaagtat acaccatata   132600
tatagccaat aatatcaaca atctcaaaaa ctaaagaag aagacattca taagatgaaa   132660
tcttcaaaac attgttgaaa ttatggacta cttctgggcc agagacaata tatatgcctt   132720
ttgataaggc caaaaatgac atacacaaat ccggaccaaa gtactactca tctgccatta   132780
cattcgcact acttcttatc gaattcagtg cttacattgc tataattacc ataaatcttt   132840
caacaaggcc aaaaatgtac agcataattg aattcattat aagatctatt tataagatgg   132900
```

```
tatgccgcca ctcaaccaca gtatgaactg ctaaaaaaaa aataatctta aacatcaatt   132960
acaccaacag atcagatcaa tccaatcacc gagccttcac actaaataat aaccaaacaa   133020
tcctcacgta acacagcatc cacaaaatta cagcacaagc tgcacaatcg acaagaaaa    133080 ctaacagatc cgcaaatacc aattgcacaa acaacacaaa acccagaatt gaaaacgaac   133140
attaatcaca gaaaaatact tttcactgtc aaaaagatt  aacactcgct tcaaacaaga   133200
taaatacata ctgaaaggca aaaaaaaaac agaaatctaa aggggtttta aagaatttac   133260
cttcaacgcc attgttgtgg aaatctgatc tggttagctt gataaaaacg agagaaaact   133320
ggagatgtga ttgtgatgga gattgaagaa gaagggtggg tatatatata tagtggagta   133380
tttagcatag gaattaacgt aaaattcgat tcgattatga taatctaaac aagttgcact   133440
tggatcactt actagtcata gtggacccaa aaattgagta tagattatgg acctatacta   133500
tgtgagctcc acaac                                                   133515

<210> SEQ ID NO 2
<211> LENGTH: 15891
<212> TYPE: DNA
<213> ORGANISM: Solanum habrochaites
<220> FEATURE:
<223> OTHER INFORMATION: >Genomic fragment 2

<400> SEQUENCE: 2
tctgtggttt gatgctttca aatcacagca atcctctgta taattatggt ttatatttta      60
ggggttttca gtttacaaag tcattttatc cttccaatca ccaaaagtat tatcttggct     120
ctagtgacta gtaacaagtt agttttgtgt tatgtggaaa tttacaacag atcaccttca     180
tactgaggag ggagatgatc attttgtcgt ggctcggccc gtctgtcttt tagccaaatg     240
ctgcgggaga gagtgggatt ataacagtaa gtattttgtg ttttaatact gcttctatca     300
gctaatgttt catagaaatg acagtgtgaa tgaaattgca aattttgtgt ggtaaatagt     360
ttcaggctcc aatctagtga tcattttttc tgggtaatca gttaacaaga tctcttaag     420 cattcaaatt tatgtatggt aggtaagtgc acatcatgtt aggaccgaaa ataagcgggt     480
gtaaatgcgg aagctagcaa agcaaacctc gaaagatcac gagtaagaag ataacgagaa     540
atataccaaa agacacaaag atttaacgtg gttcggtcaa ttgacctacg tccacaaagg     600
agatgagcaa tccactataa atatgagagt acaaatata  gagagaaaca acctcaacca     660
attcactcgg aatacatggg aggttcacac aagtgataac gtatcaagct tgtgacccac     720
aaattctccc tctaaccaaa actctcaaaa ctctttaaga ctacattgtg aatgctgatt     780
aagttagaag gaacatgtct ctatttatag agtcctaaac ttttcatac  tagaaaaaag     840 attagtcaat tcaaaacctt ttcctaaaag gaaaacctat ttatggtaag aaatcagggc     900
aaataaaacc caacacatca tggtttgaac cgtactacat aagaaaagtt ctagtattta     960
aattgagaag gatagagggg aggggcctat ccttaaatct gttaaagttt tacgtactag    1020
cccaactatt tgtgcgcgtg aagaaaagat gtgacagctc cactatagat ttcagcacta    1080
ccatttagtt tgttacaaca ttttgctgaa attgagttag gatcttcttg agtcgcagag    1140
taatatcttc catgcgaatt ctctcttcag gcaaatcatt tgtacattca agagctaatt    1200
ccatgattga tttgaagcat ctatctttag aagtaaaatt ttcttcgttc agtgaaaata    1260
gattaatgtc cactacatcc accaatcggt ctggtaatga ttggcatatc catcttttca    1320
aggtgaagtc tccaacgaat agatcatcca cagggctctt tcttgtaaaa gtctccatta    1380
```

```
acaatatacc aaagctataa acatctcccg aagttgatac tttgccttca gacccatact    1440
ctacaaaaaa aataaatcac gccatcatta atgaaaataa ttaacaacat ttaaaatcct    1500
caagtgaact tgataataac atttacctgg tgccatgtag ccgatagtac ccaaagtctt    1560
ggtatgtgct attagcgtct cagatgtaag aagtttggat atcccaaaat cactcacttt    1620
tgccaccata tcttcatcca aaagtatgtt acttggtttc aaatcacaat ggacgactac    1680
aaacaaatgt cctccatgta aatactccac agcagaagcc acatcaatca tcacctttag    1740
tctttgagtt atatccaaaa ctttgtcagt agagtgaagc caacattcga ggttttcatt    1800
aggcatgtac tctagcacca acactttata atcgaaattt gcacaactac ttatcacctt    1860
aacaaggttt ctgtgtcgaa tgctacctaa aacttgacat tccacctcga aacttctaaa    1920
tgcaagttgc agttctgtat tgaataccct tatcgccaca accattccat ctgctagtgt    1980 cccctttatac accaaaccaa ggctcccccct tccaatcaag tttgcttcat caaagttgtt    2040
tgtcccttga gaaatatcat agtacgaaat cctcttatgt acctgaccaa atgtatcaac    2100
tagaggaagt tccgtactcc tttttcggca tttcagaaac caaatgataa aaatggttgt    2160
gactacaatt cctgaggaaa ctgatgcaag aacagaagtt aggactctgt tctttctttt    2220
tctttcaaga cttgtcactc tgcattgcat cacatgaaag cgtgatgatc cacataatgc    2280
agggttaccc atgaatgatt cagctgtaaa atttacgaat ggccctccat ctggaatttc    2340
acccatgagc ccattgaacg agacattgaa atgcatgaga tgttcaagat tcctcaagga    2400
cttggggatc atgcctgata gattgttgct agatagatcc aaatattcca acgaaaccaa    2460
atcttcaaat acttcaggta tggaaccatc taacatattc tttgacaatg aaaggctaac    2520
caagctttgt agttggccaa tcgtgctagg aatctgacca gagaactgat taccatgtaa    2580
atgtaatatc cgcaaactcc ttaaattccc catttctact gcaagagacc cattcagcaa    2640
attggaggcc aaagtgagaa ttgaaatatc tttgttcctc caaaaagttg atggaatatg    2700
ggaaattagt gcattggaat ctaagtagag ttctcttaaa gatgaaagat ttccaaaaca    2760
atttggtaat tcaccagtaa gttgattttt ccccaagata atttggtaca agttttccat    2820
gttacacaag ctagttggta taattccatc taaattgttt ttctctaggc taaatctttt    2880
caacttcctc aagttcccca aatctggagg aatagatcct ataagtttat tgtctcccaa    2940
gcttaaccac tccaggttcc taaagttact gatgttaggt ggtatttttc ctgtgatacc    3000
attttgaagg gcaatgaaat attcaaggga aaaggaccag tttcctgaac ctaaagatgt    3060
tggaagactt ccattaaatt ggttacctcc tatttgaacg gttttcatat acttgcaatt    3120
agataatgaa gtcaggaaac ttaactcgcc tgtagattga tcattcgtca attggtttat    3180
ttgcaagttg atgaattgta gctgttgtag cttttccaaga ttcataggta caggtccact    3240
aaacagattg cggccaaaat caagctggat aagcatggtg gaattcacaa tggaggtagg    3300
aatcagcccg gtgaactggt tatccccaag gtaaaggcct tcaaggtttg gaagagtatg    3360
gcctatgttt gagggaagtg ttcctgaaag ctcatttgct acaaatgaaa tcttttttag    3420
tccagaaatg ttgtacaaac gccttggaac ttcacccgat aatctgtttg gaccaagata    3480
cacttctttc aaatttacaa gatgttcaaa ctcctgagga attccaccat ataaactgtt    3540
gtcacctagg tctatcatct ctagatttga caaatttcca attgatggtg gaagaattcc    3600
caccaaattg ttccgtcgta gacttaatct tcgaattgct gataggttat cgatttcact    3660
tggtatatgt cctgtaaaat atatgtcgaa ttgtgtggtt actacactga aatgtccaat    3720
actgtataac agctttatag tcactaagtt actataaata acagaaactg ttagttgtat    3780
```

```
gccttttaaa tagttcagca atcctcacaa actgttttga tgtccttttg aagatgggac   3840
taaatggatc aacatggata attaggattc atatagcaga cacaaactag aattgagcca   3900
atgtagtagt tactgttgtt gtttgaaaat gaagaacaaa gagctatacc aacattttt    3960 gctactaccc tttgaaatgc aaatactaat ttcttataaa tgagttgaag agcaagtttt   4020
taaatatcaa agatctctag tgctacaagg tgagaagtcc agcaataaag ttaggtggat   4080
tcagttaaac cagaacatta taaatacctg ttatgttatt ccatccaaga aatagatgtt   4140
gaagttttgt caagttccac atgtctctag gcaagtttcc tgtaatagga tattacgata   4200
agttatatgt acctctcacg gcctatgatt gtttaactaa aaaattgttg caatctttgt   4260
tgtcaatatg aaccaaaagt agcagagaaa gaagttggtt ccgttttttt ttacctgtga   4320
agtggttata tgacaaggac aaatatatta gctctttgca tttgtctaaa ttgcttggta   4380
gttggccaga gagttgattt cttgctattt gtaatccctc cagccgcgga agattatggc   4440
aaatgtcatt cggcaaagtc ccagatagtg cattataaat caaattgatg accttcaaag   4500
aagagacatt gaagatagac gaaggaacag atccaaagag atcattttca gaaagatcca   4560
acaactcgag ccttctcagt aatccaagac tttctggaat ttgacctgtg agattattca   4620
ttgacaagga caagtgcttc agcctcctca aatagccgag ttcatcaggg atttcaccgt   4680
tgatgctgtt gttgccaatg tccaagaaac taagaaagga gaggttccca atatctgtcg   4740
cgattgaacc tcttagtctg agaccattga ggtctagtga tgtcactctt tgatgccttt   4800
tactgcaaga tatgcctatc caattgcaaa cgtgagtccc ctttgtccag tttttcgaca   4860
acattccatt tggatctgaa gttatatgag ctttgaaagc taaagagca gcctcatcag    4920 ttgaaatgtt cgatgcatta gtattcgaga ggtacgttaa caaaactagc aatcctataa   4980
tcatagccac ggaaaccgtt ttgtgcaact tctcttgcag ctatttgtgg gggaaattta   5040
taagtgcctg atttttttatt tttcaagtga cattaatata tatttctata attaaaggca   5100 ataagaatc atgtattagc actggaatat atagaatcta gagttcaatg tcaatgatca   5160
acatatatac gtaatatgtt ttgagacatt tttttttaaa ttgaatgttg ctgaacttga   5220
ctgcaattca ttgctgaagg gaaatcattg gttgtgggat tctgtagtga tagtaaaata   5280
atttacttgg atttataagc cttgtatatt cattattcaa gaatattaaa gactaaaatc   5340
atgatataat gtcatcattc gaatgtatat agcctccgct gaatagatgt ttgacaaaag   5400
aacgtgaagt gttacggtca aattagtgaa tctaacgtgt aatgttggat ttacgtgaat   5460
tcaatagctt ttattcctat cttttatata tattaagtaa tttattaaaa atctaaaatt   5520
atcgtatatt actatcttgc agtctgtgtg agaatactat tttgataatc gtcaaataat   5580
tatctataaa tttcaaatct tgaatcacac ttatttaata ggaggaaatg gtaaaaagga   5640
agtgaggttg acaagatctc aagactcttt cttaattttg atgaaatgtt gtaaaaactt   5700
gaattagtag attgcatggc atcactatac acgtgtcagt ctagtgttta gagaaattta   5760
atcaaagaat ataagttata atatatatta tccatgagaa tcttgagaaa gattttctgt   5820
atctgtctga tgaaatagaa attggagttt cccaattcta tattacttgg cttattctaa   5880
cttctagtgc agaatctgca gatggtcaat attctttgaa tatataatag caaatttgat   5940
tattagtttc attttttaaac tattgatagt tttaaaaata tttattattt aactaattaa   6000
atttaaatat atcctcgatc ttgcaatatg agagaaatac atctctaaat tctttccttt   6060
tcaacatttc tttcgttttt ctaattaaaa gcctcatact tatacaagag tttgaaacca   6120
```

```
cttgatatgt cacgtgacaa aaaagaattg tatctaagtt tggctactca tgtagagaag    6180 tattttttaaa gcggtcaata tctcaaaaga gaaacaaata aattatgtat ctacaaatta    6240
taaaaaaagg agtctacctt tattgggaaa gtcatatgca attcatgtat gctttcctaa    6300
ttggggatac aaagtcaatc ttgttaaacc cctaaactat tacaatcatt ttaagaatta    6360
tatatatatg tactatttga gtgttgacaa aagccttaaa ttatcataaa actcatatta    6420
aaatatctct tagagtaata tgacatgtca tgtgaatatt atgtttgaca aactcaattt    6480
caaagagttc aaagtggtta tacacgtagg ttttagaaaa attctaaact cactgttttg    6540
tgactttcat acctaaaatt gttaggtgtt tatataacca cccctgaatt ataccatgaa    6600
attattgtgc caggtggcct aatttgaaat ttaatagggc tgaattaaga tttttgaagt    6660
caattaaaga aaatatttt ttaatttatc ctgaataagc ttgctatttg agggggtttga    6720 gaaatatcgg tagggcggta catgggctaa taaaattgat taaaaatata atatgatatt    6780
aaatttaaaa ttaaagagaa tccaaactca aaacaattag gttaatattt ctatttagct    6840
atttatcttt gttatcttga aaaaaactta ataaatatta taaagataat tttatttgtg    6900
gatttgatta acaagtagta acattaacat catgtaatat tgttttgtgg atattttcg    6960 ataatatttt ttaaattata atttataatt taatttaata attataaaaa aataaaaaaa    7020
aagtgggcca cggcaagttc tgtagctctc acgtacttat gggttggacc gacccatttt    7080
ctgacccata caaaaaatga gctagcctag cttaacccat aaaatatcaa aacatgtatg    7140
gattagccca ggatgagata tgttagccca tattgacagc tctattccca catcaacaag    7200
gtatttaata tgtcaacttg aaaagaaaag atattccaaa attaatctgc ttatactcta    7260
tcaattccat atctcactta gtgaaatttc gcagaatata tcgttaata tattgttgtt    7320 gtcgttgtcc tctcccatca ttctaaattt aagaacatg caatgtaaga ggtaatttag    7380
aaaacttagt tcggccgtag aagaaggatc atctgtaaat ttattcctct gcaagttgat    7440
gctctgttgg aaatttatta ctacaagata gattggttaa tttgaccgta aaacagttga    7500
cattcttttg tcaaggatct attctgggga ggttatagat atacatttga ataatgacat    7560
tgtcaagtaa attatttaac tgtcaataca gaattccaca accatggtt tatttccctt    7620 tagcaatgaa ttgcagtcaa gttcagctag caatatacga ttaaaagttg tttcaaatca    7680
ttggtattaa ttagataagt attgactcaa ttacaagtat acacacagta tatatagaat    7740
ggcgtttgaa aacgaaaaca taggcacaaa tagcagctaa agaagttgaa caaatccaaa    7800
tggttgcgaa gactattatt atagcatgcc tagttttgtt agcatgcctc tcagttacta    7860
atgcatcaaa cattacaact gatgaggctt ctcttttagc tttcaaagct catataactt    7920
cagatcccaa tgaaatgttg tcgaaaaact ggacaaaagg aactcacatt tgcaattgga    7980
taggcatatc ttgcagtaaa aagcatcaaa gagtgacatc attagtcctc aaaggtttaa    8040
ataaatgcac caaacttgaa gttctgtcct tgtcttataa caattcact ggtaattaac    8100 taacttgtaa acttttcatt tactaatttc ttcttgaatt aatcatcatt tttgtgtgtg    8160
tctgtcattt tataattgat aggaaattta ccaagagaca tgtggaacat gtcaaaggtt    8220
caagaactgt ttattggatg gaataacttt acaggtacgt gattcttgta tgtattaaat    8280
cttgaatact cttcacgaag ttcctaattt cactagatat agtcaatttg tgcattgtct    8340
agtaacaaac aaagattaat atatgttgtg gagaacattt tcgaaagaca ctctatgtct    8400
gatctttagc atgataacca tgtacttatt ttcaaaatga atttgcagga aatataccaa    8460
atgaaatgaa cctaccatct atttgcagga aagttaacaa agcttgagca tctcaactat    8520
```

```
ctgaaagtct cttacaatga gttatcaggt gaaataccag atggagggcc ttttggtaat    8580
tttcacagct gaatcattca tcggcaacga agagttatgt ggaccgccta gattccaagt    8640
caaggtgtgt gaaatccaga acaacgtgac aagaagaaac aggaagaaaa cagtactaaa    8700
atttgttctt ggaccagttg cagctggagg tttagtcata ggggttttag gcatgatatg    8760
gttgttgaat tatcggagac gtaacaacca acttattcct ttaactgatt ggtatgatca    8820
gttatcacac aaaaggtttt cttactatga acttgttcga gggactaaca actttgacga    8880
atcaaatttg attggaaagg gaagccttgg tatggtttat aagggacat ttacaaatgg     8940
gaccatagct gctgtaaagg ttttcaatgc acaactgcaa gatgcattca agaggtttga    9000
tttggagtgt aaggttttgc gtaacactcg aaataggaat cttgttaagg tgataagtag    9060
ttgtgcaaat cttgatttta aggcattggt gtttgagtac atgcctaatg gagatcttga    9120
ttattggctt tactcacaca acaatttctt ggatttaaac aagaggctga aaattatgtt    9180
tgatgtggct tgtgtcgtag agtatctaca ccaaggccat tcacttgtag tggtccattg    9240
cgacttgaac atacttttgg atgaagacat ggttgccaga gtaagtgatt ttggtatatc    9300
caaactcttg accgcgtatg atccagtggc attgacaaag actttaggca ccattggcta    9360
cacggcagca ggtactgatc aaactttat ttactaatta ctttcttcaa cttgtattcg     9420
atatgcatat atgatgtatt tcattttaat ggcagagtag ggatagtgtc aactatgggg    9480
gatgtttaca gctacggcat tttattgatg gaaaccttca caagaaagaa accagtagat    9540
gatgagtttg ttggagacct tacattgaag agatgggtcg cggaatcata tcctcataga    9600
gtcattgtta tgaaataaaa acgaatacac gctgaacgtc acttatgagt catttatcta    9660
atatgatcca ttaacaattg attaatgtaa cgcaaggaag aagaaaacaa tttgcattgt    9720
tatgaatgaa tgtgtttgta ctacaatata tacagtactg acaagtccag caaactttct    9780
aaccaactta ttctaaccaa ctctactcat tattaattta gctcacttaa tcaagaaatt    9840
aaacttaaca actaactacc attactcatt caactgatca cggaacatca acacattttg    9900
ttgatttctt tcacacacac cctctgcttc gaaaacccct cttttaaaca tgtaagcgac    9960
aatatctttt ttttaggaga gtgttcaaca ttgagcataa aaataataaa atagagaaca    10020
aaaaagatga gtataaaata aataataata taagatcgat tttaccgatt gtcaattttg    10080
tgtatggact aaagaaataa cagcttcaca tatctaaat taaatgtaat actgaatttc     10140
acatatggtc agaggtgaat ccacctgcac ccgatatatt cttttttaaa aaaattatat    10200
gtatatatat agattgttga taagacggta atatatttaa ttgtgcactc ttataacgaa    10260
caaatgattt gacttgtcca ttggaaaaac gaaaagtgtc acataaattg agacatgggg    10320
agtaacattt ctttcttaaa ttttcgtgt gaagtcaaac taattcatat aaaatgagac     10380
ggaaggagta ctgtttaata ttaattgcat atggtagtaa atttgataga catggtcccg    10440
tgggagtgtg tgttatttcc attgaataat tgagtttgta attgttacaa gtccattcta    10500
atttccaaca ccttacttca tttcaaaaat atactctatg gctgaagctt tccttcaaat    10560
tatgttagag aatctgactt gtttcatcca agggaacttg gattgattct tggttttaag    10620
gatgagttca aaaagcttca aagcacgttt actacaatcc aagctgtggt acaagatgct    10680
cagttgaagc aattgaagga caaggcaatt gaaaattggt tgcagaaact caatggtgct    10740
gcatatgaag ctgatgacat cttggacgaa tgtaaaactg aggcaccaat tatacagaag    10800
aagaataaat atgggtgtta tcatccaaac gttatcactt tccgtcacaa gattgggaaa    10860
```

```
cggatgaaaa agattatgga gaaactagat gcaattgcag cggaacgaat taagtttcat   10920
ttggatgaaa ggactataga gagacaagtt gctatacgcc aaacaggtaa atattttcct   10980
aaataacagc tttatatcat caaattcatg tgtgttttgg ggattttgtc taagtagata   11040
agtggttcaa aatctattat ctaaatctgt ttggtgaagt ctttaacata tatataaatc   11100
catagcttac tcatatgccc caaagtctaa atgacaggat aaagccagag ttgttttaga   11160
ttttataaat taacaaagat aataatgtaa attcaaaata gtgcatttgt tttatatttg   11220
aaatatgtct gctgcttctg atcaagctga tcattgtctt ttgcaaaatt cttctttgtt   11280
tttttttgctg actcttaccg atcttggacc aggttttgtt ttaaatgaac cacaagttta   11340
tggaagagac aaagataagg atgagatagt gaaaatcctg ataaacaatg cccaaacact   11400
ttcagtcctc ccaatacttg gtatgggggg actaggaaag acgacccttg cccaaatggt   11460
cttcaatgat cagagagtaa ttgagcattt ccatcccaaa atatggattt gtgtctcgga   11520
agatttaatg aaaagaggtt gataaaggaa attgtagaat ctattgaaga aaagtcactt   11580
ggtgacatgg acttggctcc acttcaaaag aagcttcggg acttgttgaa tggaaaaaga   11640
tacttgcttg tcttggatga tgtttggaat gaagatcaag ataagtgggc taagttaaga   11700
caagtcttga aggttggagc aagtggtgct tctgttctaa ccactactcg tcttgaaaag   11760
gttggatcaa ttatggcaac attgcaacca tatgaattgt caaacttttc tcaagaagat   11820
tgttggttgt tgttcatgca acgtgcattt gggcactaag aagaaataaa tcttaatctt   11880
gtggctatcg gaaaggtgat tgtgagaaaa tgtggtggtg tgcctctagc agctaaaact   11940
cttggaggta ttttgcgctt caagagagaa gaaagacagt gggaacatgt gagagatagt   12000
gagatttgga aattgcctca agaagaaagt tctattctgc ctgccctgag acttagttac   12060
catcaccttc cacttgattt gagacaatgc ttttcatatt gtgcagtatt cccaaaggat   12120
accaaaatgg aaaaggaaaa tctaatctct ctgtggatgg cacatggttt tcttttatca   12180
aaaggaaact tggagctaga ggatgtaggt aatgaagtat ggaatgaatt atacttgagg   12240
tcttttttcc aagagattga agttaaatat gatcgaactt atttcaagat gcatgatctc   12300
attcatgatt tggcaacatc tctattttca gcaagcacat caagcagcaa tatccgagaa   12360
ataaatgtag aaggttacct acatatgatg tcgattggtt tcgcaaaagt ggtgtcttct   12420
tactctcctc ctcacttgca aaagtttgtc tcattgaggg ttcttaatct aagttccatg   12480
ggacttaagc agttaccgtc ctccattgga gatctagtac atttaagata cttgaacctc   12540
tctctcaata acatgcgtac tcttccaaag cagttatgca agcttcaaaa tctgcagact   12600
cttaatgtag agtattgctg gtcactttgt tgtttgccaa aagaaacaag taaacttggt   12660
agtctccgaa atctcttact tgatggttgc gatggattgg attctatgcc accaaggata   12720
ggatctttga catgccttaa gactctaagt ttctttgtta ttggcgagag aaaagattct   12780
ctacttggtg aattacgaaa cctgaatttg tatgggtcag ttgaaatcac gcatcttgag   12840
agagtgaaga atgatagga tgcaaaagaa gccaatttat ctgcaaaaga aaatctgcat   12900
tctttaagca tgagatggaa aaaaccacat agatatgaat cagaagaagt tgaagtgctt   12960
gaatccctca aaccacaccc taatttgact tctttactaa tcactggctt cagaggattc   13020
cgtcttccaa agtggatgaa tcactcagtt ttgaaaaatg ttgtctctat tgcaattaga   13080
ggttgtgaaa actgctcatg cttaccaccg tttggtgatc tgccttgtct tgaaagtcta   13140
gagttaggag atgggtctgc ggaactgaag tatgttgaag attctggatt ccctacaaga   13200
agaaggtttc catctctgag aaaacttatt atagtcaatt ttgataatct gaaaggattg   13260
```

```
ttgaaagagg caggagaaga gcaattcccc gtgcttgaag agatgacaat tagctggtgt    13320
cctgtgcttg ttattccgac cctttcttct gtcaagaaat tggtagttta tcggaacatg    13380
tcagatgcaa taggtttgag gtccatatat aatcttaggg ctcttacttc cctcaacatt    13440
agccataact tgacagctac ttcgctccca gaagagatgt caaaagcct tgcaaatctc     13500 aaatacttgg aaatctcttt catcttcaat ctcaaagagc tgccaaacag cctggctagt    13560
ctcaatgctt tgaagcatct gaaaattgaa tattgtgacg cactcgagag tctccccgag    13620
gaaggggtga aaggtttaac ttcactcaca gaattatcca taacaaattg taagaggcta    13680
aaatgtttac cggagggatt gcagcaccta acaaatttat cagttaggga atgtccaaca    13740
ctggccaagc ggtgtgagaa gggaatagga caagactggt acaaaattgc tcacattcct    13800
catctgctta ttactaatga gatgtaattt tctgattttt cttttggaaa caatcaact    13860 atttgtaacc aattcgtatt ggacttttga gccctgcatt tgttcgaata cgcctttcaa    13920
cctgtatatc agtgtataac aaatgtatac aatatgtata ctgctgctca aatctgcaga    13980
tttgattttc cagcaacaca tttgctgatt cttccgacct gtaaattaat ttccagcagc    14040
tcattttttt gtgttcaacc tgtacgccag ttgtgagggt ctaagacttg aggaggaggt    14100
ttgagccttt acggctcagc gaggaagtgc agggatacgg gcgaaatccg ttaggactca    14160
tggcgaatgc acgtgaaacg gatcaaaagg aaacataaag aaaaacagtc aacgatgaaa    14220
acaattctgc atttatacgc ataactaagg caatgtaaat caaattgaag aatgggcagc    14280
caagataaat gaaagcaaat aaagccacaa tgcatgtttt aaaatactat aaccctgcca    14340
tgctgcatag acacacattt atattcaaga ttcaagtcat aacaaaatat aatttgaaag    14400
tttaaagctc tggatatcag cttactacag ttcaatcttc ttacttaaaa aagatgctaa    14460
aaaaaaacaa aattcaactc ttccaggcaa ctaacaatat caaacctaca aactaacata    14520
tgagcaaaaa aaaatcattg aaataaaggc atacaaatac taaatgaca accactagtt    14580 catgaaaaac aaaatggagc aggcaataaa taataaacaa gataatagat aaatatgtct    14640
tttaatttta ttttatttta tatttgtatc cttcaaattt gaatgtacac ataatttgat    14700
attttaactt gtatataatt gaacaagtac atagttaagt catatgtagc ataaatatat    14760
atatatatat atatatatat gaaacaccac ctatgacaca atttccatga agcatgtaca    14820
cttttatttg ttcatttcaa tactgagttt aagtatttta ctttgtttca tattatagtt    14880
gaacaccata aatataaaat aatatcaaat ttaaaaaata tatttatgta ttatgcttta    14940
aaaaatattt tttaaaaatc tagtaattgc cccaccataa aagagatgcc cattatacgc    15000
cgaaagaatg tttaaaatca aaagcaactg ttagttattg gattgaaaaa taaaaccaaa    15060
tactccaatt gagagacatg gcggcccat ggtggaataa ttattacaac acaccttcca     15120
taattaaagt ttgaccttac acctagagac aatcaaattt tggatttggg tcttatttta    15180
ctagttaaca tttcagataa tcacttaatt ttaaataatt tatttcgata gtcattcaac    15240
tttgaattat tctgttagaa agtcattcaa ttctatttta aagtcaaaag tcactaatat    15300
ttgagttgtt ggtttaaaag gtcattcaac tctctttata attcaaaagt aacataatta    15360
ttttttgttt cacttaaaag acatccgatc aacttaaata tttttcata aaatcttatt     15420 tttatgttaa actattcttt ttaaaaataa taagatattt atttagaaa agggaaaat     15480 atgttaaaaa gttagttatt ccaaaaaaga agaaagaagt tggaattgaa aagaaataat    15540
ataaaaaccg cagcacagtg cctttttct tattactttt tatttaaaag atagttataa     15600
```

-continued

| | | | |
|---|---|---|---|
| agaaatatta tacttcaaca aaatttaata aaataattaa aagcagctta taattttatt | 15660 |
| ttattttgt attcagtcaa atttaataaa aaatttcatt ttaaaataat tgtctgactt | 15720 |
| tctaagtaaa attagttgag taatttttag gttataaaac aaaattgagt gactttcgaa | 15780 |
| gttaactcaa atctgagtga cttctaagt gaattattcg aagttgagtg aatattaact | 15840 |
| ccttatacaa gttcgaggaa gatattgaaa aagattgtac atatggggtt c | 15891 |

<210> SEQ ID NO 3
<211> LENGTH: 85327
<212> TYPE: DNA
<213> ORGANISM: Solanum habrochaites
<220> FEATURE:
<223> OTHER INFORMATION: >genomic fragment 3

<400> SEQUENCE: 3

| | | | |
|---|---|---|---|
| gtaagctcct tcatgtcagc ttataaaagg cttcacacaa gtatatatag cgggtaaaat | 60 |
| tttattttgt gagaggtaga aatgttactc ggcagacaat acttgtatga catgcttaaa | 120 |
| gcttcatttt tttctctttc acctatttct atcttcttct tctctctttt tttctccgtg | 180 |
| cttcataaaa ttttatttta tttttcatca aaaacttgat acttaatata ttttattgaa | 240 |
| tgaaaattga tttaataatt ttattttca aatgttaaaa tcaagacaaa tcaattaagt | 300 |
| tgattttttt cattacttta tttttttcc ttgcgatttg ttttttgtgg acttctcgaa | 360 |
| aatatataat aatataaaat tatcctctga aaaaattatg cattacgaag aatttaatca | 420 |
| ttactaagaa atttgataaa aaattcccaa tgattttact atattcttac aaaaattaaa | 480 |
| gatttaaggc tgatatatta aagatgtctt gttaatattt tatttaaata aaataatcaa | 540 |
| ttaaattacg agttattttg aacatgaaaa aacactttca attttatcta aataaaaata | 600 |
| taaattaaat tacaaagtaa aaagaataat tattataaag agaaacacat gagtactcac | 660 |
| aaagagaaca aaaaaaatat ttataataat ttttttagct tcagagaagg ttatacgtat | 720 |
| aatcaaaatt attacggatc atttattaat aaaaataataa aataaaaatt ctcctaaaaa | 780 |
| attaatgtat gatcttttta taagcaaaca caaaaattat ttaattacac tatattaaat | 840 |
| ttctttaatc tcactaaaaa actattttt ctcgtttcat ttactttaag ttttccttaa | 900 |
| ataaataata taaaataaa atagttaaac attgtggcta atttttttta aaaaaaacac | 960 |
| aaagactac aaaggagaac aagagaatga gaaacaaaag tttacgggaa aagagtctga | 1020 |
| tataccccctt aactttgtca tttggagcta atatatccct cgttataaaa gtggctcata | 1080 |
| tatgccctta ccgttataca aacggctcat atataccccct gtcgttataa aatgactcac | 1140 |
| atatacccctt aatttgtgga agttaaaaat tagttttaaa tttatattta atacttctaa | 1200 |
| tttttaaaaa aaattattta gaggtatata tgattcttct atcaaagttc aaggtatatt | 1260 |
| ttaattttttt tttcatacat aaactatttt tgacttcttt tattataatt atttgagttt | 1320 |
| cttattctta ttttatttt tttctttca ttccttagtt taaagagaga gaaaaattaa | 1380 |
| actattttt ttgtatgtat tgtaatttaa tttcgtattc aaagaaaaaa atttagtcat | 1440 |
| ctacaataag ttttacaaga atattagtga aaaataaat aaatttgatt atcaaaataa | 1500 |
| taattataaa ttagtcattg aaaaaaaaag tcaaaaaaaa atgttttga gaattaaatt | 1560 |
| tattcatatg agattatatt ttatagaaaa aataataaaa atttagatta aaattatatt | 1620 |
| ttttcatttc cgttagatta aagggatatc tcgagccatt tgtttacaag tagggtatat | 1680 |
| atatgctact ttcatgttag gtatatcagc tctaaataac aaaattgatg ggtatatcag | 1740 |
| acccttttct caagtttaaa ttaatgtgaa aaagttttaa gtgtgggtcc catgttgtac | 1800 |

```
atttaaaatt ctcatacaac agacaaaagg ttagctttc acaaaataaa attttccca      1860 tgtgaaactc aaaataaaat aattgcgtac agacatattt atgcaacaca acattaattt     1920
atttatttac ccattcaata agtaaaggaa taattataaa gctttgtgct cttacttta     1980 gctgttcata tttcattcca acatcgatct tatagattta ttgctaattc acaacaattc     2040
cagcaatcta catggctgaa gctttccttc aaattttgtt gaaaaatttg acttctttca     2100
tacaagagga acttggattg ttttttggtt ttaagaacga gtttgaaaat cttaaaagca     2160
cgtttactac gatccaagct gtgcttgaag atgctcagga gaagcaactg aaggacaagc     2220
cactagaaaa ttggttgcag aaactcaata ttgctgcata tgaagttgat gacatcttgg     2280
atgaatgtca aactgaggca gcaagactca aagagactaa atatgggagt tatcatccaa     2340
aggctatcgc tttccgttac aagattggga aaaggatgaa agagataatg gagagactag     2400
atgcaattgc tgcagaacga agcaagtttc atttggaaaa aaggactaca gagagagaag     2460
ctgctagacg agaaacaggt gctcatcttt aattagttta tattcatttt tttgcgatta     2520
tcaagttcat gtgtgtttat ggacccaagg gactttttc taatctaatg tttgtctcaa     2580
gtctaaacag atttgtaatt ctaccactta tttatttagt gaagttctta aacatatata     2640
catggtgtaa gccagctcag ataaatccat agtcagttgt ttcggactga acttaacttg     2700
gatgtcaatt tttcaaagtc aatcatgttt tcaactcctc ccctgattc tcatctcttt     2760 gtagtgcaaa atcttctct ctgttttcg ctaaacatat tctcgtgtga acatatattg     2820
cttgaaacag gttttgtttt aactgaacca gaaccttatg gaagagacaa agaagaagat     2880
gagatagtga aaatcctgat aaacaatgcc caacaacttt cggtcctccc aatacttggt     2940
atgggggggc taggaaaatc gactcttgcc cagatggtct tcaatgatca gagagtaact     3000
gaccatttcc atcccaaaat atggatttgt gtctcagaag attttgatga gaagaagttg     3060
ataaaggcaa ttgttgaatc tatcgaagga aacccacttg gtgaccacat ggatttggct     3120
ccacttcaaa agaagcttca ggacatgttg aatggaaaga gatactttct cgttttggat     3180
gatgtttgga tgaaaatca agaaagtgg gataagataa aagcagtctt agaggttgga     3240
gcacgaggtg cttctgttct aaccaccact cgtcttaaaa ggttggatca attatgggaa     3300
ctttgcaacc atatgaattg tcaaatctgt ctcaagaaga ttgttggttg ttgttcatga     3360
aacgtgcatt tgagaaccaa gaaaaaaata atcctaacc ttgtggctat cggaaaggag     3420
attgtcaaaa aaagtggtgg tgtgcctcta gccgccaaga ctcttggagg tctttttgcgc     3480 ttcgtggatc aagaaagaga atgggaacat gtgagagata atgagatttg gaatctgcct     3540
caagatgaaa gttctattct gcctgccctg agacttagtt atcatcatct tccagttgat     3600
ttgacacaaa gttttgcata ttgtgcagta ttcccaaagg acacggtaat ggaaaaagga     3660
aatctaatct ctctctggat ggcacacggt tttctttat cgaaaggaaa cttggagcta     3720
gaggatgtag gtaatcaagt atggaatgaa ttatatttaa ggtctttttt ccaagagatt     3780
gaagttaaag atggtaaaac ttatttcaag atgcatgatc tcatccatga tttggcaaca     3840
tctctatttt cggcaagagc atcaagcaac aatatccgtg aaataaatgt aaaacggaac     3900
ccacatatga tgtcgattgg ttttgcaaaa gtggtgtctt cttactctcc ttctcacttg     3960
caaaagtttg tgtcgttgag ggtgcttaat ctaagtgaat taagacttaa gcatttaccg     4020
tcttccattg gagatctagt acatttaaga tacttgaacc tctaccgcaa taacatgcgt     4080
agtcttccaa agcagttatg caagcttcaa aatctacaga ctcttgatct acagtattgc     4140
```

```
gccttacttt cgtgtttgcc aaatcaaaca agtcaactta gcagtgtcag aaatctttta    4200
cttcatggtt gctataaatt gaattctatg ccaccaagga taggatcttt gacatgcctt    4260
aacactcttg gttgctttgc tgtgggaagg aagaaaagtt gtcaacttgg tgaattacga    4320
aacttgaatc tctatggctc aattcaaatc acacatcttg agagactgaa gaatgatagg    4380
gatgtaaaag aagccaattt atctgcaaaa gaaaatctgc attctttaag catgacttgg    4440
aaaggaccac atagatatga attagaagaa gttgaagtgc ttgaagccct caaaccacac    4500
tccaatgtga cttgcttaac aatccatggc ttcagaggaa tccgtttccc agagtggatg    4560
aatcactcag ttttgaaaaa tgttgtctct attgatatcc ggggttgcga aaactgctcg    4620
tgcttaccac cctttggtga gctgccttgt ctaaaaagtc ttaagttaca ggacgggtct    4680
gcggaaatgg agcatgttga ttctggattc cctacaagaa ggaggtttcc atctctgaga    4740
aatcttatta tagtcaattt tgataatctg aaaggattgc tgaaagaggc aggagaagag    4800
caattcccCg tgcttgaaga gatggatatt tggtggttcc ctgtgtttgt tattccgacc    4860
ctttcttctg tcaagaaatt gttagttcat tggaacatgt cagatgcaat aggtttgagt    4920
tccatatcaa atctcagggc tcttacttca ctccacatta gaactaactt catagctact    4980
tcgctcccag aagagatgtt caaaagcctt gcaaatctca atacttgaa aatctctttc     5040 ttctacaatc tcaaagagct gccaaacagc ctggctagtc tcaatgcttt gaagcatctg    5100
gagatgaatt gttgtcccaa actggagagt ctccccgagg aaggggtgaa aggtttaact    5160
tcactcacac agttatccat tacatactgt gagatgctaa aatgtttacc agagggattg    5220
cagcaactca caaattatc aattaagaat tgtccaacac tggccaagag gtgtgagaag     5280
ggaataggac aagactggta caaaattgct cacattcctc atctgcttat tactaatgag    5340
atgtaatttt ctgattttct tttggaaaca aatcaactat ttgtaaaatc tatttgtatt    5400
atacttgatt tttcttggtt atgtaacaat aaatatttga aaattttcat ataaaaatag    5460
ttacatttct atatgtataa ttcgccagaa taatacatat atatgtataa tatacaatta    5520
tttaaccgat atacatatat aattcacctc tctcccactc tctgtcctct ctcactcgcc    5580
tctctcctcc ctctctcaat ttcgcttttcc atatatacaa atacaattat ctaaagata    5640 tatatatata tatgcaattc atctctctcc cactctttgc ttcacttgac aactatgaca    5700
tttaacattg acaagcaca aattgacact taaaaactgg ttacagaaac tcaacgctgc     5760
tgcgtataaa gttgatgact tattgaatga atgagaatac gaggcagcaa gactaaagca    5820
gtctcgacta ggacggtatc atccaaaggc tatcaataca aactcagttg tttagaccac    5880
gaaaagactg tgaattcaat acaggagtag ttaacgatta ctctaattct atgtcacaga    5940
aagtaatttc ataagcgaga aaatcctcta gcattttttcc atttctcttt atggcgtgca    6000
aatatcgtta tctattttct gctgtctcct agctaattat cttgaatgta cgtaacactc    6060
tctatttatt tccaagagat tgaactaaaa tctggtaaaa cttatgatct ctgttttcag    6120
caaacacatc aagcagcaat atctgcgaaa ttaaacacat atgatgatgt cttcttactc    6180
accgagttat tagttatgct aaaatgttta cccgagggat tgcagcacct aacaaatctc    6240 acaattttt tttattagtg aaagcatagt tatcaaaata aaaacaaaaa atgagcaata    6300
tttatacaac agacaaaaaa aagaatgatt tttcatattc tttgcttatg ttaccgattc    6360 ataaccata taaaaacaaa tttcaatcac ccattaaacc aaaatgatt aaacaaaaaa    6420 aatcttctag atatctaact aatgaataat aacatattca gtgtagtccc acaagtggaa    6480
tctgggttaa ctatccaact aatcatagat caaaattgca gtgaaaggta ttttattaga    6540
```

```
ccacttccaa tctcaactat ttcaacacaa aacttatatt caatctttga tggataatag    6600
accatctatt tttaattccc ttttctcacc aacaaattga aatgtcagtg atgtttctga    6660
gcaacaaaaa gtactttaag atgatattct aaatgtgcac aatttcatgc tccaacaatc    6720
gaccaattag attaaaaaat atactcattg agtatttctt ctgtcacatg gtcaatacca    6780
tagaaaatga aaatataat cacaatttaa caacataact attgagatgg aatatgtttc    6840
atctagttaa aaaaaattta cttgagaatg ttgtttgtga gcattacact aatagacgtc    6900
agatgatttt cggatggtgg tcaaatgaca cttgttactg gttcaagcag agtaatggga    6960
tgtgaaattg cccttcaatc gtagaaaatg gaatatataa agcaaagtta cacaatttaa    7020
tcgtactctt gaaacttatc tctctataat ccatgtttgc tataaacaat aatattgtct    7080
tacacatatt caacaattac atatcctatt taaactaata tacgaaatat attcaataaa    7140
aagtgcatgc agacgatttt tctacaataa agactccagg tttagagtgt ttagcgactc    7200
ctgataaaga caatgagatt atagtaaaca ggagaaacag agcagctctt cataaataaa    7260
gaggaggaaa aaatctaccg attgatgcac gtaaaagagt aaatgtgaga ctaatgacaa    7320
taacctgttg ttggagagat ttatatagat gagtatttga aaagtttacg atcaaatgaa    7380
cttgagcgtc agaaaagttg tcgcttgagc agtaactgtt atagtgatca atgaggcatt    7440
ttttggagaa ttaaattagg tctcaaacta tgagcaaatt taatttataa taaattaata    7500
cttattaaaa ctgtagggtt aaaacggtaa atcaagttta tgattaaact cttcccactt    7560
ataataatat aagattaaaa ataatcataa aatagaatgg tgcattggta tcaaacaaga    7620
aatatgtgaa actaattaag agaatatagt ctctaagggt atgaatatat cgatgaatgc    7680
ttgattgaaa ataataata aatgtatata agtctttaat gaaataacaa aggcacgaga    7740
taaatttatt agaaatataa atctacatat tctaggtatt acaaaaaaga tcctaaaata    7800
tgtagcaaac aaatgactta ttcttctata aagcacgtaa ccatcgaagt ttaatgttaa    7860
tacgataaga ttgccttgag aatgcattta cttgtgataa gtccacgggt ctacgtataa    7920
gtatagttta ttgtattctt ataaaataat agtaaaaata atagtctctt tttatttcaa    7980
atttaatttt taataaacag aaaataaatt aataaaataa gacaaaaaac aataataata    8040
ttatagacat gtttatgatg agtacgtata atttgaaggg gaaaactaca aattcaaact    8100
caagagaaaa taataaaggt ttggaataaa atatctaaga tacggaaaga ttaaaatgtg    8160
ttctctaact aaaatcttca tcttcatgaa taattaacat gaaaatagag gatccaccaa    8220
aaattaaata ggagaaggaa agagacttat tagaaaaatg atgaattata aaatctaaaa    8280
gcctatatgt gaaaataaga gaacaagaat attgcataaa aaaaaattat agctacgaaa    8340
aatactatgt gtgattttaa agataaaatc tattttattg ttacatgtat catatttatt    8400
gttgaaattt caccttttaa aaaatgaaaa acaagctaag aaaaaaaaag taaaagagg    8460 aaaatgaaca aataaaagat taatagaaa aagggaaaaa taccaatgaa tatcctgatt    8520
gaaactgcat tatataaatc ttcggatcaa tccatttacc ttgaatttca agaacactgc    8580
aaattcgatc ataaattaat ctaaaagag gcatgtttat gataaagggg gggaaaacag    8640
tgttagaaga aaacaataaa gaaatagtgt tagaagtttg aaatcttcat gtttcaaaaa    8700
agaacaaatt aatcttcaat gtcaagtaaa atctcaagat ctctagtaaa gaaaatttat    8760
ttttatacta caaacaaatt aatggcatt taaacatata aagaaatatg aggatcaaca    8820
tattatagat taactacaag ttttcatgtc cttaaaagat aacttatcaa ccacaaacaa    8880
```

```
aagtaaattg aagggcaaga gatgaagaag tcttcagttt gttaacttaa ttggtgtttc    8940
tatcttccat gtcttttgaa atgtgtatga agatgaaatg tttcaagtac ttgaagatga    9000
aatatagttt cttacttgga tgcttaacaa tgttattact tcaaaaagaa cctgaaaaaa    9060
atcattattc acttggttgc ttaactattc tattacttca aaagatttat tactttcaat    9120
tggcttttca cttaccctat tcatggtgat taatatgtaa gtttcatgca atgtcttttc    9180
aattatccta attattgtaa ttgaaatgtg aatttatttt tcagataatt aaaatatatt    9240
gttttttttc atataataat gttcaagaat aaattggtaa ttcaacttta agctaaaggg    9300
cttcccactt ataataatat gatatgatat gatgattatt agatgtaatt ttctgatttt    9360
tcttttggaa acaaatcaac tatttgtaac atctatttgt attatacttg attttctttg    9420
ggtctgtaaa aataaatatt tgaatttttt catattaaga ttcataatta gtcttatagc    9480
ttaactgtaa gaaagaaatt acaaattaaa tttgacaaat aattaagcta cttaaataac    9540
ttaattgttc aatataaaat tttaaggatt gcctaaactt agaaaaaaaa aacaattaaa    9600
tttagttata tggttgcaat gtgtaatcaa atagtaataa atatgtggct gtttgtacag    9660
ctacaatatg acatgagata attaaaatat atgtgtcttt aagctctcct ctttttgttt    9720
gttttgagga aaatctgttg tattttgatg tgtataattg gttaattata cactctttta    9780
gaaacaaata gtgttgaatc tacaataaca tgtgaataca tagatttgat aaaatataaa    9840
atcgtaaata gattagacca tcttttttat tgacagaggt gaaagacaaa gcaaccccac    9900
aagaaaagat aggtatgaaa ctagctagca gttttatgaa caattaatat aaaatataaa    9960 acactttta ttttactcaa caattaattt ataagctatt tttatttta aacacttaaa    10020 ataagttaat tcgaacatgt actataaatc aaaacaaata aggaaaaaaa ggaaaagcta    10080
aaggtgtgtt tggtatgaag gaaaatgttt tcctaaaaaa taaatagatt ttggatttat    10140
tttctcatgt ttgattggta agtagaaaat attttcctgt gtttgattta tgaatgaaat    10200 taattttgg ggggtggggg tgggtggggg ctggtagggg tggataggg gctgccggg    10260 tggaggaggg taggagttta aaaataaaaa tttgaagttg aaaatatttt aaaaagcaaa    10320
attaattttt ggggagggtg aggttaggg gctggtcggt ggtgggtgga cggggtcaa    10380 ggatcgagtg aaaaaataaa ttttaaaatt gaaaatattt ttattaatat tgatattttc    10440
ctaaattttt gaagggaagt cattttcctt aattttagg aaaatgagtt gatttgaaaa    10500
atatttctta aaacttttat tccaaccaaa catgaaaaaa ttgaaaaata ttttccagaa    10560 aatgttttc ttcataccaa acacactcaa aaagagactc ttttaatcaa gtattattgc    10620 taaaaaaaa agagacaaag aataataatt taccccataa atttcgcaaa tcaatctata    10680
aaagattgag ggtgagatat tgataagata aaacaatcaa aataatagat aaatatgtct    10740
tttagtttaa tttaatttta tatttatatt ccttaattta gaatggacac ataatttgat    10800
atcttaactt gtatataatt aaacaagtat gtatatatat atatatatat atatatatat    10860
atatatatat atatatatat atatatatat ataacaccac ctatgacaca atttccatga    10920
aggatgtgca cgtttatttt attgattcta tacaagttta agtatacgct tattcatact    10980
atagttgaat aatataaata taaaataata tcaaatttaa aagatatatt tatatattat    11040
cttaaacaaa tatgttttaa aaaaaataa aatctagtaa ctaccccacc ataaaagtga    11100
tgcccttata cgccgaaaga acgtttaaaa tcaaaagcaa ctgttagtgt tattggattg    11160
aaaaataaaa ccgaatactc caattaagag acatggcggc cccatggtgg aataattatt    11220
acaacacacc ttccataatt aaagtttgac cttataccta atgacaatca aatttttgagt    11280
```

```
tcggatccta tttcatgagt taatatctca tataatcact taattttaaa taattcattt   11340
agtatgttat tcaagtttaa attgttcact taaaaagtca ttcaactcta ttttataagt   11400
aaaaaatcac taatatttga gttgttcatt tagaaagtca ttcaactctc tttataattc   11460
aaaagtaact caattatttt tgtttcactt aaaaagtcac ccgatcccaa cttaaatatt   11520
ttttttcat aaaatcttat ttttatgtta aactattctt ttaaaaaaaa aataagatat    11580
ttattttaga aaggggaaa acatgttaaa aagttagtta ttccaaaaaa gaagaaagaa    11640
gttggaattg aaaagaaata atataaaaaa aaaacgcagg acagtgcctt tttttcttat   11700
tacttttat ttaaaagata ggtataaaga aatattatac ttcaacaaaa tataataaat    11760
aattaaaata agcagcttat aattttattt tattttgta ttcagccaaa tttaattaaa    11820
aaatcattta aaaataattg aatgacttct taagtaaaat tagttgagta attttaagt    11880
tataaaataa aattgagtga ctttcaaagt gaactcaaag ctgagtaact ttctaagtga   11940
actattcgaa attgagtgaa catctgagat attaacacct tatttatac gtgaaacaat    12000
ttaaactata ttacaaaagt tggaggaaga tattgaagaa agattgtaca tatgttcgta   12060
agctcctta tgtcagctta taaaaggctt aacacaagta tatatagcgg gtaaaatttt    12120
attttgtgag aggtacaaat gttacttagc agacaatatt tgtatgacat tctctcagct   12180
tttgccaagt ggagtttggg tctcacttac agaaaatgtg cttaaagctt catttttttc   12240
tctttcacct atttctatct tcttcttctc tcttttttttc tccgttcttc ataaatttta   12300
ttttattttc tgtcaacaaa catcgatact taatatattt tattgaatga aaattgattt   12360
aataattttt attttcaaa tgttaaaatc aagacaaatc aattaagtcg atttttcatt   12420
actttttttt tccttgcgat ttgttttttg tggacttctc gaaaatatat aataatataa   12480
aattatcctc tgaaaaaatt atgcattacg aagaatttaa tcattactaa gaaatatgat   12540
aaattatttc cttacaaaaa aattaaagat ttaaggctga tatattaaag atgtcttgtt   12600
aatatctgat ttaaataaaa taatcaatta aattacgagt tatttgaac ataaaaaaac    12660
actttcagta ttatctaaat aaaaatataa gttaaactac aaagtaaaaa aaaataatta   12720
ttataaagag aaacacatga gtactcacaa agagaacaaa aaaaatattt ataatgattt   12780
ttttagcttt agataaggtt atacatataa ccaaaattat tacggaccat ttgttaatga   12840
aataataaaa tataaagatt ctcctaataa attaatgtat gatcttttttt aaacaaacac   12900
aaaaattagt taattacact atatttaatt tctttaatct cactaaaaaa actattttttt   12960
ctcatcacat ttacttttaaa ttttccttaa ataaataata taaaaataaa atagttaaac   13020
attgtggcta atttttttt tttttacaa aaaaacacaa aagactacaa aggagaacaa     13080
gagaatgaga aacgaaagtt taagggaaa aaagtctgat atacttctca actttttcat    13140
ttggagctga tatatttctc gttataaaag tgactcatat atgcccttat cgttatacaa   13200
acgactcata tatctgagtc atttgtttac aagtaaggta tcactttctt aaaaaagcaa   13260
tgatatcatc tctaaaacga caaagattga ggggtatatc gatccttttt caaagtttaa   13320
atgaatgaga aaaagtttta agtgtgggtc ccatgttgta catttaaaat tctcataaac   13380
tgacagaagg ttagcttttc acaaagtaaa attttttccca tgtgaaactc aaaataaaat   13440
aattgcgtac agacatgttt atgcaacaca acattaattt atttatttac ccattcaata   13500
agtgaaggaa taattataat gcttgtgct cttactttta gctgttcata tttcattcca    13560
acatcgatct tatagattta ttgttaattc acaacacttc cagcaatcta catggctgat   13620
```

```
gctttccttc aaattttgtt gacttctttc atacaagagg aacttggatt gaaaatctaa    13680
aaagcacgtt tactacgatc caagctgtgc ttgaagatgc tcaggagaag caactgaagg    13740
acaagccaat agaaaattgg ttgcacaaac tcaatgttgc tgcatatgaa gttgatgaca    13800
tcttagatga atgtcaaact ggaatttta accaaattaa gtcattatat aaaataattt    13860
accaaagtaa aatattttc taaaagttta caaaactaat ataaacgtat ttcatggtaa    13920
cgttttaggg tatattttat tttttaaaaa ctaatgactt taggttgata tcgttctttg    13980
taagtaacgt tttactccta aaacgttatt ttcaataaca ttttactctt aaaacgttac    14040
tcatagtaac gttttactcc taaaacgtta ttttcaataa cattttactc ctaaaacgtt    14100
actatgagta acgttttagg agtaaaacgt tactgtgagt aacgtatatc aatctgacgc    14160
catcaacttt taaaaaataa aatatatcct aaaacgttac tgtggaatac gtttatacta    14220
gttttgtaaa attttagaaa aacatattat tttggtgaat gactttatat aatgacttag    14280
tttggttaaa acctcgtcaa actgaggcag caagactcaa tcagactaaa tatgggagtt    14340
atcatcctaa ggctatcact ttccgttaca agattgggaa aaggatgaaa gagataatga    14400
agaaactaga tgcaattgct gcagaacgaa gcaagtttca tttggaaaaa aggactacag    14460
agagagaagc ttctagacga gaaacaggtg ctcatcttaa atatattagt attaattaca    14520
acaatttaat tagtttatat tcattttttt gctattatca agttcatgtg tgtttatgga    14580
cccaagggac tttttctaa tctaatgttt gtctcaagtc taaacagatt tgtaattcta    14640
ccacttattt atttactgaa gttcttaaac atatatacat ggtgtaagcc agctcagata    14700
aatccatagt cagttgtttc ggactgaatt taacttggat gtcaattttt caaagtcaat    14760
catgttttca actcctcccc ctgattctca tctctttgta gtgcaaaaat cttctctctg    14820
tttttcgcta aacatattct cgtgtgaaca tatattgctt gaaacaggtt ttgttttaac    14880
tgaaccagaa ccttatggaa gagacaaaga ggaagatgag atagtgaaaa tcttgataaa    14940
caatgcccaa caactttcgg tcctcccaat acttggtatg ggagggctag gaaattcgac    15000
gcttgcccag atggtcttca ataatcagag agtaactgac catttcaatc ccaaaatatg    15060
gatttgtgtc tcagaagatt ttgatgagaa gaagttgata aaggcaattg ttgaatctat    15120
cgaaggaaag tcagttggtg aaaacatgga tttggctcca cttcaaaaga aggcattgtg    15180
tcgatttgag ataatacgag aaaaatatac atgcgaaaaa caagacaaca gatttcgtgg    15240
ttcaccaata aattggctcg tccacgggaa gagggcgggt tttattatgg aggcaaaaac    15300
caattctgag aatagggttt gccatagcgt ctatatatag tgtaaactaa gcccctaaca    15360
ggcttgggcc caaaatataa attgaatgat aattaagggc ccaattcaag gcattcaaca    15420
aatctccacc ttgacttgaa ttctccaagc agattcttgg gcgcactatg atagtgccag    15480
gcctcccccc tcttcctcgg gttgcccttg agtataatta cttgacacga tgttgagcaa    15540
gtcaaacgag tgttgaaact tgctcacgtg gagccaagct ttgtgaacat atcagcggga    15600
ttatcaacag ttctactttc ttcaccttga ttctcttctc acttctcggg aaaatgatac    15660
ctccgtcaat atgcttggtt ctctcatgat ggacttgatc cttggctaga caaattgcgc    15720
tcaaaagctg tcaatacaca cgtgctttga gtcatgatcg agaccaagat cactaaccag    15780 ccccttcaa ccaaatccct tcttttgcag cctctgtcaa ggccatgtac tccgcttccg    15840
tagtagacaa agtcccatgt aggttgcaaa gttgccttca atgacgcgga tcctcaaggg    15900
taaacacttg agtcatccga tcttcttgtg tcaacatctc caaagatagt ctgaatcaga    15960
atagccaata accaagcact gagtatcacc tccataaatg ggaccagcgt cggatgtacc    16020
```

```
tctaaggcac cgaaaaattc tcttctgact gccaatgttc tctccacgtt gtcccatgaa    16080
tgctcactac actaatttgc atgtactaaa tctggcctta tacagaccat agcatacatc    16140
aaacttcctc agcactggca taagggactc gtgacatata ctccttctct tcttctgact    16200
gtggagccga acatggcgag tgggatggat aaaggcgtgg ggtatcaatg ggcttagatg    16260
aagacatgcc aaacctagcc aagaccttga atgtaacctt ctctgtgaca agaaaagttt    16320
ccttctctct ctgtctctaa tgatctccat ccctaaaatc ttcggctccc ggatccttca    16380
tctcaaactc agactaagta aaccettgac ttctgagatg tcatacttct tctttgcagc    16440
tatcaatata tcatctacat aaagcactag atagatgaat gaatcatcct tgagcctatt    16500
gtagtagaca caacaatcat atgagctccg agtatagccc aacttcacca tatagctgtc    16560
aaacctttta taccacatcc ttggagactg cttaagtcca tataaggact tcttcaactt    16620
caggacgtga ttttccttct ggaacttgga aaccatcctt tgagtcatgt atatctcttc    16680
ctccaactct ccatgtagaa acgctgtctt cacatcaagt tattcaagct ccattctgat    16740
gtgtaactat cgctagtaac actcggatgg aagtatgtct gaccactggt gagaagatct    16800
cattgtagtc cactccctct ctttggttga aacctctggc aacaaccctg ctttatact     16860 tgactccttc tgctggtgat atcccttcct tcttcttgaa aacccatttg caagtaataa    16920
tctttctccc cgaaggctgt atgaccagat cccatgtctg attcttgtgt agggactcca    16980
tctcatctcc catagcggca aaccattttt cagaatcaga acttaaaatg gcttctttgt    17040
aagtagacgg ctcagatgta tctacctctt cagcaacctg cagtgcataa cccaccatgt    17100
cctcaaaacc atacctcgta ggtggccgaa ctccaaccct ccttggccga tcttgagcta    17160
aactctgatg gatatctgat ggcatagatt ctggaatatc agtttctgtc tgtggctctt    17220
gatcctcctc ttcaggttct ttcaaatcgc tctcgttctg aatgacttga aactccacct    17280
gtttatcaag actcccagtt tctgacgtag ttgtaggctt cacaatggtt ctaagcagag    17340
aactttcatc aaagacaacg ttcctgctca taataaccct cttttctgga gccggattac    17400
gaaacctttc actccatctc atgccccaaa tactcctttt tggctcttgg tttctaactt    17460
accttcactg acgtgatagt aagccgtaca accaaaagct ttcagatttg aataatcggc    17520
agcttttcga ccacatctcc ataggtgttt tgcactgtgg ctgtatgtgg tcccttgatt    17580
atcagtagca aagctgtact aaccgcttct tgagaatctt ctatccccag cattgaaagc    17640
atgcaccttg ctctctccag aagtgtttga ttcatccgct cggctacacc gttctcttgt    17700
ggtgtatttc taagcacatg cgatgtcggg caatccttca tccttacgaa ttgatcaaat    17760
tcagaccaac agaattccag cccattatca gttcgcaacc tcttgatctt cttccctgtt    17820
tgattttcca tcaaaatttt ccactccttg aacttctgga aagcttcact tttatgcttc    17880
atcatgtaca cccaagtcat ccttgagtag tcatcaatca tggacacaaa aaatgggcga    17940
cctcccaaag actcaacacg gcatggaccc caacaatcag aatggatata atcaagtgtg    18000 cctttttgttc tttgaatggc ctttggaaac ttgttgcgat gtagttttcc aaagacacaa    18060
tgttcacaaa actctaggct cttaacctta tgaccagcaa gaagatcctc ttttttgatga    18120 atttgcatcc ctcttccacc catatgacca agtctattgc cataacttag tcatatcctt    18180
ctggtgaaat tctgacgatg caacatgggc tgaacctgta accggaacct tgtagaaaat    18240
ataaaagtac cacatgacac cttttcaagaa tcaatttgaa cctttccaga ccccaagact    18300
ccatcttttc ccgaccattt gaatcccttg ctgtcaaaag actgagagat atcagatttt    18360
```

```
cgtcatcaat ggaacgtgct gaccctcgtt caatgtgcca aaactaaatc gtcgtgtcct   18420
tatcttgatc agcctgtccc aaccaccttg cggtgaaact gttggccatc gagatcttgc   18480
ctcaaatcta ccactcataa gtcgtgaacc actctcccta ggacagatgt gataggatgc   18540
cccagaatcg agaacccaca tatctgaatg atgagtgtgc tcatcgtcaa ctagggcaat   18600
atcttcttga attggtgtct tcttgactag caacagcaga gaccactgat tgttttcgat   18660
tgcttcttct tcttggacaa tcaaatttca atgtcccttc tccttgcagt aattacaaac   18720
atcatccctt tgcaccttcg acatcggctt attttctttt ccgccgtttt ccttcccttt   18780
ccgctcttgg tcagcaggcc cggaaggtat aatgtcgtac ttgtgccgtt agccttatgc   18840
cgtaattccc tgctatgaag ggccgatctg acttcttcca gtgacacagt atctttccca   18900
acaatgaacg attgaacaaa attctcaaac gacattggga gagatactaa caatcaggcg   18960
acatcttcat cctcgatctt cacatcgata ttcgcaattc taataacaaa gtattcaatt   19020
gctctaagtg ttccctgagt tgtaccttga ccattcgtaa accgaatagg cgttgtttga   19080
agcagcttgt tggttagaga ttttgtcatg tacaaactct ccgacttcaa ccgagaccag   19140
acggtctctt catccgagac ctctgcgtga tgacgtcatc cgcgagacac aaagatgatc   19200
gtcagtgcgc ctttcctccg gaatctccat ctcgggagta acgacggcgt tcttgtcttt   19260
cgacaacggc gcccgtaaaa ccttgttgtt tcaacaaagc ccgcatcttg atcgccataa   19320
accaaactgg ctattcctcc accgtgaatt tgtcgatttt cacgtcaaa gcgtacatct   19380 caattctcaa gaacacccga ttaaccgaga ggctcgatac caatttgttg tgcggaattt   19440
gagataatac gagaaaatat aaacgcgaaa aacaagacaa cagatttacg tggttcacca   19500
ataaattggc tacgtccacg ggaagaggga acattttatt atggaaggca aaaccgtaa   19560 ttacgaatag ggtttgccat aagcgtctat atataactaa actaagccct taatgcttgg   19620
gccaaaatat agaattgaca gataattaag ggcccaattc aaggcattca atgaagcttc   19680
aagatatgtt gaatggaaag agatactttc tcgttttgga tgatgtttgg aatgaaaatc   19740
aagaaaagtg ggataagata aaagcagtct tagaggttgg agcacgaggt gcttctgttc   19800
taaccaccac tcgtcttaaa agggttggat caattatgga cactttgcaa ccatatgaat   19860
tgtcaaatct gtctcaagaa gattgttggt tgttgtgcat ttgagaacca agaaaaaata   19920
aatcctaacc ttatggctat cggaaaggag attgtcaaaa aaagtggtgg tgtgcctcta   19980
gccgccaaga ctcttggagg tcttttgcgc ttcgtggatc aagaaagaga atgggaacat   20040
gtgagagata atgagatttg gaatctgcct caagatgaaa gttctattct gcctgtcctg   20100
agacatagtt atcatcatct tccagttaat ttaacacaaa gttttgcata ttgtgcagta   20160
ttcccaaagg acaaggtaat ggaaaaagga aatttaatat ctctctggat ggcacacggt   20220
tttcttttat cgaaaggaaa cttggagctg gaggatgtag gtaatcaagt atggaatgaa   20280
ttatacttga ggtctttttt ccaagagatt gaagttaaag atggtaaaac ttatttcaag   20340
atgcatgatc tcatccatga tttggcaaca tctctatttt cggcaagagc atcaagcagc   20400
aatatccgag aaataaacgt agaaggttac ccacatatga tgtcgattgg tttcggaaaa   20460
gtggtgtctt cttactctcc ttctcacttg caaaagtttg tgtcgttgag ggtgcttaat   20520
ctaagtgaat taagacttaa gcgtttacca tctttggaga tctagtacat ttaagatacc   20580
tggatttgtc ttacaatagt aaaatgcgca gtcttccaaa gcagttatgc aagcttcaaa   20640
atctgcagac tcttgatcta aagtattgct ggtcactatg ttgtttgcca aaagaaacaa   20700
gtaaacttgg tagtctccga aatctttttac ttgatgattg cgatggattg aattctatgc   20760
```

```
cagcaagatt aggatctttg acatgcctta agactctaag tagatttgca gtggggagga  20820
gaaaaagttg tcaacttggt gaattctgaa acctgaatct gtatgggtca attgaaatca  20880
cgcatcttga gagagtgaag aatgataggg atgcaaaaga agccaattta tctgcaaaag  20940
aaaatctgca ttctttaagc atgagttgga atatcaacga accgcgtaga tatgaatcag  21000
aagaagttga agtgcttgaa gccctcaaac cacactccaa tgtgacttgt ttaacaatca  21060
aaggcttcag aggaatccgt ctcccagagt ggatgaatca ctcagttttg aaaaatgttg  21120
tctctattac aattggaggt tgtgaaaact tctcatgctt accactgttt ggtggtctgc  21180
cttgtctaga aagtctagag ttatggaatg ggtctgcgga attggagtat gttgaagatt  21240
ctggattccc tacaagaaga aggtttccat ctctgagaaa acttattata gtgaattttg  21300
ataatctgaa aggattgctg aaagaggcag agaagagca attccccgtg cttgaagaga  21360
tgaaaattag ctgttgtcct gttttgtta ttcagaccct ttcttctgtg aagaaattga  21420
atgcttattg gcacaagtca gatgcaacag gtttgagttc catatcaaat cttagggctc  21480
ttacttccct caacattagc cataactcca cagctacttt gctcccagaa gagatgttca  21540
aaagccttgc aactctcaaa tacttgaaaa tctcttactt cgataatctc aaagatctgc  21600
caaacagcct ggctagtctc aatgctttga agcatctgga gattaattgt tgttatgtac  21660
tagagagtct ccccgaggaa ggggtgaaag gtttaacttc actcacacag ttatccattg  21720
catactgtga gatgctaaaa tgtttatcag agggattgca gcaactcaca aatttatcaa  21780
ttacgaattg tccaacactg gccaagcgat gtgagaaggg aataggacaa gactgataca  21840
aaattgctca cattcctcat ctgctgatta catagtgtca tactaaatta aatgattctt  21900
atagcaatat tattggttca accaacaaaa ctaaatctct aattatatta cttaattgct  21960
tttagtttgc tacaattatc actcatgact aacattatgt atcaattacg tggtttgtct  22020
tcaattttgt ataattagtc atgtttttat atgtataatt cgctagaata atacagatat  22080
atgtataata tacaattatt taactgatat acatatataa ttcacctctc ttccactctc  22140
tgtcctctct cacttgcctc tgtcctctgc caatcgacga gatgagccta cgaaagattt  22200
caagttcaga ctatgatgac tgacatcctc acttacgcaa cgaaatggag ttgatggagt  22260
agccagtgcc cttgagtcat tctcttcggt atcgccttct ctcatcgtta atggcgccgc  22320
aaggcactcg actagcaagt tagaccttag ttagggcgaa agattccttg gatggttcat  22380
ttcagtctga agtcgggtca agtcatggaa ttgatgtgaa gttctctcaa tttcgctttc  22440
catatataca aatatatatg tataacatac aattatctaa atgatatata tatatatata  22500
tatatatata tataagcaa atttatctct ctcccactct ttgtttcacc tgacaactat  22560
gacaactatg tttgttaggg ctggaaggtc taacttcact caccgagtta tttgttgaac  22620
atatgctaaa atgtttaccc gaggaattgc accacctaac aaacctcaca attttttttt  22680
tataagtgaa agcatagtta aactctcaaa tgtagatgat aattaagctc ttgaagatta  22740
ttgctgaatt aagtgaattc gtcaagctat atttgtaaaa ttcttatggc caaacaagta  22800
atattgcaac aaaattgtaga aggattatta tactcttaac actaactaaa agattcttcc  22860
aattctcaaa gcaatttata ttcctttcca accaagagg ttttccaaat ttgctttcta  22920
gcaaaaaaca attttctgca cgataggaat agatctcata tatactccct ccgtttcatt  22980
ttatgtgaag tagtttaact gagtacggaa tacaaaaata aaagaaagac atttaaaatt  23040
tatggtctaa aatgaaggga aaaaggtcga tatctcctca actttgtcat tttagaaatg  23100
```

```
atataccttg ttatgaaagt ggctcatata taccectact tgtaaacaaa tggctcacat    23160
ataccttttt cctctaacgg gaaatgaaaa ataataattt tcaatctaaa ttttttattt    23220
tttttctaaa aaatataagt ccatatgagt aaatttaatt ctcgtcaaac aattttttt    23280 tttttacttt tttttgttt caatgactaa tttataatta ttagtttgat aatcaaattt     23340
atttatgttt cactaatatt cttgtaaaac ttattgtaga tgaaaaaaaa aaaatttgaa    23400
tacgaaatta aattacaata aacacaaaaa aatagtttat ttttttttt ctttaaacta    23460 aggaatgata gaaaaaata aataagaat aagaaactca aataattata ataaaagaag     23520
ttaaaaataa tttatgtatg aaaaaaaaat taaatatact ttgaactttt attgaagaat    23580
catatatacc actaaataat ttttttaaaa tttttaagt ataaatata aatttaaaac     23640 taattattta aaattttgtt aaatgaaggg tatatttgaa caattttgta acggcagggg    23700
tatatgtgag ccgtttgtat aacggtaagg gtatatacga gccacttta taacgagagt    23760 atatcagatt caaatgacaa agttgagggg tatatcaaac ccttttcccc taaaatgaat    23820 aataaaaat tgtgtgagta taaatcattt cattaagagt aaatggacaa tttaaaatta     23880
aattgttact taatatagta acgtatcttt tttgtttttg agtctgcttt aaaaagaaaa    23940
taaaccatat aaattggaac atagggagta tctacttaca aagtaaaagt tgtgtgtaga    24000
agattttggc atacaaatca aatcatatat catatcatat atcatcatat catatatcac    24060
atcatatcat atattagtaa aagcatgaat aaaaaaagtt gaaagttgaa ttcggtttt     24120 attccttcta ttaattaact tgttataaaa tatttaaata tttgatttta caagtttaat    24180
taaaatgtta aatgactttt agacttccta cgattaattt ctaattaaat atctaattta    24240
ttaatattta tcatttataa tctatatgta tataataatt ataattttt aaaataaaag    24300 tctaattata attttaatga ctttttagac ttcctaacac taattcctaa ttaaaatatct    24360 aatttattaa tattttatc atctataatg ttataataag catctttaga aggtttctct    24420
gaaatactct ttaaaagaat gcttggacta tgccatccta aggttgaaac cagtaggcaa    24480
aagaaggtcg ttatggggag taaacaaagt tgaggcgctg ttagggtaac caattaaaga    24540
agaaagctgt agtagtgact aggcgagatg attattaaat cattattatt acataataag    24600
taagtataat ttattaagag gtcggaagga ataaaacttt tagcaaaaat gaataagatg    24660
actacctacc taattgatga tgatgatgaa tataagatat tattacttta tatattaaaa    24720
aatcttaata ctgatcaagt tagcagtctc aaaaatcttt ttttacttca tggttgccat    24780
aaattgaatt ctatgccacc aagtatagga tctttgacat gccttaagac tctaggtcac    24840
tttgttgtgg gaaggaagaa aggttctcaa cttgatgaac tacgaaacct aaatctctat    24900
ggatcaattt caatcacaca actagagaga gtaaagaatg atagggatgc aaaagaagcc    24960
aatttatctg caaaagctaa tctgcattct ttaagcatga gttggaatat caacgaaccg    25020
cgtagatatg aatcagaaga agttgaagtg cttgaagccc tcaaaccaca ctccaatgtg    25080
acttgtttaa caatcaaagg cttcagagga atccgtctcc cagagtggat gaatcactca    25140
gttttgaaaa atgttgtctc tattacaatt ggaggttgtg aaaacttctc atgcttacca    25200
ctgtttggtg gtctgccttg tctagaaagt ctagagttat ggaatgggtc tgcggaattg    25260
gagtatgttg aagattctgg attccctaca agaagaaggt ttccatctct gagaaaactt    25320
attatagtga attttgataa tctgaaagga ttgctgaaag aggcaggaga agagcaattc    25380
cccgtgcttg aagagatgaa aattagctgt tgtcctgttt ttgttattca gacccttct    25440 tctgtgaaga aattgaatgc ttattggcac aagtcagatg caacaggttt gagttccata    25500
```

```
tcaaatctta gggctcttac ttccctcaac attagccata actccacagc tactttgctc    25560
ccagaagaga tgttcaaaag ccttgcaaat ctcaaatact tggaaatctc tttcttcgat    25620
aatctcaaag agctgccaaa cagcctggct agtctcaatg ctttgaagca tctgaagatt    25680
agttgttgtc ccaaactgga gactctcccc gaggaagggg tgaaaggttt aacttcactc    25740
acactgttat ccattacata ctgtgagatg ctaaaatgtt taccagtggg actgcagaca    25800
ctcacaaatt tatcaattaa gaaatgtcca acactggcca agcgatgtga aagggaata    25860 ggacaagact ggtacaaaat tgctcacatt cctcatctgc tgattactga ttagatgtaa    25920
ttttctgatt tttctttttgg aaacaaatca actatttgta acatctattt gtatgatact   25980
tgatttttct tggttatgta acaataaata tttgaaattt ttcatattaa agattcagaa    26040
tgagttttat agctaactct atattttcac agtttaataa cgtaaaaatg tgatatttat    26100
atcaaattat tacttatgtt gtcatttatc aacatgttgg agatgatttt gacagtttat    26160
taaagaattc taagttttt attgtttgca caagtaacaa gccataaatt aagtttcgag      26220
ataaaagtga tttgtgtatc atggcttaat tagtcggaat ttcaagtttt tttctcaagt    26280
tatatatatg acaatttgta aaaatagat agtattgatt ttgatttaat tcaagcattt     26340
ttaaaaatat aaacattata atatgggaga tacacacgct aaacgcgtac ccagaaacta    26400
gtatataaag aatcatgacc gaaaaataaa atgaagttct gtcaacaact atctcgacat    26460
ctttgctgat atatatatat atctaactag tgtacttatt cggacttgac atggtataaa    26520
aagatattaa atatattttt aaataattaa taaatgatat aataaaaaga aagaaataca    26580
aattcagtta tgattctgat aaaagggaaa ctaattttct gattttttctt ttggaaacaa   26640 atcaactatt tgtattatac ttgttaatgt tgcaattatt agtgaacagt tgtattttgg    26700
attatcactt acagcagatg tctaaaatgt gaataagata atacttagaa taattttatgc   26760 aatatacttt tgtttaaata caagaaattt aaataaagat tgctaaagat tattattttg    26820
aatgaaagat tttgattttg ttactttgtc gcctatgtaa catagtactg ttgcaaacat    26880
atacatatgt gttcattttt ccccttgtgt ttcattttat tttctacaac tcataaatac    26940 taaaagaaa acgttaggaa tgagttttaa ctagatttaa attttaacaa aaacaacgtg     27000
attatatttc actaaattga cttaaatata tttatactta aaaaaaaatt attaatttat    27060
aatattaatg ggaccatata tttatataaa aattttctat aaatatatta tcttatatct    27120
cctctaaatt catttcacga gaattaaaac catcctaacg gatgacgttg ccaaaaagaa    27180
tagaaatttt ctttgaaagc gtgttaagtt tttttaaaa aaaagtaatg gtctcacttt     27240
gtatatatga agaaaaaaaa aacccacccc tttcttcttc ttcttcaaac ccccacccccc   27300 gcttttcaa aacccaccag cccccttac ctgcttgtct tttcttcctc atattcccga      27360
cgtcacccta tccccaaccc accccatcct ctttctcatt tttcgaactc tacattcaaa    27420
gcacataaat aaaaagaatc acatttaaga ttcatataat tttttttactc tttactttg    27480 agatttgatt tttcttaaaa agttatgatt ttttgaaaa taaagaatag ggcataaaag     27540
aagatgaggt tttgtcaacc aatctataat gttaatggct gggaatggtg attgaagcaa    27600
tggatagaga aagatttttt tttaaaaaaa aagagaaga aaaatcacta caatcagtaa     27660
ccgcaattgc agtaggctta catcatggag tatcccaatg agtctcttca ctgttcaatc    27720
ggccatcggt aaccgcatta caatgggctt tgggtcaccc acccaatttc ttataaatag    27780
aaagagacat gagatttatg attgcaccta gatcacatag tgatttggca aagtgtaata    27840
```

```
atacgaatgg tacatgaaat agtgaaagcg ccaggatctt ccttcttctg cacaagagtt    27900
cttgtgacaa tagcactaca atgctgcatt cagttatcat cctcaaaact taccgatctc    27960
ttctttgtaa ctatatcctt catgaacttg gcataaccgg accatttgct ccaaagcttc    28020
tatcaaaggg acattgatgg aaagttgctt caacatagtg ataaaatgtt ggtatttacc    28080
attctcacta ttcttcacca atctaaaagt ggtggtggtc taggaatggg gaccactttc    28140
tagggtatct ttgcttttt cgccgctttg tccaccaatt caccactagt ttccaccacc    28200
tcttcatctt ttctcatctc atcttctacc acagacgaca taggtgaatc aatagtttgc    28260
atacctcctc aagtagtgac tgtcatgcaa tgtccatcat ttttaggatt tgaatggaat    28320
tactatgaaa agtgacagtt gtcgcgggtt ctgatagtga acaattggac catttataat    28380
tcaagatgct taatcgagac cgcatgtgca tccaccttt tcccgatatt agccaaatca    28440
cctctcaatt tcttggcgtg ctcatcacta gcatcaaacc ttctcatcat ctttagcaac    28500
atatcttcaa cttgcgccgt actacctcca ccatctcaag gagcaacttt ctgattttga    28560
ggtggaacat agggcacact tcaatcattt ctattaccat agttacccg gttgaagttg    28620 ttatctcggt tgtagtttct tctcgaactt actggccctc ttgttgtaat tcccattctg    28680 catttttcaat ttaaaattgt tgataaaaaa gacaaaaaca taaaaattga tatgaaagag    28740
ctttggttaa gtaacaatct aattatcata gtgtcatatt caattcaatg attcttatag    28800
caatattgtt ggttcaacag tttaacttta ctcgctgagt tttctattta tgatgttaaa    28860
atgtttaccg aagggttatt atacttgttt ttaatgttgt aactattagg ggtagattat    28920
cactttatga atgaatattt tggcacattg gaaaacacc aaatatagcg cgcaaaagct    28980
aaacaaggaa atttcatat attggatata gtctttgtca tttccaaagg tctccaacat    29040
agagatagta attgagagaa aacttctatt gctattaaat agaatctgca attaaaaaaa    29100
aaataaatta ttattatatt ttatattata agtgggaaga tgcttagtct aaaggtggat    29160
taagaaaacg ccttcaactt ttttaattat cattattata ttatattata aataataatt    29220
aattattttt ctataagtgt gaaactatta agttgaata accttttaat tctacaagaa    29280
ctcaccatta agttgaatga cttttttaact cttcaagaaa tcactaataa gtcttttttac    29340 acgtcgtctt ataatgataa tattgtacat ttgaatttgg tttagagagc ataaatccct    29400
tattatacta tgtgttttca agcatttctt tacatttaga ttttttttat tttttgctat    29460
aattcaagtt atattcttaa attgatattt aagtgtttga tttctcacat gaaaatatac    29520
agttaaaatt ttgttttatg aactcatgat gtaattttt ctcaggtata attttaatgt    29580
gattcttttg cagacaattg actaaaattt ttagtagaaa ttgcaccaat acaaataagg    29640
tatgcggcat gtctctccaa caattttaca ttttttgcat gattatttt taataaaattt    29700 gatatacata cgattattgt atttttaact agattttaat aacttaatgc atgttttttt    29760
ttataataga gcctccttga taactttaca attacttatt gaaatttatt tttcttcaat    29820
ctcctagctt ccgagataaa atgggtaact aatatttctc cctcaacaac atggagcaaa    29880
aaaaatcgag aaaatctatg aagaagacat attctaacaa atggagtaat ttaatttaat    29940
ttaaaggagt acttaatagt caaatatgaa tagtaaagta agagaaaaaa aaataaaaaa    30000
attagaatat gacaagtatg aaagacaacc atgaacaaat tattggagtt ttttgttcat    30060
gctacaaaga acaataaagt tactatgtca tttgaatgta atatgtagac aacatatata    30120
cttgttacaa gtatatatgg taattcaaat tttggtacaa attgagcagg tgtgttatgt    30180
gtgtattgtt cctttcttag aaaagtaaca aactaatata ttgtagattt cgacctaata    30240
```

```
acataaaaat gtaaattatt tatcacatta aattttgttg tccaaatttg acaagttatt    30300
ggaatatcta attatttgac atttacattt tacaataaag aagtcatttt tataggttga    30360
ttgtccattt atttcgttta tatttttttc gttaaatcat ttttgaaaat tttcaaactg    30420
tgattttaat atattttttt agtttaatgt aattttaata taactcctac aatatataat    30480 attttttgtgg gactgacatg caaaacacgt gtcttggact agtctttcac ataaagacag    30540
acaactaaga agattgtatc gcggataaac gctactggaa tagccctatt atgaagagtg    30600
tttgtcaaac agccaaatga ctgtagtttt tcttttcca gaaatatgac tgaaggacta    30660
tatcttggat cgatcagagt gcatgaatca ctcagttttg gaaaataaag ttttgcttga    30720
taaacacaaa tttatctatt cacaccacaa gcaatggtaa gtcatcataa aaaaaaagag    30780
agagagagaa atttgttgtt agatcgagaa agattttgat aattgacgaa tagacgaaca    30840
aatgaaagaa acaggttgca tgtacatgtt cctttcaaac caaatccgac tgggattgtc    30900
aaccatgcga attagaagtt ataaagtaat ggaagggttg cttttttcgac ccgaacgaag    30960 agtgcaaaag gtttcctttc ataaagaaat cctaagcaaa gtgggaagtg taaacgaagt    31020
aggtagcata agcgagtagg aagtataacg acgtgaataa atttcaaatc tgaatggagt    31080
agatgatcag atatgtaaaa caagtacaag atgaaaaagg ttttgaagag tccaaagttt    31140
ataaataggg caatattttc tttggagaaa attgtgcact taaacagaga gttacaagca    31200
aaatacaatc aaatagaggg agtttatatt tgagtgaatt ctgattacga actgcagcca    31260
acacaagaaa acaagaattg aagaactcat tcattggctt atgttttata gttcttaagt    31320
caagtttttt tgtattgagt ttttatcgag ttgtatattt aacccttctc aaatccagtg    31380
aagtataaac tggagtagaa atagagtctt taagttaaag acttggaaac ataaaccttg    31440
ggggattttg ttggagtcta ggaattagaa tcagttctag tattgcaaga gttggaatcc    31500
gaattcataa cttgaagtgg gatcgacgat ctagttggtt gttggtaggg ccgactcaac    31560
aagattgagg gcctaaagtc aaaccttaaa gagggctcca atatttttt aattcttttt    31620 aaaaaaaaaa aaaaaaaaac taataatcat gtatatatta tttaaaatct attttctagc    31680
ttttctagat gtgaagtcat taattactat tttctaatgg atttgtttta ataattcttt    31740
ttcaattgat aatatagcta atacattcaa tctcattgtt gatattacat atataagatt    31800
ttatcaattt aaattttaaa aaattctttc ggccgaaaca atagttctgg attgttaact    31860
ttattcgtta agcaatatat gcattaggat tagaatcaag tcttttttatt agattgcgta    31920 tttccattaa atcattatct tctacttgta ttatttctct taataataat aactaaagcg    31980
agcatgtata cttactatga atatcaacaa caacaaaagt tcaagaaaaa ttacaaaata    32040
agttagtata ataaaacttg gcttgcgaat ttgataaatt gatataacaa tactgaaata    32100
gtgtttcatt tcttcaatat aatgactgtt tgtttaaaca agacactcaa aaacaaattt    32160
tatttttttt aacatgtaag cgacaataac tttttttttag gagagtgttc aacattgagc    32220
ataaaagtaa taaatagag aataaaaaag atgagtataa gataaataat aatataagat    32280
cgattttacc tattgtcaat tttgtgtatc gactaaagaa ataacagctt cacatatgaa    32340
tttgtatttt aggctgctgt aagtactaaa agatagttat tcaaccagta gaagagatga    32400 aggtggggggg cagctgttgg caatcaataa gggcatattg agccaatttt tttcttctct    32460
gaaaactttt ggcagagaaa ttaaggctaa cgaaaagtct tgtgcagtt gtttcccaaa    32520 actttgtgaa ttgtatttca aaaatacat tatttaatac tccaacaact ttgtgattcc    32580
```

```
actctagact accatcacat atctaatatt aattataata gtgaatttca catatggcca    32640
gaggcgaacc cacctgcacc caatatattt ttaaaaaaaa ttcatatgta gattgttgat    32700
aagacgctat aatatattta attgtgcact cttataatga acaaatgatt tgacttgttc    32760
attgaaaaaa caaaaagtgt cacataaatt gagacatgaa aaataatatt tcttttttaa    32820 attttcgtg tgaagtcaaa ctaattcata tataaagcga aagcggaagg agtactgttt    32880
aatattaatt gcatatggta gtaaatttga tagacatggt cccgtggggt gtgtgttatt    32940
tccattgaat aattgagttt gtaattgtta caagtccatt ctaatttcca acaccttact    33000
tcatttcaaa aatatagatt cattgcttac tcaccacata ctcgatggct gaagcttttcc   33060 ttcaaattct gttagaaaat ttaacatctt tcatacaagg ggaacttgga ttgttttttg    33120
gttttaagga cgaatttgaa aatctgaaaa gctcgtttac tacgatccaa gctgtgcttg    33180
aagatgctca ggagaagcaa ctgaaggaca agccactaga aaattggttg cagaaactca    33240
atgttgctgc atatgaagtt gatgacatct tggatgaata tcaaactgag gcagcaagac    33300
tcaatcagac taaatatggg agttatcatc caaaggctat cgctttccgc tacaagattg    33360
ggaaaaggat gaaagagata atgaagaaac tagatgcaat tgctgcagaa cgaagcaagt    33420
ttcatttgga aaaaaggact acagagagag aagctgctag acgacaaaca ggtgctcatc    33480
ttaaatatat tagtcttagt tacaacaatt taattagttt atattcattt tttggcgatt    33540
atcaagttca tctgtgttta tggactgaac ttaacttgga tgtcaatttt tcaaagtcaa    33600 tcatgtttc aactcccccc tgattcttat ctctttgtag tgcaaaaatc ttctctctgt    33660
ttttcgctaa acatattctc gtgtgaacat atgttgcttg aaacaggttt tgttttaact    33720
gaaccagaac tttatggaag agacaaagag gaagatgaga tagtgaaaat cctgataaac    33780
aatgcccaac aactttcggt cctcccaata cttggtatgg gggggctagg aaaatcgacg    33840
cttgcccaga tggtcttcaa tgatcagaga gtaactgacc atttccatcc caaaacgtgg    33900
atttgtgtct cagaaggttt tgatgagaag aagttgataa aggcaattgt tgaatctatc    33960
gaagaaaacc cacttggtga cgacatggat ttggctccac ttcaaaagaa gcttcaggat    34020
aggttgaatg gaaagagata ctttctcgtt tggatgatg tttggaatga aaatcaagaa    34080
aagtgggata agataaaagc agtcttagag gttggagcac gaggtgcttc tgttctaacc    34140
accactcgtc ttaaaagggt tggatcaatt atgggaactt gcaaccata tgaattgtca    34200 aatctgtctc aagaagattg ttggttgttg ttcatgaaac gtgcatttga gaaccaagaa    34260
aaaataaatc ctaaccttgt ggctatcgga aaggagattg tcaaaaaaag tggtggtgtg    34320
cctctagccg ccaaaactct tggaggtctt ttgcgcttcg tggatcaaga aagagaatgg    34380
gaacatgtga gagataatga gatttggaat ctgcctcaag atgaaagttt tattctgcct    34440
gccctgagac ttagttatca tcatcttcca gttgatttaa cacaaagttt tgcatattgt    34500
gcagtattcc caaaggatac ggtaatggaa aaaggaaatc taatctgtct ctggatggca    34560
cacggttttc ttttatcgaa aggaaactta gagctggagg atgtaggtaa tcaagtatgg    34620
aatgaattat acttgaggtc ttttttccaa gagattgaag ttaaagatgg taaaacttat    34680
ttcaagatgc atgatctcat ccatgatttg gcaacatctc tatttttggc aagagcatca    34740
agcagcaata tccgagaaat aaacgtagaa ggttacccac atatgatgtc gattggtttc    34800
gcaaaagtgg tgtcttctta ctctcccttct cacttgcaaa agtttgtgtc gttgagggtg    34860
cttaatctaa gtgaattaag acttaagcgt ttaccatctt ccattggaga tctagtacat    34920
ttaagatact tgaacctctc tcgcaataac atgcgtagtc ttccaaagca gttatgcaag    34980
```

```
cttcaaaatc tacagactct tgatctacag tattgctggt cactttgttg tttgccaaat   35040
caaacaagtc aagttagcag tctcagaaat cttttacttc atggttgcca taaattgaat   35100
tctatgccac caaggatagg atctttgaca tgccttaaga ctcttggttg ctttgctgtg   35160
ggaaggaaga aaagttgtca acttggtgaa ttacgaaacc tgaatctgta tggctcaatt   35220
caaatcacac atcttgagag agtgaagaat gatagggatg taaaagaagc caatttatct   35280
gcaaaagaaa atctgcattc tttaatcatg gaatgggacg acgatgaacg tccacataga   35340
tatgaatcag aagaagttga agtgcttgaa gctctcaaac cacactccaa tgtgacttgt   35400
ttaaaaatct atagattcag aggaatccgt ctcccagagt ggatgaatca ctcagttttg   35460
aaaaatgttg tctctattag aattggaggt tgtgaaaact gctcatgctt accaccgttt   35520
ggtgatttgc cttgtctaga aagtctagag ttatggagtg ggtctgcgga agtggagtat   35580
gttgaacatt ctggattccc aacaagaaga aggtttccat ctctgagaaa acttattata   35640
gacaattttg ataatctgaa aggattgctg aaagaggcag gagaagagca attccccgtg   35700
cttgaagagt tgacaattag ttgttgtcct gtgtttgtta ttccgaccct ttcttctgtc   35760
aagaaattgg tagtttatgg gaacatgtca gatgcaacag ttttaggtc catatataat   35820 cttagggctc ttacttccct caacattagc cttaactcca tagctacttc gctcccagaa   35880
gagatgttca aaagccttgc aaatctcaaa tacttggcaa tctctttctt cgacaatctc   35940
aaagagctgc caaacagcct ggctagtctc aatgctttga agcatctgaa aattgaatct   36000
tgttatgcac tcgagagtct ccccgaggaa gcggtgaaag gtttaacttc actcacacag   36060
ttatccatag aatactgtga gatgctaaaa tgtttaccgg aggaattgca gcaactcaca   36120
aatttatcaa ttcgaattg tccaacactg gccaagcgat gtgagaaggg aataggacaa   36180
gactggtaca aaattgctca cattcctcat ctgctgatta catagtgtca tactaaatta   36240
aataattctt atagcaatat tattggttca accaacaaaa ctaaatctct agttatatta   36300
tttacttgct catcatagct atagtttgct ataatcatca ctcgcgatta acattatgca   36360
tcaattacgc gggctgactt cgattttgta taattagtca cgtttttatg tgtataattc   36420
gccagaatat acggatatat gtataatata taattattta accgatatac atatataatt   36480
cacctctctc ccactctatg tcatctctca ctcgcctctc tcctccctct cttaattttg   36540
cttttcatat atacaaatac atatgtgtaa tatacaatta tctaaacgat atatatatat   36600
gcaattcatc tctctcccgc tcttttgctt cacctgacaa ctatgacatt aactttgga   36660 tatgcacatt taaaaactgg ttacagaaac tcaatgttgc tgcgtataaa gttgatgact   36720
tattggatga acgtgaatac gaggcagcaa gactaaagca gtctcgatta ggacgttatc   36780
atccaaaggc tatcaaatac gaactcagtt gtttagacca caaaaagact gtgaattcaa   36840
tacaggagta gttaacgatt tagaagagat ctactcttaa cgctaactaa aagattattc   36900
caattctcaa agaaaattta tattcctttc caaccaaaga ggttttccaa atttgctttc   36960
tagtaatttt ttttttttc tgcacgatag gaatagatct catatactcc ctccgtccca   37020
ttttatgtga agtagtttaa ctcgtacgga atacaaaaat gaaagaaaga catttaaaat   37080
ttatggtcta aatgaataat aaaaaatcgt gtgactataa atcatttcat taagagaaaa   37140
tagacaattt aaaattaaat tgttacttag tatagtaacg tgtctttttt ttttttaaact   37200 gtctaaaaaa gaaaataaat tatataaatt ggaacatagg gagtatctac ttacaaagta   37260
aaagttatgt gtagaagatt ttggcataca aatcatatca tatatcatca tatcatatat   37320
```

```
cacatcatat catcatatat tattataagc atgaagttca aaacttaaaa gttgaattac    37380
cattttagcc ttatactaaa ttaaaatatt ataaaataat taattaatta aatattaaat    37440
atgcttaaat tgttaattaa gttgattcac ttattgttaa aataaatagg agaatgaata    37500
gttgtaaaaa taattaatta taaagttatt acaaaaactt attagagaaa cgtttcattt    37560
ctctatcgat cgattttagg tgtaattttg tcataatgtg tattaatacc acacctccac    37620
tatctcatca ttaatatcca caccttcata atcttccaca ctctcaagaa gttgatggca    37680
taattatgag acttttgatt ttactcaatg atgtcctata aattgcggta tttgacacaa    37740
caatctatac actttgaaga tatttaggta cagtttggaa gaaattaaaa aaaatgtcta    37800
tatttctatt gttttatcc tttagtatat atttaaatca cttttaaac tgctcataac    37860 accgattcat taattttcct tatcttcatt tgttgtttat aggaaggaaa tgtgtacaaa    37920
ttgttagatc ttctaatgga gtttacaacg agagaaggga tgttcaagtc ttccggaggt    37980
tgaaatcaat tttaatttca agtattatat tcatgctttt agatgtttat atatatatat    38040
atatatatat atatatatat atatatatat atatattcaa atgagtcaac atagactaat    38100
atgagactta aaggtcggaa aattggagta tcacaattag tagtaaaaca aagtaagaaa    38160
tctcaattag atatatttta ttattttta agaaataata cactcatggg tataagtgtg    38220
aagctccaaa atgcaaaaag ttgaattact attgtatccc tataatagtt aattattttt    38280
aaatattagt tcatatgata ttattaaatt atacttcttt gaaattaata acataataaa    38340
aaccaaattc atctttgaag tgcaaattta tcgtccttca ttattgataa tttgaatgca    38400
ctaaaaacta tttaatatcc cggaaggtgg aagagtgaaa gtattcataa ttaatttcta    38460
gataaaattt tactagataa aaaagtatac atgcattgga attaataatt taaaaataaa    38520
gaaataatga tttagccttt taagttacct acttttatta tgctctttaa accattgtta    38580 ttattttta aaaaaaaaac tcatattaag gtgttagctt gattagtcta aagatatcaa    38640
aatgtcattt cttggatcac ttaatttgta acgttttat cttctattag cgtgattctc    38700
cattttccta tattatatat tatactttct catgtaatca tgttatctat atttattttt    38760
ttatataagt ttgttatgct caatgtttta tttatcttta tttgaactca tctaaattgt    38820
tgaatatttc aactactaat aaatttttta aatttgactt ttttttttatg aaaatacaat    38880 taagaaatga cgctaatatt tcatagtgat gatgcagtaa gtgaagcaac acagattgaa    38940
ctgtttcaag tggtatcaat tttcaggtaa taaatcattg ttccttatat gcaattaatt    39000 attttttgtgt aagttgatat gttcttaata aaattttggt ttgattttta aataaaaatt    39060
attttataga agttgagacg gtacacttaa ttggattatc caaaaaaaga atcttttaca    39120
caaggacaag aagaaagact tctagcttta tcactgcatt catgacaatc aatggaatat    39180
cctacaagac aaaaagttga tgtgattctg tacaagtgaa tccaactcac taacaaaaaa    39240
attaaagaaa gaaaaaaatg aacatgaaga gaataaaaat gaagatgaag agaatcaatg    39300
gtgtcttata agttgatgaa ccactgtaac ttcattattt tttaaattta cgaggaaatg    39360
aattattgac gaaatttatg aaatgtacat atataccttt gggtcggtaa caaatgtgat    39420
tgaaagtagt atttttcat gcataatagc taattcttga tatatatatt gtttaaattt    39480
attatttgta ctacaaacat tgtatgatat attttaggat aagcgtaacg catgcgacgt    39540
ggaaactagt atattagtaa aagcatgaat aaaaaagttg aaagttgaat tacgattta    39600 ttccttctat aattaacttg ttataaaata tttaaatatt tgattgtaca agtttaatta    39660
aaatgttaaa tgacttttag acttcataag attaatttat aattaaatat ctattttatt    39720
```

```
aatatttatc atttataatc tatatgtata taataattat attttttttt aaataaaagt   39780
ctaattaaaa tattaatgac ttttagactt cctaacacta atttctaatt aaatatctaa   39840
tttattaata tttttatcat ctattatctc tctctatata ataattttac aaaaattaac   39900
aaaaaaagtc tctacgtaaa tttttatact tttttttttta ttctcataaa tttttcctaa   39960
ataacaaaat ttaataattt gaaggatgca aatctgcaaa atggagacac acacatttga   40020
taatgtcctc ttaattatca ttaaagaatg actctaacta gcttcacaaa tttaaattca   40080
ttgatactta attactcgga gaaaagtaga tgaagactct taattttgat agtatatgga   40140
aggagtcaat aaagtttcgt agattttatgc aataattttg tacttattt ttcatctaca    40200 tatacatagt cttatgagaa tgatgtctac attgtatttt ttcttaaatc tgtttctttt   40260 gtctttatc cccaattaga cttcttaatt taatttata caaatgtttt attgtcataa      40320
gtctttatac ttattttgta attgtagcat tttattgttc attacaattt gcatatatat   40380
atttccatga aatattagta attctatcat atctataaaa attcacatga aatacacgtg   40440
caaagcacgt gttcagaaac tagttaggaa aacaacacaa atatacatct gaactatcgt   40500
aaatgatata cagataccat catcatactt ttgggacatt ggtgtccatg tcgtcaaaaa   40560
aatagagcaa atatattaat ggacatcacg tgtcagaatc atatcaattg atccaacatt   40620
tattaaatgt ttgatcgaag aatagattgt gtcacatgtc cctatttagt catctgttaa   40680
aatgaatgac atatgggttg ggccgaccat tttctgaccc acacaaaaaa tgggctagcc   40740
cggtttaacc cgtaaaatat caaaacatgt atggattagc ccggataagg tgtgttagcc   40800
atattgacag ctttatcccc acatcaagaa ggtatttata tgtcaacttg aaaagaaaaa   40860
attttccaaa tatgatctgc ttatactcta tcaattccat atctcactta gtgaaatttc   40920
actgaatata ttgttgttgt tggtgtcctc tcccatcatt ataaatttaa agaacatgca   40980
atgtaagacg taatttagaa aacttggttc gcccgtagaa gaaggatcat ctgtaaattt   41040
attcctctgc aagttgatgc tttgaatctg ttggtacatt tcctctaaac atgttagatt   41100
ggattgaatc ttaagtcatc atgtgttact atctgaaaga ccaatatttta aatttattgc   41160 tcacaagtaa aaattagaac taaaaatata caaacatgaa gttcaacata tattataact   41220
taattcataa aagaaaaatt atttgcatgc ataatatttg tttattcatt tcttagtgta   41280
catattttaa ctttatcagc gtagtaattt ggtttgattt gtttgtttgt tataatgtaa   41340
ttacaagtgt acttagcttg tttgattaca caagtgtaat catataatta tactgaattt   41400
taaagataaa agttaattat ttgaaacaaa aaaattatat taggcaaata agagccttta   41460
taaatgatat tcaattgaat atttaagata tatagtgtct tttaaaaaat atgttattta   41520
ataaacatat gttcttaatt aatattataa aaaagcaaa tgatttatat atttcaatgt   41580 agtatttta aagtaaatta atcataaaaa ttaaaaatgc atgaacatca tgaaatgctt   41640
gtttcacaaa aaaattaata ttataaatat aatgtcataa aatcatagaa aaataattga   41700
caaaagaact aatttatcaa gtctaactta aaaagaatag gttgcaatgg aatatcaagt   41760
caatactcct aaaacaaatg aaattgaaaa tataatataa gttctaaatt taaaataaaa   41820
aatttaacat aatactttta tgtcaaattt caacataata tgattaaaag aaaaggaaaa   41880
tttaagtccg taactttgtt caacaataaa ttctacttta attcaaaaat tagaatacta   41940
acaaaattat actaataatt tttttagata ttatgaagaa ttgcatgaaa tcacatgaag   42000
taaaagttaa aaataagaag gaaatgaaat ataaataata aaggaaaact ttcatatata   42060
```

```
gccacttaaa aataattaat tactctccat agctatagtt tgataattac aatttgtagc    42120
tacatgttat gtggaggaga gagaggcgag cgtcacttgg agagagaggc gagagagaga    42180
gggggaaaag agtgggagaa aggtgaattg tatatgtata ttggctagat aattgtatat    42240
tatacatatg taattgtata tatggcaaga gagattgaga gagggaggag agaggcgagt    42300
gagactgtga gagagagaga gaggcgagcg agatcaagag agggaggaga gaggtgagcg    42360
agagagggca gagagtgaga gggatgtgaa ttgtatatgt atataatttt atataactgt    42420
atattataca tatacatttg tataaatggc aagcgagatt gggagaggga tgagagagac    42480
gagcgagaga gggcagagag tgggagagag gtgaattgta tatgtatata ggctaaaaaa    42540
ttgtatatta tacatattta tttgtatatc ctggcaaatt atacatatat aaacatgata    42600
attatacaaa catgaagtca acccacgtaa ttaatgtata atgttagtcg cgagtggtaa    42660
ttataacaaa ctatagttat gatgcataat taaaataata taagtttgtt tattcgcata    42720
atttttcctt ttttaaaattc ctccttctat tcaacttgca tttttttgtca aatataatca    42780 tcgttaaaaa ttatttgatg ttgaattaac aaacatccat ctttattata tcacatgttg    42840
tgacatgcac caaaacgata aaaacgacac cttcaaaatg atttttttta aaataagcct    42900
agttaattga tgtttaacat ataaataatc aactaataag gttaaaggct tacacataca    42960
aactaaaaat tagatcaaat gcactaaaaa taaataatat gaggaaaatc tgttttaggg    43020
attatagtgt cccccaacga ccaagtctta tttttaatgg agcatcattg attggtctat    43080
tgacaaagaa aatttggaaa ttaatgattt tgttttatcc tctggaaatt tattatgtta    43140
tcacaactat ttgttaattt gaactgcata aaagttttg ttcgaacttc atatatgaaa    43200
attctaaaca agaattggaa acttgaaatg aatccaacat ttaaatcaat agataattat    43260
tgattgaatt tcttaatacg tatatataca aaagatctga ataaaagcta ttgaatacat    43320
tacatgttat attggttaat ttgaccgtaa aacagttgac attcttttgt caagcatcta    43380
ttctggggag gttatatata tatacatttg aataatgacg ttatactata gcctaaaact    43440
acataaaaaa tgtcaagtaa attatttaac tgtcaataca gaattccaca accaatagtt    43500
tatttccctt tagcaatgaa ttgcagtcaa gttcagctag caatatacaa ttaaaagatg    43560
tttcaaatca ttggtattaa ttagataagt attgactcaa ttacaagtat acacacagta    43620
tatatagatg gcgtttgaaa acgaaaacat aggcacaaat agcagctaaa gaagttgaac    43680
aaatcaaaat ggttgcgaag actattatta tagcatgcct agttttgtta acatgcctct    43740
cagttactaa tgcatcgaac attacaactg atgaggcaca aatgactata tctagtgaaa    43800
ttaacatgca gatgaatagg catatcttgc agtaaaaagc atcaaagagt gacatcatta    43860
gtcctcaata gctttggatt tagaggttca atcgcgacag atattgggaa tctctccttc    43920
cttaactttt tggacattgg aaacaacagt ttccatggcc aaatacctga tgaaataggg    43980
cgtttgaggc gtttaaaata catgtatttg cagatgaata atctcgctgg tcaaatccca    44040
gaaagccttg gatttctcac aaggcttcaa gttcttcatc tttctgaaaa tcgtctattt    44100
ggaaatgttc cagcttccat tttcagcgtg tcttctttaa aggacattga tttgtctcag    44160
aattacgagt taactgggag tttaccaaat gagatatgca ctaatcttcc agtgttggaa    44220
tatatatccc tgcaagataa tcaatttgta ggtgaacttc ctaaaggttt aaataaatgc    44280
tccaaacttg aagttctgtc cttgtcttat aacaaattca ctggtaatta actaacttgt    44340 aaactttttca tttactaatt tcttcttgaa ttaatcatca tttttgtgtg tgtctgtgat    44400
tttataattg ataggaaact taccaagaga catgtggaac atgtcaaagg ttcaagaact    44460
```

```
ttttattgga tggaataact taacaggtac gtgattctgt atgtattaaa tcttgaatac    44520
tcttcacgaa gttcctaatt tcactagata tagccaattt gtgcattgtc tagtaataaa    44580
caaagattaa tatattttgt ggagaacatt ttcgaaagac actctatgta tgatctttag    44640
catgataacc atatacttat tttcaaaatg aatttgcagg aaatatacca aatgaaatga    44700
acctaccatc tatttgcagg aaagttaaca aagcttgagc atcttgttgg gttatgggtc    44760
tttttcccct cctatttgga taactaaaag cccaatttgg accaatccat ttttgcctat    44820
aagcccattc ttatgaggca aatataaact gattttaggg tctgattttc agaacatata    44880
gagagttctt cagcagccaa aaagagagaa agagagattt tcgcaggcaa aattcagatc    44940
taatagacaa cttcaaattg cgattcccgc ttcttttctt atccgattga gttgattttt    45000
ggacagcata ttgtcttcat ctcaatcttt gattagaaac tgacagagtt ggatttggtg    45060
gcctgcgact ttcagttttg cttttgtcgt gagcgaagct gcaaaattgg tgattttgct    45120
cctttaattt tctagatttg gtgcaatctt attttgttgt tgctcgttgt ttggcacttg    45180
ttttgtggcc aattttggag aacaatattg taactcttgg tgattatagt ggagcttttg    45240
gtccgtggtt tttactcttc acatgaaggg ttttcaacgt aaatcttggt gtcttatgtg    45300
attggtttca cattgtcttg ttatatttgt ttggttgaat tggaatcgcc ttactatcat    45360
attgcttgtg gttgtttgtc ttctcttggt tcaaatcgaa aaagggaaag tatagacttg    45420
gatattcttc cgttatctgt cgtcagcatt cttggtagtg tcttgtcttt cccaacaaag    45480
tggtatcaga gcattgggta ttgttgattg tcgttttgaa tgatggagac aaatatgagc    45540
aaaatggtgt ttttaaatgg tagtaactat catatttgga aaggcaagat gaaagatctt    45600
ctatttgtca agaagatgca tttacctgtg tttgtttcta ataagcctaa gtctttgaat    45660
gatgaagaat gggaatttga gcatcatgca ggtttggcta tattatacaa tgggttgaag    45720
ataatgttat tagaaatcag tattgtgaat gagacatgcc aaaagtttgt ggacaagtcg    45780
agacacttta tgcttcaaga ttgtgtaaca actgctccta ttgaacaatt aatgaatatc    45840
gtataaagag ggcactccta tttctgatca tattaatgat tttagggggt tcttgaccgg    45900
ctgtccgaaa tgggtgtaaa gtttgatgat gagatacagg gactttggct tcttaatacc    45960
gccagatctt gggaaactct tcagtttctt tgaccaatct gctcccaaag ggtgttgtaa    46020
ccatcggaat atactaaaag tagtgtcttg aatgaagaaa taagaagaag atctgacctc    46080
atcttcagac ttctacactc cgatgttttt ccactgaaga tagggggaga aacaagtcgg    46140
taggaggaat gatagaggta aaagtgtatg tcaaagtcta agtctaacac aagaatatta    46200
catgtgacta ttgccacaag aatgggcata tcatgaaata ttgttacaag cctgagagat    46260
atgagacaac aaaaaagaga aggcgataat gaaaatcgtg ttgttgttgt tgctaatgat    46320 cttcttttctt tttttcttga tgcaaatgcc attaatcttg ttcgtgatga gtctagctgg    46380
tttgtggatt cgggtgctac ttctcatgtc atgccaaaga aggaattcta tttcttatac    46440
tccggggtaa ttttgaaacg ttgaaatggg caataatcat gaagttgaag ttattggcat    46500
tgggacagtt tgtttggaaa ataacaatgg ttcaaaacta gttctcaata atgtcaagca    46560
tactccggat gttcgcttga atttgattta cgtaggatat cttgatgatg aggttatgtt    46620
aaacacattt ggtgttggct agtggaagct tactagaggt ttgatggttg tggcccgtgg    46680
tgacaagttg tctaactttg tatgtatttg gggctccgtt tcgagagact caagaatttg    46740
gtagagaatg atacttatcg aagttatggc atgtaaaatt tgagtcatat gagcgagaag    46800
```

```
aggattgata gtttggctaa gaaaaatttg ctttctggag tgaaacaagc aaagttgaag    46860
aaatgtgttc attgcttagc cggtaaacat aaagagtttc ttttgaaatc atccgccttc    46920
aagaaagctt gatttgcttg gagttggtac attcccgatt ttgtggtcct tttaaggtaa    46980
gatcccatag tggtgcaatt ttactttgtg actttttatt gatgatcatt ctcgcaaact    47040
cggggtattt cctttgaagt ccaaggatca agtacttgat gtgttcaaga gttttcaggc    47100
cttggttgaa agacaaacag gaagacattg aaatgcatcc gctcgaataa tggtggtgag    47160
tatattggtc cttttttgata gatattgaag agagcggggt attaggcacg aaaactcctc    47220
caaaactcgc ggttaaatgg tttagcaagg aggatgggca gaactctagt tgagaggctt    47280
agatgtatgc tctcggatgc taatttgcca ttcctttagg cggaagcact taatctgccg    47340
cttatgttat cgatttatct cctttgttgc tttagataga tggtgatgtc acagcggagt    47400
ttgggtggta agaatgtttc ttatgatcat cttagagtct ttgggtgtaa agcctttgta    47460
catgtttcta aggatgaaag gtcaaagttg gatgttaaaa ctaggcgagg tatcttcatt    47520
ggttatagtc aagatgaatt tggctatcgt ttctatgatc tgttgagaag aaacttgtta    47580
gaagccatga tgttgagttc tttgaagacc aaacaattga agattttgac aaaagtgaca    47640
aggctgattt tcgagtagtg agagcttagt tgatgttgat ccggttcctt tgactattgc    47700
cgaagaaaat cttcttaatg aagaaatca agttgataat gaagatggtg atcatgttct    47760
aatgaccggc atgatgttgt ttatgctccc aagaagatga tgtggttgtc caacaaccaa    47820
ttatagatgc tccggagagt tctctcgcac gatctagtag agaattcctt catctcgtga    47880
ttctcctaat gagtatgtac ttgacttacg gggagaaccc agagtcttga tgaggccatg    47940
gaaagtgaag aaaaagaaag gtggtttgat gctatggaag atgagattaa atccttgcat    48000
gataatcata cctttgattt gttgttacct aaactgaaaa acttttttgaa aaaaggtggg    48060 ttttttcggg tgaaacatga agatggtaat ccggttccac cagacaaagc tagattagtt    48120
gtcaagggat ttaatcagaa aagggagttg atttttgatga aatattctct ccgattgtga    48180
agatatcatc cattcggtgt ggttctaggt cagctgcaag tctagattta gaggttgagc    48240
aaatggatgt taaaaaccgc tttcctccat ggtgacttag actaagaaat ttatatggag    48300
caaccggaag gttttgaagt caaggtaaaa gagaattatg tttgcaaatt aaagaagagc    48360
ttgtatggtt tgaaacaagc tcccgtgcaa aggggtacag tgaagtttgg tttttttatga    48420 gtcaaagggg cttcaagaag acttcttaac cattgtgttt tgtgcaaagt tctctgatgg    48480
tgacttttat tgttgcggtt gctttatgtt gatgacacgc ttgttgtcgg gtcataatac    48540
ttgcagtagg atcaagttga agcaaggagt cgaggcaagt cttttttgcat gaaagactta    48600 gaccaaagaa ggcagattct tggcatgcag attgcccgtg atagaaaaag ccaagaaatt    48660
ggtattatca caagagaaag tacatttta aagtacttca agcagattca aagatggaca    48720
aagctaaggt tgtcaagaca ccttagctat gccttcaaat tgaaagcatg gaaatgctgt    48780
cctttctagc gatgatggaa aggaagatat gaagaaagtt ccttatgctt caaattggta    48840
gtttgatgta tgcgatggtt tgtacaagac cgatattgct cacgctgttg agttgttaag    48900
cgggtttctt tctaatccag gaagagaaca ttggaatctt tgtgaagtgg gttatgagat    48960
atctcatggc acttctagtc cgagtttgtt tttggcaggg aagcctatt ttttgattta    49020 tcttgattag gacatggttg gtgatgttga tactcgcaag tctacttggt gcttggttac    49080
tttaggggga gtattgtctt ggcaatctag attgcaaaat gtgttactct atctctacta    49140
tggaaggctt attctttttcg tgaagcttgt aaagaattgc tttggatgaa gagattatta    49200
```

```
agaacttggt ttgtgctcaa agaggtatgt actttattgt gaccggtcaa agtgctatac   49260
atcttggcaa gaattctacg ttccatggtc ggttaaacac attgatgtga gataccattt   49320
gattcgagat gtattggatt ctaagttgct tgagcttgaa aaagattcat acaaatgaca   49380
atggttccga tatgatgact aaagctttgc caagaggaag tttgaagatt gttgcatggt   49440
cgtggggacg ggcggtcctc cacatagtcg tgagggagaa ttgttgggtt atgggtcttt   49500
tttccttcta tgtggataaa taaaagccca atttggacca acctattttt gcctataagc   49560
ccattcttat gaggcaaata taaactgatt ttagggtctg attttcagaa catatagaga   49620
gttcttcagc agccaaaaag agagaaagag agatttcgc aggcaaaatt caaatctaat    49680
agccaacttc aaattgcgat tcccgcttcg tttcttatcc gattgagttg attttggac    49740 agcatattgt attcatctca atatttgatt aggaactgac agagttggat ttggtggcct   49800
gcagcttcag ttttattgtg aggaattagc tgcaaaattg gtgattttgc tcctttaatt   49860
ttctagattt ggtgcaatct tattttgttt tgttgctcat tgtttggcac ttgttttggc   49920
caattttgga gaacaatatt gtaactcttg gtgattatag tggagctttt ggtcccgtgg   49980
ttttactctt cacatcgaag ggttttccac gtaaatcgtg gtgtcttgtg tgattggttt   50040
catattgtct cgttatattt gtttggttga attacctgct gccttagtat catattgctt   50100
gtggttgttt gtcttctctt ggttcaaatc gaaaaaggga agtatagac ttgggtattc    50160 ttccgctgtt atcctgtcag gcattcttgg tagtgccttg tctttcccaa cacatctcaa   50220
ctatctgaat gtctcttaca atgagttatc aggtgaaata ccagatggag gccttttgg    50280 taattttcac agctgaatca ttcatcggca atgaagagtt atgtggaccg cctagattcc   50340
aagtcaagat ttgtgaaatc cgaacaacgt gacaagaaga acaggaaaaa acaagacta    50400 aaatttgttc ttggaccagt gcagctggag gtttagtcat ggggttttag gcatgatatg   50460
gttgttgaat tatcggagac gtaacaacca acttattcct ttaactgatt agtatgatcg   50520
gttatcacac aaaaagttttt cttactatga acttgtttga gggactaaca actttgactt   50580
taatcaaatt tgattggaaa gggaagcctt ggtatggttt ataagggac atttacaaat    50640 gggactatag ccaactgtaa aaggttttcaa tgctggcgca agatgcattc aagaggtttg   50700
atttggagtg taaggttttg cgtaacaccg aaataggaat cttgttgggt gataagtagt   50760
tgttcaaatc ttgattttaa ggcattggtg tttgagtaca tgcctaatgg agatcttaat   50820
tattggcttt actcacacaa caatttcttg gatttaaaca aaatttgaaa attatgtttg   50880
atgtggcttt gtgtcagaga gtatctacac caaggccatt caaaacatag tggtccatca   50940
tgacttgaac atactttggg atgaagacat ggttgccgag taagtgattt tggtatattc   51000
aaactcttga ccgccagatg atccaaaggg cattgacaaa gactttaggc accattatcc   51060
tggcactgtg cccgatcaaa tttttattta ctaattactt tcttcaactt gtattcgata   51120
tgcatatatg atgtatttca ttttaatggt agagtacggg tcagaaggga tagtgtcaac   51180 tatggggat gtttacagct acggcatttt atttatggaa accttcataa gaaagaaatg    51240
atagatgatg agtttgttgg agaccttaca ttgaagagat gggtcatgga atcatatcct   51300
catagagtca ttgttatgaa ataaaaacga atacaagttg aacgtcaatt atgagtcatt   51360
tatctaatat gatccattaa caattgatta atgtaacgca ggaagaagaa aacaatttgc   51420
attgttatga atgaatgtgt ttgtactaca atatatacaa agatcgacaa gtctagcaaa   51480
ctttctaacc aacttattct aaccaactct actcattatt catttagctc acttaatcaa   51540
```

```
gaaattagac ctaacaacta actaccatta actcattcaa ctgattgttg ggttataggt    51600 cttttttccct tcctatgtgg ataaataaaa gcccaatttg gaccaaccca tttttgccca   51660
taggcccatt cttatgaggc aaatataagc ctatttaggg tcttattttc agacaaaaca   51720
gatcagtttt tcagcagcca aaagagaga aagagagatt ttcgcaggca aaaatttaga    51780
tctaatagct aacttcaaat tgcgattttc acttcgtttc ttatccgatt gagctgattt   51840
ttggacagca tattgtcttc atctaaatat ttgactagga actgacagag ttggatttgg   51900
tggcctgtag cttcagtttt gctgtcgtga acagtagctg cgaaattggt gattttgctc   51960
cctttaattc tctagatttg gtgcaatctt attttgttgt tgctcattgt ttggcacttg   52020
ttttgtggcc aattttggag aacaatattg taactctttg gtgattatag tggagctgtt   52080
ggtccgtggt ttttactctt cacatcaaga gttttccacg aaatcttggt gtctttgtga   52140
ttggtttcac attgtcttgt tatatttgtt tggttaaatt acttgccgcc ttactatcat   52200
attgcttgtg gttgtttgtc ttctcttggt tcaaatcgaa aagagaagta tagacttgga   52260
tattcttcat ttgttatccc gtcgagcatc atttgttatt gccttgtctt ttcccaacaa   52320
agtggtatgt caggagcatt ggttattgtt gattgtcgtt ttgaatgatg gaggcaaata   52380
tgagcaaaat ggtgtgtttta aatggtagta actatcatat ttggaaaggc aagatgaaag   52440
atctttattt gtcgaagatg aatttacatg tttgcttcta ataagcctaa gtctttgaat   52500
gatgaagaat tggaatttga gcatcctggg tttcggctat attagacaat gggttgaaga   52560
taatgttaga aatcatattg tgaatgaaac acatgccaaa gtttgtggga caagctcgag   52620
acactttatc ttgaagacgg caacaaacaa gttgttctat tgaaacaatt aatgaatatc   52680
ggtataaaga gggcactcta tttctacgat catattaatg attttcaggg tgttcttgac   52740
cagcctgtcc ggaatgggtg taaagtttga tgatgagatc acaggggact ttggcttctt   52800
aatactcatc cggactcttg ggaaacttct tctagtttct ttgactaatt gctcccggtg   52860
gtgttgtaac catggaatat actaagagtg gtgtcttgaa tgaagaaaat gagaagaaga   52920
tcttgcctca tcttcttaaa cttcactccg atgttttggt tcttgaagat ggggagaaac   52980
aagtcagtag atcgaatgat agaggtaaaa gtagaagcaa gtcaaagtct aaatacaaga   53040
atattacttg tgactattgc cacaagaatg ggcatatcat gaaatattgt tacaagcaca   53100
agagatatga gacaacaaaa caagagaagg cgataatgaa aatcgtggtt gctgttgttg   53160
ctaatgatga tcttctttttt tcttgtgatg caaatgccat taatcttgtt catgatgagt   53220
ctatttggtt tgtggattcg gtgctacttc tcatgtcacg ccaaagaagg aattattttc   53280
ttcttatact ccgggtaatt ttgaaacgtt gaaaatgggc aataatcatg aagttgaagt   53340
tattggcatt gggacgtttt gtttggaaag taacaatggt tcaaaactag ttctcaataa   53400
tgtcaagcac acccaaatgt tcgcttgaat ttgatttccg tgggatatct tgacgatgag   53460
ggttatgtta atacacttgg tgttggcggt ggaagctcac tagaggtttg atggttgtgg   53520
cccgtggtga caagttgtct aacttgtatg tatttagggg ctccatatcc ggagactcca   53580
agaatttggt ggagaatgat acttcatcga gttatggcat gaaggtcgag tcatagagaa   53640
ggggattgat agtttggcta agaaaaattt tcttctctgga ttgaaacaag caagttgaa   53700 gaaatgtgtt cattgcttag cgggtaaata gaaaagagtt ttttttagt catccgcctt   53760 caagaaagct tgatttcttt ggagttggta cattccgatt ttgtgtggtc ctttaaggta   53820
agatctcatg gtggtgcact ttactttgtg acttttattg atgatcattc tcgcaaactc   53880
taggtatttc cttttgaagtc caatgatcaa gtacttgatg tgttcaagag ttttcgtgcc   53940
```

```
ttggtttaaa gacaagcagt ggaagacatt gaaatgcatc cattaagata atggtggtga   54000
gtatattggt cctttttgata gatatttgca gagcgggggta ttaggcatga aaaacctcca   54060
aagactccct cggttaaatg gtttagaagc agaggatgag cgagaactct agttgagagg   54120
gttagatgta tgcttttaga tgttgtcgtc gattcctttt gggcggaagc acttaacatc   54180
gctgcttatg ttatcaattt atctccgttg ctttagatgg tgatgtcctc gatgtagttt   54240
ggatcgtaag aatgttttta catcatcttg tagtctttgg gtgtaaagcc tttgtacatg   54300
ttcctaagga tgaaaggtca aagttggatg ttaaaactag gcaaagatat cttcattgga   54360
tatggtcaag atgaatttgg ctatcgcttt ctatgatccc gttgagaaga aaacttgtta   54420
gaagtcgtgg atgttatgtt cttttgaaga ccaaacaatt gaagattttg acaaactgac   54480
aaggctgatt tgagagtag tgagagctta gttgatgttg atccggttcc tttgactatc   54540
aacttgggaa gaaaattttc ataatgatga aaatcaagtt gataatgaag atggtgatca   54600
tgttcagtaa tgacctatga cgatgacgct ttttgatgct cgatgcagaa gatgacgggt   54660
tgtccaacaa ccaattatag attctccgag agttctctca gacgcatcta gtagagagag   54720
atttcttcat ctcgttattc tcccaatgag tatgtactct tggtgacggg gagaacccga   54780
gagtcttatg aagccatgga aagtgaagaa aaagaaaggt ggtttgatgc tatggaagat   54840
gagattaaat ccttgcatga taatcatacc tttgatttgg ttaagttacc taaaagcgta   54900
aaaagctttg aaaaaaaagg gttttttttg ttgaaacatg aagatggtaa tcaagttcca   54960
cggtataaaa gtagttgtca agggatttaa tcggaaaagg gagttgattt tgatgagata   55020
ttctctccgg gttgtgaaga tgtcatccat tcgtgtggtt ctaggcttgg tacgcaagtc   55080
tagatttaag ttgagcaaat ggatgttaaa ccgcttccca tggtgactta gatgaagaaa   55140
tttatatgga gcaaccggaa ggttttgaag tcaagggtaa agagaattat gtttgcaaat   55200
tgaagaagag cttgtacggg tttggaaaca agctcccaaa gcaaattggt acagaagttt   55260 tggttctta tgctggggaa aggcttcaag aagacttctt cagaccattg tgtttttgtg   55320
caaaagttct ctgatggtga ctttattatt gtgttgcttt tatgttgatg acatgcttgt   55380
tgttgggtca taatacttgc ggggattcag aagttgaagc aagagttgag taagtctttc   55440
tttatgaaag acttaggacc aaagaagaca gattcttggc atgcagattg tccgtgtgat   55500
agaaaggcta aaaattggta ttatcacaag agaagtacat tcagaaagta cttccacagt   55560
attcaagatg gacaaagcta aaggttgtca gtgacacact tttagctatg cacttcaaat   55620
tgagcactag cttaggtgtc cttctagtga cagatgagaa ggaagatatg aagaaagttc   55680
ttatgcctag ctgggttggt agtttgatgt cacgatggtt ttgtacaaga ccggatgttg   55740
ctccatattt ggggttatta accgttttct tttctaatcg ggaagagaga acattggaat   55800
ctttgtagtg ggttatgaga tatctttgtg gcacttctag taaagtttgt gttttagtgc   55860
agaagcctat tctttgtggt tatccggatt cggacatggc tggtgatgtt gatactacgc   55920
aagtctactt gatgcttaat tcttttttgt ggggagctgt gtcttggcaa tctaggttgc   55980
aaaatgtgtt gctctatcta ctctctgctg gaggcttatt cttttatcgtt gaagcttgta   56040 aaattacttt ggatgaaaga ttaacacggg aacttggttg tgctcaagag aggtatgtgc   56100
tttattgtgg tcaaaagtgc tatacatctt ggcaagaatt ccacgttcaa tagtcggtct   56160
aaacacgttg atgtgagata ccattggatt cgagatgtgt tggattctaa gttgcttgag   56220
cttgaaaaga ttcatacaaa tgacaatggt tacgatatga tgactaaagc tttgccaaga   56280
```

```
gggaagtttc aagattgttg catggtgctt gggatggcgg gcctccacat agtcgtgagg    56340
ggggagaatt gttgggttat aggtcttttt tccttcctat gtgataataa aaagcccaat    56400
ttgaccaacc cattttttgct catagcccat tcttatgagg caaatataag ccttatttag   56460
gatcttattt cggaaaatga cagttagttt tttggtgagc caaaatagag aaagagagat    56520
tttcgcaggc aaaaattcag atctaataac caactttaaa ttgtgattcc cgcttcgttt    56580
cttatccgat tgagctgatt tttggtcaga atattgtctt catctcaatc tttgactagg    56640
aaccgacaga gttggatttg gtggttcggt aacttcagtt ttctttgcga atgagcgatg    56700
gctaaattgg tgattttgct cctttaattc tctagatttg gtgcaatctt tttgttgttg    56760
tcgttgtttg acacttgttt tgtggccaat tttggagaac aatattgtaa ctcttggtga    56820
ttactggtgg gagcttttgg tcctgtggtt ttttactctt cacatcgggc cgattttccg    56880
taaatcttga tgtcttgtgt gattggtttc acattgtctt gttatatttg tttggttgaa    56940
ttcttgctgc cttactatca tattgcttgt ggttgtttct tctcttggtt caaatcaaaa    57000
ggaagtatac ttgggtattc ttccatcgtt atcctgtcga ggcattctta tttgtgcctt    57060
gtctttccta acactgatca cggaacatca acacattttg ttgatttctt tcacacacac    57120
ctcctcaaaa aaccctcttt tttaacatgt aagcgacaat atctttttta ggagagtgtt   57180
caacattgag cataaaaata ataaaataga gaacaaaaaa agatgagtat aaaataataa    57240
ataataatat aagatcgatt ttaccgattg tcaattttgt gtatgaacta agaaataac    57300 agcttcacat atgaatttgt attttaggct gctgtaagta ctaaaaatag ttattcaacc    57360 agtagaaagat atgaaggtgg gggccagctg ttggcaatca ataagggaaa gaaaagacaa    57420
ggaatattga gccaattttt tttcttctgt ggaaaacttt ggcagagaaa ttaaggctaa    57480
cgaaaagtct ttgtgcaatg accccatggg catgtgcagt tgtttcccac aactttgtga    57540
attatattcc aaaaaataca aattcattat ttaatactcc aacaactttt tgattccact    57600
ctagactacc atcacatatc taatattaaa tgtaatactg aatttcacat atggtcagag    57660
gcgaatccat cagcacctga tatattcttt ttttaaaaaa attatatcta tatatacaga    57720
ttgttgataa gacggtaata tatttaattg tgcactctta taacgaacaa atgatttgac    57780
ttgtccattg gaaaaacaaa aagtgtcaca taaattgaga catggcgaat aatatttctt    57840
tcctaaattt ttcgtgtgaa gtcaaattaa ttcatataaa attagacgaa aggagtaatg    57900
tttaatagta attgcatatg gtagtaaatt tgatagacgt ggtcccgtgg gagtgtgtgt    57960
tatttccatt gaataattga gtttgtaatt gttacaagtc cattctaatt tccaacacct    58020
tacttcattt caaaaatata ctctatggct gaagctttcc ttcaaattat gttagagaat    58080
ctgacttgtt tcatccaagg ggaacttgga ttgattcttg gttttaagga tgagttcgaa    58140
aagcttcaaa gcacgtttac tacaatccaa gctgtggtac aagatgctca gttgaagcaa    58200
ttgaaggaca aggcaattga aaattggttg cagaaactca atggtgctgc atatgaagct    58260
gatgacatct tggacgaatg taaaactgag gcaccaatta tacagaagaa gaataaatat    58320
gggtgttatc atccaaacgt tatcactttc cgtcgcaaga ttgggaaaag gatgaaaaag    58380
attatggaga aactagatgc aattgcagcg gaacgaatta gtttcatttt ggatgaaagg    58440
actatagaga gacaagttgc tacacgccaa acaggtaaat attttttctaa ataacagctt    58500 tatatcatca aattcatgtg tgttttgggg attttgtcta agtagataag tggttcaaaa    58560
tctattatct aaatctgttt ggtgaagtct ttaacatata tataaatcca tagcttactc    58620
atatgcccca aagtctaaat gacaggataa agccagagtt gttttagatc ttataaatta    58680
```

```
acaatgataa taatgtgaat tcaaaatagt gcatttgttt tatatttgaa atatgtctgc    58740
tgcttctgat caagctgatc attgtctttt gcaaaattct tctttgtttt ttttgctgac    58800
tcttaccgat cttggaccag gttttgtttt aaatgaacca caagtttatg gaagagacaa    58860
agataaggat gagatagtga aaatcctgat aaacaatgcc caaacacttt cagtcctccc    58920
aatacttggt atgggggac taggaaagac gacccttgcc caaatggtct tcaatgatca    58980
gagagtaatt gaacatttcc atcccaaaat atggatttgt gtctcggaag attttaatga    59040
aaagaggttg ataagaaaa ttgtagaatc tattgaagaa aagtcacttg gtgacatgga    59100
cttggctcca cttcaaaaga agcttcagga cttgctgaat ggaaaaaaat atttgcttgt    59160
cttagatgat gtttggaatg aagatcaaga taagtgggct aagttaagac aagtcttgaa    59220
ggctggagca agtggtgctt atgttctaac cactacccgt cttgaaaagg ttggatcaat    59280 catgggaca ttgcaaccat atgaattgtc aaatttgtct caagaagatt gttggttgtt    59340
gttcatgcaa tgtgcatttg ggcaccaaga agaaatgaat cttaatctag tggctatcgg    59400
aaaggtgatt gtgaaaaaat gtggtggtgt gcctctagca gctaaaactc ttggaggtat    59460
tttgcgcttc aagagagaag aaagacagtg ggaacatgtg agagatagtg agatttggaa    59520
tttacctcaa gatgaaagtt ctattctgcc tgccctgaga cttagttacc atcaccttcc    59580
acttgatttg agacaatgct tttcatattg tgcagtattc ccaaaggata ccaaaatgga    59640
aaaggaaaat ctaatctctc tctggatggc acatggtttt cttttatcaa aaggaaactt    59700
ggagctagag gatgtaggta atgaagtatg gaatgaatta tacttgaggt ctttttttcca    59760 agagattgaa gttcaatatg atcgaactta tttcaagatg catgatctca ttcatgattt    59820
ggcaacatct ctattttcag caagcacatc aagcagcaat atccgagaaa taatgtaga    59880 aggttaccta catatgatgt cgattggttt tataaaagtg gtgtcttctt actctcctcc    59940
tcacttgcaa aagtttgtct cattgagggt tcttaatcta agttccatgg gacttaagca    60000
gttaccgtcc tccattggag atctagtaca tttaagatac ttgaacctct ctctcaataa    60060
catgcgtact cttccaaagc agttatgcaa gcttcaaaat ctgcagactc ttaatgtaga    60120
gtattgctgg tcactttgtt gttttccaaa agaaacaagt aaacttggta gtctccgaaa    60180
tctcttactt gatggttgcg atggattgga ttctatgcca ccaaggatag gatctttgac    60240
atgccttaag actctaagtt tatttgttat tattagagaa aagattctct acttggtgaa    60300
ttacttaaac ctgaatctgt atgggtcaat tgaaatcacg atcttgagag agtgaagaat    60360
gatagggatg caaagaagc caatttatct gcaaaaaaga aaatctgcat tctttaagca    60420
tgagatggga aggaccacat agatatgaat cagaagaagt tgaagtgctt gaatccctca    60480
aaccacactc caatgtgact tgtttaacaa tcactggctt cagaggaatc cgtctcccag    60540
agtggatgaa tcactcagtt ttgaaaaatg ttgtctctat tgcaattaga ggttgtgaaa    60600
actgctcatg cttaccaccg tttggtgatc tgccttgtct agaaagtcta gagttacgga    60660
gtgggtctgc ggaagtggag tatgttgaag attctggatt cccaacaaga agaaggtttc    60720
catctatgag aaaacttact atagaaaatt ttgataatct gaaaggattg ctgaagagg    60780 caggagaaga gcaattcccc gtgcttgaag agttgacaat tagatgttgt cctgtgtttg    60840
ttattccgac cctttcttct gtcaagaaat tggtagttca tgggaacaag tcagatgcaa    60900
tagttttgag gtccatatat aatcttaggg ctcttacttc cctcaacatt agccataact    60960
tcacagctac ttcgctccca gaagagatgt tcaaaagcct tgcaaatctc aaatacttgg    61020
```

```
aaatcgcttt catctccaat ctcaaagagc tgccaaacag cctggctagt ctcaatgctt    61080
tgaagcatct gtttattaat tgttgttttg cactagagag tctccccgag gaagcggtga    61140
aaggtttaac ttcactcaca cagttatcca taacatactg taagaggcta aaatgtttac    61200
cagagggatt gcagcaacta acaaatttat cagttaggta ttgtccaaca ctggccaagc    61260
gatgtgagaa gggaatagga caagactggt acaaaattgc tcacattcct catctgctga    61320
ttactgatta gatgtaattt tctgatttttt cttttggaaa caaatcaact atttataaca    61380
tctatttgta ttatacttga ttttttcttga ttatgtaaca ataaatattt gaaatttttc    61440
atattaaaga ttcagaatga gttttacagc taactctata ttctcacagt ttaataacgt    61500
aaatatgata tttatatcaa attattactt atgttgtgat ttgatttatc aacatgttgg    61560
agatgatttt gacagtttat taagaatttt ctaagttttt attgttttgca caagtaacaa    61620 gccataaatt aagtttcgag ataaaagtaa tttgtgtatc atggcttaat tagtcggaat    61680 ttcaagttttt ttctcaagtt atatatatgg caatttgtaa aaatagata gtattcattt    61740 tgatttaatt caagtatttt taaaaatata tacaaataat atgggggata cacacgctaa    61800
acgcgtaccc aaaaattagt atataaagaa taatgacgaa aaaataaaat gaagttctat    61860
caccaactat ctctacatct tttgctgata tatatatata tatatatata tatatatata    61920
tatatatata tatatatata tatatatata tatatatata tatatatata tatatatata    61980
tatatatata tatatatata tatatatata tatatatatc taactagtgt acttattcgg    62040
acttgacatg gtataaaaag atattaaata tattttaaat aattaataaa tgatataata    62100
aaaagagaaa tacaaaataa gttatgattc tgataaaagg aaacttacat aaatgtgtta    62160
taataaaaaa atatttacca tttatagcta taattttttt tttcactcga tcacttttaa    62220
ttaatttata atacaagttt aatatatatt acaaagaaca atttattatt cacatacaat    62280
acaagtttta atgatggatt ttatcacaca ttttaataca cttataatat aatgttacta    62340
ttttttacca aacaaacaca atatatttca aaaacaatta taattcaaat atattgcata    62400
aataattcac ttttaataaa tattacagat ttatcacaat attgctataa atgataataa    62460
acaaaagtat cgctaaaatc agtaattatt ttttaacata tattaattca tgtaattttt    62520
cttattatct attcagaaaa attgcttaaa aaatctcatt tgacattttc aatttaaaat    62580
tgttgataaa aaagacaaaa acataaaaat tgatatgaaa gagctttggt taagtagcaa    62640
tctaattaca tagtggcata ctaaattaaa tgattcttat agcaatatta ttggttcaac    62700
caacaaaact aaatctctag ttatattact taattgctca tcatagctat agtttgttat    62760
aatcatcact cgcggttaac attatgcatc aattacgtgg gctgacttcg attttgtata    62820
attagtcatg ttttttatatg tactagattc tgagaacatg ccttgcacgt ttgtccttta    62880
ttattattaa cttttttatat actaaaaagt taagtaatta aaaagatgct taaataaaca    62940 ataaagttt aaccatttat cttttattcg ctaaataata actaatataa tatgaagaac    63000
attaaataga tgataatatc taccttagta attggttctt aaaaagcata ttaaaaattt    63060
aattctcaaa gtgttttac ataaatagtg gagaatgact cttcacattg agcttttaat    63120
tttaaaaaat tatgtgtatg agaaataatt aacattcaat aattaggtag aataatatca    63180
cattatcata aataaaataa tatctctaag tcaaagtag acattctagt ttggaaaata    63240
attactacta actattttatg ggtccagctc caatcaataa tctatagatg ggagtttgac    63300
aatttttcag ctatagttaa aattttacat caacaataaa taacttatta tcacagtaga    63360
tagacgtttg atgcataaaa gttataaatg ctaaaagatt ttgtcaatgt agtacatatg    63420
```

```
caaacttatg ataaaaacac ttggtatatt acgaaacaca cttgaagcca ttaccatgat    63480
taacatatca attatttta tcattatatc acatatacgt cttctttta accttaaaag    63540
tattgtacac atgatttatg aagagaaaag aatagtactc cttttttcat gtaacgacct    63600
gtttagtcgt tttgagcagc agaatttatt tctggaaaaa ctgtctgagt caacggaacc    63660
cacgacggac cgtcatgggc acgacggacc gtcgatggtg tctcattcca aaacacttag    63720
aattttgaaa tttgggtctg aaatcgactc tccaacttcg tgcttgagat ggccggggcg    63780
aacaagtaag tggagccgca cggctgcacc gtcacaaatc ttccatgggg aagtgatccg    63840
aatgtgtgga tttggcgggg agatgccgtc cacgatccac gacggacgt cactgttgcg    63900
cgtaatcccg gtgggtcgga tttctgttaa gtgatttaag gggcgttttg gactattcct    63960
gctttaatta taaagttagt gggttaatgt taataagttt aattacttgg gggttaaaag    64020
aggtaacctt gagttaatta gtgggttatt attgacatct ttatacttaa ttatattcta    64080
attagggtaa aagaaagagg gtttgaataa gaaacaatag aaagaacaat gagagggaaa    64140
gagaaacgag aaagagagaa acgaacgaag aggaaaacac aagctttggg aaaattgctt    64200
tcttgatcaa aattcttcgg tggaggtagg ttattgtttt tatactattc gtagtaaact    64260
cttaatagcg aatgatatgt gttgggttgt attgtaaagt cttctatatg cttaattgta    64320
tgcttgtata aatgtgatta tataattgtg ataaataag caagataaag ctattgaatc    64380
ccaaatcttg aaaccccctt gttaatgatg atgccttggt ataaagaag cttgatgaa    64440
ctaaagtaat gatattgatg atgtcttggt ataaagaag cttgatgaa ctaaagtaat    64500
ggggttgatg atgccttggt ataaagaag gattgatgaa ttaatagaat gagattagtg    64560
gagcgggtgt cacgaaccga cacatagtat taggggacc gggtgtcacg aaccgacacg    64620
tagtattagg gggaccgagt gtcacgaacc gacacataga attaggggat cgggtgtcac    64680
gaaccgacac gtagaattag gggatcgggt gtcacgaacc cacatgtata attggggatc    64740
gggtgtccga accgacacgt gggaattagg agatcggtgt cacgtgcgga caaatagtag    64800
taggggcggg tgtcacatac caaaccaaga ggaataaaga taatgaatct tgaaagatgt    64860
taatatactc aatctaatga acctaatccc aaataggtat ggtattgagg cttgagtctc    64920
atgtgaactt ggcggtgctt attaatgatt atagtacttg ttgttgttac acatattgag    64980
tattgtagtt gatttatgat attatcagta tatcttttgt tttctatttt gagttggccg    65040
atgataccta cctcgatgcc cgtgttttat cttgaccta cttgtatttg ttttctttgt    65100
tatttgtgga gtgtagcaag cgtaccgtcg tcttcaactc attgccaact ctgtgatctt    65160
cattacaccg gattttaggg tgagctaatg cttctagctt ggactggatc ttcttcctca    65220
tgtcttgatg ccttgaagtt ccggcatgga ctagattttg tttattttag cttctttaga    65280
atactcttag tttagtaatt tgatcataga tgttcttgtg gtgatgacgg gattttgggg    65340
aatactagtt gttgaatttt agaagttatt gaattggttt tattaatgag tttaagtctt    65400
catattactt ctgttgatat tatattgaaa tgttggggtt tagattggtt ggttcgctaa    65460
cataggatgg taagtgtggg tgcgttggct cggttttggg tcgtgacaaa cttggtatcg    65520
agcattaggt tcgttggtct catcacacaa gagaaccagt ctagtagagt cttaaggagc    65580
gtagggggggg ccttttactt ttctttgaga ggctataaga ctttaggaaa ttttcctttc    65640
ttttcttttt ctttattact tggatccaat tggtatctag gtgatacaaa ttggtaatcg    65700
accatcttca ctctatttt cgcaaatggt tagaacaaaa gcgacgacta acaacagcac    65760
```

```
cgatagcgcg ggcggagcga ggtgcgtccc gggcgtgctg gggagtacat ggctgggaag   65820
gcggctgaca gaggccgtgg tgaaattagg tggggagacg tctacagggg acaaacaccg   65880
ccccatagta ctgggcggtg actcactcca cccggtaggt ggtaagagag ggtgaggaag   65940
gaggcccggc aagtgcgagg agatgaggaa ctaccgctga cctacccgga gatgataaat   66000
caggttctgc ttaccttagt aggttgctct gatcaaggtc aaacacctcg atgtttctgc   66060
tgcttctctc gggttttgga aatacgacgg gcaaaatctg tttcacgcat ggatatgcca   66120
ttggaagcga aactatttcc tcgtttgact acggggccta tgatgacaag cggtgacaaa   66180
gatgaaccaa gaagggattg aaattgaaac ctccgtcttc aagggtgcta accgggatgc   66240
ctacgatttt ccgtcgattg tcatgagtta ccaagataaa atgggcatag tggaacgatt   66300
cggtgttgag ttttttggact tatcagtttc aaaggaacgc caaatgcgcg gcggtcacat   66360
gttgagtgtc aaccaacgga ggaaccacct atgacttggc cattctctag cttatttatg   66420
gaagtatatc ccctgacctt gagggatagg aggagatgag ttttttggct tagagcaagt   66480
agaacgacgg tcacttcata tgaaggctaa gtttcgtgca ttatctaggt atgtcacttt   66540
gcgcccgggt tcacaagaag cggattcaaa ccgttttgtg aaaggggttg aggtcagttt   66600
tcagcccttt tgtagcggtg gcaaaatgaa atccttccag aaagtggtag acttctgtga   66660
tagaggtgga ggagtaaagt aggatgactt caccatggca tcgacatcaa aaaggtttga   66720
aaagggagag gtttaatggt tcttacacta cagggcgaga gttcgaggat tttcggtggg   66780
ccgttgtctg ctcaggaggc tgtggtgggg tccgctaccg gaccgtgaca tttctgcggg   66840
agtagggtca ttccagacct caatcattct cacaaatact atactgggct ccagagaatg   66900
ttatggatgt gggaggctgg accataatgg gaagttatga cgaggtccca tgggccaggc   66960
cagctaggtg gggtggtggt aggagaggca gttgataagg aggccagtgg ccaggtaatg   67020
ggtgagtcct gaaggcagcc aggagtgagg acaagtgaac tacaaccttc ccacatggtg   67080
agggcagccg aggcagcagg caaattagta ggggctacgg ctgtgcagcc tcgcagtctg   67140
gcggggacat cagatgttgt tatcaccggt aatctttttgg tttgtgattg catggctacg   67200
tcattatcgg atcctgatcc acatttcata tgtatcttcc tatttgttac tggtgtaatt   67260
tacattgtga attgcttgac atgctatttg tgtttctact ccgttggtga gtcatgatag   67320
ttgaaaaggt ataggtct tgtccgtgac ttttgtgggg agcacactca tgtagatttg   67380 gttatttag aaatggttga tttctgatgt aattacgggt atgacttgct ttccaaattt   67440
tgcaatctta gattgtaatg ctaaaagcgt aacgttggcc aagccaggga catccagatt   67500
agtaatggga gtgtgactac acttccgctc cagataaata tcatatcctt tttcgtgcta   67560
agagaatggt tagtaaaggg tgtttagcct tcttggcacc tcagtgatga tactaagtac   67620
cttcgagtga gcctggggtt tcggtagttc gtgagttta gacgtgttcc ctcgcacctt   67680
ctccggtatg ccaccgacga ggatattgac ttttgcattg atttgggccg agtactcatt   67740
cccatttccc ccccttatag aatggctcaa acgagttaag gagttaaaag cccaacttca   67800
aaaactgtta ggggaagagc tttattaggc cgagtgcatc cccttagggt gctttgtttt   67860
tgtttgtgaa gaagaagatg gggagtcttcg gatgtgcata gattactggc aactaaataa   67920
agtaactgtt aagaacaggt accctcttcc ctcgcattga tgacttgacc gatcgatttc   67980
taaggtgcta tgtcttctct aagattgact tgagatggtt atcatcaatt gaaaatccag   68040
gcgtgagata tgccaaggcc ttttcgaag acgtatggg cattatgaat tcttggtaat   68100
gtcctttgga ctaacaaaat gcccctgcta cttttctgcga gcttgatgag cattttttaa   68160
```

```
gccatatcta tggatctctt tagatcgtat ttattgatga tatcttgata tactcaagag    68220
aaagaaggaa catgaggagc atttgagagt tgtgttggaa atgttgagga gaaaaagctt    68280
tatgccaaat tctccaagta tgagttttgg ctagattgat tgtccttctt gaggcaacgt    68340
agtttctaag ggaggagtga tgtagatcct tctaagatca agtagttaga agaattgggt    68400
aagacctact aatatgtcgt aaataagaag ctttgttggt ttaaccattc taccgtcgat    68460
ttgtcaaggg attctcttcc attgcttccc aattcgaact taactaagca gaatgttcca    68520
tttgtatggt cggatgaatg tgaggaaatc tttcgtaaac tcaagacctt gtttgacttc    68580
accgcaccta tccttacctt tccaaagaga gagggtaaga acttcattgt gtattgtgat    68640
gcatcatatt ctggttcgca aaaaaaaaaa aaaagtgct aatgcaagag aagaacgtaa     68700
ttgtgtatgc ttcgaggcaa ttaaaggtgc atgaacgtaa ttatccaacc cacgtatttg    68760
gagttggtca tggatagtgt ttgcattaaa caatggagac actatctata tgggggtta    68820 agtgaagtct atcacggatc atcgtagcct acagtatgtc tttaccggaa agatttgaat    68880
ttgagacgga gggaggtgga tggaactaat gcgaaggatt atgatgttta ccatcttgta    68940
tcacccagaa aggctaatct tgtggcggta taggtagaaa aagcaggagc atggtagttt    69000
agctcacttg caagcttcta ggcgcccatt ggcctagaga ggtgagacta cggctaataa    69060
ctttatgaga ttggaagtaa aaaatgagaa gggagtgatt ttttggcggt gtggaggcgt    69120
agatattctt ttcttgacaa gatcaaagga aaaacagttt ttaatgatga gaaattgatc    69180
cgaattaggg atatggtgtt atgagggaga gtctaaaaaa gcaacaatcg atgaggaagg    69240
tgttttgaga atcaagggaa gggtgatgtg taccctgcgt tgatgacttg atcaacacta    69300
ttatgagagg ctcatagttc aaggtatttt atacacctgg tgcaaccaag atgtatcgtg    69360
acctaaagca acacttttgg tggagtagaa tggtagcgac attgttgatt tgttgccaa     69420 atgtccaaat tgtcaacaag taaagtatga acaccggagg caggaggaac actttcagag    69480
aatgcccatt ctgaatggaa atgggagaaa ttgcaatgga tttcgtggtt ggtcttccaa    69540
agacaatggg taaatgactc tatttgggtg attgttgata ggttaactaa gtctgctcat    69600
ttcattcgtc aaggtgactt acaatgctga gaaattagcc aaactttaca tccagtagat    69660
tgttaggttc atggagttcc actctccatc atatcggata aattaccagt ttactttaag    69720
ttttggagaa cattgcatgc ggaattaggt actaggttga accttagtgc gcatttcacc    69780
cctcgagacg atggagatga tcggcgagcg attcaagtgt tggaggatat gccgtgcatg    69840
tgtgatagaa tttggtggcc atgggatagc ttcttacccct tagcggagtt ttcatacaat    69900
aatagctatc actcaagtat tgacatggcc ccatttgaag cattgtatgg taggagatat    69960
aggtctccca ttgggtggtt tgatgcattt gaggttagac cttgggggtc ttgacctttt    70020
gaggttatta gaggcggtga aatctattca gaaaagcttt taagcggtaa agtaggcaaa    70080
aataatgtcc ggatcgaagg ttagagactt aaggtttatg gagggtgagc aagtcttctt    70140
tgaaggtttt cgccaaagaa aggggtgatg cggtttggta aagaggtaag ctaagcccaa    70200
ggtatattgg accatttgaa gtacttagcg aataggggag gtggcttatg aattagcctt    70260
gcctcggggt tgtcagagtg catccggtat ttcatgtgtc tatgttgaaa agttaccatg    70320
gggatggaaa cacatcatcg ttgggattga tctggctttg atgagaattt gtcccataag    70380
tatgagcctt tgtgccattc tagatagaga aattcgcaag ttaagatcaa gtgagattgc    70440
atccatcaaa gttcaatgga agaatcgacc cgattgaaga ggccacttgg ggagaaggaa    70500
```

```
gtcgatgtgc aaagaaagat acccacaacc tacttacgta ttcgtgtact cccgctttt    70560
tttttggcgt gatcgttcga ggacgaacga tgggtaaatt ggtatctatt gtaacgactg   70620
cttagtcgct tttgagtatt gattttattt ccccgaaaaa ctgaagtcat cggaacccac   70680
gacggaccgt cacgggcaca cgacggaccg agggtgtctc attccaaaac acttagaatt   70740
ctggaatttg ggtaccgaat cgactctctc gaacttcgta acgatggcga cggaccgtcg   70800
tgagcggcgg accgtcacac atcttccata ggaattgagt ctacgaactt ctgtgtgacg   70860
gcggcggaga cggaccgtcg cagtacccgt cactgcaatc ccgtaatccc agctggccgg   70920
tcacattaag tgatttaagg ggcgttttgg actattccct ttaattataa agttagtggg   70980
ttaatgttaa taagtctaat tactgagggt taaaagagg taaccttgag ttaatttggg    71040
ttattattga catctttata cttaattata ttctaattag ggtaaaagaa agagggtttg   71100
aataagaaac aatagaaaag agcgagagga agagaatgag aaagagagaa aacaagcgag   71160
cgaaaaaaca caagatttga aattgctttt tgcttgatca aaattcttga ttggaggtag   71220
gttattgttt ttatactatt attagtaaac tcttaatagc gaatgatatg tgttgggttg   71280
tattgtaaag tcttctatat gcttaattgt atgcttgtat gaatgtgatt atataattgt   71340
gataaaataa gcaagataaa gctattgaat cccaaatctt gaaaacccct tgttaatgat   71400
gatgccttgg tataaaagaa ggcttgatga actaaagtaa tgagattgat gatgccttgg   71460
tataaaaaaa gggttgatga tgccttggta taaaagaagg attgatgaat aatagaatg    71520
agattagtgg agcgggtgtc acgaaccgac acgtagtatt aggggggaccg ggtgtcacga   71580
accgacacgt agtattaggg ggaccgggtg tcatgaaccg acacatagaa ttaggggatc   71640
gggtgtcacg aaccgacacg tgggaattgg ggggatcggg tgtcacgaac cggccacgta   71700
taattggggg atcgggtgtc accgaaccga gccgcgtaga attagggatt cggagtgtca   71760
cgcatcgacc acatagtagt aggggagcgg gtgtcgtcgc accgacacaa gaggaataaa   71820
gataatgaat cttgaaagat gttaatatac tcaatctaat gaacctaatc ccaaatgagt   71880
atggtattga ggcttgagtc cgcatgtgtg aacttggcgg tacttattaa tgattatagt   71940
acttgttgtt gttacatgtt gagtattgta gttgatttat gatattatct gatatatata   72000
ctattttcta ttttgagttg gccgatgata cctactcagt acccgtgttt tgtactgacc   72060
cctacttgta tttgttttct tgttatttg tggagtgtag caaacgtacc gtcgtcttca    72120
actcaaccgc aactctagcc agtcttcatt acaccggatt ttagggtgag ctaatgcttc   72180
tagcttggac tggatcttct tcctcatgtc ttgatgcctt gaagttccgg catggactag   72240
attttgttta ttttagcttc ttagaatact cttagtttag taatttgatc atagatgttc   72300
ttgtggtgat gacttccaga ttttggggaa tattagttgt tgaattttag aagctattga   72360
attggttttt attaatgagt ttatgtcttc cgcattactt ctgttgatat tatattgaaa   72420
tgttaaggtt tagattggtt ggttcgctca cataggaggg taagtgtggg tgccagtcgc   72480
ggctcggttt tgggtcgtga catttcataa cattactctt tgaataatta atataaattg   72540
agcaatataa acttttcaaa atgacttatt ctagatatat gatcaatttg aggaatgaat   72600
gttccaacaa acatataata gactaataag atcaataaat tatacatata aacgaaaagt   72660
ttaaataaaa atacaacctc aaaatcacat atatactaca tagaatatga ttcattcttt   72720
atctccaatt aggtgggtca ttttatttt agttcatata tatatgtgtg tgtgtgtgtg   72780
tgtgcgtgtg tgtgtgtgtg tggcgtcttg gcgtcttggc gtgtcttggt gtgttaatgt   72840
gcgtgtgcgt gtgtgtgtgt gtgtatgaat ttcatcagta attaagatac atagtagaac   72900
```

```
atgaattgta tattactatt ttcttcatgt aggatacaaa atattctaat aaaaaaatct   72960
aagaaagtac atcaacatat ataaaaagga aatatataat acttaggacg gacaaaagga   73020
gcggataaaa acaaaaaata attactacac atacaaaatg atttgcaaag ttcattttg    73080
catgataatc tctcatcctc ttcttgtcat atacatgaag atcatgctag ataatttata   73140
gaagtagcta tgatgacctt tgaatagata attaatttgc attaaattag ttcaatggtt   73200
ttagtccata tcaaatttgt ttaatggaaa aaattttcaa atactcctga ttttcacaat   73260
agagtaatta attattaatg tgaatttgat acatgcatca atctaaatga gttatttatc   73320
aaaaataaaa tgaaatagag tagactaaaa ataataaaat agctaatgaa ttctaaaact   73380
tttaaataac aaaaattaaa gaaagaaata gttctagttt ataagaatag tggaacttcc   73440
tcaataacta acaaaaacat aaacaaatct atatcttttt tattgcatat gttatgaaca   73500
attacattca tcaacaatta tccatcaata attatacatt agaataacaa agcatatgca   73560
tcaacaaaaa gtaattgtgt tgaacaatgt gtcaagtgta attacatcca ccaataatta   73620
ttcataaaca attatacatc ggaataacta agtgtgcatt aatataaagt gattttgaag   73680
ataattttt ggtatttata gttacaagtt tggaattgta aaagtcattt aaaaattaat    73740
gatatacata acgtttatga gaattagatt gtttaaagtt gagcatatgt aaagtttctt   73800
actaaaatct aaatgtgtca tattaagatg tatggtaatt caaggacat ttttgttctt    73860
taatgttaat tgatattttg aatataattt atcatcttt tgttatgaaa tacttcatct    73920
cttgaactct attttagaat aaaagacaaa ttaaacatt cttaattat ttctacctag     73980
aaacataatg gattaatacc atataagtat tatttaagta atattttatt aattatttct   74040
ttaataatat ttaaattagt aaaagggtag aatcataatc ctatttaaa gttaagatct    74100
tctcacttat aataaaataa taataattta cggactagcc ccgcttgttt acctatatta   74160
gtcaatacat ttttaaaaaa aagtataaat attattaata atattgtttt atgttaaaa    74220
attaaaagga gtatatactc cttaaaatga gtaaaagaat ctatgagatt ttttatccaa   74280
atacttttt tttctagata gaataaatga aataataagt tctaaattta atcaataaaa    74340
acataaagtt gcagaatata aaaatattta gcaatactgt ttttcttctt caacgctacc   74400
tcgtctttcg ttattagggg tatttattta caaacatgaa atcacaccat gattttattt   74460
tcatacaagt agtaaatcat ttataaattc taaaaaaaca cattaaatat aatgcatgct   74520
aatttttgt agatttaatt atgagaaaaa actaattaca tcaattattc aattctctta    74580
tccaataacc tagagtgttc actacatgat aatcaacttg ttataacaaa cataatcttt   74640
aaagaagat ttgtacatca gacatgtaaa tgaaaaattt tcttttcttt tttcactgcc    74700
attattcaag aaaagtagt caatttacct tccttcaacc gaaaattga atgtaacaaa     74760
taatgaacta agtaaaaata tgcaacattg aaatgaaaaa taatacttac caaacaacaa   74820
ataaatgtcc atgacgcctt taaccttctt gaagaatgca tcgaatgcac tgaaatgatt   74880
aaattctaat tcagatacta tattctccaa gatttaccgt caataaatta acaaaacaac   74940
atacatattt tttctcacac aagtaggttt gttttacctc atgaacgttg agcagactat   75000
ttgtccaaat gaaaaactct ctagaattat ttatcacctg tttgcgttga aaacataaat   75060
tttcgatgaa aagaataaaa caaaacatgt aatattagtt ctatctatat acatatatgc   75120
ctaaaattta ttgatcaaaa gaaacatgaa aattttgaag aagaatttt gagataaatc    75180
aattcacatg ctattgtcat gagaagacat caaaataatg tattttgttg gaaaaatcat   75240
```

```
gtatataatt ttatcaatgg aactcttcaa attctttaac ttaaaattaa ataaaagatg    75300
ttttgaaatg tttgaacttc atttgtttga atgactattt atctttcatt atatctttat    75360
tactttaaag tttattatct aattatttat taaaaatact tttacatttt aaaaaataga    75420
aaaaatttaa gtgaatggta aaatggtaat ttaactttga ggttaggagc ttcccactta    75480
taataatata tgatgataat tcgccagaat aatacagata tatgtataat atacaattat    75540
ttaaccgata tcatatctga ttcctctctt ccactctctc tcctctctca cccgcctctc    75600
tcctcccact ctcaattttc ctttccatat atacaaatac atatgtataa tatacaatta    75660
tctaaacgat atatatatat atatgcaatt catctctctc tcactctttg cttcacttga    75720
caactatgac acttaacttt ggatatgcac aaattgacat ttaaaaactg gttacagaga    75780
aacttaatgc tgttgcgtat aaagttgatg acttattgga tgaacttgaa tatgaggcag    75840
caagactctg tttttcagca aacacatcaa gcagcaatat ctgagaaatt aaacacatat    75900
gatgatgtct tcttactcac cgagttatta gttatgctaa aatgtttacc cgagggattg    75960
cagcacctaa caaatctcac aattttttt gataagtgaa agcatagtta aactctcaaa    76020
tgtagatgat aattaagctc ttgaagatta tcgctgaatt aagtgaattc gttattagtt    76080
tcaaaatgtt tagcctcctt gggacctgac gaatgattta aatttcaaac acaaggtcaa    76140
gctatatttg taaaattctt atggccaaac aagtcatact gcaacaaatt gtaaaggat    76200 tattatactc caaaagtaaa gatttagaag agatctactc ttaacactaa ctaaaagatt    76260
attccaattc tcaaagcaaa tttatattcc tttccaacca agaggtttt ccaaatttgc    76320 tttctagtaa ttttttttt ctgcacgata ggaatagatc tcatatactc cctccgttcc    76380
atattatgtg gtgtagttta attcaatacg gaatataaaa atgaaagaaa gacttttaaa    76440
atttatagtc taaaatgaat aataaaaaat tgtatgacta taaatcatt cattaagagt    76500 aaatgtacaa tttaaaataa aattgttact taatatagta acgtgtcttt ttttttggaa    76560
actgcctaaa aaaaaaaaaa tagtcatata aattgaacac agggagtatc tacttacaaa    76620
gtaaaagttg tgtgtagaag attttggcat ataaatcata tcatatatca tcatatcata    76680
tattagtaaa agcatgaatt aaaaaaagtc aaaaagttaa attacgattt tatcccttct    76740
attaattaac ttgttataaa atatttaaat atttgattgt acaagtttaa ttaaaatgtt    76800
aaatgaattt taaacttcct aatattaatt tctaattaaa tatctaattt attaatattt    76860
atcatttata atccatatgt atataataat tataattttt taataaaagt ctaatcaaaa    76920
tattaatgac ttttagactt cctaacacta attcctaatt aaatatctaa tttattaata    76980
tttttatcat ctataatctc tctatatata ataatttac aaaaattaat aaaaagtctc    77040
tacgtaaatt tttatacttt tcttattctc ataactttta ccctaaataa caaaatttaa    77100
taattttaag ggtgcaaatc ttcaaaatgg agacacacac attgataatg tcctcttaat    77160
tattattaaa gaatgactct agcttcacaa atttaaattc attaatgctt aattacttag    77220
agaaaagtag atgaagactc ttaatttga tagtatatgg aaggattgtg tactaatttt    77280
gtacttattt tttcatctac atatacatag tcttataaaa atgatgtcta cattgtattt    77340
tttcttaatc tgtttctttt tgtctttttc ccccaattag acttcttaat ttagttttct    77400
acaaatgttt tattgtcgta agtctcttta cttattttgt aattgtagca ttttattatt    77460
cattataatt tgcatatatg tatttccatg aaatattagt aattctatca tatctataaa    77520
aattcacatg aaatacacgt gctcagaaac tagtaaggaa aacaacacaa atatacatcc    77580
gaactatcgt aaaaatgata tgcagatacc atcctcatac ttttgggaca ttgctgtcca    77640
```

```
ttacgtcaaa aaaatatagc atatatatta acggacatca cgtgtcataa tcatatcaat    77700
tgatccaaca tttaataaat attcgatcga cgaatagatt gtgtcacatg tccctattta    77760
gtcatatgtt aaagtgaatg acatatatgc tctagttttg aaactttctt gtaaaattta    77820
agtatatgcc ctaaattttt aacaatattt tgctacattt tacgttttttt ccattcacgt   77880 attttcttat ttactaaaca agtttctatc gtcctcagag tatttcctta attagcacta    77940
aatgttgtga tgttttttctt caactaagtt tcattgaagg attgagatta aacctatttc   78000
ggtatccacg atctttgaat gaatcgccaa actctatcta tgaatttaat agcaaaagct    78060
cagattttgt tccaaattga gatataatat ttctataaag aaatttaaat taatgatgtg    78120
atataatgat aatgaattca gttttttacat tagaaagact ctattttttct ctcttacttc   78180 acaacaatgc aagaattctt aaagacctaa aaatggggta ggggtggggg aaggggggcca   78240 acaacaacaa gattctaaat tcttgaatat ttttaactaa aaaattaatt ctttttcccaa    78300 tggattcaaa ttgaaaagga aaactacaac tttgtgatta tcgcgctttc aaaatgttga    78360
atagattgtc ttcaggtgtg agaagaatga gagtgagatg gagaaccata cgaataaaga    78420
aattctcaag tacgattcca atggaaggaa ttgaactacc tattttgatc ggagataaca    78480
agtcattcga tagagagatt ttgaaactgc atatgtttcc taaatgaaag ttatatatta    78540
gctagatagg gatatagatg ggttgaattc tcaaaatcta agaataattt tggatatgtc    78600
taaagtgatt ggaaagtgaa tatatttagg acaaattaca tgattcgata tacttcacta    78660
ttatatatat tatttttaca tatacttttta aaacactagt ttctggacac gtgcattgaa    78720
cgtgtatctc aaatatatga aatagatatt tttgaaattg taagacaatt ctaaaatatg    78780
gttgtgatgt ttagttatgt atgagagcaa tttaataaaa tatgtatgag actttttttaa   78840 tttgtttccc atttggtgtt ccgctagcta attcaaattc atgtgtgaca ttccactttg    78900
aggatacttc ctataaagtc tttccatcat caagaattga attcaaaaga ttgaatttag    78960
aacgaacgaa tatttatcaa tcaatcaact tatttgatga aaacatatat gaatttcagt    79020
ttgcacatat tataaaaggg caaacttcat atttcaaggg tactacctat aaggtctttc    79080
cattatcaag aattgaattc aaaagattga atttagaacg aacgaatatt tatcaatcaa    79140
ccaacatatt cgatgaaata tatatgaatt tcggtctgca catattttaa aagggcaaac    79200
ttcaaaattt atcgtatatg ccccaaattt ttaacaatat tttgctagtt tttagttttt    79260
tccattcacg cattttctta tttactaaac aagttcctat cgtcctcagg tatttttctt    79320
aattcagcac taaatgttgc gatgtttctc ttcaacaaag ttttcattga aggactgaga    79380
ttaaacctat ttgggtatcc atgatctttg aatgaatcgc caaactccat ctaagaattt    79440
aatagcaaaa gctcagattt tgttcaaaat tgagatataa catttctata tagaaattta    79500
aatcaatgat gtgatataat gataaatatg aattcagttt ttacattaga aggattcttt    79560
ttttctctct tatttcacaa caatgctaga attcataaaa acctaaaaat gggaatatta    79620
tcatattata attaaaagta aaactctatt ttagaaatag tggactaaac atctaaacta    79680
ataattcaat ggcctacgtt gatgtaagtt acgttatttt agcaaaatta agaagaaatt    79740
ccttcatttg agggtagaat cataaaaata aaaatagaa aaatacatat gaaatatctt    79800
accgcaatca tgtgccctct ttgtattttt cattactatt gtctctcccc ccaacttgat    79860
caattacttt ttttaggaaa aataatccac gatgaatgta ttcgtcaatt ttcactgatt    79920
atgtgaacac aaattattaa gttctctctt gaatgaaaac aaaaaaaaaa gaaattattt    79980
```

-continued

```
aaagaatcaa aaaaaattaa acgtaaatcc ccttgcacta tttagagaaa ttttctatgt    80040
gaagcatatt tcacaattaa ttgcacattt ctctgttctc ttcttctctt cttgaataaa    80100
aagtcaatac ctaaattccc atgataagag tatcaaagaa acatattact ggattaggga    80160
tgaatcattt atgaaattgt gaagtgattt tagatactca cagaaaaaaa atcaccaaga    80220
atttataagg agtggatgat tgtgatttat gatcgaaaaa agatgaaggt taaaattgtt    80280
gtgactatta atacgaaata tgtcttcttt aacaaataaa agtttattta attttaaatg    80340
atacaaataa tattgaagta tgtacatgat gaaaatcgta agaagaaata caagtatgat    80400
tgatgaataa gttgctataa tttattcacc gattctttct tatgtagtac ctcgagtttg    80460
gttgaatttc gaacttgatc aatagttgca aacaacactt gagatatttt aagaagaaga    80520
aatataaaaa tgtgaagaaa cacttcaatt tatagctaac aaattgtgtt atgaatatgt    80580
gttaattgtg tcttttagt aaagctacaa cccttcgaaa aaggcattgc tcatgagaaa     80640
gtcacaatac tgagaaaaag ttacaactta tcaaaaaaga cacaatgctt tcgaaaactc    80700 aaaaccttttt gaaaaaatca caacccttct gaaaagtcac aactcaccga aaatgtcaca   80760
actgtcaatt tcaacccttc aaaaagttac aattcatagc aaaaattcac aaaccgttta    80820
atgaaaaaaa actatctata tttaatataa tataagtaaa taaaataaaa ataaattaat    80880
tgtgtatttt tttttaattg gggatattat agtaatttaa cattcatttt gggagttcat    80940 gcttttttagg tagtgctagt ttcgagcacg tgttttgcac gtgtgatcca tgtgaatttt   81000
atagatatgt tagaatgact aaaaattaat ggcaatatat atgtaaattg taatgaaaaa    81060
taaaatgtaa caattacaaa tctagtataa agacttacgg caataaaaca ttcatagaaa    81120
actaaattaa gaagtctata gagagaaaaa aagacaaaaa gaaacagatt taagaaaaat    81180
acaatgtaga cattattctt ataagactga taaatatata gctgaaagaa taagtataaa    81240
attagtacat ataactctct gagttcttca actccttcta tatcctatca aaattcaaga    81300
gtcttcttca tctacttttaa caatagaata aaattaatag cctaataatc ttggtagggg    81360
tttcatgaga taaaaagttg aattttatag atagagtaga aggaatatca aaagatatct    81420
ttaagtttaa gttagatat ttggaagtta tgaatatgaa aagattagag ttatgaatgt     81480
tgagagtaaa aaagttgaat aagtaattat aaaataataa taaataagta aataatatga    81540
aaaagaaaat taaaggtagc aaaccatgta gaaagaacaa ctaaagttct tatcacgtaa    81600
ttaattttaa tttaaattttg ttaagctaga gtcattcttt aataataatc aagaggacat   81660
tatcaatgtg tgtctccatt ttgcagattt gcacctttta aattactaaa tttcgttatt    81720
tatcataaag aataatactt tatccacata aattatatta ttcatgagag gggttaagga    81780
aagttatgag aagaggaaaa gtatagcaat ttaggtatag acttttttaat tttattttt    81840 ttttataatt attatataca tatagattat atgataatta ttaataaatt agatatttaa    81900
ttaggaatta atcttagaaa gtctaaaagt cattaagatt ttaattaaat aaacaatcaa    81960
atatttaaat attttataac atttaattta tagaagagat aaaaccgtaa ttcaacttc     82020 aacttttttt gttcttgctt ttagtaatac tagcaattat aacaaactca tcagcatcaa    82080
ctcgacctgt atatttcata atcaataatg tcttgtaaat attcatcgat gtgtcgaaac    82140
aaagcccccc acgtataata caatcatctt ctaattaatt gagctcaagc actttgatga    82200
aaaatcgaat ggcaggattc cacaagtaaa tatgcttgtt tataccaatc agtataaaac    82260
tatgactgtt aggttgtgga gcctgattaa tatttgatgt attatttatt ctctgtaact    82320
aaatatactc tgaattatta atatatacc caccgccgtg gaagtttacc cacggggtg     82380
```

```
ttaccacgaa atattggttt ctctctttct agatctctct agatctctca tctctctcaa   82440
aagtttttgt gttcttcatt catcaagtgt gtgtggattc gatcctaaca acgacaagaa   82500
cctaaaatca tacaagttgg gggaaaagct cattatcatg acttagagga taggtgagtt   82560
cttccacaat gagttgttgg tttatttatt gaaagcaagg gttagagttc tacgttgcat   82620
tgacaattgc tcctccttct cgacgttgat ttgagagatg aataaaattt ggacttgaaa   82680
ttcaagaatg tcatgatcgt gaaacacact tgaatcgtaa tagagatttc acagataaaa   82740
ttgaaagaat tatcataatg gtttcattgg gtagatacac catcttgaca agtagtagat   82800
tttctgggta atttttaattc tcgtatttct gatatagaca tatgctcaca aattgacgtg   82860
aaaccgcatg cgaaatttag gaacttatgc aggtgtttgg gcgcagtttt gactgtctat   82920
tgttgttccc taattaaata tacaccttct ctgtttcaac tttccaacag ttttgtgcta   82980
aagtatttgt tgttgcattt atttattcaa acttaatttg ttccaaaata tcatcagagt   83040
acaaactaaa ggattcaaca tgccttgagt acatttata ctgtcaatgg caatgctaca   83100
gcaattaagc accagtacat gaagcaaccg tttattggtt gagatttgag tgtcagtgtc   83160
attccttttc cattctttgt ttttggtagt aactatgata ttgccattgt ttataacttc   83220
aatgatctgc tgatattgtg gagcatgcaa aactaaaagc tatcgagtaa aagtgatcat   83280
aatgtgctag ttcatataag accatctaaa agctatcaat taaaacttat cgcagtgtgc   83340
taggaagtta agggtgtaca tatatttgca attggcagca aaacagagca aaagcaaagc   83400
attaagatca gaaaaagtag attaaccta acaaatcgag ctcgcctatt gtcccctaca   83460
gcaaagttaa acacctgcag tgtttaaaaa ccacaaacaa catttaacaa aagtgaatga   83520
ttaaaagtaa aaaagaaaa aatcgagaaa gataaaaaag aacagaagac ggcataaact   83580
acaatatatg ttttccatca caggttattc atatcatccc ccataaaact ttctacttga   83640
gcactaccaa gaaactattg aggatgtggg accttgggat ggttagtcaa aatgagcttc   83700
tattatatcc ttctgtgtcc ttctattaaa gctctcctct tcttgtttat tttgtggagt   83760
cccaattttg gcgtggccaa ttccatgatg ccaaattggt aacaaatact tgaaagagtg   83820
atgactcaag agagatggtg aagaaagtag acatagttca acgaattgaa gtcatattcg   83880
agaacaatat tatccagata gttcaatgaa gtcatttatt caaaattcat aagcaaatat   83940
taatgtggaa aagttctatt catttccaaa ttgaacaaaa gaagcaaaca atagataagg   84000
tctccaacat ggagataata attgagagta aaaacttcta ttgctattaa atagaatctg   84060
caattaaaaa aaaaattaca tagatacaat atggaacttc aatatgtaca acttggaaac   84120
cctttcaatg cttgaggtct cagttttac cacattcaga tacaaaaatg tagtaacaat   84180
ggcaattgtg cgcgattcta aaatggcaaa aaaataatgc caacttaact atggaaatta   84240
tgtacagata taactaacta taaaacttaa atcgtacagt ggcatatcaa cagagccttc   84300
ttaggctctg ctgctatcat caaaaaaagc ttttgactga ttctggcagt tcatggagta   84360
gtataagctt cggacgattt gaactgattc acacagcatg taactgattt aaaaattcag   84420
ttttactcta tcagagtcac caactccttt cttcccagaa gaactagcag ccgcttgttc   84480
cttcaaagct tccttctcca gtttcttctt ttcagcatca gctgcttgtt cattctcatc   84540
acgtgatttt ttaaacatct tcatgaacac caccaaaatt tgtgtcactg catccagaaa   84600
gtaaggaaat gaaaactgac aaagttcgtc acaaacattg tccggttaaa gagttggtga   84660
ggaaaaatct gttgaagcaa ttctcacacc agttaaaaca agatctcaag gacaaacgca   84720
```

```
attcgagaaa tctagccgat ggctatatgc actcaacaaa agctacaaag gccataaatg    84780
ttgcatccca taatcttcac ataaagatag acaactaaaa agcatcactg ataaacgcta    84840
ctggaatatc tatattacca agactgtttg aacgactgta gttttttctt ttccagatga    84900
ctgataagtg ataatacagc aagaaaataa cgtatgtatc tctaaccttg ctcaaagggg    84960
catcgagctg gatcttcgcc aaaatacagg gatagggagt ctgcactcct tccctgcaga    85020
tttacaggat agaaaaacaa tcaataaact tggcatggct tatacatcca ggaggcttta    85080
aaatatgaca taatggatgc aagaaactca ccacttcaat ataagagta gtgagagact     85140 tgacttcagc ctcagcagta tcaaggaaat tctttaacac ctgagaagga atgcacgagt    85200
cacaaaccgc atatttcaga tgtttataac aaaattatat gtacaccaaa tcacagacat    85260
cgcaatcaag tttgactgca tcaccagact ccactctaaa accatgtcca acacaaacca    85320
aattggg                                                             85327
```

<210> SEQ ID NO 4
<211> LENGTH: 33516
<212> TYPE: DNA
<213> ORGANISM: Solanum habrochaites
<220> FEATURE:
<223> OTHER INFORMATION: >Genomic fragment 4

<400> SEQUENCE: 4

```
caacttggaa acccttttcaa tgcttgaggt ctcagttttt accacattca gatacaaaaa     60
tgtagtaaca atggcaattg tgcgcgattc taaaatggca aaaaaataat gccaacttaa    120
ctatggaaat tatgtacaga tataactaac tataaaactt aaatcgtaca gtggcatatc    180
aacagagcct tcttaggctc tgctgctatc atcaaaaaaa gcttttgact gattctggca    240
gttcatggag tagtataagc ttcggacgat ttgaactgat tcacacagca tgtaactgat    300
ttaaaaattc agttttactc tatcagagtc accaactcct ttcttcccag aagaactagc    360
agccgcttgt tccttcaaag cttccttctc cagtttcttc ttttcagcat cagctgcttg    420
ttcattctca tcacgtgatt ttttaaacat cttcatgaac accaccaaaa tttgtgtcac    480
tgcatccaga aagtaaggaa atgaaaactg acaaagttcg tcacaaacat tgtccggtta    540
aagagttggt gaggaaaaat ctgttgaagc aattctcaca ccagttaaaa caagatctca    600
aggacaaacg caattcgaga aatctagccg atggctatat gcactcaaca aaagctacaa    660
aggccataaa tgttgcatcc cataatcttc acataaagat agacaactaa aaagcatcac    720
tgataaacgc tactggaata tctatattac caagactgtt tgaacgactg tagttttttc    780
ttttccagat gactgataag tgataataca gcaagaaaat aacgtatgta tctctaacct    840
tgctcaaagg ggcatcgagc tggatcttcg ccaaaataca gggatagggt gtctgcactc    900
cttccctgca gatttacagg atagaaaaac aatcaataaa cttggcatgg cttatacatc    960
caggaggctt taaatatga cataatggat gcaagaaact caccacttca atataaagag    1020
tagtgagaga cttgacttca gcctcagcag tatcaaggaa attctttaac acctgagaag    1080
gaatgcacga gtcacaaacc gcatatttca gatgtttata acaaaattat atgtacacca    1140
aatcacagac atcgcaatca gtttgactgc atcaccagac tccactctaa aaccatgtc    1200 caacacaaac caaattggga gttttcccag cgcaagcctt tttcacttga ccttgttaag    1260
aacacaaatg tcatccatcc attggggaca cctatcactc ttctaaaaca gtggtacact    1320
gcttccttac tttgttttct caaactatct agaataaagc tttttgatag taaataggga    1380
tccttgtaat gtataatgaa ggaaacctgg ggaaagagga atccgcacaa cgccgttcat    1440
```

```
ttcatatctg gcgtaagaaa atctcgagaa tttgataata catttagggg tcgtttggta    1500
gagcgtatta agaaaaatca tggatgcatt agccttgttt attgctagta ccatgtttgg    1560 tactctttc  taaactatgt acaactagtg ttgcattagt tatacactat cgtttattaa    1620
agtagattat gatatgacct tcaaagttaa aatttaaaac taaaagaaa  cattatcttg    1680 gaagtacaag taactcattt ggtttgtagg aataattcac atgttaccat tctcttttct    1740
caccttctga atcctgaag  atattgtacc atcattgtcg gatgcagtaa gttcttgttc    1800
aactttctca agacctttac tcactgcttg catttcttca gccaaagact tcagttgaat    1860
ctaaccatat aatatgatgt aaacaaacat ttcagttcac caaatacca  gtagtactgc    1920 aaaggaagac cataataaat agcaagggta ccttagaagc agcttccaag tgaagaagat    1980
ccttgtcaaa atcaagcaac tctggcattt tctcagcaag gagctgacaa aaaacgaat    2040 ttacacattt ggcatcacat tgagaagtgc aaacatatat atgccgaaga gtaaagacta    2100
aggctggtca agccagctat agttgatagc taaaggctat caactaaagt tcactgatgg    2160
ttgggcaaaa gaacagcata acgtagaat  actgaaagta gaaataaat  acaaaaacat    2220 atagttttct acagaactca accttctata ttacaggaac ctcatgggtg caccaaaaag    2280
caataaggga caagaggcta ttccttaact gtgcaaatta ctctacactt tcaaaagctc    2340
tcctaattct cactctccac aaaacccaca taagtgcaaa agcataccct tcacgccttg    2400
tgtctcctcc ttcatcttcc gccatttcag ttgagcaaca ttacttatac agtgacgggc    2460
atcacccaaa tttaccaaac gaacaccaca tttcccacca taaccgagaa gttatcgcac    2520
aatctagaag acgattcgcg tcttcacctg accccttac  acataaaaca ccgcccaaca    2580
taagtagttc tcctcttcat tcttttatca tccatcaaga tcacccctct tgttcctaac    2640
caagtgaaaa aacctacctt tctcagtacc ttagggatcc atatcaaaat atatggaagg    2700
ctatctttct tctcattgat caaaaatttg tccaaagaaa aggacttag  caaatttatt    2760 cttaggcggc caaaatgaaa cttagattac aatgaaacct taacaaagac aagaattcaa    2820
tgaaacctaa acaaagacaa ggaccagaca atagagtcta gctaaaaaga atctgggctt    2880 gcttttcaa  ttcaaatctg tgagcgagga ttcctctttc tcttctccac aaaaatttga    2940
agtggtttat aacttacgga gtatccgata atctcttgca atcttgtata agcctgtgca    3000
gatgaaataa cttgaacatt tccaggagtc aatcgatttg caccagtcga ccagtgggag    3060
cgataatttt aagatataaa catcatataa ccttcctttt agcctattcc cacttgagcg    3120
tacttcacag ctgatacgct cataatactt gacgccccga ataatgaac  agggatagat    3180 atggagatac aatttaagaa aatgaacctt aggcacttca atataagaga agagagaagt    3240
agaacaaaat aaagaacaat gcaactgaa  aaatgttgaa aataaagtga acgatataag    3300
atggattagt tttcagattt tcatctttaa gagctgctga ctctcaaaaa tctgctacac    3360
cgccttgccg ccgccttctt gtttgagtgc tcaacagaag cacctatacg cacttggact    3420
ttccttaggg tgatttaata gatttttgt  gtattttatt tccaattgtt tcatttggca    3480
agatactcta agcttgaaat ttttaatttc tatttagata gtcttgtatg cctaatttca    3540
tgtttgatct tctatttcat tttagagtat tggagttgat actggatcta gctatcaccg    3600
acctactgtc gtactagcgt caagtgcagc acttagccaa taatcccaa  taatagggc     3660 tacacttaga caaagtatga atcaagaagt tgtaagtgtt agatgcatgt gtggcattta    3720
gctatgttta acctctttg  ctggagtaat ctctcctttg taaatgatat ggatcaatca    3780
```

```
acccaccaat agttctagta attcctgaac tactaagtgt actaccaagc attctaaagc    3840
ctcatgcatc ttccttgatt gtgtagaaca tgccatactt atgtggtgag ccttgcttgt    3900
gcactatggc tcccacttgt gcatcaccat gcctcgtgca tgctacatca tcagaccatg    3960
ctcttgtgct aacactatca ccataccagc ccagccatgc ctccatgaaa cagttcctaa    4020
ttttctttgc gttactacta agacaacgaa tcgtttgatc ttgaaattcc ttgcctcctc    4080
tctgttagcc tggtccatgg cttttgttgca cttgcgcatc atgccacact tatgtttgtg    4140
aaccgtgctt gtacactatg gcttccacta gtgcttcttc accatgcctc atgcatgctt    4200
catcttagta gcatcctctt gtgccaaaac aaccacgcct accagccatg cctaacatgg    4260
aactgttccc caatttcttt aactttctaa ttaaaactta aacaagaat catttggttt    4320
ttgagtgttg aaaccttgaa agcgctcgcc tcctctaaag tagccccctt catggtttta    4380
gatgggttat gacatagacc tcaaatacac ttggcacttt ttcaatccaa tcatgagcta    4440
ctcaacaatt attactgagc caaaactaat ctgattcaac ttacgcttaa gtcacctcca    4500
actcttccca attcagagct aattgatcaa tactaattac ataaaggtaa aaacagaaag    4560
gcatcataat gcagtaattc taccttgcac agataatgca tcaaggtcat tttgttgttt    4620
ctcgcacgag tgtcagaaag cttaagaaga ctgtccaact tgaaccctac agcagatcct    4680
gtaacgtaat tacaaaacaa agatgttagt cacgatgcct ccacccaaca actgattatt    4740
ttcttataga gatatagatc ttagaaaact gtacctcgtg ctgtaccctg attcagtgca    4800
ttacccaatg ttagaatggt ctgcattatc tgacgtaatt tggcagattc tttcacctac    4860
ttgaccagga aattcagtta gagcctagtt aaatcagaat gtgccaaatc aaacttcata    4920
aggtattaaa aatacctctc tagtagcatc attgattgta ctcaggttac ttctcaagtc    4980
cttcacctga acaattcaac atattatagt caacagaaaa ttaatggcag aatccataga    5040
cattagatca ctaagaagta caagagaaaa tacctgatta gagaaagtga tagtaaatga    5100
aaacactcgt aacttggact caactcgtgg gaccttcatc agctccagga aaaactgaaa    5160
cgggtattac ttatccggtt aattacttat aacttaaagg ataggaaaac ttgtacttcc    5220
ccacatatat ggtcaaaatg gagaagacct gctcacactt tccaagcatc cccttgtccc    5280
cattatagtt ctggaaaata gaacataacc agtaagatca aattgtgaaa tcaagaataa    5340
caattaaata tcaaattgca agtatagact gtcaagaaac taacataact aagttcacaa    5400
agagagggg aaatcaagca gaaacaagta tggatctaca tacacaaaag actaagatat    5460
atgcctatgt ttatacacat ccacacccac cgggaaagga agttcccagg aaaaggtatc    5520
tgcatgatta gacattgaaa cagacacatg agcatgcacg cacagcatag atgcaagtac    5580
atactgtata agcatgaaac cgccaaatgg gtcattgact tatgggcatc aacctacaca    5640
gctacttgca acaaatggca catcaacaaa actataggct cctgctgttc ctacgactca    5700
cttaactatt cttacgttaa gtacaattgc agaatgtgaa ggttccgact cttgtttcca    5760
aatactatgg gcaaaaaact tcaatatgga gtatttctc taaacgggaa aagttaaaag    5820
aagaatcaaa gcaaacttca gaacatacct ctaatattac ttgtgaactc aaaataaatg    5880
actagacaca cattataagc atattattgt aacttaaact ttgccatgat aggcaagcac    5940
agtaggatga gaaagagatt atacccctcag tgtctccatt tcttcttttg ttgggcaaaa    6000
ttttatcaga ttttcaacct gatcaatgtc cagagctgat gaatccaaag ccaaatagc    6060
attctgtatg acatgcatac aaatataatt tgtaagaaat ccgcggtaaa ttttcctttg    6120
taaacagaaa ttttatttgc atttgcataa tactggccgc gagttcaaat agcggacccc    6180
```

```
aacttgtctg gaactgaggc gcaactgttg ttataatatt agtaaaaaga aatccatggc    6240
aaatatttca ttcatttcaa tgtacctcca ttaaaactca aaataaggaa aaagaacttt    6300
ccaaagaaac catgcatgag catcctaaag aaatgctcgt cagtcattac acttattgaa    6360
cacatgcatg aatcagcata ttgatactgt gcattatgaa acatgatttt gaccaaaggc    6420
caaaggatag aatattttat acaatttcta tcatgattcc tttgaatttc aaaggaaaaa    6480
tatccataag agttcaattt tgaactcttc aagttcggtg aaattacatg atcttttcaa    6540
cacaataaaa ttatcaaaaa tataaaaaat aagaaagtct tttggataaa tagttctaca    6600
gctacttcca tagaaagctc cttttctcct tgtacaaaat aaaggtttct ttatccattt    6660
cattgaactc cggctaaaaa atatttctaa taacgatagt gtctgatcct acttgtgctc    6720
gtatcttgac taatttatag ggtacttgac acctcctatc aacataggta tgggaacta    6780 tgccctccaa aatgcaatca gatgaggaaa accaccaagt cttagttttg gtcgctacta    6840
gaaaaaccac ttggccacac tctaaagtgc tcattgaact ccaccaatat gagaaaagca    6900
taactaactt gaaactgaat tacaaggaga actgttatag gttaatggct aacataaaaa    6960
tagtcaaact accaaactcc tctgtgtatg acctaaatgt tatgtgtagt taaccgattt    7020
atacgttctt cattcctttg ttgagaaaaa atatagatag ttaatcaata tattgtactt    7080
ctattaagca gaaacgaaga tacttcaatt tagagttcag tacataatat aatcttttg    7140 atctagtaaa aagattatag catgaagagt tcaatacata caagatacaa caatctttc    7200 cttttttttg ttgttgagaa tggacttta gtcaaaccca ttaagctgat tcaataattt    7260
tgcagatcta tttgattcat cagatacata cttctatagt tttagcaaat gtacaaaggg    7320
attaaaaaaa actaaaatac taaattgtaa tcttttggaa aataaagtca acaacatat    7380 gcattcaatt gcatatgtaa tttgttactt gatttcaatt gataaacaca tcaggattcg    7440 ttaatttaa tggctgttta gtttgtgtta ctttttaaat tattagcagc tcaatttcca    7500
aatatctgat tgtcctaaag cccaagtaaa gatcacataa tctaatagtt tcatctgata    7560
aacaataata gattattatc aaaagaccca cctgttggct agaagacata aattagtgcg    7620
caatagataa aagtatcgaa gctcatagta gaaacgagaa gacacaaaaa gaactcacaa    7680
gcatatcagg caggggaatc ttgattttg taagcatgat ttcacaattg tatgccctgc    7740
gcaaatcaat ctggcaaaag catatgttaa gaatcatcc cggtcttta acagttagac    7800 caaaatgtaa cacttccagt ctttcactat aaataatggg agttgtgtaa aataaacctc    7860
aatacctcag gaagaaaaag aagccaacac caatagactg ttcaccaact attccatagt    7920
gatctcatat tatacagtga agctttgaa aactatcagt ttctttctat agaagttttc    7980
tatctctttc ccaatttagc actaacagat aaattaagaa gcaagtgaac tgcaattcat    8040
tcatggtcaa tggccatccc catgggacac agtgcccatt atgagcacag cctccgcaac    8100
tctttcatta gatctagaca tgtatcgcag cctaataaaa ttactctgtt gcatgaattt    8160
acatctcaaa gtattaacac aacttttaag aattttttcaa aggcaaccat tatttttta    8220 tatgattgac tccatccact aaaccctctg cctaagacgc ccaagagagg tttccccctt    8280
tatcccttcg ttaatcaaac ccccaacctt atggttggag atgaaggacc ttaccctagg    8340
atatcactcc agtcaaagat aattgtctta actttcatga aacagaaatg gtattaccta    8400
caggatggag aaaggaggac ttttccaccc aaagttatg taatcatcca catccaggct    8460
gaaaaaacat aagttcttct ctataagggc atgcttgttt cgaaacgtca cctatgttaa    8520
```

```
acccatttaa gcctttctat ttacttcttt tcttccacct tgttagccac aagataccac   8580
aaaaagtgct ctttaaaacc tatctaatat ttaattgttt tgttaaacta gtaaagaaag   8640
gagatacact catcctacaa cactcacttt actacatgaa agacttgcta gataatgcct   8700
actggagaat aacagttgta gagactggaa acaagataaa gcatatataa cttgccaatt   8760 gcacttttc tggtttgttg attttgaac cacgtcggcc tccacctttg ctagtgccat    8820
cagtagctga agccaccgaa aacaaattct caagctccgt aatatcaatt tcaggtgctc   8880
tgtcatgtac attaataaaa tcttatcaga actacccata acagacagat aacaaataaa   8940
agttgcagta cccaacacaa actaggttaa gctcaaaggg ctcagaacta ctatatctgt   9000
aatctattaa gcattcgaag ttgaaaccat gagaatgata gtgcttatga caacctgtta   9060
aggggtttca cgagacacga gaaatagcga acaatttagc tctgactatt aacttgaaat   9120
gacacacaaa gttctcattg taattttca tccccaaaaa taaaatcttt atacctggaa    9180
gtattttcct tgttttgcgt atcagcccat aaactcccctt gcatagcccg tgtaactttc   9240
gaccaatgta agggcttcaa tgaagctttt ttcggaggaa ttgaagtacc tcctgtacct   9300
cgcccttttc ctagagcagt tgaacctaca gaggctctta cacgtccggt agatggaggt   9360
ggtggcgctg gcacactaag gccctttcca ccaggcgggg gaggtggagt gggtgtcaaa   9420
ccccgcctag ggggtggtgg agcattagga gcctttggtg ctggtggagg tgctggtgga   9480
gtggaacctt gcctaggaac tcccaaagga ggtggaggag gtgcaggtgg ccttgtagaa   9540
ttgtttgacg gtggaggtgg tggcggtgga ggtgccaacg gagtaggcct atttgatgaa   9600
gaaggcggag gtggaggcgg tggtggtgga ggtgccaacg gagttggcct atttgacgta   9660
gaggatggag gtggaggcgg tggtggtgga ggtgccaaca gagttggcct atttgacgta   9720
gaggatggag gtggaggtgg aggaggtgga ggtggaggtg ccaacgaagt tggccttttt   9780
gacgtagaag atggaggtgg aggtggaggc ggtggaggtg gaggtgccaa cagagttggc   9840
ctatttgaag tagaggacgg aggtggaggt ggaggtggag gtggagcggg aggtggaggg   9900
cctttggaaa gggctgaagg ggtaagcggg ggaggtggag aaggcgggga agttacacaa   9960
agcaagggtg aacacttcaa tgacatgaaa gggagggga ggggtggagg aggagctgat   10020
aaattacagt tagatggacc ccgaggagga ggaggtggag gtggaggtgg aggcaaggca   10080
cttctagaag tagaaaacgt agggacagat ggtggatgtg gaggagcaga agagcataaa   10140
aggctctgat taggaagtgg tggaggtggt ggaggtggcg gaggtcctct agaaaagcta   10200
tcaggggaag ttgaagaagt aggttgtctt ggcggtgaat gttctctatg gctaccaatt   10260
gaaggtggtg gtggtggtgg tggtgaggt ggaggtggag gtgatctatt agaacttgca    10320
agtggtggaa gcgacgagt acgttggaca aagaaggga caccaattat aggaggaggt    10380
ggaggtggtg gaggaggcgg aggaggtaat gagacctcct tgctaggaga accaaacaga   10440
gagggtggtg aaggggagaa tggagctgat gattgagtga cttttatact agaaatcaca   10500
gaggcaggtg acggaggtgg tgaaggtagc ggagaagaag aggaagtcct tgtatcgcaa    10560
attgaactcc cctttaaacg ttcaggagaa atggcagtat ccaattgaca gttactttca   10620
gaaagagact gaacaggacc aagatctgac tttgaaagct tcatttgacc ctcagaaatc   10680
ttgggatcag aagttccatc agaagctgaa tcctgttcat ctaaaaagtt gacatctgtt   10740
gtattagcat aactaatact actagctttc tctgagtcca gaaaatccaa actgtcggca   10800
atgctcgatg cattattttc ttcttcagaa tcaaatgggg atgaatacccc actcatccta    10860 cttttgcaaaa ttgacaaatc tttcatatca ttcagcaccg atagctgttt aaacaaccac   10920
```

| | | | | | |
|---|---|---|---|---|---|
| aacgcagcat | catcaccagt | atcaacccaa | tcagcaccac | taaaaagttc | ttgtaccctt | 10980 |
| gaaaaggctt | caataggaag | tccaccagtc | tcctcaccat | tgagagctgc | agtgggagct | 11040 |
| tttagtggag | atatgctctc | aacatcacca | aataaaacct | gcaaagcaga | aagtataagt | 11100 |
| tagaggagaa | atatgaagag | caaaggtgat | ccaataaaac | aaaactaatc | agacagtttg | 11160 |
| taaataagta | ttcacctcag | ctcgaaagcc | ttttggatag | cgtgcctttg | aatcccatag | 11220 |
| aatatccagg | ttatcgcagt | ttaacatcaa | aatgttagag | cgaataaaag | cagtgttaaa | 11280 |
| cacaatacgg | aacatcatga | cttccctttc | aggatccagg | tctaagtgga | cacactccaa | 11340 |
| aactacatct | ccttgcacca | aacactgaat | atcaatcttg | atgacatcac | tgtccttctg | 11400 |
| caaaacaata | acaatcatgt | tgccacagag | cagaattgaa | gaagacaaca | aacaagatgc | 11460 |
| agtgatagca | atttttcacc | tggcgataat | gtcgaaggct | tctacctttc | ttcggcatgg | 11520 |
| agtacaacat | atgagttgac | aatccatcct | tgctgagaag | gttccttcca | aaaatgcgca | 11580 |
| caattggcct | acaccctttt | tgattgtcaa | atcttggaat | ggcacgaaga | atgaggcaat | 11640 |
| ccagagaaag | agcttgttca | ggaggaggcc | actcgggaga | tatatttctt | cttgatatat | 11700 |
| attgcaggta | acgaagctga | gaagggaatg | ggttcaaagg | tgacaacaat | tgcgataaac | 11760 |
| ctttaggtgc | ctcacgataa | accatctcga | gagtttttct | ctctccgctt | tgtaactttc | 11820 |
| tgaaaaccaa | gaaactggcg | aaaatgaagg | ctagaagggg | ccaaccacct | ctctcacagt | 11880 |
| gtaacaaaat | tacattgtta | tgattttgaa | gagagagcca | actctcacag | atacatagaa | 11940 |
| aatgatgtat | caatgacaat | ggcagtacag | gacagccttc | atattgtctt | gggtaatcca | 12000 |
| ttacagtcac | atcatactcg | cataaaatct | cagcaaactg | gctccttttc | tcgccttctc | 12060 |
| tgaaattgaa | agcaagaaag | gaggaatctg | gaaattcttc | atgtagttca | tttatgattt | 12120 |
| cgtgcaagta | aagctgataa | attccctcag | gcagtacttc | agtcgaaaaa | caagaatcaa | 12180 |
| aaactgcaga | tattcaacat | aagataaaaa | gatgttgaga | aaactacaat | gcacttccaa | 12240 |
| tgttcaataa | aaaacacatt | ataaagtcaa | agctagttcc | tttaccatat | actctatcat | 12300 |
| caagttccag | caacccatct | gggggccttc | tatagaaaaa | tctactcaac | agcgacataa | 12360 |
| tactgagcca | atatatcacc | taaatttacc | tgacatcaaa | gaaattcaaa | cccattttca | 12420 |
| ttcctttggt | gtcccaatat | caaaagggtc | agagaatcag | ctcgtacaaa | ttcaagaaaa | 12480 |
| tgtgaaattc | ataagaagaa | ctcaaaatta | atctcaaatt | cagaataccc | acaaagctaa | 12540 |
| aaagggattg | aactatattt | caggcgaaaa | aattggaact | tgacaccaaa | taaactacaa | 12600 |
| caagactgaa | acacacacaa | aactcacatg | gaaaatattt | gcatataaaa | caccaaaaaa | 12660 |
| ggaaatcttt | gaactgaagc | aaaccgacag | aagccgttga | ggaaggattc | gagatgtgag | 12720 |
| gtgaagaacc | gacagtgttg | ccagtaaagt | ttcacctgc | gctttccgat | ttagtatga | 12780 |
| attttttttt | ttttctgatt | acggatttga | actctttgga | gttcaaaatt | ttgggaacga | 12840 |
| aaaaaaggg | gctgattttt | tattttaaca | tatggttgtt | ttcaatttt | gaaattacag | 12900 |
| aaccaaccca | atacttgtat | ggataacttt | tagttagtgt | ttatttttcg | aaaactctac | 12960 |
| gatgaaggat | cgatcggaaa | taatttttat | tttctactca | taattaggaa | taagattata | 13020 |
| atgtgaaata | ttcaatgatg | attaatgaat | agtgttatat | ttaattgatt | attattgact | 13080 |
| tgaataataa | taaaaatata | aattacaaat | atatataaat | taaatacgaa | tgagtataat | 13140 |
| ataactttct | taaacaatt | gagtgcgatg | gcttaatggt | caagatgaat | atattgtact | 13200 |
| ggatgatcat | gtctttgaat | ccccatttat | atcagggtca | aatacataaa | gagatttcta | 13260 |

```
aacttgttgg gttttttttct tcacgtactt taactacgtc attttttctat tgaatcattg    13320 aaccatccaa aaatttattc ctttaagaac attgttggtt tattttgatc ggctattcta    13380
ttgtaaatgc ctttaattgg gttcgaattg taatgatttt gattgaagga atgaagacaa    13440
cccgttttag tctcatttgt tttttaacgt cttcaaatga cttaattaaa atacaattat    13500
tctcgaacat ttttactatc aattggacta atgatttctg aaacaacata tatatcctct    13560
atcaatcccc ctcacaaatc tggtttcaca tcagacaaca gtgttatttt aaatggaaca    13620
aattataggg gtttaatgat tcaataggaa aatgacgtag ttaaagtacc tgaggagaaa    13680
aaacacaagt ttagagattt gcttatgtat ttgaccttaa atcagctatc caacatgcac    13740
ttttgagctt tctatgggtg cgctaatact tgtgtgtcaa ctttttttaaa gatatatatg    13800 aataaaatata tataacatga ttttttttttt gaaattaaca ggtatacgtg cacctcattt    13860
atacatgtta ggtctgtctc taaaatcaga tctacaaagt tacatcgggt atgttttttaa    13920 tattattgtg gttgtttgta ataaatattt taattagagt tgttcaaaat caaatcgaaa    13980
ttgataattc gaattggaaa aaaaagttat tgatttatca gtattgggtt attgatttag    14040
cgatttagtt aagggtctga ttttttttgt tatcgggtta tcagtttgaa gttttttctc    14100
ccgatagtaa attaaataat tatatttata ccatttatg tttgactcga agtttgcttt    14160 cctacttta ttttttggtta ttcaatgtat ctgcttttga gtaagatgta acttgtgaac    14220
tgatgtgcat agtttatttg gtttgtcacc ttgtttctaa gtgattttta atataaattt    14280
ttgtgtcaaa tcttaaccag ttaaactgat aaccaaatcg atagcgataa aaaatcgata    14340
agccaatatg ttaatagttc tataacgatt taacatctct acacactatc aaccaataag    14400
ccaatcaata aactttaaaa ccgaatcgaa cagaccgata cgcagagcta attctaatga    14460
caataatcga ttgtggaatc tatattaatg catggctgca ttgaactcta aattgaagta    14520
tcttcttttc tgcttaaatt acctccaaaa ggtaccaatg ataccaaaat ttccaggctt    14580
ggttgatggg ccaaagtgac catgtgatcg cctttattgg gcttttagcc cagttaaact    14640
tagggcccaa tgacgcatat tctatcagca acaagaagta ttgttggtga ctagagaatt    14700
ttagaatgta attaaactat ttttggccaa caaaaaatat aaatgatata caatatttaa    14760
tataaaacta gaaaaagtta acattattcc tcaatgagta tgattcgaaa tgcatagacg    14820
aggctatata caaaaataga ggaagattgg atcgccatt tgaatctggt ttggtgttag    14880
aaattcgtag ataaatcgag ttgaaaaaaa cgttgtgaca cgtgttttac gtatgagagc    14940
caaatgatat ggactttgat caacttttca agatgtattt tttcgtcata ttgatattga    15000
gaaagattgc aatttatagt attgtcctca ttgttttaga aaaccaaaag attttaagtt    15060
tgaagtatag aattaatcca atcaaattta gttttgaaag tcaattaaag tgactctcaa    15120
aaacgcaaat catgataata ttttgaaata aattagggtg ttttttttttat tgttctatct    15180 catttgtttg aaatatagta tttagaaatt acgcgaacat tctaatcgtt attcattgag    15240
taatatacct gattataaga cgattaatat tgagattgtg agacaaaagg aagaaaatat    15300
aaatttatag tactaaggac aagggcggac ccacaaggtg tcaagtcggg tgctcgaaac    15360
acccattaac cgttattgaa atatgtatat ctatgttaaa atcgatagct atttgtataa    15420
aattaacata gagcacccaa tgaataaatc atatagttgg cccaatggtt ctagaatggg    15480
tacttaagac tcttttaatg ttattgtacc aaggttcgaa ttccgccact gactaaggat    15540
cacgatggag tcatggagat cattatttgg ataaataac aagcaaatgc aacttaaatt    15600
caaatttctt ttattcaatt acaattaatt aaattatgat taaatcattt tataagtgga    15660
```

```
gatcattatt tggataatat aacaagcaaa tgcaacttaa attcaaattt ctttttattca   15720 attacaatta attaaattat gattaaaaaa tcattttata agtaaaaata cttctataaa   15780
aggaaatttt atccttaaaa ttcaaatatt aaacttcaaa ttaacaacac atgcaacctt   15840
atacaaaaca aatcaactag gatacctccc ccaataatta aattggtggt caataaaatt   15900
gtactccata attatgaatt gtagttggca ataataaata tgcattgtat tgtcctcatc   15960
gactagtcaa tggaacattt atgaaaccaa aaaacatgaa tcaatgttct ctacttgcac   16020
caaagttttt atgaatgaga ataatatta gatttgtccg ttaaggattt caaatgtttt   16080
aaatattgta cttggggtat aaatgagctt ttttttatca gtaaattttt atcgtatatc   16140
tgatgattat agatctccat tctcagaaac atcacttgaa aatagttgtt actccatccg   16200
ctcacccaat tataacatcg atcttaataa aaatacataa aaatcattta gttcaaatgg   16260
tttccctcac tttatatttt tatcattttt ttctattacc aattaattag ttttgttata   16320
aaatcgttga tggtcaacaa ttataactct atcttgattg tcatacgatt gttaagatgg   16380
agtttcagcg aggttaaaaa ttaactcgtt ggtataatta tgcattattt aaattttatt   16440
tgagatgatt ttatagatta atggtaatta atttagtctt gaggagtaaa ataaaatcgt   16500
tataggtttt tgagtgttcc taacatcaga atggtgacat cattatgaag ttataaagac   16560
atataatata atttaaacta ggaaaaaaga taaatatcct tttgaattat cgtaaatagt   16620
atgtaaatgc tctctgtcaa ttttttggga cactgatgct cctgtcgttc aaaaactaga   16680
aataatatat actctttaca ctaacggaca cacacgtgtc ataatcttat tcaccaattc   16740
tacatttatt gacggagaag attgcgccat gtgtttctat ttagtcttcc tttagagtta   16800
acggcatata aactttagtt tttttttttac agcaggaaca tcaatgtccc aaaaatatga   16860
caaagaatat ttccatatca tttacgatag tttgagatat attttcccctt tttccattta   16920 aactaatatg caaaatacga tcctgctcct ctttatttct cttctctcca ttttccccaa   16980
gtttccattt ggattaatga cacatgtcat gggttaaaat aaatggttaa aatttaattt   17040
ttcaaagtaa acctctaaac atgatttagt taatatatat attatatatc aagtatcaaa   17100
atttttataa tttcacaatc ttagcaaaca tattattttg tccatattat ttatgtaaaa   17160
agttttcttc ctataatttt ttttttttcgt aggatctttt ttatttttta ttttatacaa   17220
tattttaatt gtaatctttt gttaaaggta tattggtccg tgattaataa attacctaga   17280
gataatcaaa tcattttgac aaactaattt taatttcata ataagattaa gaatacggtg   17340
ataccaagac atacgataga ttaattatag ttttcatact tctattcagt tgcttattct   17400
tctaattaga taaaaaaaaa tttatataaa gggaaaaaaa agatcctacg taaaagaaa   17460 taataggaag aaaactttt ttacctatat ttatggacaa aataatatgt tcctaagatt   17520
gtgagattat ataatttttg atgcttgata tataatatat ttattaacta aatctgtcac   17580
gacccaaacg ggtcgcgagt ggcacccaca tttactctcc tatgtgagcg aaccaaccaa   17640
tctaatccca acatttcaac cataataaac agaaataaa gcgaaagact taaaactcat   17700
taacgaaatc aattaataac ttctaaaatt taatattcat catccccaaa atctggaagt   17760
catcaccaca agaacatcta tcctcaaaat actaaatcta agaatgtcta gaaaactaaa   17820
ataataaaca gctagtctat gccgaaactt caaggcatca agacacacga aggaagatcc   17880
gtcaagctgc taaagcgtta gctcaccccg agatccgacg tgatgaagac cggctagagt   17940
tacggttgag ttgaagacga tgatacgttt gtgcgactcc acaaataaca aagaaaacaa   18000
```

```
ttacaagtag ggtcaagata aaaaacagta atcgaaagta gtatcattgc caactcaaaa    18060
tagaaagcaa tatatttcag ataatatcat aaaatcaact aatattctta acaggtgata    18120
gcaacaagta taaaactcat ttataacaaa ccaaccacat ccatgaggac tcaagcctcc    18180
ataccatact ctttagggaa acaagttctt tggattgact atattaacat atttcaagat    18240
tcattatctt tctatctccg gtgtcggaac gtgacaccga tcctcatcat actatctggt    18300
gctctaacgt gacacccgat ccatattcta tcctgcgtgg gaacgtggca ccgatcctca    18360
ttctatctcg gtgccgaatg tggcaccgat cctcattcta tcccagtgcc gaacgtgggc    18420
actccgatcc tcattctatc acggtgcggg aacgtgacac ccgatcctct attactatcc    18480
cggtgctcaa cgtgacaccc gatcctctaa tctcattact ttagttcatc aagccttctt    18540
ttataccaag acatcatcat taacaaagta aaatttagga tttaagattc aacagcctca    18600
tcatgctagt ttcatcacaa ttatatatat aaactcatca tgctagtttc atcacagtta    18660
tatatataaa ctcatcatgc atacacacaa ttaagcatat agaagagttt acaatactac    18720
ccaaaacata tcattcgcta ttaagagttt actatgaaat agcataaacc ataacctacc    18780
tccaccgaag aatcgcgatc gacaagctat cttcccaaag ctgcgttctt cctctctctc    18840
tttgttcttt ctattttcct tattcaaacc ccctttctt ttaccctaat tagcataaa     18900 ttaagtataa aagatgataa aatacccccac tacttgtttc caaggttatc tcttttaacc   18960
cccaagtaat tgaattatta acattaaacc actaacttta taattataag caggaatagt    19020
ccaaaacgtc ccttaaaata tttaacagaa atccgaccca ttcggtcacg cgttttagac    19080
ggcccgtcgt gctgcgacgg tcaaatctct ttgcttccgt acaaagttcg ggagactcaa    19140
ttcattaaaa agtccagcgg cggcccgtta tgctcggaga cggtcgcccc gccacccgtc    19200
gtgacgttcg atcgatctcg gtacccaaat ttttaaattc taagtgtttt agaacgagac    19260
ccctcgacgg tccggtcgtg cccatgacgg tccatcgtgg gatccgtcga ctcaccagct    19320
ttttccggaa ataaaaatca cgctaaaaac gactaaacag gtcgttacaa aatcatggtt    19380
aaaggtttac tttgaaaaat taaatcttaa ctatttattt taacctataa catgtgtcat    19440
taatccaaat agaaacttga aaaaaatgaa gagaaagaga aatggagagg agccgaatcc    19500
cgcaaagtag aaatatattt gaccctgct attaactatt aaaacgttct tgtttcattt     19560
tgaacttgca aatatctgtg gtacactaca aatttaaggg ttataatatc tattaataaa    19620
cctaattagt aagggctaat gagactttaa acacaatagg caaatgacag gtaagccctc    19680
agattttgat tctcctatat cacacatgac gttgtcagag gtcaaaactg tcattatatg    19740
tccaaaatac gtgagtatga ttttttagca gcaagaaacc aaaaaaaaaa aaagagatac    19800
agattttggc aatttatacc ttttgaatt gaaatgatta cacaccttt tcacattgtc       19860 agtttatttt cttttgggg tctaaaagtt ttggttttg aaaaaaaaaa tatccgttga       19920
tttaattttg gagtaattta aggggatgt ttggttatga aaatataaaa atattcattt      19980
tatttaaaaa aaattaaagt tgaagtttga attgtgttgg gttatatttt ttgtaaataa    20040
tatgtataat tggttatgtt tttgggtgac taaaagtatt tactttagaa aagaagatat    20100
ttatgtcaag aaaataagtg ttgcttaaga gtagaaaaat attatttga caaaaaaat       20160 gcacttaaaa acactttgaa gaaatgcaat taaacactaa ttgtcgtgta agaggtcttt    20220
aaaaattaat tggtcaatgc attatgatca caaaagtatt tttaaaaaat taaacctta     20280 ctaaaataaa ttaattttag aaattcgacc taacaagtca taaaaataaa ataaactttt    20340
acttatttaa tgtttgaagg ccattaacaa ttgaattaat attgcttttt caataaagat    20400
```

```
ttgatttaa ccaacctcaa ttaataccaa ttaaagttta attttgtaaa ttggattgaa   20460
gttgcacaaa tgagtatatt tagttatgta ctaacatctt ccatattaat tctcctaaat   20520
ctttaggtac atatttttct tttccatatt tttaacgatt ttactttcta agttttaaac   20580
tttaactttt ttaaattaat tagttcaatc ttcttcttct tctttttttt ttggagggac   20640
ataatttgat cgatctatta atcataaaac atgtcttttt ttttgtccaa tattatatga   20700
attttatgaa ataaatttat tttagaactt tttaacgtat tttgacttta agctttattc   20760
aatccgcctt cactgacaaa aattccaaat aaaaataaag tgctaaagta taatttatat   20820
actctctctg ttttataaag aatggtctaa tttgacttga tacgatattt ctcctatttt   20880
ataaagaatg atctaatttg atttgatacg aaattaaata tacaacccct acatgccacg   20940
tggaaagtta ttgtcagaaa aaaaaaatta ttcttttga tatggactat aaaaaaaagg   21000
tcattccttt ttaaaacgag cagaataata tatatcccaa aactttatta ttgagaaagc   21060
atctaaaatt tgatatggca attgcatgaa tgtggagtaa aattattcta atacaccaga   21120
tatgatgcca tgcagaaatg atgtggaaac tatatatagc acaattccca atgaaattta   21180
atgtactgtc tcataactat atagtatagg cttttcctcta actatacata aagttacccc   21240
taaaatatag gctagctacc cttctagctt tcccccaaat tctaaattag aacaaaaaaa   21300
tatttctaca tctttttaca gtttttagtc cctttcactc tttggggtta tttgaggta   21360
aattatttat agtaatttag aattttatat gtataaatta taaaaactta tatttgtggc   21420
atctttggag gtaaattatt aatagtaatt tagaatttta tgcgtatgag ttataaaac   21480
ttatatcatt catataaggt agaagatata ataattaaat tttatataat aattatctgt   21540
attactaata tttgtataac tttaatcaat cattctttaa tgagcaattt tcacatataa   21600
caaataaaaa aaatcatatt tgtatgttat aacaaagttt gcttaattaa ggctccataa   21660
agaacataga aacatataat tcgctataca tatacggttg aagcaaattg tataaaacga   21720
agtgtataaa acaagaaaga gaaagacatc aagagaatcg tataaaaata aattgtatta   21780
ttataagtgt atagaacgat tatatacaat ttgaatttgt ataaaatgag aaatagagaa   21840
agacaaaaga gacttgacag ggaatataca attgaatcga attgtataaa acgagaaaag   21900
agaaattaga tacaatttga aaattgtata aaacgagaaa gagagaaaga caaagaaac   21960
tggtcagatg agtattttta ttgtataatt ataagtgtat aggacgaaaa tatatgtact   22020
tgtatgtgta tatacaattt tctcacgctt tatacaaaca taaacacaat ttatacattt   22080
agcttctgtt tgtataagtg agaaaggcga gggtggtgag cgagatttgg gagagtggcg   22140
agcgagatct ggaagaggag agagagggga acaaaaatat atgtattata caattttctc   22200
tgctttaaac aattagaaat aattttata tacttgtgtt tgtataaaaa ataaggaagc   22260
gagtgagaga ttagaggaaa gtggcgagcg agataattgg gagagaggcg cctggcaatt   22320
tttcgcaaat atttgcgatg gagcacaatt atatcaaact ctaactacat ttattttaga   22380
ttattagttt gctattatat ataattttct ttttttaat tgtttagtac ttgaaagttg   22440
agtaagtgtt ctaacccaaa atgagttata tttatacact gatactccta tttaaagttt   22500
agtaatagta cttatgtaga ccattgtata agttttttaac tggccaacaa tctatttcat   22560
acaatatatt tggacttaca aacactatag aacttatctt taagtattaa agataatttt   22620
ttatcacata agcaggagcc tctatttgat ctatttcgct ttaatataac gtgcaatatc   22680
ctatttgatt ttcttatta ctttaattat agactcgaga tttgtaaaac ttcttatttt   22740
```

```
gaggataact agtgtatcaa tatcactttc ctatttacct tatgtgacgc gacacataac   22800
ttccatttaa tgtactttct tttagtcccg ctcatccaaa aatatttaaa ctctttggtc   22860
ggtctccaaa tctcttatat atcattaatt caatagcatg actcatcaat aaaatattat   22920
atcatctaca cataacatac attgtgatac ttccactcga atatgtcatg ttaattcatc   22980
gatcatcaaa gcaaataaaa acaaattgag aactaattcc tagtgcatcc catctcgatt   23040
ggtatcaagg tcttttctt taacagtcct tacttagatc ttgactccat tatacatgcc   23100
tttaattact ctaatatata tcgtaattat atttctagac tccaaacatc ttcgtaaaac   23160
ctctctcata atcaccatat aaataaaaga taactcaaac ttgacctatt aagagttgat   23220
tggttgaaat tccatgttaa agatctgaaa aaggccttat ataaaatgg tcctttgtac   23280 agtctgttga ttctgattcc aaattgttta tgcctaaaac aaacatgatc taaatattta   23340
attaaaaggt ctctaattca atcaagatcc attttgtagt caaaatatat actattttgg   23400
tggaattttg gacataagaa ttaatgaaaa atagtccatt atatttttt catagttaaa   23460 caacacactt tatactacat gcctattttt tgctagtaat ttcgcctaag aattaaaatt   23520
aaaagtgcta attaattaag acattaagct gtaaaaatat ttaaatatgc aaaggctaat   23580
cattaatgca aaaacaatag gctccccaac cgcactttca tatataaata gcaagaagga   23640
aataataagt aaaatggata aaaatatgat aacgtctaga tacacaaaga ctatcttatt   23700
tgaaaaaatt gttatataa tagcaaccta ttagtttaaa ttaaatgtta taaccatagt   23760
ttgatttaac tgtaactctt attaaattct tgttgttcac atcccgttca ccactctcac   23820
tcgtctctcc actttataga aacacaaatg tatacattgc gtttgtgttt gtataaagca   23880
aaaaaaattg tatatacaaa aataatgcat atattttcgt tcgatacact tatgattatg   23940
aaaatacaat ttttccttgc ccaatttctt ttgtctttct atcttttcg ttttataaac   24000 acaaattata caattgattc ttttgtatat gtataccgaa acatattata taatttttt   24060 tttgtatata agtataacga aatatccata gcaaacataa agtttgctat aaagcgtaat   24120
taatgtaaac tatagttata acttacaaat ataattttg tatttcttat atgtgaaagt   24180 tgctctttt tttcaagtgt gtgaataaat taatacttaa agtatgtaat cacttttaat   24240
tgggaaaatg cataagtatc ccaacaacct atgtccgaaa tcacagagac acacttatac   24300
tatactaagg tcctattacc ctatgaactt gttttataaa taactttata ccctttttcg   24360
gccttgatgc gggagaggca tgagtgcaat tcaatcttgt ggtgtattcg tttgtagtga   24420
gtagggcctc tttctcgttg atctgacact atcaaccaca taacttaaaa aaattgtcag   24480
cacactttgg gcccacaaga gagtgtcacg taggccgtaa agggatagaa agttatttat   24540
aaaataagtt tacatgggta atatgacctt agtatattat gagtgtatct ctaaaatttc   24600
ggacatatgt tgaagggta cttaagcatt tctcccttt aattatatgc attaacctct   24660
attagttata aaaaaaaac ttattttgag attgaagcat ataatgaaat gcaataacac   24720
atattattca catttttaaa acgttcaaca taattatata tcgtggatct tgctttcgaa   24780
ataactggaa tcggcatgct agtccgaaat tctcgtggaa gcttcattag aggccacact   24840
cgtcggttag gatgacaaca agatccactt atggccgagg aactgggtgt tcaagaagca   24900
ctaagctggt tgaaggacac tttacggcaa acaacccaga tagttataga gatggacaat   24960
ctttttggtt aaacaagaga taaaaaggt gcaaaaacta ctcttacttt tatgttatta   25020
ttcatgattg taaagcattc gtgtgtgact ttacttctat ttcttgtct ttcgataaaa   25080 gatgagcaaa ccagtgtacc catcagttag ctcaaatttt gggttttatg actaatgcta   25140
```

```
taaagcggat aatagatctc catctttaat tcaagatgta ctcaatttta atttgatcaa    25200
taattaatta aaatgtttga ttaaaaaaaa aagaatgtt  catcatacta aacctactt     25260 gtaatgacat atataactaa ctattttgat gaataatcaa actactcaac tttctttaaa    25320
ggttttgaag aacaaaaatg tcatattggc tatttacact tcatttagct aataagaaat    25380
tgattttcct ttcttataat ttttttttgtg ttttctttc  tcacctccat tttttctgac    25440
ttagagctcg ttttgattga tttaaaagaa tagttttaa  atcaaactta ataattta       25500 aattaaaaaa taaaagtag  aaggagatct acttttaatt ttaaacttat tttaagtcat    25560
ttataatctt gtcaatcata taaagtcaaa attctgactc aaaataagt  ttgattaact    25620 cttgagtcaa ttcaaacacc ctcttagttt taattgacat ctataacctc taattttagg   25680
tatgtacaaa taaatactta aatttatata aaaattaaac aaattaatat tgtgatatg     25740 tgacattgca taagacaatt ttatatcaac gtgatgtcct acctatatta cgccacataa   25800
attacatata tattgatctt tcaattttat atcgtttaaa ttatacatat atacccatc     25860 aaaaaagtat tatgcttgtt gaatagttct aacttgtaac atccactttc ctctttccac    25920
ttcaatccca aaaacatttc ttacaaattt gcaaaaaca  atgaaaagga cttaattagc    25980
aaaagagacc acaaaatgaa agggtcacat ggggtgtgtt aaaactcaag cctaaaaga    26040 ctttgttttg tttttgaata gatatatcac tcaaaaccc  aaaaagcaaa ccagtaaaag   26100
gtgaccccaa aaagcttccc cacacacaca ctgaagacaa ctttccagta atggcggcac   26160
atgaagaaca acaccaccat catcaacaac aagaacaaga gaaccccatt tcctctttat    26220
ccttaaaacc caacaataaa cacttggaga agattttctc ctcatatttg ggtctaagtt   26280
tcgctgtctt tcttgggtct ttaccaagaa atgcagtttc tttggttggg agacttcaga   26340
accgtaacaa ggagctaact tttcagctta ttgatacaga ggagcagtta aagcagctac   26400
ttttcaggag aaaagaggat tcaaaggcaa atgcaagagt tgtggaaatc tttgcaagtc   26460
atagacatgc ctggcagcaa aagagaaga  ggttgttaca gcagatcgat gagtgtgatg   26520
aagaaattgc tgagttaaga gggagagctg agcagtttga gacaatgaa  agtgagttga   26580 gggctaatat tgaggacttg aaaagggaga ttagtgaaag agatgaaatg ttgaacttta    26640
tgagtagaag gggttgtgag atggagaata gtactagtgg agatggtggg agtgatggtg    26700
ttggagattg ttatgctgaa atgggtttga ggtttgggaa agtgggata  tctgaaggga   26760 tggatttggg ggtagggatg gaagagtgtt acttggctaa tgggattcct aatgctgaac    26820
aaatgagtgg tgtttatgga cagagtaatg ggtttaactc agaatacttg aattctgctt    26880
ctaagttttg ggctgaaaaa gctagtcctt ggcaggtatg atccattcat tatttctttt    26940
tgggaacttt ttttgttcttt atagttgttg ttatttgggg  ttttatagtg agtggtgtca   27000
taatgtggta aaaataaacg caaaagtcct ttccaggatc ttcatatgta ggaagaactt    27060
ggactaaagt ttgtcgcttt aatgtttgtc ttatatatgg ttttttcatgg tgaaacttat   27120 gaataaagtt gcttctttta tttaaccatg ggattgtact ttaagtacta ccacctgata   27180
ttctttcttt tagtgtttat ctgtttgttc atcttgaggc tgtggaattt gttttttgtat   27240 gtgatatctg atgaaacaaa tgatccagag caattgagga tgaacgaaat taagtaataa   27300
aatgtttggc ttatagggtt cttggtgaag tacaggcctt tatgatcttt cttcacatac    27360
ctgaaaattt cacaggaata tccacttcta attgttctg  ataaagctga atgaaggtg     27420 tttctccagg agtagttcag cgccaaattc aaattgaatt gtataatgat tacattctga    27480
```

```
gatgcttatt aatgaaatat gtagtttagt gtgtactcag tgacctccta cttgtcttgt   27540
gatttgtctt tattgttgag actcttgtct ctattatcta aaattttgaa tggtttgatc   27600
ttcttagtgg ctgctgaaag ttcaaactac ccaggatatg gttttctgtt tactgaaaga   27660
taatactcac ctcaactgtt cattttacc ctatactggt gttatggacc actgcttgaa   27720
aaccaggtca ccgttttgta cttttcttct ttcaccgttt tcgtcctatt agaggtttgc   27780
aattcttgct tcaagaatgg tccccttttgg ctgaatactt tgcatgaagg ttggtttcct   27840
ggttatgaag gaagctcaaa aaaatgtatt cgggtaactc tagaaatccg aaatccgttt   27900
aaaacggacc gttttgttgg catagaccac tgtgcctcta aaataccaac taatgacatc   27960
caattatata tccccttttgg tttgggaagt tcaattctgg ttaaaatgga tccgtatatc   28020
agcaaaggat gggctgttat cagtcaacat ctagtccatc tgttatattt ctgtttaaga   28080
ttcatcaacc tcaatggaaa gatgtcctct ccctttcttg ttgcaagctg tatcttgtcc   28140
ttgtctgtct ctgtatctta ttttccaatt acaatgttat ctttggtaat tcgttacaca   28200
tccttgaaat aaagcaaatg cctccatgaa acttgaactc cccgcggcct ctaatccagg   28260
cactaatctt tcccgttcaa aaggatcact ggaacatttt cctatacttg gtggatgtgt   28320
caaagtttgg actaggtaga gatcacacat tcaatttatg gctgtgtttt ttgtcttttta   28380 tcattttgt ctttttatat tatatagaaa agaagatctg gattttctta cccttggtac   28440 agtcacccctt ttcatttatt tggaaccaga gggaactgga gcatttcact atgttgtctt   28500
caactttaat agaaaggcta aagaaaacac acaaccttaa aaataaacct aaattgccta   28560
actattagtt gatctatgcc ttgtgagctg gttaaggatt agtcatattt acaatggtta   28620
gagcaaaaag agaaataaac atctagatca caatgcttat attctagttt caagcttgaa   28680
tggtaggaga aatgaggttc ttttgactct tattcagctt cttccttcta tgtgagatgt   28740
cctacctatc ttagtaaaac cagcttggta tttaggatgc tattgggtct taagaaaatg   28800
tgttttcttc atgcaggata tgcagtatga ttctggcgat tcacttcacc atttaaagca   28860
ttttgtagca aggtaaacat tctgtgatta gttagacaga tgcttagatg tttgcatttt   28920
gatgttgaat caactaacta gggtgagccc ttttgctttc tcagacggga ggcccccttgg   28980 aagatagatg gtgaatcaac aggagtctcc tccaaactaa agttacttga gcaggagcta   29040
ctgaatttgg aaaaaattgg gaagactgat ttatctaagg taccatcatc aacgcggaag   29100
caagtgaaga gataccaagc tctagctggc aagattgatg atttatgcag aagaatggta   29160
attactgcat ctctgcaagc ttattggtta aactttagt atatggattt caaagcttgt   29220
tacatgcatg cttaggtttc tctaagaatg gacaatagtc ttgattacat ctgctaactc   29280
aaatatttag atgttgggtt atactcttag cttgcacgac taggccttac aattagcttt   29340
ttacctaaca caaacataca tctgataatg atctccctcc ctcttagcag caggccagtg   29400
atccttgcga atcaaacctg agtcctgagt tccggaccca aagacagacc gagttttttgc   29460 ttgaagcatt tcgacttcag cagcgtgcat ctgaaactgc acagaagctg atggtactac   29520
aaactgacag tggaaaaagt tattacgggg acgaatttga agggcaagcc caactagcca   29580
ctaaacgatc ctttgactcc atccggaaca acttaaaaga aatccaacgg aatttagaga   29640
tatggcttgc cagaattatt ggggatctgg agggaatcct ttctcgagat ggtgcttctc   29700
gtgtaaggga ttattacata tctagatatc cttttgttca atagttatgt cttaacatgc   29760
tcagtaaaat catgattgaa aaaatgatgt ataggtcctt cctgttatgt taacaagata   29820
gctccagctg aatgaacaat atgaggttga taagtccatt tatgcacata aatctgcttc   29880
```

```
acagaagcaa actattaatg ctaactagta cttaaagag tgaagatttt tgacagaatt    29940
attgctggat gtcactgttc ctgatctgga tgcttgtcat ttactagttt tacttggtcc    30000
cggtctttct ggattaaaaa gttgaaagga tggtgtggcc ctttgcaact ggataaatgt    30060
catgtctaca caaatctggc aaacattaaa tatttgtgga ccaagtttac agccccattt    30120
gatttgaaat cagattgatt ttaagttgat atttgttttg atttggattc ttaagctgta    30180
ttgattattc ttaagcttag caaatgagca aatcatattt tcatgaataa gatatcaaaa    30240
tattctagga agttgaatta acaagttata tagcttcatg ttactttttt tataaataaa    30300
tatttgtaat tatatgttat tataaacttt caaatatgtt caataaacca aacaacagta    30360
atactttctt ttgataaaag ttattcgctt ggtacaaaca atttcttccg ctagattttc    30420
ttttttaaat tttaaaatta tgggtctttt cttgtaaaaa ttaggtttct ttttctcacc    30480
taacctagtc gtggacatga gttcataagt tgaataatct ctaactaaaa ggatagtcaa    30540
ggatgtgcca ccgtcgaaca agaaggatag ttaaggacac tctcaagcaa aggccagtag    30600
catgtactct aaatttagtc aaagttccaa tacaagcttt ttgagcgcca ctgtgacttt    30660
gataggtgga aaaataatta aaatttatct ttaatatata atactcccct cattttacca    30720
caatacctat taattgatgt aatggcctga ggttataact tttaaccatc tctgttctat    30780
ttatgtcaag aagtgcaatc aggttttgaa ccaagtagct aatcactcaa tataaagaaa    30840
ccaaattcaa acttttttag gggtttatta tagaaggttc agacatactt atagcagtaa    30900
ttttttttcc tagccaggaa aaggcataca cctgctgtta cactaaaatc aaacaagcca    30960
cataatccaa ttccaataac aatttaacaa catagataga tgagccttat gctgaagcag    31020
caccttcttc cagcaactgt ttcaccttgg tgatgtagtc gttcatggct tcatcggtgg    31080
attttcctgt catagatgca tgcagtgcaa ttagttgtgt ttctcataca accaagagaa    31140
aggaagtcaa tctgaacact gttgttagat cacataccctt caacagcctt ccatgcatcc    31200
cactttgctc tgtctctcat gttgaaaatg ccaggacggc ctgcccataa gaaagggcgt    31260
aagaacaaag tgtagctagt ttgagacagc atgtacatat gcataagaca tttcaagcat    31320
tatactcact tgtgttgaca ctgccaacgg tggcttgctt gtaaagtccg taagaataa    31380 gcttgttctc attggtggta ctctcaggca atgtcttagc tttctcagca tgtgcttcaa    31440
attcctcctg aaacccaaat agttcagtaa aaggtgtgg tagctgaagt tacaaagata    31500
aatttccagg tatactttct tagtgataaa ataaggatga gaatccaact taatagttga    31560
gatcgaaact atttgtgaat taagagggaa ctgaacttat ggaaatctaa aatacaaatt    31620
gagtgttcct tcattgggta aatgaaaagt ttgcagttca ggatatcaaa tatgtacgaa    31680
ttcattgatg gactttagca caagtgtacg cttagcctag cggtgaaaag ggttcattct    31740
atttagccaa cccgagttca attctcgctt tatttattt tataacttga atccgcttcg    31800
tgaaaatcct aggtccgcca ctggttagtg aaagagtatt tgcaagaatg ttagacaaga    31860
aaagcacaac aatacattcc tcaacattgt aagagattct gctggccaac attttgcttt    31920
gacaatgtta agacgcaaat tttagacaca tgtgttaatc atacaattct ccaacctttt    31980
cctcttctag aaatgcttct atttacagat cacagtgaag caccaaaaac atcctcagat    32040
aatgtattat gacctcttca gtttgtttac tggtttgccc tgtttgttac cctacgattc    32100
aaccattacc actcagtagc ctacatactt gtggtaacag gaatccttt agtgcgaggc    32160 gattggccaa ccaacaattt ttgtagtcac ttaaaaatag gtcagactaa attacatcca    32220
```

```
ctataggtta tgaacagcag agaaatttca aagacaggct gaacacaaag tgcacatttc    32280
cttcaacttt tccccttccc caataaaaga aatatggaag ggtgatgata ggttttttgac   32340 caggaaacaa aaactagtct tggactaggc aatacaggat aggaaagaga aagaagcggg   32400
cgctatctca tattcaattt ttgctagact atttacacag aagttggcca atgtagcacc   32460
atataaattt gagaaagagc catttgttca ctactaacat tttgatggcc ctaactgcac   32520
atgaactaat agtaatctga ttctaacatc tcgttcccctg ggtttagtca tcgacttaag  32580
cttcaaagta tacaccatat atatagccaa taatatcaac aatctcaaaa actaaaagaa   32640
gaagacattc ataagatgaa atcttcaaaa cattgttgaa attatggact acttctgggc   32700
cagagacaat atatatgcct tttgataagg ccaaaaatga catacacaaa tccggaccaa   32760
agtactactc atctgccatt acattcgcac tacttcttat cgaattcagt gcttacattg   32820
ctataattac cataaatctt tcaacaaggc caaaaatgta cagcataatt gaattcatta   32880
taagatctat ttataagatg gtatgccgcc actcaaccac agtatgaact gctaaaaaaa   32940
aaataatctt aaacatcaat tacaccaaca gatcagatca atccaatcac cgagccttca   33000
cactaaataa taaccaaaca atcctcacgt aacacagcat ccacaaaatt acagcacaag   33060
ctgcacaatc gacaaagaaa actaacagat ccgcaaatac caattgcaca aacaacacaa   33120
aacccagaat tgaaaacgaa cattaatcac agaaaaatac ttttcactgt caaaaaagat   33180
taacactcgc ttcaaacaag ataaatacat actgaaaggc aaaaaaaaaa cagaaatcta   33240
aaggggtttt aaagaattta ccttcaacgc cattgttgtg gaaatctgat ctggttagct   33300
tgataaaaac gagagaaaac tggagatgtg attgtgatgg agattgaaga agaagggtgg   33360
gtatatatat atagtggagt atttagcata ggaattaacg taaaattcga ttcgattatg   33420
ataatctaaa caagttgcac ttggatcact tactagtcat agtggaccca aaaattgagt   33480
atagattatg gacctatact atgtgagctc cacaac                             33516
```

<210> SEQ ID NO 5
<211> LENGTH: 4900
<212> TYPE: DNA
<213> ORGANISM: Solanum habrochaites
<220> FEATURE:
<223> OTHER INFORMATION: >Genomic fragment 5

<400> SEQUENCE: 5

```
cctacgtcca caaggagat gagcaatcca ctataaatat gagagtacaa aatatagaga      60
gaaacaacct caaccaattc actcggaata catgggaggt tcacacaagt gataacgtat    120
caagcttgtg acccacaaat tctccctcta accaaaactc tcaaaactct ttaagactac    180
attgtgaatg ctgattaagt tagaaggaac atgtctctat ttatagagtc ctaaactttt    240
tcatactaga aaaagatta gtcaattcaa aaccttttcc taaaaggaaa acctatttat     300
ggtaagaaat cagggcaaat aaaacccaac acatcatggt ttgaaccgta ctacataaga    360
aaagttctag tatttaaatt gagaaggata gaggggaggg gcctatcctt aaatctgtta    420
aagttttacg tactagccca actatttgtg cgcgtgaaga aaagatgtga cagctccact    480
atagatttca gcactaccat ttagtttgtt acaacatttt gctgaaattg agttaggatc    540
ttcttgagtc gcagagtaat atcttccatg cgaattctct cttcaggcaa atcatttgta    600
cattcaagag ctaattccat gattgatttg aagcatctat cttttagaagt aaaattttct   660 tcgttcagtg aaaatagatt aatgtccact acatccacca atcggtctgg taatgattgg    720
catatccatc ttttcaaggt gaagtctcca acgaatagat catccacagg gctctttctt   780
```

```
gtaaaagtct ccattaacaa tataccaaag ctataaacat ctcccgaagt tgatactttg    840
ccttcagacc catactctac aaaaaaaata aatcacgcca tcattaatga aaataattaa    900
caacatttaa aatcctcaag tgaacttgat aataacattt acctggtgcc atgtagccga    960
tagtacccaa agtcttggta tgtgctatta gcgtctcaga tgtaagaagt ttggatatcc   1020
caaaatcact cacttttgcc accatatctt catccaaaag tatgttactt ggtttcaaat   1080
cacaatggac gactacaaac aaatgtcctc catgtaaata ctccacagca gaagccacat   1140
caatcatcac ctttagtctt tgagttatat ccaaaacttt gtcagtagag tgaagccaac   1200
attcgaggtt ttcattaggc atgtactcta gcaccaacac tttataatcg aaatttgcac   1260
aactacttat caccttaaca aggtttctgt gtcgaatgct acctaaaact tgacattcca   1320
cctcgaaact tctaaatgca agttgcagtt ctgtattgaa tacctttatc gccacaacca   1380
ttccatctgc tagtgtccct ttatacacca aaccaaggct ccccttcca atcaagtttg    1440 cttcatcaaa gttgtttgtc ccttgagaaa tatcatagta cgaaatcctc ttatgtacct   1500
gaccaaatgt atcaactaga ggaagttccg tactcctttt tcggcatttc agaaaccaaa   1560
tgataaaaat ggttgtgact acaattcctg aggaaactga tgcaagaaca gaagttagga   1620
ctctgttctt tcttttttctt tcaagacttg tcactctgca ttgcatcaca tggaagcgtg   1680
atgatccaca taatgcaggg ttacccatga atgattcagc tgtaaaattt acgaatggcc   1740
ctccatctgg aatttcaccc atgagcccat tgaacgagac attgaaatgc atgagatgtt   1800
caagattcct caaggacttg gggatcatgc ctgatagatt gttgctagat agatccaaat   1860
attccaacga aaccaaatct tcaaatactt caggtatgga accatctaac atattctttg   1920
acaatgaaag gctaaccaag ctttgtagtt ggccaatcgt gctaggaatc tgaccagaga   1980
actgattacc atgtaaatgt aatatccgca aactccttaa attccccatt tctactgcaa   2040
gagacccatt cagcaaattg gaggccaaag tgagaattga aatatctttg ttcctccaaa   2100
aagttgatgg aatatgggaa attagtgcat tggaatctaa gtagagttct cttaaagatg   2160
aaagatttcc aaaacaattt ggtaattcac cagtaagttg attttccccc aagataattt   2220
ggtacaagtt ttccatgtta cacaagctag ttggtataat tccatctaaa ttgttttttct  2280 ctaggctaaa tcttttcaac ttcctcaagt tccccaaatc tggaggaata gatcctataa   2340
gtttattgtc tcccaagctt aaccactcca ggttcctaaa gttactgatg ttaggtggta   2400
tttttcctgt gataccattt tgaagggcaa tgaaatattc aagggaaaag gaccagtttc   2460
ctgaacctaa agatgttgga agacttccat taaattggtt acctcctatt tgaacggttt   2520
tcatatactt gcaattagat aatgaagtca ggaaacttaa ctcgcctgta gattgatcat   2580
tcgtcaattg gttatttgc aagttgatga attgtagctg ttgtagcttt ccaagattca    2640
taggtacagg tccactaaac agattgcggc caaaatcaag ctggataagc atggtggaat   2700
tcacaatgga ggtaggaatc agcccggtga actggttatc cccaaggtaa aggccttcaa   2760
ggtttggaag agtatggcct atgtttgagg gaagtgttcc tgaaagctca tttgctacaa   2820
atgaaatctt ttttagtcca gaaatgttgt acaaacgcct tggaacttca cccgataatc   2880
tgtttggacc aagatacact tctttcaaat ttacaagatg ttcaaactcc tgaggaattc   2940
caccatataa actgttgtca cctaggtcta tcatctctag atttgacaaa tttccaattg   3000
atggtggaag aattcccacc aaattgttcc gtcgtagact taatcttcga attgctgata   3060
ggttatcgat ttcacttggt atatgtcctg taaaatatat gtcgaattgt gtggttacta   3120
```

| | | | | |
|---|---|---|---|---|
| cactgaaatg | tccaatactg | tataacagct | ttatagtcac | taagttacta taaataacag | 3180 |
| aaactgttag | ttgtatgcct | tttaaatagt | tcagcaatcc | tcacaaactg ttttgatgtc | 3240 |
| cttttgaaga | tgggactaaa | tggatcaaca | tggataatta | ggattcatat agcagacaca | 3300 |
| aactagaatt | gagccaatgt | agtagttact | gttgttgttt | gaaatgaag aacaaagagc | 3360 |
| tataccaaca | ttttttgcta | ctaccctttg | aaatgcaaat | actaatttct tataaatgag | 3420 |
| ttgaagagca | agttttaaa | tatcaaagat | ctctagtgct | acaaggtgag aagtccagca | 3480 |
| ataaagttag | gtggattcag | ttaaaccaga | acattataaa | tacctgttat gttattccat | 3540 |
| ccaagaaata | gatgttgaag | ttttgtcaag | ttccacatgt | ctctaggcaa gtttcctgta | 3600 |
| ataggatatt | acgataagtt | atatgtacct | ctcacggcct | atgattgttt aactaaaaaa | 3660 |
| ttgttgcaat | ctttgttgtc | aatatgaacc | aaaagtagca | gagaaagaag ttggttccgt | 3720 |
| tttttttac | ctgtgaagtg | gttatatgac | aaggacaaat | atattagctc tttgcatttg | 3780 |
| tctaaattgc | ttggtagttg | gccagagagt | tgatttcttg | ctatttgtaa tccctccagc | 3840 |
| cgcggaagat | tatggcaaat | gtcattcggc | aaagtcccag | atagtgcatt ataaatcaaa | 3900 |
| ttgatgacct | tcaaagaaga | gacattgaag | atagacgaag | gaacagatcc aaagagatca | 3960 |
| ttttcagaaa | gatccaacaa | ctcgagcctt | ctcagtaatc | caagactttc tggaatttga | 4020 |
| cctgtgagat | tattcattga | caaggacaag | tgcttcagcc | tcctcaaata gccgagttca | 4080 |
| tcagggattt | caccgttgat | gctgttgttg | ccaatgtcca | agaaactaag aaaggagagg | 4140 |
| ttcccaatat | ctgtcgcgat | tgaacctctt | agtctgagac | cattgaggtc tagtgatgtc | 4200 |
| actctttgat | gccttttact | gcaagatatg | cctatccaat | tgcaaacgtg agtccccttt | 4260 |
| gtccagtttt | tcgacaacat | tccatttgga | tctgaagtta | tatgagcttt gaaagctaaa | 4320 |
| agagcagcct | catcagttga | aatgttcgat | gcattagtat | tcgagaggta cgttaacaaa | 4380 |
| actagcaatc | ctataatcat | agccacggaa | accgttttgt | gcaacttctc ttgcagctat | 4440 |
| ttgtgggga | aatttataag | tgcctgattt | ttattttc | aagtgacatt aatatatatt | 4500 |
| tctataatta | aaggcaataa | agaatcatgt | attagcactg | gaatatatag aatctagagt | 4560 |
| tcaatgtcaa | tgatcaacat | atatacgtaa | tatgttttga | gacatttttt tttaaattga | 4620 |
| atgttgctga | acttgactgc | aattcattgc | tgaagggaaa | tcattggttg tgggattctg | 4680 |
| tagtgatagt | aaaataattt | acttggattt | ataagccttg | tatattcatt attcaagaat | 4740 |
| attaaagact | aaaatcatga | tataatgtca | tcattcgaat | gtatatagcc tccgctgaat | 4800 |
| agatgtttga | caaagaacg | tgaagtgtta | cggtcaaatt | agtgaatcta acgtgtaatg | 4860 |
| ttggatttac | gtgaattcaa | tagctttat | tcctatcttt | | 4900 |

<210> SEQ ID NO 6
<211> LENGTH: 2684
<212> TYPE: DNA
<213> ORGANISM: Solanum habrochaites
<220> FEATURE:
<223> OTHER INFORMATION: >Genomic fragment 6

<400> SEQUENCE: 6

| | | | | |
|---|---|---|---|---|
| gttgatgctc | tgttggaaat | ttattactac | aagatagatt | ggttaatttg accgtaaaac | 60 |
| agttgacatt | cttttgtcaa | ggatctattc | tggggaggtt | atagatatac atttgaataa | 120 |
| tgacattgtc | aagtaaatta | tttaactgtc | aatacagaat | tccacaacca atggtttatt | 180 |
| tcccttagc | aatgaattgc | agtcaagttc | agctagcaat | atacgattaa agttgtttc | 240 |
| aaatcattgg | tattaattag | ataagtattg | actcaattac | aagtatacac acagtatata | 300 |

```
tagaatggcg tttgaaaacg aaaacatagg cacaaatagc agctaaagaa gttgaacaaa    360
tccaaatggt tgcgaagact attattatag catgcctagt tttgttagca tgcctctcag    420
ttactaatgc atcaaacatt acaactgatg aggcttctct tttagctttc aaagctcata    480
taacttcaga tcccaatgaa atgttgtcga aaaactggac aaaaggaact cacatttgca    540
attggatagg catatcttgc agtaaaaagc atcaaagagt gacatcatta gtcctcaaag    600
gtttaaataa atgcaccaaa cttgaagttc tgtccttgtc ttataacaaa ttcactggta    660
attaactaac ttgtaaactt ttcatttact aatttcttct tgaattaatc atcattttg     720 tgtgtgtctg tcattttata attgatagga aatttaccaa gagacatgtg aacatgtca     780 aaggttcaag aactgtttat tggatggaat aactttacag gtacgtgatt cttgtatgta    840
ttaaatcttg aatactcttc acgaagttcc taatttcact agatatagtc aatttgtgca    900
ttgtctagta acaaacaaag attaatatat gttgtggaga acattttcga agacactct     960 atgtctgatc tttagcatga taaccatgta cttattttca aaatgaattt gcaggaaata   1020
taccaaatga aatgaaccta ccatctattt gcaggaaagt taacaaagct tgagcatctc   1080
aactatctga aagtctctta caatgagtta tcaggtgaaa taccagatgg agggcctttt   1140
ggtaattttc acagctgaat cattcatcgg caacgaagag ttatgtggac cgcctagatt   1200
ccaagtcaag gtgtgtgaaa tccagaacaa cgtgacaaga agaaacagga agaaaacagt   1260
actaaaattt gttcttggac cagttgcagc tggaggttta gtcataggg ttttaggcat    1320 gatatggttg ttgaattatc ggagacgtaa caaccaactt attcctttaa ctgattggta   1380
tgatcagtta tcacacaaaa ggttttctta ctatgaactt gttcgaggga ctaacaactt   1440
tgacgaatca aatttgattg gaaagggaag ccttggtatg gtttataagg ggacatttac   1500
aaatgggacc atagctgctg taaaggtttt caatgcacaa ctgcaagatg cattcaagag   1560
gtttgatttg gagtgtaagg ttttgcgtaa cactcgaaat aggaatcttg ttaaggtgat   1620
aagtagttgt gcaaatcttg attttaaggc attggtgttt gagtacatgc ctaatggaga   1680
tcttgattat tggctttact cacacaacaa tttcttggat ttaaacaaga ggctgaaaat   1740
tatgtttgat gtggcttgtg tcgtagagta tctacaccaa ggccattcac ttgtagtggt   1800
ccattgcgac ttgaacatac ttttggatga agacatggtt gccagagtaa gtgattttgg   1860
tatatccaaa ctcttgaccg cgtatgatcc agtggcattg acaaagactt taggcaccat   1920
tggctacacg gcagcaggta ctgatcaaac ttttatttac taattacttt cttcaacttg   1980
tattcgatat gcatatatga tgtatttcat tttaatggca gagtagggat agtgtcaact   2040 atggggatg tttacagcta cggcattta ttgatggaaa ccttcacaag aaagaaacca     2100
gtagatgatg agtttgttgg agaccttaca ttgaagagat gggtcgcgga atcatatcct   2160
catagagtca ttgttatgaa ataaaaacga atacacgctg aacgtcactt atgagtcatt   2220
tatctaatat gatccattaa caattgatta atgtaacgca aggaagaaga aaacaatttg   2280
cattgttatg aatgaatgtg tttgtactac aatatataca gtactgacaa gtccagcaaa   2340
ctttctaacc aacttattct aaccaactct actcattatt aatttagctc acttaatcaa   2400
gaaattaaac ttaacaacta actaccatta ctcattcaac tgatcacgga acatcaacac   2460
attttgttga tttctttcac acacaccctc tgcttcgaaa accctctctt ttaacatgta   2520
agcgacaata tctttttttt aggagagtgt tcaacattga gcataaaaat aataaaatag   2580
agaacaaaaa agatgagtat aaaataaata ataatataag atcgattta ccgattgtca    2640
```

| | |
|---|---:|
| attttgtgta tggactaaag aaataacagc ttcacatatc taat | 2684 |

<210> SEQ ID NO 7
<211> LENGTH: 4297
<212> TYPE: DNA
<213> ORGANISM: Solanum habrochaites
<220> FEATURE:
<223> OTHER INFORMATION: >Genomic fragment 7

<400> SEQUENCE: 7

| | |
|---|---:|
| ataaataata atataagatc gattttaccg attgtcaatt ttgtgtatgg actaaagaaa | 60 |
| taacagcttc acatatctaa tattaaatgt aatactgaat ttcacatatg gtcagaggtg | 120 |
| aatccacctg cacccgatat attctttttt aaaaaaatta tatgtatata tatagattgt | 180 |
| tgataagacg gtaatatatt taattgtgca ctcttataac gaacaaatga tttgacttgt | 240 |
| ccattggaaa aacgaaaagt gtcacataaa ttgagacatg gggagtaaca tttctttctt | 300 |
| aaattttcg tgtgaagtca aactaattca tataaaatga gacggaagga gtactgttta | 360 |
| atattaattg catatggtag taaatttgat agacatggtc ccgtgggagt gtgtgttatt | 420 |
| tccattgaat aattgagttt gtaattgtta caagtccatt ctaatttcca acaccttact | 480 |
| tcatttcaaa aatatactct atggctgaag cttccttca attatgtta gagaatctga | 540 |
| cttgtttcat ccaagggaac ttggattgat tcttggtttt aaggatgagt tcaaaaagct | 600 |
| tcaaagcacg tttactacaa tccaagctgt ggtacaagat gctcagttga agcaattgaa | 660 |
| ggacaaggca attgaaaatt ggttgcagaa actcaatggt gctgcatatg aagctgatga | 720 |
| catcttggac gaatgtaaaa ctgaggcacc aattatacag aagaagaata atatgggtg | 780 |
| ttatcatcca aacgttatca cttccgtca caagattggg aaacggatga aaaagattat | 840 |
| ggagaaacta gatgcaattg cagcggaacg aattaagttt catttggatg aaaggactat | 900 |
| agagagacaa gttgctatac gccaaacagg taaatatttt tctaaataac agctttatat | 960 |
| catcaaattc atgtgtgttt tggggatttt gtctaagtag ataagtggtt caaaatctat | 1020 |
| tatctaaatc tgtttggtga agtctttaac atatatataa atccatagct tactcatatg | 1080 |
| ccccaaagtc taaatgacag gataaagcca gagttgtttt agattttata aattaacaaa | 1140 |
| gataataatg taaattcaaa atagtgcatt tgttttatat ttgaaatatg tctgctgctt | 1200 |
| ctgatcaagc tgatcattgt cttttgcaaa attcttcttt gttttttttg ctgactctta | 1260 |
| ccgatcttgg accaggtttt gttttaaatg aaccacaagt ttatggaaga gacaaagata | 1320 |
| aggatgagat agtgaaaatc ctgataaaca atgcccaaac actttcagtc ctcccaatac | 1380 |
| ttggtatggg gggactagga aagacgaccc ttgcccaaat ggtcttcaat gatcagagag | 1440 |
| taattgagca tttccatccc aaaatatgga tttgtgtctc ggaagattta atgaaaagag | 1500 |
| gttgataaag gaaattgtag aatctattga agaaaagtca cttggtgaca tggacttggc | 1560 |
| tccacttcaa aagaagcttc gggacttgtt gaatggaaaa agatacttgc ttgtcttgga | 1620 |
| tgatgtttgg aatgaagatc aagataagtg ggctaagtta agacaagtct tgaaggttgg | 1680 |
| agcaagtggt gcttctgttc taaccactac tcgtcttgaa aaggttggat caattatggc | 1740 |
| aacattgcaa ccatatgaat tgtcaaactt ttctcaagaa gattgttggt tgttgttcat | 1800 |
| gcaacgtgca tttgggcact aagaagaaat aaatcttaat cttgtggcta tcggaaaggt | 1860 |
| gattgtgaga aaatgtggtg gtgtgcctct agcagctaaa actcttggag gtattttgcg | 1920 |
| cttcaagaga gaagaaagac agtgggaaca tgtgagagat agtgagattt ggaaattgcc | 1980 |
| tcaagaagaa agttctattc tgcctgccct gagacttagt taccatcacc ttccacttga | 2040 |

```
tttgagacaa tgcttttcat attgtgcagt attcccaaag gataccaaaa tggaaaagga    2100
aaatctaatc tctctgtgga tggcacatgg ttttctttta tcaaaaggaa acttggagct    2160
agaggatgta ggtaatgaag tatggaatga attatacttg aggtcttttt tccaagagat    2220
tgaagttaaa tatgatcgaa cttatttcaa gatgcatgat ctcattcatg atttggcaac    2280
atctctattt tcagcaagca catcaagcag caatatccga gaaataaatg tagaaggtta    2340
cctacatatg atgtcgattg gtttcgcaaa agtggtgtct tcttactctc ctcctcactt    2400
gcaaaagttt gtctcattga gggttcttaa tctaagttcc atgggactta agcagttacc    2460
gtcctccatt ggagatctag tacatttaag atacttgaac ctctctctca ataacatgcg    2520
tactcttcca aagcagttat gcaagcttca aaatctgcag actcttaatg tagagtattg    2580
ctggtcactt tgttgtttgc caaaagaaac aagtaaactt ggtagtctcc gaaatctctt    2640
acttgatggt tgcgatggat tggattctat gccaccaagg ataggatctt tgacatgcct    2700
taagactcta agtttctttg ttattggcga gagaaaagat tctctacttg gtgaattacg    2760
aaacctgaat ttgtatgggt cagttgaaat cacgcatctt gagagagtga agaatgatag    2820
ggatgcaaaa gaagccaatt tatctgcaaa agaaaatctg cattctttaa gcatgagatg    2880
gaaaaaacca catagatatg aatcagaaga gttgaagtg cttgaatccc tcaaaccaca    2940
ccctaatttg acttctttac taatcactgg cttcagagga ttccgtcttc caagtggat     3000
gaatcactca gttttgaaaa atgttgtctc tattgcaatt agaggttgtg aaaactgctc    3060
atgcttacca ccgtttggtg atctgccttg tcttgaaagt ctagagttag gagatgggtc    3120
tgcggaactg aagtatgttg aagattctgg attccctaca agaagaaggt ttccatctct    3180
gagaaaactt attatagtca attttgataa tctgaaagga ttgttgaaag aggcaggaga    3240
agagcaattc cccgtgcttg aagagatgac aattagctgg tgtcctgtgc ttgttattcc    3300
gacccttttct tctgtcaaga aattggtagt ttatcggaac atgtcagatg caataggttt    3360
gaggtccata tataatctta gggctcttac ttccctcaac attagccata acttgacagc    3420
tacttcgctc ccagaagaga tgttcaaaag ccttgcaaat ctcaaatact tggaaatctc    3480
tttcatcttc aatctcaaag agctgccaaa cagcctggct agtctcaatg ctttgaagca    3540
tctgaaaatt gaatattgtg acgcactcga gagtctcccc gaggaagggg tgaaaggttt    3600
aacttcactc acagaattat ccataacaaa ttgtaagagg ctaaaatgtt taccggaggg    3660
attgcagcac ctaacaaatt tatcagttag ggaatgtcca acactggcca agcggtgtga    3720
gaagggaata ggacaagact ggtacaaaat tgctcacatt cctcatctgc ttattactaa    3780
tgagatgtaa ttttctgatt tttcttttgg aaacaaatca actatttgta accaattcgt    3840
attggacttt tgagccctgc atttgttcga atacgccttt caacctgtat atcagtgtat    3900
aacaaatgta tacaatatgt atactgctgc tcaaatctgc agatttgatt ttccagcaac    3960
acatttgctg attcttccga cctgtaaatt aatttccagc agctcatttt tttgtgttca    4020
acctgtacgc cagttgtgag ggtctaagac ttgaggagga ggtttgagcc tttacggctc    4080
agcgaggaag tgcagggata cgggcgaaat ccgttaggac tcatggcgaa tgcacgtgaa    4140
acggatcaaa aggaaacata aagaaaaaca gtcaacgatg aaaacaattc tgcatttata    4200
cgcataacta aggcaatgta aatcaaattg aagaatgggc agccaagata aatgaaagca    4260
aataaagcca caatgcatgt tttaaaatac tataacc                            4297
```

<210> SEQ ID NO 8

<211> LENGTH: 4357
<212> TYPE: DNA
<213> ORGANISM: Solanum habrochaites
<220> FEATURE:
<223> OTHER INFORMATION: >Genomic fragment 8

<400> SEQUENCE: 8

```
aattaaattt attcatatga gattatattt tatagaaaaa ataataaaaa tttagattaa      60
aattatattt tttcatttcc gttagattaa agggatatct cgagccattt gtttacaagt     120
agggtatata tatgctactt tcatgttagg tatatcagct ctaaataaca aaattgatgg     180
gtatatcaga ccccttttctc aagtttaaat taatgtgaaa agttttaag tgtgggtccc     240
atgttgtaca tttaaaattc tcatacaaca gacaaaaggt tagcttttca caaaataaaa     300
tttttcccat gtgaaactca aaataaaata attgcgtaca gacatattta tgcaacacaa     360
cattaattta tttatttacc cattcaataa gtaaggaat aattataaag ctttgtgctc     420
ttacttttag ctgttcatat ttcattccaa catcgatctt atagatttat tgctaattca     480
caacaattcc agcaatctac atggctgaag ctttccttca aattttgttg aaaaatttga     540
cttctttcat acaagaggaa cttggattgt ttttggttt taagaacgag tttgaaaatc     600
ttaaaagcac gtttactacg atccaagctg tgcttgaaga tgctcaggag aagcaactga     660
aggacaagcc actagaaaat tggttgcaga aactcaatat tgctgcatat gaagttgatg     720
acatcttgga tgaatgtcaa actgaggcag caagactcaa agagactaaa tatgggagtt     780
atcatccaaa ggctatcgct ttccgttaca agattgggaa aaggatgaaa gagataatgg     840
agagactaga tgcaattgct gcagaacgaa gcaagtttca tttggaaaaa aggactacag     900
agagagaagc tgctagacga gaaacaggtg ctcatcttta attagtttat attcattttt     960
ttgcgattat caagttcatg tgtgtttatg gacccaaggg acttttttct aatctaatgt    1020
ttgtctcaag tctaaacaga tttgtaattc taccacttat ttatttagtg aagttcttaa    1080
acatatatac atggtgtaag ccagctcaga taaatccata gtcagttgtt tcggactgaa    1140
cttaacttgg atgtcaattt ttcaaagtca atcatgtttt caactcctcc ccctgattct    1200
catctctttg tagtgcaaaa atcttctctc tgtttttcgc taaacatatt ctcgtgtgaa    1260
catatattgc ttgaaacagg ttttgtttta actgaaccag aaccttatgg aagagacaaa    1320
gaagaagatg agatagtgaa atcctgata aacaatgccc aacaactttc ggtcctccca    1380
atacttggta tgggggggct aggaaaatcg actcttgccc agatggtctt caatgatcag    1440
agagtaactg accatttcca tcccaaaata tggattgtg tctcagaaga ttttgatgag    1500
aagaagttga taaaggcaat tgttgaatct atcgaaggaa acccacttgg tgaccacatg    1560
gatttggctc cacttcaaaa gaagcttcag gacatgttga atggaaagag atactttctc    1620
gttttggatg atgtttggaa tgaaaatcaa gaaaagtggg ataagataaa agcagtctta    1680
gaggttggag cacgaggtgc ttctgttcta accaccactc gtcttaaaag gttggatcaa    1740
ttatgggaac tttgcaacca tatgaattgt caaatctgtc tcaagaagat tgttggttgt    1800
tgttcatgaa acgtgcattt gagaaccaag aaaaaaataa atcctaacct tgtggctatc    1860
ggaaaggaga ttgtcaaaaa aagtggtggt gtgcctctag ccgccaagac tcttggaggt    1920
cttttgcgct tcgtggatca agaaagagaa tgggaacatg tgagagataa tgagatttgg    1980
aatctgcctc aagatgaaag ttctattctg cctgccctga gacttagtta tcatcatctt    2040
ccagttgatt tgacacaaag ttttgcatat tgtgcagtat tcccaaagga cacggtaatg    2100
gaaaaaggaa atctaatctc tctctggatg gcacacggtt ttctttatc gaaaggaaac    2160
```

```
ttggagctag aggatgtagg taatcaagta tggaatgaat tatatttaag gtcttttttc    2220
caagagattg aagttaaaga tggtaaaact tatttcaaga tgcatgatct catccatgat    2280
ttggcaacat ctctattttc ggcaagagca tcaagcaaca atatccgtga aataaatgta    2340
aaacggaacc cacatatgat gtcgattggt tttgcaaaag tggtgtcttc ttactctcct    2400
tctcacttgc aaaagtttgt gtcgttgagg gtgcttaatc taagtgaatt aagacttaag    2460
catttaccgt cttccattgg agatctagta catttaagat acttgaacct ctaccgcaat    2520
aacatgcgta gtcttccaaa gcagttatgc aagcttcaaa atctacagac tcttgatcta    2580
cagtattgcg ccttacttte gtgtttgcca aatcaaacaa gtcaacttag cagtgtcaga    2640
aatcttttac ttcatggttg ctataaattg aattctatgc caccaaggat aggatctttg    2700
acatgcctta acactcttgg ttgctttgct gtgggaagga agaaaagttg tcaacttggt    2760
gaattacgaa acttgaatct ctatggctca attcaaatca cacatcttga gagactgaag    2820
aatgataggg atgtaaaaga agccaattta tctgcaaaag aaaatctgca ttctttaagc    2880
atgacttgga aaggaccaca tagatatgaa ttagaagaag ttgaagtgct tgaagccctc    2940
aaaccacact ccaatgtgac ttgcttaaca atccatggct tcagaggaat ccgtttccca    3000
gagtggatga atcactcagt tttgaaaaat gttgtctcta ttgatatccg gggttgcgaa    3060
aactgctcgt gcttaccacc ctttggtgag ctgccttgtc taaaaagtct taagttacag    3120
gacgggtctg cggaaatgga gcatgttgat tctggattcc ctacaagaag gaggtttcca    3180
tctctgagaa atcttattat agtcaatttt gataatctga aaggattgct gaaagaggca    3240
ggagaagagc aattccccgt gcttgaagag atggatattt ggtggttccc tgtgtttgtt    3300
attccgaccc tttcttctgt caagaaattg ttagttcatt ggaacatgtc agatgcaata    3360
ggtttgagtt ccatatcaaa tctcagggct cttacttcac tccacattag aactaacttc    3420
atagctactt cgctcccaga agagatgttc aaaagccttg caaatctcaa atacttgaaa    3480
atctctttct tctacaatct caaagagctg ccaaacagcc tggctagtct caatgctttg    3540
aagcatctgg agatgaattg ttgtcccaaa ctggagagtc tccccgagga aggggtgaaa    3600
ggtttaactt cactcacaca gttatccatt acatactgtg agatgctaaa atgtttacca    3660
gagggattgc agcaactcac aaatttatca attaagaatt gtccaacact ggccaagagg    3720
tgtgagaagg gaataggaca agactggtac aaaattgctc acattcctca tctgcttatt    3780
actaatgaga tgtaattttc tgattttctt ttggaaacaa atcaactatt tgtaaaatct    3840
atttgtatta tacttgattt ttcttggtta tgtaacaata aatatttgaa aatttttcata    3900
taaaaatagt tacatttcta tatgtataat tcgccagaat aatacatata tatgtataat    3960
atacaattat ttaaccgata tacatatata attcacctct ctcccactct ctgtcctctc    4020
tcactcgcct ctctcctccc tctctcaatt tcgctttcca tatatacaaa tacaattatc    4080
taaaagatat atatatatat atgcaattca tctctctccc actctttgct tcacttgaca    4140
actatgacat ttaacattgg acaagcacaa attgacactt aaaaactggt tacagaaact    4200
caacgctgct gcgtataaag ttgatgactt attgaatgaa tgagaatacg aggcagcaag    4260
actaaagcag tctcgactag gacggtatca tccaaaggct atcaatacaa actcagttgt    4320
ttagaccacg aaaagactgt gaattcaata caggagt                             4357
```

<210> SEQ ID NO 9
<211> LENGTH: 2561
<212> TYPE: DNA

<213> ORGANISM: Solanum habrochaites
<220> FEATURE:
<223> OTHER INFORMATION: >Genomic fragment 9

<400> SEQUENCE: 9

| | | | | | |
|---|---|---|---|---|---|
| aagtctgata | tacttctcaa | cttttttcatt | tggagctgat | atatttctcg | ttataaaagt | 60 |
| gactcatata | tgcccttatc | gttatacaaa | cgactcatat | atctgagtca | tttgtttaca | 120 |
| agtaaggtat | cactttctta | aaaaagcaat | gatatcatct | ctaaaacgac | aaagattgag | 180 |
| gggtatatcg | atccttttc | aagtttaaa | tgaatgagaa | aaagttttaa | gtgtgggtcc | 240 |
| catgttgtac | atttaaaatt | ctcataaact | gacagaaggt | tagcttttca | caaagtaaaa | 300 |
| tttttcccat | gtgaaactca | aaataaaata | attgcgtaca | gacatgttta | tgcaacacaa | 360 |
| cattaattta | tttatttacc | cattcaataa | gtgaaggaat | aattataatg | ctttgtgctc | 420 |
| ttacttttag | ctgttcatat | ttcattccaa | catcgatctt | atagatttat | tgttaattca | 480 |
| caacacttcc | agcaatctac | atggctgatg | ctttccttca | aattttgttg | acttcttca | 540 |
| tacaagagga | acttggattg | aaaatctaaa | aagcacgttt | actacgatcc | aagctgtgct | 600 |
| tgaagatgct | caggagaagc | aactgaagga | caagccaata | gaaaattggt | tgcacaaact | 660 |
| caatgttgct | gcatatgaag | ttgatgacat | cttagatgaa | tgtcaaactg | gaattttaa | 720 |
| ccaaattaag | tcattatata | aataattta | ccaaagtaaa | atattttct | aaagtttac | 780 |
| aaaactaata | taaacgtatt | tcatggtaac | gttttagggt | atattttatt | ttttaaaaac | 840 |
| taatgacttt | aggttgatat | cgttctttgt | aagtaacgtt | ttactcctaa | aacgttattt | 900 |
| tcaataacat | tttactctta | aaacgttact | catagtaacg | ttttactcct | aaaacgttat | 960 |
| tttcaataac | attttactcc | taaaacgtta | ctatgagtaa | cgttttagga | gtaaaacgtt | 1020 |
| actgtgagta | acgtatatca | atctgacgcc | atcaactttt | aaaaaataaa | atatatccta | 1080 |
| aaacgttact | gtggaatacg | tttatactag | ttttgtaaaa | ttttagaaaa | acatattatt | 1140 |
| ttggtgaatg | actttatata | atgacttagt | ttggttaaaa | cctcgtcaaa | ctgaggcagc | 1200 |
| aagactcaat | cagactaaat | atgggagtta | tcatcctaag | gctatcactt | tccgttacaa | 1260 |
| gattgggaaa | aggatgaaag | agataatgaa | gaaactagat | gcaattgctg | cagaacgaag | 1320 |
| caagtttcat | ttggaaaaaa | ggactacaga | gagagaagct | tctagacgag | aaacaggtgc | 1380 |
| tcatcttaaa | tatattagta | ttaattacaa | caatttaatt | agtttatatt | cattttttg | 1440 |
| ctattatcaa | gttcatgtgt | gtttatggac | ccaagggact | ttttctaat | ctaatgtttg | 1500 |
| tctcaagtct | aaacagattt | gtaattctac | cacttattta | tttactgaag | ttcttaaaca | 1560 |
| tatatacatg | gtgtaagcca | gctcagataa | atccatagtc | agttgtttcg | gactgaattt | 1620 |
| aacttggatg | tcaattttc | aaagtcaatc | atgttttcaa | ctcctcccc | tgattctcat | 1680 |
| ctctttgtag | tgcaaaaatc | ttctctctgt | ttttcgctaa | acatattctc | gtgtgaacat | 1740 |
| atattgcttg | aaacaggttt | tgttttaact | gaaccagaac | cttatggaag | agacaaagag | 1800 |
| gaagatgaga | tagtgaaaat | cttgataaac | aatgcccaac | aactttcggt | cctcccaata | 1860 |
| cttggtatgg | gagggctagg | aaattcgacg | cttgcccaga | tggtcttcaa | taatcagaga | 1920 |
| gtaactgacc | atttcaatcc | caaaatatgg | atttgtgtct | cagaagattt | tgatgagaag | 1980 |
| aagttgataa | aggcaattgt | tgaatctatc | gaaggaaagt | cagttggtga | aaacatggat | 2040 |
| ttggctccac | ttcaaaagaa | ggcattgtgt | cgatttgaga | taatacgaga | aaaatataca | 2100 |
| tgcgaaaaac | aagacaacag | atttcgtggt | tcaccaataa | attggctcgt | ccacgggaag | 2160 |
| agggcgggtt | ttattatgga | ggcaaaaacc | aattctgaga | atagggtttg | ccatagcgtc | 2220 |

```
tatatatagt gtaaactaag cccctaacag gcttgggccc aaaatataaa ttgaatgata    2280
attaagggcc caattcaagg cattcaacaa atctccacct tgacttgaat tctccaagca    2340
gattcttggg cgcactatga tagtgccagg cctccccct cttcctcggg ttgcccttga    2400
gtataattac ttgacacgat gttgagcaag tcaaacgagt gttgaaactt gctcacgtgg    2460
agccaagctt tgtgaacata tcagcgggat tatcaacagt tctactttct tcaccttgat    2520
tctcttctca cttctcggga aaatgatacc tccgtcaata t                        2561
```

```
<210> SEQ ID NO 10
<211> LENGTH: 3203
<212> TYPE: DNA
<213> ORGANISM: Solanum habrochaites
<220> FEATURE:
<223> OTHER INFORMATION: >Genomic fragment 10

<400> SEQUENCE: 10
```

```
acgtcatccg cgagacacaa agatgatcgt cagtgcgcct ttcctccgga atctccatct      60
cgggagtaac gacggcgttc ttgtcttcg acaacggcgc ccgtaaaacc ttgttgtttc     120
aacaaagccc gcatcttgat cgccataaac caaactggct attcctccac cgtgaatttg     180
tcgattttca cgttcaaagc gtacatctca attctcaaga cacccgatt aaccgagagg      240 ctcgatacca atttgttgtg cggaatttga gataatacga gaaatataaa acgcgaaaaa     300
caagacaaca gatttacgtg gttcaccaat aaattggcta cgtccacggg aagagggaac     360
attttattat ggaaggcaaa aaccgtaatt acgaatagg tttgccataa gcgtctatat     420
ataactaaac taagcccctta atgcttgggc caaaatatag aattgacaga taattaaggg    480
cccaattcaa ggcattcaat gaagcttcaa gatatgttga atggaaagag atactttctc     540
gttttggatg atgtttggaa tgaaaatcaa gaaaagtggg ataagataaa agcagtctta     600
gaggttggag cacgaggtgc ttctgttcta accaccactc gtcttaaaag ggttggatca     660
attatggaca ctttgcaacc atatgaattg tcaaatctgt ctcaagaaga ttgttggttg     720
ttgtgcattt gagaaccaag aaaaaataaa tcctaacctt atggctatcg gaaaggagat     780
tgtcaaaaaa agtggtggtg tgcctctagc cgccaagact cttggaggtc ttttgcgctt     840
cgtggatcaa gaaagagaat gggaacatgt gagagataat gagatttgga atctgcctca     900
agatgaaagt tctattctgc ctgtcctgag acatagttat catcatcttc cagttaattt     960
aacacaaagt tttgcatatt gtgcagtatt cccaaaggac aaggtaatgg aaaaaggaaa    1020
tttaatatct ctctggatgg cacacggttt tcttttatcg aaaggaaact tggagctgga    1080
ggatgtaggt aatcaagtat ggaatgaatt atacttgagg tcttttttcc aagagattga    1140
agttaaagat ggtaaaactt atttcaagat gcatgatctc atccatgatt tggcaacatc    1200 tctatttcg gcaagagcat caagcagcaa tatccgagaa ataaacgtag aaggttaccc    1260
acatatgatg tcgattggtt tcggaaaagt ggtgtcttct tactctcctt ctcacttgca    1320
aaagtttgtg tcgttgaggg tgcttaatct aagtgaatta agacttaagc gtttaccatc    1380
tttggagatc tagtacattt aagatacctg gatttgtctt acaatagtaa aatgcgcagt    1440
cttccaaagc agttatgcaa gcttcaaaat ctgcagactc ttgatctaaa gtattgctgg    1500
tcactatgtt gtttgccaaa agaaacaagt aaacttggta gtctccgaaa tctttactt    1560 gatgattgcg atggattgaa ttctatgcca gcaagattag gatctttgac atgccttaag    1620
actctaagta gatttgcagt ggggaggaga aaaagttgtc aacttggtga attctgaaac    1680
```

```
ctgaatctgt atgggtcaat tgaaatcacg catcttgaga gagtgaagaa tgatagggat    1740
gcaaaagaag ccaatttatc tgcaaaagaa aatctgcatt ctttaagcat gagttggaat    1800
atcaacgaac cgcgtagata tgaatcagaa gaagttgaag tgcttgaagc cctcaaacca    1860
cactccaatg tgacttgttt aacaatcaaa ggcttcagag gaatccgtct cccagagtgg    1920
atgaatcact cagttttgaa aatgttgtc tctattacaa ttggaggttg tgaaaacttc     1980
tcatgcttac cactgtttgg tggtctgcct tgtctagaaa gtctagagtt atggaatggg    2040
tctgcggaat tggagtatgt tgaagattct ggattcccta caagaagaag gtttccatct    2100
ctgagaaaac ttattatagt gaattttgat aatctgaaag gattgctgaa agaggcagga    2160
gaagagcaat tccccgtgct tgaagagatg aaaattagct gttgtcctgt ttttgttatt    2220
cagacccttt cttctgtgaa gaaattgaat gcttattggc acaagtcaga tgcaacaggt    2280
ttgagttcca tatcaaatct tagggctctt acttccctca acattagcca taactccaca    2340
gctactttgc tcccagaaga gatgttcaaa agccttgcaa ctctcaaata cttgaaaatc    2400
tcttacttcg ataatctcaa agatctgcca aacagcctgg ctagtctcaa tgctttgaag    2460
catctggaga ttaattgttg ttatgtacta gagagtctcc ccgaggaagg ggtgaaaggt    2520
ttaacttcac tcacacagtt atccattgca tactgtgaga tgctaaaatg tttatcagag    2580
ggattgcagc aactcacaaa tttatcaatt acgaattgtc caacactggc caagcgatgt    2640
gagaagggaa taggacaaga ctgatacaaa attgctcaca ttcctcatct gctgattaca    2700
tagtgtcata ctaaattaaa tgattcttat agcaatatta ttggttcaac caacaaaact    2760
aaatctctaa ttatattact taattgcttt tagtttgcta caattatcac tcatgactaa    2820
cattatgtat caattacgtg gtttgtcttc aattttgtat aattagtcat gttttatat    2880 gtataattcg ctagaataat acagatatat gtataatata caattattta actgatatac    2940
atatataatt caccctctctt ccactctctg tcctctctca cttgcctctg tcctctgcca    3000
atcgacgaga tgagcctacg aaagatttca agttcagact atgatgactg acatcctcac    3060
ttacgcaacg aaatggagtt gatggagtag ccagtgccct tgagtcattc tcttcggtat    3120
cgccttctct catcgttaat ggcgccgcaa ggcactcgac tagcaagtta gaccttagtt    3180
agggcgaaag atttcttgga tgg                                           3203
```

<210> SEQ ID NO 11
<211> LENGTH: 4181
<212> TYPE: DNA
<213> ORGANISM: Solanum habrochaites
<220> FEATURE:
<223> OTHER INFORMATION: >Genomic fragment 11

<400> SEQUENCE: 11

```
atacattatt taatactcca acaactttgt gattccactc tagactacca tcacatatct     60
aatattaatt ataatagtga atttcacata tggccagagg cgaacccacc tgcacccaat    120
atatttttaa aaaaaattca tatgtagatt gttgataaga cgctataata tatttaattg    180
tgcactctta taatgaacaa atgatttgac ttgttcattg aaaaaacaaa aagtgtcaca    240
taaattgaga catgaaaaat aatatttctt tttaaattt ttcgtgtgaa gtcaaactaa     300
ttcatatata aagcgaaagc ggaaggagta ctgtttaata ttaattgcat atggtagtaa    360
atttgataga catggtcccg tggggtgtgt gttatttcca ttgaataatt gagtttgtaa    420
ttgttacaag tccattctaa tttccaacac cttacttcat ttcaaaaata tagattcatt    480
gcttactcac cacatactcg atggctgaag cttcccttca aattctgtta gaaaatttaa    540
```

```
catctttcat acaaggggaa cttggattgt ttttggtttt taaggacgaa tttgaaaatc    600
tgaaaagctc gtttactacg atccaagctg tgcttgaaga tgctcaggag aagcaactga    660
aggacaagcc actagaaaat tggttgcaga aactcaatgt tgctgcatat gaagttgatg    720
acatcttgga tgaatatcaa actgaggcag caagactcaa tcagactaaa tatgggagtt    780
atcatccaaa ggctatcgct ttccgctaca agattgggaa aaggatgaaa gagataatga    840
agaaactaga tgcaattgct gcagaacgaa gcaagtttca tttggaaaaa aggactacag    900
agagagaagc tgctagacga caaacaggtg ctcatcttaa atatattagt cttagttaca    960
acaatttaat tagtttatat tcattttttg gcgattatca agttcatctg tgtttatgga   1020
ctgaacttaa cttggatgtc aattttcaa agtcaatcat gttttcaact cccccctgat   1080
tcttatctct ttgtagtgca aaaatcttct ctctgttttt cgctaaacat attctcgtgt   1140
gaacatatgt tgcttgaaac aggttttgtt ttaactgaac cagaacttta tggaagagac   1200
aaagaggaag atgagatagt gaaaatcctg ataaacaatg cccaacaact ttcggtcctc   1260
ccaatacttg gtatggggg gctaggaaaa tcgacgcttg cccagatggt cttcaatgat   1320
cagagagtaa ctgaccattt ccatcccaaa acgtggattt gtgtctcaga aggttttgat   1380
gagaagaagt tgataaaggc aattgttgaa tctatcgaag aaaacccact tggtgacgac   1440
atggatttgg ctccacttca aaagaagctt caggataggt tgaatggaaa gagatacttt   1500
ctcgttttgg atgatgtttg gaatgaaaat caagaaaagt gggataagat aaaagcagtc   1560
ttagaggttg gagcacgagg tgcttctgtt ctaaccacca ctcgtcttaa aagggttgga   1620
tcaattatgg gaactttgca accatatgaa ttgtcaaatc tgtctcaaga agattgttgg   1680
ttgttgttca tgaaacgtgc atttgagaac caagaaaaaa taaatcctaa ccttgtggct   1740
atcggaaagg agattgtcaa aaaagtggt ggtgtgcctc tagccgccaa aactcttgga   1800
ggtcttttgc gcttcgtgga tcaagaagga gaatgggaac atgtgagaga taatgagatt   1860
tggaatctgc ctcaagatga aagttttatt ctgcctgccc tgagacttag ttatcatcat   1920
cttccagttg atttaacaca aagttttgca tattgtgcag tattcccaaa ggatacggta   1980
atggaaaaag gaaatctaat ctgtctctgg atggcacacg ttttctttt atcgaaagga   2040
aacttagagc tggaggatgt aggtaatcaa gtatggaatg aattatactt gaggtctttt   2100
ttccaagaga ttgaagttaa agatggtaaa acttatttca agatgcatga tctcatccat   2160
gatttggcaa catctctatt tttggcaaga gcatcaagca gcaatatccg agaaataaac   2220
gtagaaggtt acccacatat gatgtcgatt ggtttcgcaa aagtggtgtc ttcttactct   2280
ccttctcact tgcaaaagtt tgtgtcgttg agggtgctta atctaagtga attaagactt   2340
aagcgtttac catcttccat tggagatcta gtacatttaa gatacttgaa cctctctcgc   2400
aataacatgc gtagtcttcc aaagcagtta tgcaagcttc aaaatctaca gactcttgat   2460
ctacagtatt gctggtcact tgttgttttg ccaaatcaaa caagtcaagt tagcagtctc   2520
agaaatcttt tacttcatgg ttgccataaa ttgaattcta tgccaccaag gataggatct   2580
ttgacatgcc ttaagactct tggttgctttt gctgtgggaa ggaagaaaag ttgtcaactt   2640
ggtgaattac gaaacctgaa tctgtatggc tcaattcaaa tcacacatct tgagagagtg   2700
aagaatgata gggatgtaaa agaagccaat ttatctgcaa agaaaatct gcattcttta   2760
atcatggaat gggacgacga tgaacgtcca catagatatg aatcagaaga agttgaagtg   2820
cttgaagctc tcaaaccaca ctccaatgtg acttgtttaa aaatctatag attcagagga   2880
```

| atccgtctcc cagagtggat gaatcactca gttttgaaaa atgttgtctc tattagaatt | 2940 |
| ggaggttgtg aaaactgctc atgcttacca ccgtttggtg atttgccttg tctagaaagt | 3000 |
| ctagagttat ggagtgggtc tgcggaagtg gagtatgttg aacattctgg attcccaaca | 3060 |
| agaagaaggt ttccatctct gagaaaactt attatagaca attttgataa tctgaaagga | 3120 |
| ttgctgaaag aggcaggaga agagcaattc cccgtgcttg aagagttgac aattagttgt | 3180 |
| tgtcctgtgt ttgttattcc gacccttttct tctgtcaaga aattggtagt ttatgggaac | 3240 |
| atgtcagatg caacagtttt taggtccata tataatctta gggctcttac ttccctcaac | 3300 |
| attagcctta actccatagc tacttcgctc ccagaagaga tgttcaaaag ccttgcaaat | 3360 |
| ctcaaatact tggcaatctc tttcttcgac aatctcaaag agctgccaaa cagcctggct | 3420 |
| agtctcaatg ctttgaagca tctgaaaatt gaatctgtt atgcactcga gagtctcccc | 3480 |
| gaggaagcgg tgaaaggttt aacttcactc acacagttat ccatagaata ctgtgagatg | 3540 |
| ctaaaatgtt taccggagga attgcagcaa ctcacaaatt tatcaattac gaattgtcca | 3600 |
| acactggcca agcgatgtga aagggaata ggacaagact ggtacaaaat tgctcacatt | 3660 |
| cctcatctgc tgattacata gtgtcatact aaattaaata attcttatag caatattatt | 3720 |
| ggttcaacca acaaaactaa atctctagtt atattattta cttgctcatc atagctatag | 3780 |
| tttgctataa tcatcactcg cgattaacat tatgcatcaa ttacgcgggc tgacttcgat | 3840 |
| tttgtataat tagtcacgtt tttatgtgta taattcgcca gaatatacgg atatatgtat | 3900 |
| aatatataat tatttaaccg atatacatat ataattcacc tctctcccac tctatgtcat | 3960 |
| ctctcactcg cctctctcct ccctctctta attttgcttt tcatatatac aaatacatat | 4020 |
| gtgtaatata caattatcta aacgatatat atatgcaa ttcatctctc tcccgctctt | 4080 |
| ttgcttcacc tgacaactat gacatttaac tttggatatg cacatttaaa aactggttac | 4140 |
| agaaactcaa tgttgctgcg tataaagttg atgacttatt g | 4181 |

<210> SEQ ID NO 12
<211> LENGTH: 1479
<212> TYPE: DNA
<213> ORGANISM: Solanum habrochaites
<220> FEATURE:
<223> OTHER INFORMATION: >Genomic fragment 12

<400> SEQUENCE: 12

| acattacaac tgatgaggca caaatgacta tatctagtga aattaacatg cagatgaata | 60 |
| ggcatatctt gcagtaaaaa gcatcaaaga gtgacatcat tagtcctcaa tagctttgga | 120 |
| tttagaggtt caatcgcgac agatattggg aatctctcct tccttaactt tttggacatt | 180 |
| ggaaacaaca gtttccatgg ccaaatacct gatgaaatag ggcgtttgag gcgtttaaaa | 240 |
| tacatgtatt tgcagatgaa taatctcgct ggtcaaatcc cagaaagcct tggatttctc | 300 |
| acaaggcttc aagttcttca tctttctgaa atcgtctat ttggaaatgt tccagcttcc | 360 |
| atttcagcg tgtcttcttt aaaggacatt gatttgtctc agaattacga gttaactggg | 420 |
| agtttaccaa atgagatatg cactaatctt ccagtgttgg aatatatatc cctgcaagat | 480 |
| aatcaatttg taggtgaact tcctaaaggt ttaaataaat gctccaaact tgaagttctg | 540 |
| tccttgtctt ataacaaatt cactggtaat taactaactt gtaaacttttt catttactaa | 600 |
| tttcttcttg aattaatcat catttttgtg tgtgtctgtg attttataat tgataggaaa | 660 |
| cttaccaaga gacatgtgga acatgtcaaa ggttcaagaa cttttttattg gatggaataa | 720 |
| cttaacaggt acgtgattct gtatgtatta aatcttgaat actcttcacg aagttcctaa | 780 |

```
tttcactaga tatagccaat ttgtgcattg tctagtaata aacaaagatt aatatatttt      840
gtggagaaca ttttcgaaag acactctatg tatgatcttt agcatgataa ccatatactt      900
attttcaaaa tgaatttgca ggaaatatac caaatgaaat gaacctacca tctatttgca      960
ggaaagttaa caaagcttga gcatcttgtt gggttatggg tcttttccc ttcctatttg      1020 gataactaaa agcccaattt ggaccaatcc attttgcct ataagcccat tcttatgagg      1080
caaatataaa ctgattttag gtctgatttt tcagaacata tagagagttc ttcagcagcc     1140
aaaaagagag aaagagagat tttcgcaggc aaaattcaga tctaatagac aacttcaaat     1200
tgcgattccc gcttcttttc ttatccgatt gagttgattt ttggacagca tattgtcttc     1260
atctcaatct ttgattagaa actgacagag ttggatttgg tggcctgcga ctttcagttt     1320
tgcttttgtc gtgagcgaag ctgcaaaatt ggtgattttg ctcctttaat tttctagatt     1380
tggtgcaatc ttattttgtt gttgctcgtt gtttggcact tgttttgtgg ccaatttttgg    1440 agaacaatat tgtaactctt ggtgattata gtggagctt                            1479
```

<210> SEQ ID NO 13
<211> LENGTH: 2084
<212> TYPE: DNA
<213> ORGANISM: Solanum habrochaites
<220> FEATURE:
<223> OTHER INFORMATION: >Genomic fragment 13

<400> SEQUENCE: 13

```
agcatattgt attcatctca atatttgatt aggaactgac agagttggat ttggtggcct       60
gcagcttcag ttttattgtg aggaattagc tgcaaaattg gtgattttgc tcctttaatt      120
ttctagattt ggtgcaatct tattttgttt tgttgctcat tgtttggcac ttgttttggc      180 caatttttgga gaacaatatt gtaactcttg gtgattatag tggagctttt ggtcccgtgg     240
ttttactctt cacatcgaag ggttttccac gtaaatcgtg gtgtcttgtg tgattggttt      300
catattgtct cgttatattt gtttggttga attacctgct gccttagtat catattgctt      360
gtggttgttt gtcttctctt ggttcaaatc gaaaaaggga agtatagac ttgggtattc       420 ttccgctgtt atcctgtcag gcattcttgg tagtgccttg tctttcccaa cacatctcaa      480
ctatctgaat gtctcttaca atgagttatc aggtgaaata ccagatggag ggccttttgg     540
taattttcac agctgaatca ttcatcggca atgaagagtt atgtggaccg cctagattcc     600
aagtcaagat ttgtgaaatc cgaacaacgt gacaagaaga aacaggaaaa aacaagacta     660
aaatttgttc ttggaccagt gcagctggag gtttagtcat gggtttttag gcatgatatg    720
gttgttgaat tatcggagac gtaacaacca acttattcct ttaactgatt agtatgatcg    780
gttatcacac aaaaagttttt cttactatga acttgtttga gggactaaca actttgactt   840
taatcaaatt tgattggaaa gggaagcctt ggtatggttt ataagggac atttacaaat     900 gggactatag ccaactgtaa aggttttcaa tgctggcgca agatgcattc aagagggtttg    960 atttggagtg taaggttttg cgtaacaccg aaataggaat cttgttgggt gataagtagt    1020
tgttcaaatc ttgatttttaa ggcattggtg tttgagtaca tgcctaatgg agatcttaat   1080
tattggcttt actcacacaa caattccttg gatttaaaca aaatttgaaa attatgtttg    1140
atgtggcttt gtgtcagaga gtatctacac caaggccatt caaaacatag tggtccatca    1200
tgacttgaac atacttttgg atgaagacat ggttgccgag taagtgattt tggtatattc    1260
aaactcttga ccgccagatg atccaaaggg cattgacaaa gactttaggc accattatcc    1320
```

-continued

| | |
|---|---|
| tggcactgtg cccgatcaaa tttttattta ctaattactt tcttcaactt gtattcgata | 1380 |
| tgcatatatg atgtatttca ttttaatggt agagtacggg tcagaaggga tagtgtcaac | 1440 |
| tatgggggat gtttacagct acggcatttt atttatggaa accttcataa gaaagaaatg | 1500 |
| atagatgatg agtttgttgg agaccttaca ttgaagagat gggtcatgga atcatatcct | 1560 |
| catagagtca ttgttatgaa ataaaaacga atacaagttg aacgtcaatt atgagtcatt | 1620 |
| tatctaatat gatccattaa caattgatta atgtaacgca ggaagaagaa acaatttgc | 1680 |
| attgttatga atgaatgtgt tgtactaca atatatacaa agatcgacaa gtctagcaaa | 1740 |
| ctttctaacc aacttattct aaccaactct actcattatt catttagctc acttaatcaa | 1800 |
| gaaattagac ctaacaacta actaccatta actcattcaa ctgattgttg ggttataggt | 1860 |
| cttttttccct tcctatgtgg ataaataaaa gcccaatttg gaccaaccca ttttttgccca | 1920 |
| taggcccatt cttatgaggc aaatataagc ctatttaggg tcttatttc agacaaaaca | 1980 |
| gatcagtttt tcagcagcca aaagagaga aagagagatt ttcgcaggca aaaatttaga | 2040 |
| tctaatagct aacttcaaat tgcgattttc acttcgtttc ttat | 2084 |

<210> SEQ ID NO 14
<211> LENGTH: 4300
<212> TYPE: DNA
<213> ORGANISM: Solanum habrochaites
<220> FEATURE:
<223> OTHER INFORMATION: >Genomic fragment 14

<400> SEQUENCE: 14

| | |
|---|---|
| tattccaaaa aatacaaatt cattatttaa tactccaaca acttttttgat tccactctag | 60 |
| actaccatca catatctaat attaaatgta atactgaatt tcacatatgg tcagaggcga | 120 |
| atccatcagc acctgatata ttctttttt aaaaaaatta tatctatata tacagattgt | 180 |
| tgataagacg gtaatatatt taattgtgca ctcttataac gaacaaatga tttgacttgt | 240 |
| ccattggaaa aacaaaaagt gtcacataaa ttgagacatg gcgaataata tttctttcct | 300 |
| aaattttttcg tgtgaagtca aattaattca tataaaatta gacgaaagga gtaatgttta | 360 |
| atagtaattg catatggtag taaatttgat agacgtggtc ccgtgggagt gtgtgttatt | 420 |
| tccattgaat aattgagttt gtaattgtta caagtccatt ctaatttcca acaccttact | 480 |
| tcatttcaaa aatatactct atggctgaag ctttccttca aattatgtta gagaatctga | 540 |
| cttgtttcat ccaaggggaa cttggattga ttcttggttt taaggatgag ttcgaaaagc | 600 |
| ttcaaagcac gtttactaca atccaagctg tggtacaaga tgctcagttg aagcaattga | 660 |
| aggacaaggc aattgaaaat tggttgcaga aactcaatgg tgctgcatat gaagctgatg | 720 |
| acatcttgga cgaatgtaaa actgaggcac caattataca gaagaagaat aaatatgggt | 780 |
| gttatcatcc aaacgttatc actttccgtc gcaagattgg gaaaaggatg aaaaagatta | 840 |
| tggagaaact agatgcaatt gcagcggaac gaattaagtt tcatttggat gaaaggacta | 900 |
| tagagagaca agttgctaca cgccaaacag gtaaatattt ttctaaataa cagctttata | 960 |
| tcatcaaatt catgtgtgtt tgggggattt tgtctaagta gataagtggt tcaaaatcta | 1020 |
| ttatctaaat ctgtttggtg aagtctttaa catatatata aatccatagc ttactcatat | 1080 |
| gccccaaagt ctaaatgaca ggataaagcc agagttgttt tagatcttat aaattaacaa | 1140 |
| tgataataat gtgaattcaa aatagtgcat ttgttttata tttgaaatat gtctgctgct | 1200 |
| tctgatcaag ctgatcattg tcttttgcaa aattcttctt tgttttttt gctgactctt | 1260 |
| accgatcttg gaccaggttt tgttttaaat gaaccacaag tttatggaag agacaaagat | 1320 |

```
aaggatgaga tagtgaaaat cctgataaac aatgcccaaa cactttcagt cctcccaata    1380
cttggtatgg ggggactagg aaagacgacc cttgcccaaa tggtcttcaa tgatcagaga    1440
gtaattgaac atttccatcc caaaatatgg atttgtgtct cggaagattt taatgaaaag    1500
aggttgataa agaaaattgt agaatctatt gaagaaaagt cacttggtga catggacttg    1560
gctccacttc aaaagaagct tcaggacttg ctgaatggaa aaaaatattt gcttgtctta    1620
gatgatgttt ggaatgaaga tcaagataag tgggctaagt taagacaagt cttgaaggct    1680
ggagcaagtg gtgcttatgt tctaaccact acccgtcttg aaaaggttgg atcaatcatg    1740
gggacattgc aaccatatga attgtcaaat ttgtctcaag aagattgttg gttgttgttc    1800
atgcaatgtg catttgggca ccaagaagaa atgaatctta atctagtggc tatcggaaag    1860
gtgattgtga aaaatgtgg tggtgtgcct ctagcagcta aaactcttgg aggtattttg    1920
cgcttcaaga gagaagaaag acagtgggaa catgtgagag atagtgagat ttggaattta    1980
cctcaagata aagttctat tctgcctgcc ctgagactta gttaccatca ccttccactt    2040
gatttgagac aatgcttttc atattgtgca gtattcccaa aggataccaa aatggaaaag    2100
gaaaatctaa tctctctctg gatggcacat ggttttcttt tatcaaaagg aaacttggag    2160
ctagaggatg taggtaatga agtatggaat gaattatact tgaggtcttt tttccaagag    2220
attgaagttc aatatgatcg aacttatttc aagatgcatg atctcattca tgatttggca    2280
acatctctat tttcagcaag cacatcaagc agcaatatcc gagaaataaa tgtagaaggt    2340
tacctacata tgatgtcgat tggtttata aaagtggtgt cttcttactc tcctcctcac    2400
ttgcaaaagt ttgtctcatt gagggttctt aatctaagtt ccatgggact taagcagtta    2460
ccgtcctcca ttggagatct agtacattta agatacttga acctctctct caataacatg    2520
cgtactcttc caaagcagtt atgcaagctt caaaatctgc agactcttaa tgtagagtat    2580
tgctggtcac tttgttgttt tccaaaagaa acaagtaaac ttggtagtct ccgaaatctc    2640
ttacttgatg gttgcgatgg attggattct atgccaccaa ggataggatc tttgacatgc    2700
cttaagactc taagtttatt tgttattatt agagaaaaga ttctctactt ggtgaattac    2760
ttaaacctga atctgtatgg gtcaattgaa atcacgatct tgagagagtg aagaatgata    2820
gggatgcaaa agaagccaat ttatctgcaa aaaagaaaat ctgcattctt taagcatgag    2880
atgggaagga ccacatagat atgaatcaga agaagttgaa gtgcttgaat ccctcaaacc    2940
acactccaat gtgacttgtt taacaatcac tggcttcaga ggaatccgtc tcccagagtg    3000
gatgaatcac tcagttttga aaaatgttgt ctctattgca attagaggtt gtgaaaactg    3060
ctcatgctta ccaccgtttg gtgatctgcc ttgtctagaa agtctagagt tacggagtgg    3120
gtctgcggaa gtggagtatg ttgaagattc tggattccca acaagaagaa ggtttccatc    3180
tatgagaaaa cttactatag aaaattttga taatctgaaa ggattgctga agaggcagg    3240 agaagagcaa ttccccgtgc ttgaagagtt gacaattaga tgttgtcctg tgtttgttat    3300
tccgaccctt tcttctgtca agaaattggt agttcatggg aacaagtcag atgcaatagt    3360
tttgaggtcc atatataatc ttagggctct tacttccctc aacattagcc ataacttcac    3420
agctacttcg ctcccagaag agatgttcaa aagccttgca atctcaaat acttggaaat    3480 cgctttcatc tccaatctca aagagctgcc aaacagcctg gctagtctca atgctttgaa    3540
gcatctgttt attaattgtt gttttgcact agagagtctc cccgaggaag cggtgaaagg    3600
tttaacttca ctcacacagt tatccataac atactgtaag aggctaaaat gtttaccaga    3660
```

```
gggattgcag caactaacaa atttatcagt taggtattgt ccaacactgg ccaagcgatg    3720
tgagaaggga ataggacaag actggtacaa aattgctcac attcctcatc tgctgattac    3780
tgattagatg taattttctg attttctttt tggaaacaaa tcaactattt ataacatcta    3840
tttgtattat acttgatttt tcttgattat gtaacaataa atatttgaaa tttttcatat    3900
taaagattca gaatgagttt tacagctaac tctatattct cacagtttaa taacgtaaat    3960
atgatattta tatcaaatta ttacttatgt tgtgatttga tttatcaaca tgttggagat    4020
gattttgaca gtttattaaa gaatttctaa gttttttattg tttgcacaag taacaagcca    4080
taaattaagt ttcgagataa aagtaatttg tgtatcatgg cttaattagt cggaatttca    4140
agttttttct caagttatat atatggcaat ttgtaaaaaa tagatagtat tcattttgat    4200
ttaattcaag tattttttaaa aatatataca aataatatgg gggatacaca cgctaaacgc    4260
gtacccaaaa attagtatat aaagaataat gacgaaaaaa                         4300

<210> SEQ ID NO 15
<211> LENGTH: 9902
<212> TYPE: DNA
<213> ORGANISM: Solanum habrochaites
<220> FEATURE:
<223> OTHER INFORMATION: >Genomic fragment 15

<400> SEQUENCE: 15
aagaaactat tgaggatgtg ggaccttggg atggttagtc aaaatgagct tctattatat      60
ccttctgtgt ccttctatta aagctctcct cttcttgttt attttgtgga gtcccaattt     120
tggcgtggcc aattccatga tgccaaattg gtaacaaata cttgaaagag tgatgactca     180
agagagatgg tgaagaaagt agacatagtt caacgaattg aagtcatatt cgagaacaat     240
attatccaga tagttcaatg aagtcattta ttcaaaattc ataagcaaat attaatgtgg     300 aaagttcta ttcatttcca aattgaacaa aagaagcaaa caatagataa ggtctccaac     360
atggagataa taattgagag taaaaacttc tattgctatt aaatagaatc tgcaattaaa     420
aaaaaaatta catagataca atatggaact tcaatatgta caacttggaa acccctttcaa     480 tgcttgaggt ctcagttttt accacattca gatacaaaaa tgtagtaaca atggcaattg     540
tgcgcgattc taaaatggca aaaaaataat gccaacttaa ctatggaaat tatgtacaga     600
tataactaac tataaaactt aaatcgtaca gtggcatatc aacagagcct tcttaggctc     660
tgctgctatc atcaaaaaaa gcttttgact gattctggca gttcatggag tagtataagc     720
ttcggacgat ttgaactgat tcacacagca tgtaactgat ttaaaaattc agttttactc     780
tatcagagtc accaactcct ttcttcccag aagaactagc agccgcttgt tccttcaaag     840
cttccttctc cagtttcttc ttttcagcat cagctgcttg ttcattctca tcacgtgatt     900
ttttaaacat cttcatgaac accaccaaaa tttgtgtcac tgcatccaga aagtaaggaa     960
atgaaaactg acaaagttcg tcacaaacat tgtccggtta aagagttggt gaggaaaaat    1020
ctgttgaagc aattctcaca ccagttaaaa caagatctca aggacaaacg caattcgaga    1080
aatctagccg atggctatat gcactcaaca aaagctacaa aggccataaa tgttgcatcc    1140
cataatcttc acataaagat agacaactaa aaagcatcac tgataaacgc tactggaata    1200
tctatattac caagactgtt tgaacgactg tagttttttc ttttccagat gactgataag    1260
tgataataca gcaagaaaat aacgtatgta tctctaacct tgctcaaagg ggcatcgagc    1320
tggatcttcg ccaaaataca gggataggga gtctgcactc cttccctgca gatttacagg    1380
atagaaaaac aatcaataaa cttggcatgg cttatacatc caggaggctt taaaatatga    1440
```

```
cataatggat gcaagaaact caccacttca atataaagag tagtgagaga cttgacttca   1500
gcctcagcag tatcaaggaa attctttaac acctgagaag gaatgcacga gtcacaaacc   1560
gcatatttca gatgtttata acaaaattat atgtacacca atcacagac atcgcaatca    1620 agtttgactg catcaccaga ctccactcta aaaccatgtc caacacaaac caaattggga   1680
gttttcccag cgcaagcctt tttcacttga ccttgttaag aacacaaatg tcatccatcc   1740
attggggaca cctatcactc ttctaaaaca gtggtacact gcttccttac tttgttttct   1800
caaactatct agaataaagc tttttgatag taaataggga tccttgtaat gtaataatgaa  1860 ggaaacctgg ggaagagga atccgcacaa cgccgttcat ttcatatctg gcgtaagaaa    1920
atctcgagaa tttgataata catttagggg tcgtttggta gagcgtatta agaaaaatca   1980
tggatgcatt agccttgttt attgctagta ccatgtttgg tactcttttc taaactatgt   2040
acaactagtg ttgcattagt tatacactat cgtttattaa agtagattat gatatgacct   2100
tcaaagttaa aatttaaaac taaaagaaa cattatcttg gaagtacaag taactcattt    2160
ggtttgtagg aataattcac atgttaccat tctctttttct caccttctga atcctgaag   2220 atattgtacc atcattgtcg gatgcagtaa gttcttgttc aactttctca agaccttttac  2280 tcactgcttg catttcttca gccaaagact tcagttgaat ctaaccatat aatatgatgt   2340
aaacaaacat ttcagttcac caaaatacca gtagtactgc aaaggaagac cataataaat   2400
agcaagggta ccttagaagc agcttccaag tgaagaagat ccttgtcaaa atcaagcaac   2460
tctggcattt tctcagcaag gagctgacaa aaaacgaat ttacacattt ggcatcacat    2520
tgagaagtgc aaacatatat atgccgaaga gtaaagacta aggctggtca agccagctat   2580
agttgatagc taaaggctat caactaaagt tcactgatgg ttgggcaaaa gaacagcata   2640
aacgtagaat actgaaagta gaaaataaat acaaaaacat atagtttctc acagaactca   2700
accttctata ttacaggaac ctcatgggtg caccaaaag caataaggga caagaggcta   2760
ttccttaact gtgcaaatta ctctacactt tcaaaagctc tcctaattct cactctccac    2820
aaaacccaca taagtgcaaa agcataccct tcacgccttg tgtctcctcc ttcatcttcc   2880
gccatttcag ttgagcaaca ttacttatac agtgacgggc atcacccaaa tttaccaaac   2940
gaacaccaca tttcccacca taaccgagaa gttatcgcac aatctagaag acgattcgcg   3000
tcttcacctg acccccttac acataaaaca ccgcccaaca taagtagttc tcctcttcat   3060
tcttttatca tccatcaaga tcacccctct tgttcctaac caagtgaaaa aacctacctt   3120
tctcagtacc ttagggatcc atatcaaaat atatggaagg ctatctttct tctcattgat   3180
caaaaatttg tccaaagaaa aggactttag caaatttatt cttaggcggc caaaatgaaa   3240
cttagattac aatgaaacct taacaaagac aagaattcaa tgaaacctaa acaaagacaa   3300
ggaccagaca atagagtcta gctaaaaga atctgggctt gcttttttcaa ttcaaatctg   3360 tgagcgagga ttcctctttc tcttctccac aaaaatttga agtggtttat aacttacgga   3420
gtatccgata atctcttgca atcttgtata agcctgtgca gatgaaataa cttgaacatt   3480
tccaggagtc aatcgatttg caccagtcga ccagtgggag cgataatttt aagatataaa   3540
catcatataa ccttcctttt agcctattcc cacttgagcg tacttcacag ctgatacgct   3600
cataatactt gacgccccga ataatgaac agggatagat atggagatac aatttaagaa   3660
aatgaacctt aggcacttca atataagaga agagagaagt agaacaaaat aaagaacaat   3720
gcaactggaa aaatgttgaa aataaagtga acgatataag atggattagt tttcagattt   3780
```

```
tcatctttaa gagctgctga ctctcaaaaa tctgctacac cgccttgccg ccgccttctt    3840
gtttgagtgc tcaacagaag cacctatacg cacttggact ttccttaggg tgatttaata    3900
gatttttgt gtattttatt tccaattgtt tcatttggca agatactcta agcttgaaat    3960
ttttaatttc tatttagata gtcttgtatg cctaatttca tgtttgatct tctatttcat    4020
tttagagtat tggagttgat actggatcta gctatcaccg acctactgtc gtactagcgt    4080
caagtgcagc acttagccaa taatccccaa taatagggc tacacttaga caaagtatga    4140
atcaagaagt tgtaagtgtt agatgcatgt gtggcattta gctatgttta acctcttttg    4200
ctggagtaat ctctcctttg taaatgatat ggatcaatca acccaccaat agttctagta    4260
attcctgaac tactaagtgt actaccaagc attctaaagc ctcatgcatc ttccttgatt    4320
gtgtagaaca tgccatactt atgtggtgag ccttgcttgt gcactatggc tcccacttgt    4380
gcatcaccat gcctcgtgca tgctacatca tcagaccatg ctcttgtgct aacactatca    4440
ccataccagc ccagccatgc ctccatgaaa cagttcctaa ttttctttgc gttactacta    4500
agacaacgaa tcgtttgatc ttgaaaattcc ttgcctcctc tctgttagcc tggtccatgg    4560
ctttgttgca cttgcgcatc atgccacact tatgtttgtg aaccgtgctt gtacactatg    4620
gcttccacta gtgcttcttc accatgcctc atgcatgctt catcttagta gcatcctctt    4680
gtgccaaaac aaccacgcct accagccatg cctaacatgg aactgttccc caatttcttt    4740
aactttctaa ttaaaactta aacaaagaat catttggttt ttgagtgttg aaaccttgaa    4800
agcgctcgcc tcctctaaag tagccccctt catggtttta gatgggttat gacatagacc    4860
tcaaatacac ttggcacttt ttcaatccaa tcatgagcta ctcaacaatt attactgagc    4920
caaaactaat ctgattcaac ttacgcttaa gtcacctcca actcttccca attcagagct    4980
aattgatcaa tactaattac ataaaggtaa aaacagaaag gcatcataat gcagtaattc    5040
taccttgcac agataatgca tcaaggtcat tttgttgttt ctcgcacgag tgtcagaaag    5100
cttaagaaga ctgtccaact tgaaccctac agcagatcct gtaacgtaat tacaaaacaa    5160
agatgttagt cacgatgcct ccacccaaca actgattatt ttcttataga gatatagatc    5220
ttagaaaact gtacctcgtg ctgtaccctg attcagtgca ttaccccaatg ttagaatggt    5280
ctgcattatc tgacgtaatt tggcagattc tttcacctac ttgaccagga aattcagtta    5340
gagcctagtt aaatcagaat gtgccaaatc aaacttcata aggtattaaa aatacctctc    5400
tagtagcatc attgattgta ctcaggttac ttctcaagtc cttcacctga acaattcaac    5460
atattatagt caacagaaaa ttaatggcag aatccataga cattagatca ctaagaagta    5520
caagagaaaa tacctgatta gagaaagtga tagtaaatga aaacactcgt aacttggact    5580
caactcgtgg gaccttcatc agctccagga aaaactgaaa cgggtattac ttatccggtt    5640
aattacttat aacttaaagg ataggaaaac ttgtacttcc ccacatatat ggtcaaaatg    5700
gagaagacct gctcacactt tccaagcatc cccttgtccc cattatagtt ctggaaaata    5760
gaacataacc agtaagatca aattgtgaaa tcaagaataa caattaaata tcaaattgca    5820
agtatagact gtcaagaaac taacataact aagttcacaa agagagggg aaatcaagca    5880
gaaacaagta tggatctaca tacacaaaag actaagatat atgcctatgt ttatacacat    5940
ccacacccac cgggaaagga agttcccagg aaaaggtatc tgcatgatta gacattgaaa    6000
cagacacatg agcatgcacg cacagcatag atgcaagtac atactgtata agcatgaaac    6060
cgccaaatgg gtcattgact tatgggcatc aacctcacaca gctacttgca acaaatggca    6120
catcaacaaa actataggct cctgctgttc ctacgactca cttaactatt cttacgttaa    6180
```

```
gtacaattgc agaatgtgaa ggttccgact cttgtttcca aatactatgg gcaaaaaact    6240
tcaatatgga gtattttctc taaacgggaa aagttaaaag aagaatcaaa gcaaacttca    6300
gaacatacct ctaatattac ttgtgaactc aaaataaatg actagacaca cattataagc    6360
atattattgt aacttaaact ttgccatgat aggcaagcac agtaggatga gaaagagatt    6420
ataccctcag tgtctccatt tcttcttttg ttgggcaaaa ttttatcaga ttttcaacct    6480
gatcaatgtc cagagctgat gaatccaaag ccaaaatagc attctgtatg acatgcatac    6540
aaatataatt tgtaagaaat ccgcggtaaa ttttcctttg taaacagaaa ttttatttgc    6600
atttgcataa tactggccgc gagttcaaat agcggacccc aacttgtctg gaactgaggc    6660
gcaactgttg ttataatatt agtaaaaaga aatccatggc aaatatttca ttcatttcaa    6720
tgtacctcca ttaaaactca aaataaggaa aaaagaactt ccaaagaaac catgcatgag    6780
catcctaaag aaatgctcgt cagtcattac acttattgaa cacatgcatg aatcagcata    6840
ttgatactgt gcattatgaa acatgatttt gaccaaaggc caaaggatag aatattttat    6900
acaatttcta tcatgattcc tttgaatttc aaaggaaaaa tatccataag agttcaattt    6960
tgaactcttc aagttcggtg aaattacatg atcttttcaa cacaataaaa ttatcaaaaa    7020
tataaaaaat aagaaagtct tttggataaa tagttctaca gctacttcca tagaaagctc    7080
cttttctcct tgtacaaaat aaaggtttct ttatccattt cattgaactc cggctaaaaa    7140
atatttctaa taacgatagt gtctgatcct acttgtgctc gtatcttgac taatttatag    7200
ggtacttgac acctcctatc aacataggta tggggaacta tgccctccaa aatgcaatca    7260
gatgaggaaa accaccaagt cttagttttg gtcgctacta gaaaaaccac ttggccacac    7320
tctaaagtgc tcattgaact ccaccaatat gagaaaagca taactaactt gaaactgaat    7380
tacaaggaga actgttatag gttaatggct aacataaaaa tagtcaaact accaaactcc    7440
tctgtgtatg acctaaatgt tatgtgtagt taaccgattt atacgttctt cattcctttg    7500
ttgagaaaaa atatagatag ttaatcaata tattgtactt ctattaagca gaaacgaaga    7560
tacttcaatt tagagttcag tacataatat aatcttttg atctagtaaa aagattatag    7620
catgaagagt tcaatacata caagatacaa caatctttc ctttttttg ttgttgagaa    7680 tggactttta gtcaaaccca ttaagctgat tcaataattt tgcagatcta tttgattcat    7740
cagatacata cttctatagt tttagcaaat gtacaaaggg attaaaaaaa actaaaatac    7800
taaattgtaa tcttttggaa aataaagtca aacaacatat gcattcaatt gcatatgtaa    7860
tttgttactt gatttcaatt gataaacaca tcaggattcg ttaattttaa tggctgttta    7920
gtttgtgtta ctttttaaat tattagcagc tcaatttcca aatatctgat tgtcctaaag    7980
cccaagtaaa gatcacataa tctaatagtt tcatctgata aacaataata gattattatc    8040
aaaagaccca cctgttggct agaagacata aattagtgcg caatagataa aagtatcgaa    8100
gctcatagta gaaacgagaa gacacaaaaa gaactcacaa gcatatcagg caggggaatc    8160 ttgattttg taagcatgat ttcacaattg tatgccctgc gcaaatcaat ctggcaaaag    8220
catatgttaa gaaatcatcc cggtctttta acagttagac caaaatgtaa cacttccagt    8280
ctttcactat aaataatggg agttgtgtaa aataaacctc aatacctcag gaagaaaaag    8340
aagccaacac caatagactg ttcaccaact attccatagt gatctcatat tatacagtga    8400
aagctttgaa aactatcagt ttctttctat agaagtttc tatctctttc ccaatttagc    8460
actaacagat aaattaagaa gcaagtgaac tgcaattcat tcatggtcaa tggccatccc    8520
```

| | |
|---|---|
| catgggacac agtgcccatt atgagcacag cctccgcaac tctttcatta gatctagaca | 8580 |
| tgtatcgcag cctaataaaa ttactctgtt gcatgaattt acatctcaaa gtattaacac | 8640 |
| aacttttaag aattttttcaa aggcaaccat tattttttta tatgattgac tccatccact | 8700 |
| aaaccctctg cctaagacgc ccaagagagg tttccccctt tatcccttcg ttaatcaaac | 8760 |
| ccccaacctt atggttggag atgaaggacc ttaccctagg atatcactcc agtcaaagat | 8820 |
| aattgtctta actttcatga aacagaaatg gtattaccta caggatggag aaaggaggac | 8880 |
| ttttccaccc aaagtttatg taatcatcca catccaggct gaaaaaacat aagttcttct | 8940 |
| ctataagggc atgcttgttt cgaaacgtca cctatgttaa acccatttaa gcctttctat | 9000 |
| ttacttcttt tcttccacct tgttagccac aagataccac aaaaagtgct ctttaaaacc | 9060 |
| tatctaatat ttaattgttt tgttaaacta gtaaagaaag gagatacact catcctacaa | 9120 |
| cactcacttt actacatgaa agacttgcta gataatgcct actggagaat aacagttgta | 9180 |
| gagactggaa acaagataaa gcatatataa cttgccaatt gcacttttc tggtttgttg | 9240 |
| attttttgaac cacgtcggcc tccacctttg ctagtgccat cagtagctga agccaccgaa | 9300 |
| aacaaattct caagctccgt aatatcaatt tcaggtgctc tgtcatgtac attaataaaa | 9360 |
| tcttatcaga actacccata acagacagat aacaaataaa agttgcagta cccaacacaa | 9420 |
| actaggttaa gctcaaaggg ctcagaacta ctatatctgt aatctattaa gcattcgaag | 9480 |
| ttgaaaccat gagaatgata gtgcttatga caacctgtta aggggtttca cgagacacga | 9540 |
| gaaatagcga acaatttagc tctgactatt aacttgaaat gacacacaaa gttctcattg | 9600 |
| taattttca tccccaaaaa taaaatcttt atacctggaa gtattttcct tgttttgcgt | 9660 |
| atcagcccat aaactcccctt gcatagcccg tgtaactttc gaccaatgta agggcttcaa | 9720 |
| tgaagctttt ttcggaggaa ttgaagtacc tcctgtacct cgcccttttc ctagagcagt | 9780 |
| tgaacctaca gaggctctta cacgtccggt agatggaggt ggtggcgctg cacactaag | 9840 |
| gccctttcca ccaggcgggg gaggtggagt gggtgtcaaa ccccgcctag ggggtggtgg | 9900 |
| ag | 9902 |

<210> SEQ ID NO 16
<211> LENGTH: 2863
<212> TYPE: DNA
<213> ORGANISM: Solanum habrochaites
<220> FEATURE:
<223> OTHER INFORMATION: >Genomic fragment 16

<400> SEQUENCE: 16

| | |
|---|---|
| ggggaggggt ggaggaggag ctgataaaatt acagttagat ggaccccgag gaggaggagg | 60 |
| tggaggtgga ggtggaggca aggcacttct agaagtagaa aacgtaggga cagatggtgg | 120 |
| atgtggagga gcagaagagc ataaaaggct ctgattagga agtggtggag gtggtggagg | 180 |
| tggcggaggt cctctagaaa agctatcagg ggaagttgaa gaagtaggtt gtcttggcgg | 240 |
| tgaatgttct ctatggctac caattgaagg tggtggtggt ggtggtggtg gaggtggagg | 300 |
| tggaggtgat ctattagaac ttgcaagtgg tggaagcgga cgagtacgtt ggacagaaga | 360 |
| agggacacca attataggag gaggtggagg tggtggagga ggcggaggag gtaatgagac | 420 |
| ctccttgcta ggagaaccaa acagagaggg tggtgaaggg ggagatggag ctgatgattg | 480 |
| agtgactttt atactagaaa tcacagaggc aggtgacgga ggtggtgaag gtagcggaga | 540 |
| agaagaggaa gtccttgtat cgcaaatttg aactcccttt aaacgttcag gagaaatggc | 600 |
| agtatccaat tgacagttac tttcagaaag agactgaaca ggaccaagat ctgactttga | 660 |

```
aagcttcatt tgaccctcag aaatcttggg atcagaagtt ccatcagaag ctgaatcctg    720
ttcatctaaa aagttgacat ctgttgtatt agcataacta atactactag ctttctctga    780
gtccagaaaa tccaaactgt cggcaatgct cgatgcatta ttttcttctt cagaatcaaa    840
tggggatgaa tacccactca tcctactttg caaaattgac aaatctttca tatcattcag    900
caccgatagc tgtttaaaca accacaacgc agcatcatca ccagtatcaa cccaatcagc    960
accactaaaa agttcttgta cccttgaaaa ggcttcaata ggaagtccac cagtctcctc   1020
accattgaga gctgcagtgg gagcttttag tggagatatg ctctcaacat caccaaataa   1080
aacctgcaaa gcagaaagta taagttagag agaaatatg aagagcaaag gtgatccaat    1140
aaaacaaaac taatcagaca gtttgtaaat aagtattcac ctcagctcga aagcctttg    1200 gatagcgtgc ctttgaatcc catagaatat ccaggttatc gcagtttaac atcaaaatgt   1260
tagagcgaat aaaagcagtg ttaaacacaa tacggaacat catgacttcc ctttcaggat   1320
ccaggtctaa gtggacacac tccaaaacta catctccttg caccaaacac tgaatatcaa   1380
tcttgatgac atcactgtcc ttctgcaaaa caataacaat catgttgcca cagagcagaa   1440
ttgaagaaga caacaaacaa gatgcagtga tagcaatttt tcacctggcg ataatgtcga   1500
aggcttctac ctttcttcgg catggagtac aacatatgag ttgacaatcc atccttgctg   1560
agaaggttcc ttccaaaaat gcgcacaatt ggcctacacc cttttttgatt gtcaaatctt   1620 ggaatggcac gaagaatgag gcaatccaga gaaagagctt gttcaggagg aggccactcg   1680
ggagatatat ttcttcttga tatatattgc aggtaacgaa gctgagaagg gaatgggttc   1740
aaaggtgaca caattgcga taaaccttta ggtgcctcac gataaaccat ctcgagagtt    1800
tttctctctc cgctttgtaa ctttctgaaa accaagaaac tggcgaaaat gaaggctaga   1860
aggggccaac cacctctctc acagtgtaac aaaattacat tgttatgatt ttgaagagag   1920
agccaactct cacagataca tagaaaatga tgtatcaatg acaatggcag tacaggacag   1980
ccttcatatt gtcttgggta atccattaca gtcacatcat actcgcataa aatctcagca   2040
aactggctcc ttttctcgcc ttctctgaaa ttgaaagcaa gaaaggagga atctggaaat   2100
tcttcatgta gttcatttat gatttcgtgc aagtaaagct gataaattcc ctcaggcagt   2160
acttcagtcg aaaacaaga atcaaaaact gcagatattc aacataagat aaaaagatgt    2220
tgagaaaact acaatgcact tccaatgttc aataaaaaac acattataaa gtcaaagcta   2280
gttcctttac catatactct atcatcaagt tccagcaacc catctggggg ccttctatag   2340
aaaaatctac tcaacagcga cataaactg agccaatata tcacctaaat ttacctgaca    2400
tcaaagaaat tcaaacccat tttcattcct ttggtgtccc aatatcaaaa gggtcagaga   2460
atcagctcgt acaaattcaa gaaaatgtga aattcataag aagaactcaa aattaatctc   2520
aaattcagaa tacccacaaa gctaaaagg gattgaacta tatttcaggc gaaaaaattg    2580
gaacttgaca ccaaataaac tacaacaaga ctgaaacaca cacaaaactc acatggaaaa   2640
tatttgcata taaaacacca aaaaggaaa tctttgaact gaagcaaacc gacagaagcc    2700
gttgaggaag gattcgagat gtgaggtgaa gaaccgacag tgttgccagt aaagtttca    2760 cctgcgcttt ccgattttag tatgaatttt tttttttttc tgattacgga tttgaactct   2820
ttggagttca aaattttggg aacgaaaaaa aagggggctga ttt                    2863
```

<210> SEQ ID NO 17
<211> LENGTH: 4781
<212> TYPE: DNA

<213> ORGANISM: Solanum habrochaites
<220> FEATURE:
<223> OTHER INFORMATION: >Genomic fragment 17

<400> SEQUENCE: 17

```
attctgactc aaaaataagt ttgattaact cttgagtcaa ttcaaacacc ctcttagttt      60
taattgacat ctataacctc taattttagg tatgtacaaa taaatactta aatttatata     120
aaaattaaac aaattaatat ttgtgatatg tgacattgca taagacaatt ttatatcaac     180
gtgatgtcct acctatatta cgccacataa attacatata tattgatctt tcaattttat     240
atcgtttaaa ttatacatat ataccctatc aaaaagtat tatgcttgtt gaatagttct      300
aacttgtaac atccactttc ctcttccac ttcaatccca aaaacatttc ttacaaattt      360
gcaaaaaaca atgaaagga cttaattagc aaaagagacc acaaaatgaa agggtcacat      420
ggggtgtgtt aaaactcaag cctaaaaaga ctttgttttg ttttgaata gatatatcac      480
tcaaaaccc aaaaagcaaa ccagtaaaag gtgaccccaa aaagcttccc cacacacaca     540
ctgaagacaa ctttccagta atggcggcac atgaagaaca acaccaccat catcaacaac     600
aagaacaaga gaaccccatt tcctctttat ccttaaaacc caacaataaa cacttggaga     660
agattttctc ctcatatttg ggtctaagtt tcgctgtctt tcttgggtct ttaccaagaa     720
atgcagtttc tttggttggg agacttcaga accgtaacaa ggagctaact tttcagctta     780
ttgatacaga ggagcagtta aagcagctac ttttcaggag aaaagaggat tcaaaggcaa     840
atgcaagagt tgtggaaatc tttgcaagtc atagacatgc ctggcagcaa gaagagaaga     900
ggttgttaca gcagatcgat gagtgtgatg aagaaattgc tgagttaaga gggagagctg     960
agcagtttga gacaatggaa agtgagttga gggctaatat tgaggacttg aaaagggaga    1020
ttagtgaaag agatgaaatg ttgaacttta tgagtagaag gggttgtgag atggagaata    1080
gtactagtgg agatggtggg agtgatggtg ttggagattg ttatgctgaa atgggtttga    1140
ggtttgggaa agttgggata tctgaaggga tggatttggg ggtagggatg gaagagtgtt    1200
acttggctaa tgggattcct aatgctgaac aaatgagtgg tgtttatgga cagagtaatg    1260
ggtttaactc agaatacttg aattctgctt ctaagttttg ggctgaaaaa gctagtcctt    1320
ggcaggtatg atccattcat tatttctttt tgggaactt tttgttcttt atagttgttg     1380
ttatttgggg ttttatagtg agtggtgtca taatgtggta aaaataaacg caaaagtcct    1440
ttccaggatc ttcatatgta ggaagaactt ggactaaagt ttgtcgcttt aatgtttgtc    1500
ttatatatgg ttttttcatgg tgaaacttat gaataaagtt gcttcttta tttaaccatg    1560
ggattgtact ttaagtacta ccacctgata ttctttcttt tagtgtttat ctgtttgttc    1620
atcttgaggc tgtggaattt gttttttgtat gtgatatctg atgaaacaaa tgatccagag    1680
caattgagga tgaacgaaat taagtaataa aatgtttggc ttataggggtt cttggtgaag    1740
tacaggcctt tatgatcttt cttcacatac ctgaaaattt cacaggaata tccacttcta    1800
attgtttctg ataaagctga aatgaaggtg tttctccagg agtagttcag cgccaaattc    1860
aaattgaatt gtataatgat tacattctga gatgcttatt aatgaaatat gtagtttagt    1920
gtgtactcag tgacctccta cttgtcttgt gatttgtctt tattgttgag actcttgtct    1980
ctattatcta aaattttgaa tggtttgatc ttcttagtgg ctgctgaaag ttcaaactac    2040
ccaggatatg gttttctgtt tactgaaaga taatactcac ctcaactgtt cattttacc     2100
ctatactggt gttatggacc actgcttgaa aaccaggtca ccgttttgta cttttcttct    2160
ttcaccgttt tcgtcctatt agaggtttgc aattcttgct tcaagaatgg tcccctttgg    2220
```

```
ctgaatactt tgcatgaagg ttggtttcct ggttatgaag gaagctcaaa aaaatgtatt    2280
cgggtaactc tagaaatccg aaatccgttt aaaacggacc gttttgttgg catagaccac    2340
tgtgcctcta aaataccaac taatgacatc caattatata tcccctttgg tttgggaagt    2400
tcaattctgg ttaaaatgga tccgtatatc agcaaaggat gggctgttat cagtcaacat    2460
ctagtccatc tgttatattt ctgtttaaga ttcatcaacc tcaatggaaa gatgtcctct    2520
ccctttcttg ttgcaagctg tatcttgtcc ttgtctgtct ctgtatctta ttttccaatt    2580
acaatgttat ctttggtaat tcgttacaca tccttgaaat aaagcaaatg cctccatgaa    2640
acttgaactc cccgcggcct ctaatccagg cactaatctt tcccgttcaa aaggatcact    2700
ggaacatttt cctatacttg gtggatgtgt caaagtttgg actaggtaga gatcacacat    2760
tcaatttatg gctgtgtttt ttgtctttta tcattttttgt cttttttatat tatatagaaa    2820 agaagatctg gattttctta cccttggtac agtcacccct ttcatttatt tggaaccaga    2880
gggaactgga gcatttcact atgttgtctt caactttaat agaaaggcta agaaaaacac    2940
acaaccttaa aaataaacct aaattgccta actattagtt gatctatgcc ttgtgagctg    3000
gttaaggatt agtcatattt acaatggtta gagcaaaaag agaaataaac atctagatca    3060
caatgcttat attctagttt caagcttgaa tggtaggaga aatgaggttc ttttgactct    3120
tattcagctt cttccttcta tgtgagatgt cctacctatc ttagtaaaac cagcttggta    3180
tttaggatgc tattgggtct taagaaaatg tgttttcttc atgcaggata tgcagtatga    3240
ttctggcgat tcacttcacc atttaaagca ttttgtagca aggtaaacat tctgtgatta    3300
gttagacaga tgcttagatg tttgcatttt gatgttgaat caactaacta gggtgagccc    3360
ttttgctttc tcagacggga ggccccttgg aagatagatg gtgaatcaac aggagtctcc    3420
tccaaactaa agttacttga gcaggagcta ctgaatttgg aaaaaattgg gaagactgat    3480
ttatctaagg taccatcatc aacgcggaag caagtgaaga gataccaagc tctagctggc    3540
aagattgatg atttatgcag aagaatggta attactgcat ctctgcaagc ttattggtta    3600
taactttagt atatggattt caaagcttgt tacatgcatg cttaggtttc tctaagaatg    3660
gacaatagtc ttgattacat ctgctaactc aaatatttag atgttgggtt atactcttag    3720
cttgcacgac taggccttac aattagcttt ttacctaaca caaacataca tctgataatg    3780
atctccctcc ctcttagcag caggccagtg atccttgcga atcaaacctg agtcctgagt    3840
tccggaccca agacagacc gagttttttgc ttgaagcatt tcgacttcag cagcgtgcat    3900
ctgaaactgc acagaagctg atggtactac aaactgacag tggaaaaagt tattacgggg    3960
acgaatttga agggcaagcc caactagcca ctaaacgatc ctttgactcc atccggaaca    4020
acttaaaaga aatccaacgg aatttagaga tatggcttgc cagaattatt ggggatctgg    4080
agggaatcct ttctcgagat ggtgcttctc gtgtaaggga ttattacata tctagatatc    4140
cttttgttca atagttatgt cttaacatgc tcagtaaaat catgattgaa aaaatgatgt    4200
ataggtcctt cctgttatgt taacaagata gctccagctg aatgaacaat atgaggttga    4260
taagtccatt tatgcacata aatctgcttc acagaagcaa actattaatg ctaactagta    4320
ctttaaagag tgaagatttt tgacagaatt attgctggat gtcactgttc ctgatctgga    4380
tgcttgtcat ttactagttt tacttggtcc cggtctttct ggattaaaaa gttgaaagga    4440
tggtgtggcc ctttgcaact ggataaatgt catgtctaca caaatctggc aaacattaaa    4500
tatttgtgga ccaagtttac agccccattt gatttgaaat cagattgatt ttaagttgat    4560
```

-continued

| | |
|---|---|
| atttgttttg atttggattc ttaagctgta ttgattattc ttaagcttag caaatgagca | 4620 |
| aatcatattt tcatgaataa gatatcaaaa tattctagga agttgaatta acaagttata | 4680 |
| tagcttcatg ttactttttt tataaataaa tatttgtaat tatatgttat tataaacttt | 4740 |
| caaatatgtt caataaacca aacaacagta atactttctt t | 4781 |

<210> SEQ ID NO 18
<211> LENGTH: 3271
<212> TYPE: DNA
<213> ORGANISM: Solanum habrochaites
<220> FEATURE:
<223> OTHER INFORMATION: >Genomic fragment 18

<400> SEQUENCE: 18

| | |
|---|---|
| taggaagttg aattaacaag ttatatagct tcatgttact tttttataa ataaatattt | 60 |
| gtaattatat gttattataa actttcaaat atgttcaata aaccaaacaa cagtaatact | 120 |
| ttcttttgat aaaagttatt cgcttggtac aaacaatttc ttccgctaga ttttctttt | 180 |
| taaattttaa aattatgggt cttttcttgt aaaaattagg tttcttttc tcacctaacc | 240 |
| tagtcgtgga catgagttca taagttgaat aatctctaac taaaaggata gtcaaggatg | 300 |
| tgccaccgtc gaacaagaag gatagttaag gacactctca agcaaggcc agtagcatgt | 360 |
| actctaaatt tagtcaaagt tccaatacaa gcttttgag cgccactgtg actttgatag | 420 |
| gtggaaaaat aattaaaatt tatctttaat atataatact ccttcattt taccacaata | 480 |
| cctattaatt gatgtaatgg cctgaggtta aactttaa ccatctctgt tctatttatg | 540 |
| tcaagaagtg caatcaggtt ttgaaccaag tagctaatca ctcaatataa agaaaccaaa | 600 |
| ttcaaacttt tttagggggtt tattatagaa ggttcagaca tacttatagc agtaattttt | 660 |
| tttcctagcc aggaaaaggc atacacctgc tgttacacta aaatcaaaca agccacataa | 720 |
| tccaattcca ataacaattt aacaacatag atagatgagc cttatgctga agcagcacct | 780 |
| tcttccagca actgtttcac cttggtgatg tagtcgttca tggcttcatc ggtggattt | 840 |
| cctgtcatag atgcatgcag tgcaattagt tgtgtttctc atacaaccaa gagaaaggaa | 900 |
| gtcaatctga acactgttgt tagatcacat accttcaaca gccttccatg catcccactt | 960 |
| tgctctgtct ctcatgttga aaatgccagg acggcctgcc cataagaaag ggcgtaagaa | 1020 |
| caaagtgtag ctagtttgag acagcatgta catatgcata agacatttca agcattatac | 1080 |
| tcacttgtgt tgacactgcc aacggtggct tgcttgtaaa gtccgtaaag aataagcttg | 1140 |
| ttctcattgg tggtactctc aggcaatgtc ttagctttct cagcatgtgc ttcaaattcc | 1200 |
| tcctgaaacc caaatagttc agtaaaaagg tgtggtagct gaagttacaa agataaattt | 1260 |
| ccaggtatac tttcttagtg ataaaataag gatgagaatc caacttaata gttgagatcg | 1320 |
| aaactatttg tgaattaaga gggaactgaa cttatggaaa tctaaaatac aaattgagtg | 1380 |
| ttccttcatt gggtaaatga aaagtttgca gttcaggata tcaaatatgt acgaattcat | 1440 |
| tgatggactt tagcacaagt gtacgcttag cctagcggtg aaaagggttc attctattta | 1500 |
| gccaacccga gttcaattct cgctttattt tatttataa cttgaatccg cttcgtgaaa | 1560 |
| atcctaggtc cgccactggt tagtgaaaga gtatttgcaa gaatgttaga caagaaaagc | 1620 |
| acaacaatac attcctcaac attgtaagag attctgctgg ccaacatttt gctttgacaa | 1680 |
| tgttaagacg caaattttag acacatgtgt taatcataca attctccaac cttttcctct | 1740 |
| tctagaaatg cttctattta cagatcacag tgaagcacca aaaacatcct cagataatgt | 1800 |
| attatgacct cttcagtttg tttactggtt tgccctgttt gttaccctac gattcaacca | 1860 |

```
ttaccactca gtagcctaca tacttgtggt aacaggaatc cttttagtgc gaggcgattg    1920
gccaaccaac aatttttgta gtcacttaaa aataggtcag actaaattac atccactata    1980
ggttatgaac agcagagaaa tttcaaagac aggctgaaca caaagtgcac atttccttca    2040
acttttcccc ttccccaata aagaaatat ggaagggtga tgataggttt ttgaccagga    2100
aacaaaaact agtcttggac taggcaatac aggataggaa agagaaagaa gcgggcgcta    2160
tctcatattc aattttgct agactatta cacagaagt ggccaatgta gcaccatata    2220
aatttgagaa agagccattt gttcactact aacatttga tggccctaac tgcacatgaa    2280
ctaatagtaa tctgattcta acatctcgtt ccctgggttt agtcatcgac ttaagcttca    2340
aagtatacac catatatata gccaataata tcaacaatct caaaaactaa agaagaaga    2400 cattcataag atgaaatctt caaaacattg ttgaaattat ggactacttc tgggccagag    2460
acaatatata tgcctttga taaggccaaa aatgacatac acaaatccgg accaaagtac    2520
tactcatctg ccattacatt cgcactactt cttatcgaat tcagtgctta cattgctata    2580
attaccataa atctttcaac aaggccaaaa atgtacagca taattgaatt cattataaga    2640
tctatttata agatggtatg ccgccactca accacagtat gaactgctaa aaaaaaaata    2700
atcttaaaca tcaattacac caacagatca gatcaatcca atcaccgagc cttcacacta    2760
aataataacc aaacaatcct cacgtaaac agcatccaca aaattacagc acaagctgca    2820
caatcgacaa agaaaactaa cagatccgca ataccaatt gcacaaacaa cacaaaaccc    2880
agaattgaaa acgaacatta atcacagaaa aatacttttc actgtcaaaa aagattaaca    2940
ctcgcttcaa acaagataaa tacatactga aaggcaaaaa aaaaacagaa atctaaaggg    3000 gtttttaaaga atttaccttc aacgccattg ttgtggaaat ctgatctggt tagcttgata    3060
aaaacgagag aaaactggag atgtgattgt gatggagatt gaagaagaag ggtgggtata    3120
tatatatagt ggagtattta gcataggaat taacgtaaaa ttcgattcga ttatgataat    3180
ctaaacaagt tgcacttgga tcacttacta gtcatagtgg acccaaaaat tgagtataga    3240 ttatggaccct atactatgtg agctccacaa c                                   3271
```

<210> SEQ ID NO 19
<211> LENGTH: 20
<212> TYPE: DNA
<213> ORGANISM: Artificial Sequence
<220> FEATURE:
<223> OTHER INFORMATION: Synthetic Construct

<400> SEQUENCE: 19

```
ggtacaacaa ttgaccaagg                                                   20
```

<210> SEQ ID NO 20
<211> LENGTH: 23
<212> TYPE: DNA
<213> ORGANISM: Artificial Sequence
<220> FEATURE:
<223> OTHER INFORMATION: Synthetic Construct

<400> SEQUENCE: 20

```
gctaattaaa aaggaacatc agc                                               23
```

<210> SEQ ID NO 21
<211> LENGTH: 20
<212> TYPE: DNA
<213> ORGANISM: Artificial Sequence
<220> FEATURE:

<223> OTHER INFORMATION: Synthetic Construct

<400> SEQUENCE: 21
gctatggcgg agaagtcaag      20

<210> SEQ ID NO 22
<211> LENGTH: 20
<212> TYPE: DNA
<213> ORGANISM: Artificial Sequence
<220> FEATURE:
<223> OTHER INFORMATION: Synthetic Construct

<400> SEQUENCE: 22
agtcacctcc atagtagacc      20

<210> SEQ ID NO 23
<211> LENGTH: 21
<212> TYPE: DNA
<213> ORGANISM: Artificial Sequence
<220> FEATURE:
<223> OTHER INFORMATION: Synthetic Construct

<400> SEQUENCE: 23
ggatccaagt tgtgttcgaa c      21

<210> SEQ ID NO 24
<211> LENGTH: 24
<212> TYPE: DNA
<213> ORGANISM: Artificial Sequence
<220> FEATURE:
<223> OTHER INFORMATION: Synthetic Construct

<400> SEQUENCE: 24
cttctcatca atgtatgtga tttc      24

<210> SEQ ID NO 25
<211> LENGTH: 20
<212> TYPE: DNA
<213> ORGANISM: Artificial Sequence
<220> FEATURE:
<223> OTHER INFORMATION: Synthetic Construct

<400> SEQUENCE: 25
tgtataacac ctggtgctcc      20

<210> SEQ ID NO 26
<211> LENGTH: 24
<212> TYPE: DNA
<213> ORGANISM: Artificial Sequence
<220> FEATURE:
<223> OTHER INFORMATION: Synthetic Construct

<400> SEQUENCE: 26
ccattttctg ttacaaaatt tcag      24

<210> SEQ ID NO 27
<211> LENGTH: 21
<212> TYPE: DNA
<213> ORGANISM: Artificial Sequence
<220> FEATURE:
<223> OTHER INFORMATION: Synthetic Construct

<400> SEQUENCE: 27
gcttcccaat ttatgctgaa g      21

```
<210> SEQ ID NO 28
<211> LENGTH: 21
<212> TYPE: DNA
<213> ORGANISM: Artificial Sequence
<220> FEATURE:
<223> OTHER INFORMATION: Synthetic Construct

<400> SEQUENCE: 28
gagcctccca ctatagtaat c                                              21

<210> SEQ ID NO 29
<211> LENGTH: 22
<212> TYPE: DNA
<213> ORGANISM: Artificial Sequence
<220> FEATURE:
<223> OTHER INFORMATION: Synthetic Construct

<400> SEQUENCE: 29
agaattatca tttgcaggat cg                                             22

<210> SEQ ID NO 30
<211> LENGTH: 20
<212> TYPE: DNA
<213> ORGANISM: Artificial Sequence
<220> FEATURE:
<223> OTHER INFORMATION: Synthetic Construct

<400> SEQUENCE: 30
ctatggttcg catgtcatgc                                                20

<210> SEQ ID NO 31
<211> LENGTH: 21
<212> TYPE: DNA
<213> ORGANISM: Artificial Sequence
<220> FEATURE:
<223> OTHER INFORMATION: Synthetic Construct

<400> SEQUENCE: 31
cacaacggca atataccttg c                                              21

<210> SEQ ID NO 32
<211> LENGTH: 22
<212> TYPE: DNA
<213> ORGANISM: Artificial Sequence
<220> FEATURE:
<223> OTHER INFORMATION: Synthetic Construct

<400> SEQUENCE: 32
tggaagtatt agaaaggtcc ag                                             22

<210> SEQ ID NO 33
<211> LENGTH: 22
<212> TYPE: DNA
<213> ORGANISM: Artificial Sequence
<220> FEATURE:
<223> OTHER INFORMATION: Synthetic Construct

<400> SEQUENCE: 33
ccattgagaa taactactgt ac                                             22

<210> SEQ ID NO 34
<211> LENGTH: 20
<212> TYPE: DNA
<213> ORGANISM: Artificial Sequence
<220> FEATURE:
<223> OTHER INFORMATION: Synthetic Construct
```

```
<400> SEQUENCE: 34
ccacaggatg actaacttgg                                              20

<210> SEQ ID NO 35
<211> LENGTH: 23
<212> TYPE: DNA
<213> ORGANISM: Artificial Sequence
<220> FEATURE:
<223> OTHER INFORMATION: Synthetic Construct

<400> SEQUENCE: 35
tgcagtattg atcgcatctt cta                                          23

<210> SEQ ID NO 36
<211> LENGTH: 19
<212> TYPE: DNA
<213> ORGANISM: Artificial Sequence
<220> FEATURE:
<223> OTHER INFORMATION: Synthetic Construct

<400> SEQUENCE: 36
gtttgttgct gccctcaaa                                               19

<210> SEQ ID NO 37
<211> LENGTH: 27
<212> TYPE: DNA
<213> ORGANISM: Artificial Sequence
<220> FEATURE:
<223> OTHER INFORMATION: Synthetic Construct

<400> SEQUENCE: 37
tgatcaagaa ttttgtttta gcataga                                      27

<210> SEQ ID NO 38
<211> LENGTH: 24
<212> TYPE: DNA
<213> ORGANISM: Artificial Sequence
<220> FEATURE:
<223> OTHER INFORMATION: Synthetic Construct

<400> SEQUENCE: 38
taaagcatca attttgcatt gtct                                         24

<210> SEQ ID NO 39
<211> LENGTH: 26
<212> TYPE: DNA
<213> ORGANISM: Artificial Sequence
<220> FEATURE:
<223> OTHER INFORMATION: Synthetic Construct

<400> SEQUENCE: 39
tcgaagacta acaaagtcct tgtaga                                       26

<210> SEQ ID NO 40
<211> LENGTH: 19
<212> TYPE: DNA
<213> ORGANISM: Artificial Sequence
<220> FEATURE:
<223> OTHER INFORMATION: Synthetic Construct

<400> SEQUENCE: 40
gacactccgg cagttcctt                                               19

<210> SEQ ID NO 41
<211> LENGTH: 23
```

```
<212> TYPE: DNA
<213> ORGANISM: Artificial Sequence
<220> FEATURE:
<223> OTHER INFORMATION: Synthetic Construct

<400> SEQUENCE: 41
ttcttatgtg aaaaattggg tgg                                             23

<210> SEQ ID NO 42
<211> LENGTH: 20
<212> TYPE: DNA
<213> ORGANISM: Artificial Sequence
<220> FEATURE:
<223> OTHER INFORMATION: Synthetic Construct

<400> SEQUENCE: 42
actacgcagt cccacagctt                                                 20

<210> SEQ ID NO 43
<211> LENGTH: 20
<212> TYPE: DNA
<213> ORGANISM: Artificial Sequence
<220> FEATURE:
<223> OTHER INFORMATION: Synthetic Construct

<400> SEQUENCE: 43
ttgtttggtg gatccatgtg                                                 20

<210> SEQ ID NO 44
<211> LENGTH: 18
<212> TYPE: DNA
<213> ORGANISM: Artificial Sequence
<220> FEATURE:
<223> OTHER INFORMATION: Synthetic Construct

<400> SEQUENCE: 44
agggaaaggg caaggatg                                                   18

<210> SEQ ID NO 45
<211> LENGTH: 22
<212> TYPE: DNA
<213> ORGANISM: Artificial Sequence
<220> FEATURE:
<223> OTHER INFORMATION: Synthetic Construct

<400> SEQUENCE: 45
gatctaccaa tggctattca tc                                              22

<210> SEQ ID NO 46
<211> LENGTH: 21
<212> TYPE: DNA
<213> ORGANISM: Artificial Sequence
<220> FEATURE:
<223> OTHER INFORMATION: Synthetic Construct

<400> SEQUENCE: 46
gcaaaactta accggtctaa g                                               21

<210> SEQ ID NO 47
<211> LENGTH: 23
<212> TYPE: DNA
<213> ORGANISM: Artificial Sequence
<220> FEATURE:
<223> OTHER INFORMATION: Synthetic Construct

<400> SEQUENCE: 47
```

-continued

```
tctcgatggt tgataatttg ttc                                          23

<210> SEQ ID NO 48
<211> LENGTH: 21
<212> TYPE: DNA
<213> ORGANISM: Artificial Sequence
<220> FEATURE:
<223> OTHER INFORMATION: Synthetic Construct

<400> SEQUENCE: 48
ggaatcgatt aacactggtt c                                            21

<210> SEQ ID NO 49
<211> LENGTH: 21
<212> TYPE: DNA
<213> ORGANISM: Artificial Sequence
<220> FEATURE:
<223> OTHER INFORMATION: Synthetic Construct

<400> SEQUENCE: 49
catcttattg aagctctgct g                                            21

<210> SEQ ID NO 50
<211> LENGTH: 21
<212> TYPE: DNA
<213> ORGANISM: Artificial Sequence
<220> FEATURE:
<223> OTHER INFORMATION: Synthetic Construct

<400> SEQUENCE: 50
caaacagtcc ctattcaaca c                                            21

<210> SEQ ID NO 51
<211> LENGTH: 20
<212> TYPE: DNA
<213> ORGANISM: Artificial Sequence
<220> FEATURE:
<223> OTHER INFORMATION: Synthetic Construct

<400> SEQUENCE: 51
ggtcttgcgc taatcaaaag                                              20

<210> SEQ ID NO 52
<211> LENGTH: 22
<212> TYPE: DNA
<213> ORGANISM: Artificial Sequence
<220> FEATURE:
<223> OTHER INFORMATION: Synthetic Construct

<400> SEQUENCE: 52
gcgttgtggt gaaagtttta tc                                           22

<210> SEQ ID NO 53
<211> LENGTH: 20
<212> TYPE: DNA
<213> ORGANISM: Artificial Sequence
<220> FEATURE:
<223> OTHER INFORMATION: Synthetic Construct

<400> SEQUENCE: 53
cttgtttgga tggttgtcac                                              20

<210> SEQ ID NO 54
<211> LENGTH: 24
<212> TYPE: DNA
<213> ORGANISM: Artificial Sequence
```

```
<220> FEATURE:
<223> OTHER INFORMATION: Synthetic Construct

<400> SEQUENCE: 54
caacaaaaaa tatacaatcc gtcc                                         24

<210> SEQ ID NO 55
<211> LENGTH: 21
<212> TYPE: DNA
<213> ORGANISM: Artificial Sequence
<220> FEATURE:
<223> OTHER INFORMATION: Synthetic Construct

<400> SEQUENCE: 55
gagatagaag gaaacttacc g                                            21

<210> SEQ ID NO 56
<211> LENGTH: 20
<212> TYPE: DNA
<213> ORGANISM: Artificial Sequence
<220> FEATURE:
<223> OTHER INFORMATION: Synthetic Construct

<400> SEQUENCE: 56
caattatccc ctcagttctg                                              20

<210> SEQ ID NO 57
<211> LENGTH: 20
<212> TYPE: DNA
<213> ORGANISM: Artificial Sequence
<220> FEATURE:
<223> OTHER INFORMATION: Synthetic Construct

<400> SEQUENCE: 57
tatgcctgtc cctgaaaagg                                              20

<210> SEQ ID NO 58
<211> LENGTH: 22
<212> TYPE: DNA
<213> ORGANISM: Artificial Sequence
<220> FEATURE:
<223> OTHER INFORMATION: Synthetic Construct

<400> SEQUENCE: 58
agggtcttgg atcaaatctt ga                                           22

<210> SEQ ID NO 59
<211> LENGTH: 20
<212> TYPE: DNA
<213> ORGANISM: Artificial Sequence
<220> FEATURE:
<223> OTHER INFORMATION: Synthetic Construct

<400> SEQUENCE: 59
tgtggacttg gagtggtatc                                              20

<210> SEQ ID NO 60
<211> LENGTH: 21
<212> TYPE: DNA
<213> ORGANISM: Artificial Sequence
<220> FEATURE:
<223> OTHER INFORMATION: Synthetic Construct

<400> SEQUENCE: 60
gtagaaaggg taggcatgtt c                                            21
```

```
<210> SEQ ID NO 61
<211> LENGTH: 21
<212> TYPE: DNA
<213> ORGANISM: Artificial Sequence
<220> FEATURE:
<223> OTHER INFORMATION: Synthetic Construct

<400> SEQUENCE: 61
taccaaagca aacactgcca c                                              21

<210> SEQ ID NO 62
<211> LENGTH: 22
<212> TYPE: DNA
<213> ORGANISM: Artificial Sequence
<220> FEATURE:
<223> OTHER INFORMATION: Synthetic Construct

<400> SEQUENCE: 62
agccacgaga tatatattgg ag                                             22

<210> SEQ ID NO 63
<211> LENGTH: 21
<212> TYPE: DNA
<213> ORGANISM: Artificial Sequence
<220> FEATURE:
<223> OTHER INFORMATION: Synthetic Construct

<400> SEQUENCE: 63
gataagaccg ccaataacta g                                              21

<210> SEQ ID NO 64
<211> LENGTH: 20
<212> TYPE: DNA
<213> ORGANISM: Artificial Sequence
<220> FEATURE:
<223> OTHER INFORMATION: Synthetic Construct

<400> SEQUENCE: 64
gtgatctcca tgagcaaatg                                                20

<210> SEQ ID NO 65
<211> LENGTH: 21
<212> TYPE: DNA
<213> ORGANISM: Artificial Sequence
<220> FEATURE:
<223> OTHER INFORMATION: Synthetic Construct

<400> SEQUENCE: 65
tgagttgaga tgctgttcta g                                              21

<210> SEQ ID NO 66
<211> LENGTH: 21
<212> TYPE: DNA
<213> ORGANISM: Artificial Sequence
<220> FEATURE:
<223> OTHER INFORMATION: Synthetic Construct

<400> SEQUENCE: 66
agtccaccaa gacttaaaga g                                              21

<210> SEQ ID NO 67
<211> LENGTH: 20
<212> TYPE: DNA
<213> ORGANISM: Artificial Sequence
<220> FEATURE:
<223> OTHER INFORMATION: Synthetic Construct
```

<400> SEQUENCE: 67
gtctgccttc tcttgcatgc                                              20

<210> SEQ ID NO 68
<211> LENGTH: 21
<212> TYPE: DNA
<213> ORGANISM: Artificial Sequence
<220> FEATURE:
<223> OTHER INFORMATION: Synthetic Construct

<400> SEQUENCE: 68
gttgctccag acagaataag c                                            21

<210> SEQ ID NO 69
<211> LENGTH: 20
<212> TYPE: DNA
<213> ORGANISM: Artificial Sequence
<220> FEATURE:
<223> OTHER INFORMATION: Synthetic Construct

<400> SEQUENCE: 69
catcgaagag atgtgtaggg                                              20

<210> SEQ ID NO 70
<211> LENGTH: 21
<212> TYPE: DNA
<213> ORGANISM: Artificial Sequence
<220> FEATURE:
<223> OTHER INFORMATION: Synthetic Construct

<400> SEQUENCE: 70
tgcagttgaa gtagacttca g                                            21

<210> SEQ ID NO 71
<211> LENGTH: 22
<212> TYPE: DNA
<213> ORGANISM: Artificial Sequence
<220> FEATURE:
<223> OTHER INFORMATION: Synthetic Construct

<400> SEQUENCE: 71
tcaacgttag tggtgatgct ag                                           22

<210> SEQ ID NO 72
<211> LENGTH: 21
<212> TYPE: DNA
<213> ORGANISM: Artificial Sequence
<220> FEATURE:
<223> OTHER INFORMATION: Synthetic Construct

<400> SEQUENCE: 72
caattgcaga aagtgaagct g                                            21

<210> SEQ ID NO 73
<211> LENGTH: 22
<212> TYPE: DNA
<213> ORGANISM: Artificial Sequence
<220> FEATURE:
<223> OTHER INFORMATION: Synthetic Construct

<400> SEQUENCE: 73
gtggattcag ttaaaccaga ac                                           22

<210> SEQ ID NO 74

```
<211> LENGTH: 22
<212> TYPE: DNA
<213> ORGANISM: Artificial Sequence
<220> FEATURE:
<223> OTHER INFORMATION: Synthetic Construct

<400> SEQUENCE: 74
gacatgtgga acttgacaaa ac                                              22

<210> SEQ ID NO 75
<211> LENGTH: 21
<212> TYPE: DNA
<213> ORGANISM: Artificial Sequence
<220> FEATURE:
<223> OTHER INFORMATION: Synthetic Construct

<400> SEQUENCE: 75
gcgagagaaa agattctcta c                                               21

<210> SEQ ID NO 76
<211> LENGTH: 22
<212> TYPE: DNA
<213> ORGANISM: Artificial Sequence
<220> FEATURE:
<223> OTHER INFORMATION: Synthetic Construct

<400> SEQUENCE: 76
cattcttcac tctctcaaga tg                                              22

<210> SEQ ID NO 77
<211> LENGTH: 23
<212> TYPE: DNA
<213> ORGANISM: Artificial Sequence
<220> FEATURE:
<223> OTHER INFORMATION: Synthetic Construct

<400> SEQUENCE: 77
cgtttggtga tctgccttgt ctt                                             23

<210> SEQ ID NO 78
<211> LENGTH: 24
<212> TYPE: DNA
<213> ORGANISM: Artificial Sequence
<220> FEATURE:
<223> OTHER INFORMATION: Synthetic Construct

<400> SEQUENCE: 78
tcttcttgta gggaatccag aatc                                            24

<210> SEQ ID NO 79
<211> LENGTH: 21
<212> TYPE: DNA
<213> ORGANISM: Artificial Sequence
<220> FEATURE:
<223> OTHER INFORMATION: Synthetic Construct

<400> SEQUENCE: 79
gtgtcctgtg cttgttattc c                                               21

<210> SEQ ID NO 80
<211> LENGTH: 23
<212> TYPE: DNA
<213> ORGANISM: Artificial Sequence
<220> FEATURE:
<223> OTHER INFORMATION: Synthetic Construct

<400> SEQUENCE: 80
```
cctcaaacct attgcatctg aca                                            23

<210> SEQ ID NO 81
<211> LENGTH: 21
<212> TYPE: DNA
<213> ORGANISM: Artificial Sequence
<220> FEATURE:
<223> OTHER INFORMATION: Synthetic Construct

<400> SEQUENCE: 81
cggctcagcg aggaagtgca g                                              21

<210> SEQ ID NO 82
<211> LENGTH: 21
<212> TYPE: DNA
<213> ORGANISM: Artificial Sequence
<220> FEATURE:
<223> OTHER INFORMATION: Synthetic Construct

<400> SEQUENCE: 82
cgttgactgt ttttctttat g                                              21

<210> SEQ ID NO 83
<211> LENGTH: 20
<212> TYPE: DNA
<213> ORGANISM: Artificial Sequence
<220> FEATURE:
<223> OTHER INFORMATION: Synthetic Construct

<400> SEQUENCE: 83
gtaagctcct tcatgtcagc                                                20

<210> SEQ ID NO 84
<211> LENGTH: 22
<212> TYPE: DNA
<213> ORGANISM: Artificial Sequence
<220> FEATURE:
<223> OTHER INFORMATION: Synthetic Construct

<400> SEQUENCE: 84
caagtattgt ctgccgagta ac                                             22

<210> SEQ ID NO 85
<211> LENGTH: 23
<212> TYPE: DNA
<213> ORGANISM: Artificial Sequence
<220> FEATURE:
<223> OTHER INFORMATION: Synthetic Construct

<400> SEQUENCE: 85
gcgtacagac atatttatgc aac                                            23

<210> SEQ ID NO 86
<211> LENGTH: 22
<212> TYPE: DNA
<213> ORGANISM: Artificial Sequence
<220> FEATURE:
<223> OTHER INFORMATION: Synthetic Construct

<400> SEQUENCE: 86
gaacagctaa aagtaagagc ac                                             22

<210> SEQ ID NO 87
<211> LENGTH: 21
<212> TYPE: DNA

```
<213> ORGANISM: Artificial Sequence
<220> FEATURE:
<223> OTHER INFORMATION: Synthetic Construct

<400> SEQUENCE: 87
gttcatgtgt gtttatggac c                                         21

<210> SEQ ID NO 88
<211> LENGTH: 24
<212> TYPE: DNA
<213> ORGANISM: Artificial Sequence
<220> FEATURE:
<223> OTHER INFORMATION: Synthetic Construct

<400> SEQUENCE: 88
cttcactaaa taaataagtg gtag                                      24

<210> SEQ ID NO 89
<211> LENGTH: 22
<212> TYPE: DNA
<213> ORGANISM: Artificial Sequence
<220> FEATURE:
<223> OTHER INFORMATION: Synthetic Construct

<400> SEQUENCE: 89
tatggatttg tgtctcagaa ga                                        22

<210> SEQ ID NO 90
<211> LENGTH: 21
<212> TYPE: DNA
<213> ORGANISM: Artificial Sequence
<220> FEATURE:
<223> OTHER INFORMATION: Synthetic Construct

<400> SEQUENCE: 90
tgtggtcacc aagtgggttt c                                         21

<210> SEQ ID NO 91
<211> LENGTH: 23
<212> TYPE: DNA
<213> ORGANISM: Artificial Sequence
<220> FEATURE:
<223> OTHER INFORMATION: Synthetic Construct

<400> SEQUENCE: 91
gtcttccaga gcagttatgc aag                                       23

<210> SEQ ID NO 92
<211> LENGTH: 25
<212> TYPE: DNA
<213> ORGANISM: Artificial Sequence
<220> FEATURE:
<223> OTHER INFORMATION: Synthetic Construct

<400> SEQUENCE: 92
tgagactgct aagttgactt gtttg                                     25

<210> SEQ ID NO 93
<211> LENGTH: 22
<212> TYPE: DNA
<213> ORGANISM: Artificial Sequence
<220> FEATURE:
<223> OTHER INFORMATION: Synthetic Construct

<400> SEQUENCE: 93
gtacaccaaa tcacagacat cg                                        22
```

<210> SEQ ID NO 94
<211> LENGTH: 22
<212> TYPE: DNA
<213> ORGANISM: Artificial Sequence
<220> FEATURE:
<223> OTHER INFORMATION: Synthetic Construct

<400> SEQUENCE: 94
cccaatttgg tttgtgttgg ac                                          22

<210> SEQ ID NO 95
<211> LENGTH: 20
<212> TYPE: DNA
<213> ORGANISM: Artificial Sequence
<220> FEATURE:
<223> OTHER INFORMATION: Synthetic Construct

<400> SEQUENCE: 95
gaaattcctt gcctcctctc                                             20

<210> SEQ ID NO 96
<211> LENGTH: 21
<212> TYPE: DNA
<213> ORGANISM: Artificial Sequence
<220> FEATURE:
<223> OTHER INFORMATION: Synthetic Construct

<400> SEQUENCE: 96
gtggaagcca tagtgtacaa g                                           21

<210> SEQ ID NO 97
<211> LENGTH: 23
<212> TYPE: DNA
<213> ORGANISM: Artificial Sequence
<220> FEATURE:
<223> OTHER INFORMATION: Synthetic Construct

<400> SEQUENCE: 97
catattatac agtgaaagct ttg                                         23

<210> SEQ ID NO 98
<211> LENGTH: 21
<212> TYPE: DNA
<213> ORGANISM: Artificial Sequence
<220> FEATURE:
<223> OTHER INFORMATION: Synthetic Construct

<400> SEQUENCE: 98
gaattgcagt tcacttgctt c                                           21

<210> SEQ ID NO 99
<211> LENGTH: 22
<212> TYPE: DNA
<213> ORGANISM: Artificial Sequence
<220> FEATURE:
<223> OTHER INFORMATION: Synthetic Construct

<400> SEQUENCE: 99
ccacaaagct aaaagggat tg                                           22

<210> SEQ ID NO 100
<211> LENGTH: 21
<212> TYPE: DNA
<213> ORGANISM: Artificial Sequence
<220> FEATURE:

<223> OTHER INFORMATION: Synthetic Construct

<400> SEQUENCE: 100
tccatgtgag ttttgtgtgt g                                              21

<210> SEQ ID NO 101
<211> LENGTH: 23
<212> TYPE: DNA
<213> ORGANISM: Artificial Sequence
<220> FEATURE:
<223> OTHER INFORMATION: Synthetic Construct

<400> SEQUENCE: 101
gccacataaa ttacatatag ctg                                            23

<210> SEQ ID NO 102
<211> LENGTH: 23
<212> TYPE: DNA
<213> ORGANISM: Artificial Sequence
<220> FEATURE:
<223> OTHER INFORMATION: Synthetic Construct

<400> SEQUENCE: 102
gaactattca acaagcataa tac                                            23

<210> SEQ ID NO 103
<211> LENGTH: 21
<212> TYPE: DNA
<213> ORGANISM: Artificial Sequence
<220> FEATURE:
<223> OTHER INFORMATION: Synthetic Construct

<400> SEQUENCE: 103
accgttcaac ggcaatttag c                                              21

<210> SEQ ID NO 104
<211> LENGTH: 22
<212> TYPE: DNA
<213> ORGANISM: Artificial Sequence
<220> FEATURE:
<223> OTHER INFORMATION: Synthetic Construct

<400> SEQUENCE: 104
cctatacacc ttaaaaccac tg                                             22

<210> SEQ ID NO 105
<211> LENGTH: 24
<212> TYPE: DNA
<213> ORGANISM: Artificial Sequence
<220> FEATURE:
<223> OTHER INFORMATION: Synthetic Construct

<400> SEQUENCE: 105
gtcttacaat agtaaaatgc gcag                                           24

<210> SEQ ID NO 106
<211> LENGTH: 21
<212> TYPE: DNA
<213> ORGANISM: Artificial Sequence
<220> FEATURE:
<223> OTHER INFORMATION: Synthetic Construct

<400> SEQUENCE: 106
gcggttcgtt gatattccaa c                                              21

<210> SEQ ID NO 107
<211> LENGTH: 20
<212> TYPE: DNA
<213> ORGANISM: Artificial Sequence
<220> FEATURE:
<223> OTHER INFORMATION: Synthetic Construct

<400> SEQUENCE: 107
agcgaaagcg gaaggagtac                                               20

<210> SEQ ID NO 108
<211> LENGTH: 22
<212> TYPE: DNA
<213> ORGANISM: Artificial Sequence
<220> FEATURE:
<223> OTHER INFORMATION: Synthetic Construct

<400> SEQUENCE: 108
tgtggtgagt aagcaatgaa tc                                            22

<210> SEQ ID NO 109
<211> LENGTH: 25
<212> TYPE: DNA
<213> ORGANISM: Artificial Sequence
<220> FEATURE:
<223> OTHER INFORMATION: Synthetic Construct

<400> SEQUENCE: 109
gtgtataatt cgccagaata tacgg                                         25

<210> SEQ ID NO 110
<211> LENGTH: 29
<212> TYPE: DNA
<213> ORGANISM: Artificial Sequence
<220> FEATURE:
<223> OTHER INFORMATION: Synthetic Construct

<400> SEQUENCE: 110
cgtttagata attgtatatt acacatatg                                     29

<210> SEQ ID NO 111
<211> LENGTH: 26
<212> TYPE: DNA
<213> ORGANISM: Artificial Sequence
<220> FEATURE:
<223> OTHER INFORMATION: Synthetic Construct

<400> SEQUENCE: 111
caaattatta cttatgttgt gatttg                                        26

<210> SEQ ID NO 112
<211> LENGTH: 24
<212> TYPE: DNA
<213> ORGANISM: Artificial Sequence
<220> FEATURE:
<223> OTHER INFORMATION: Synthetic Construct

<400> SEQUENCE: 112
attaagccat gatacacaaa ttac                                          24

<210> SEQ ID NO 113
<211> LENGTH: 232
<212> TYPE: DNA
<213> ORGANISM: Artificial Sequence
<220> FEATURE:
<223> OTHER INFORMATION: Synthetic Construct

```
<400> SEQUENCE: 113
ggaagatttt aatgaaaaga ggttgataaa gaaaattgta gaatctattg aagaaaagtc    60
acttggtgac atggacttgg ctccacttca aaagaagctt caggacttgc tgaatggaaa   120
aaaatatttg cttgtcttag atgatgtttg gaatgaagat caagataagt gggctaagtt   180
aagacaagtc ttgaaggctg agcaagtgg tgcttatgtt ctaaccacta cc            232

<210> SEQ ID NO 114
<211> LENGTH: 235
<212> TYPE: DNA
<213> ORGANISM: Artificial Sequence
<220> FEATURE:
<223> OTHER INFORMATION: Synthetic Construct

<400> SEQUENCE: 114
agaagatttt gatgagaaga agttgataaa ggcaattgtt gaatctatcg aaggaaaccc    60
acttggtgac cacatggatt tggctccact tcaaaagaag cttcaggaca tgttgaatgg   120
aaagagatac tttctcgttt tggatgatgt ttggaatgaa atcaagaaa gtgggataa    180 gataaaagca gtcttagagg ttggagcacg aggtgcttct gttctaacca ccact       235

<210> SEQ ID NO 115
<211> LENGTH: 2940
<212> TYPE: DNA
<213> ORGANISM: Solanum habrochaites
<220> FEATURE:
<223> OTHER INFORMATION: coding sequence TBRFV resistance gene

<400> SEQUENCE: 115
atggctgaag ctttccttca aattatgtta gagaatctga cttgtttcat ccaaggggaa    60
cttggattga ttcttggttt taaggatgag ttcgaaaagc ttcaaagcac gtttactaca   120
atccaagctg tggtacaaga tgctcagttg aagcaattga aggacaaggc aattgaaaat   180
tggttgcaga aactcaatgg tgctgcatat gaagctgatg acatcttgga cgaatgtaaa   240
actgaggcac caattataca gaagaagaat aaatatgggt gttatcatcc aaacgttatc   300
actttccgtc gcaagattgg gaaaaggatg aaaaagatta tggagaaact agatgcaatt   360
gcagcggaac gaattaagtt tcatttggat gaaaggacta tagagagaca gttgctaca   420 cgccaaacag gtttttgtttt aaatgaacca caagtttatg gaagagacaa agataaggat   480
gagatagtga aaatcctgat aaacaatgcc caaacacttt cagtcctccc aatacttggt   540 atgggggac taggaaagac gacccttgcc caaatggtct tcaatgatca gagagtaatt   600
gaacatttcc atcccaaaat atggatttgt gtctcggaag attttaatga aaagaggttg   660
ataaagaaaa ttgtagaatc tattgaagaa agtcacttg gtgacatgga cttggctcca   720
cttcaaaaga gcttcagga cttgctgaat ggaaaaaaat atttgcttgt cttagatgat   780
gtttggaatg aagatcaaga taagtgggct aagttaagac aagtcttgaa ggctggagca   840
agtggtgctt atgttctaac cactacccgt cttgaaaagg ttggatcaat catggggaca   900
ttgcaaccat atgaattgtc aaatttgtct caagaagatt gttggttgtt gttcatgcaa   960
tgtgcatttg ggcaccaaga agaaatgaat cttaatctag tggctatcgg aaaggtgatt  1020
gtgaaaaaat gtggtggtgt gcctctagca gctaaaactc ttggaggtat tttgcgcttc  1080
aagagagaag aaagacagtg ggaacatgtg agagatagtg agatttggaa tttacctcaa  1140
gatgaaagtt ctattctgcc tgccctgaga cttagttacc atcaccttcc acttgatttg  1200
agacaatgct tttcatattg tgcagtattc ccaaaggata ccaaaatgga aaggaaaat  1260
```

-continued

```
ctaatctctc tctggatggc acatggtttt cttttatcaa aaggaaactt ggagctagag    1320
gatgtaggta atgaagtatg gaatgaatta tacttgaggt cttttttcca agagattgaa    1380
gttcaatatg atcgaactta tttcaagatg catgatctca ttcatgattt ggcaacatct    1440
ctattttcag caagcacatc aagcagcaat atccgagaaa taatgtaga aggttaccta    1500
catatgatgt cgattggttt cgcaaaagtg gtgtcttctt actctcctcc tcacttgcaa    1560
aagtttgtct cattgagggt tcttaatcta agttccatgg gacttaagca gttaccgtcc    1620
tccattggag atctagtaca tttaagatac ttgaacctct ctctcaataa catgcgtact    1680
cttccaaagc agttatgcaa gcttcaaaat ctgcagactc ttaatgtaga gtattgctgg    1740
tcactttgtt gttttccaaa agaaacaagt aaacttggta gtctccgaaa tctcttactt    1800
gatggttgcg atggattgga ttctatgcca ccaaggatag gatctttgac atgccttaag    1860
actctaagtt tatttgttat tggcgagaga aaagattctc tacttggtga attacgaaac    1920
ctgaatctgt atgggtcaat tgaaatcacg catcttgaga gagtgaagaa tgataggggat    1980
gcaaaagaag ccaatttatc tgcaaagaa atctgcatt ctttaagcat gagatgggaa      2040
ggaccacata gatatgaatc agaagaagtt gaagtgcttg aatccctcaa accacactcc    2100
aatgtgactt gtttaacaat cactggcttc agaggaatcc gtctcccaga gtggatgaat    2160
cactcagttt tgaaaaatgt tgtctctatt gcaattagag gttgtgaaaa ctgctcatgc    2220
ttaccaccgt ttggtgatct gccttgtcta gaaagtctag agttacggag tgggtctgcg    2280
gaagtggagt atgttgaaga ttctggattc ccaacaagaa gaaggtttcc atctatgaga    2340
aaacttacta tagaaaattt tgataatctg aaaggattgc tgaaagaggc aggagaagag    2400
caattccccg tgcttgaaga gttgacaatt agatgttgtc ctgtgtttgt tattccgacc    2460
cttcttctg tcaagaaatt ggtagttcat gggaacaagt cagatgcaat agttttgagg    2520
tccatatata atcttagggc tcttacttcc ctcaacatta gccataactt cacagctact    2580
tcgctcccag aagagatgtt caaaagcctt gcaaatctca atacttgga aatcgctttc    2640
atctccaatc tcaaagagct gccaaacagc ctggctagtc tcaatgcttt gaagcatctg    2700
tttattaatt gttgttttgc actagagagt ctccccgagg aagcggtgaa aggtttaact    2760
tcactcacac agttatccat aacatactgt aagaggctaa atgtttacc agagggattg     2820
cagcaactaa caaatttatc agttaggtat tgtccaacac tggccaagcg atgtgagaag    2880
ggaataggac aagactggta caaaattgct cacattcctc atctgctgat tactgattag    2940
```

<210> SEQ ID NO 116
<211> LENGTH: 979
<212> TYPE: PRT
<213> ORGANISM: Solanum habrochaites
<220> FEATURE:
<223> OTHER INFORMATION: TRBFV resistance protein

<400> SEQUENCE: 116

```
Met Ala Glu Ala Phe Leu Gln Ile Met Leu Glu Asn Leu Thr Cys Phe
1               5                   10                  15

Ile Gln Gly Glu Leu Gly Leu Ile Leu Gly Phe Lys Asp Glu Phe Glu
            20                  25                  30

Lys Leu Gln Ser Thr Phe Thr Thr Ile Gln Ala Val Val Gln Asp Ala
        35                  40                  45

Gln Leu Lys Gln Leu Lys Asp Lys Ala Ile Glu Asn Trp Leu Gln Lys
    50                  55                  60
```

```
Leu Asn Gly Ala Ala Tyr Glu Ala Asp Asp Ile Leu Asp Glu Cys Lys
 65                  70                  75                  80

Thr Glu Ala Pro Ile Ile Gln Lys Lys Asn Lys Tyr Gly Cys Tyr His
                 85                  90                  95

Pro Asn Val Ile Thr Phe Arg Arg Lys Ile Gly Lys Arg Met Lys Lys
                100                 105                 110

Ile Met Glu Lys Leu Asp Ala Ile Ala Ala Glu Arg Ile Lys Phe His
            115                 120                 125

Leu Asp Glu Arg Thr Ile Glu Arg Gln Val Ala Thr Arg Gln Thr Gly
130                 135                 140

Phe Val Leu Asn Glu Pro Gln Val Tyr Gly Arg Asp Lys Asp Lys Asp
145                 150                 155                 160

Glu Ile Val Lys Ile Leu Ile Asn Asn Ala Gln Thr Leu Ser Val Leu
                165                 170                 175

Pro Ile Leu Gly Met Gly Gly Leu Gly Lys Thr Thr Leu Ala Gln Met
                180                 185                 190

Val Phe Asn Asp Gln Arg Val Ile Glu His Phe His Pro Lys Ile Trp
            195                 200                 205

Ile Cys Val Ser Glu Asp Phe Asn Glu Lys Arg Leu Ile Lys Lys Ile
210                 215                 220

Val Glu Ser Ile Glu Glu Lys Ser Leu Gly Asp Met Asp Leu Ala Pro
225                 230                 235                 240

Leu Gln Lys Lys Leu Gln Asp Leu Leu Asn Gly Lys Lys Tyr Leu Leu
                245                 250                 255

Val Leu Asp Asp Val Trp Asn Glu Asp Gln Asp Lys Trp Ala Lys Leu
                260                 265                 270

Arg Gln Val Leu Lys Ala Gly Ala Ser Gly Ala Tyr Val Leu Thr Thr
275                 280                 285

Thr Arg Leu Glu Lys Val Gly Ser Ile Met Gly Thr Leu Gln Pro Tyr
            290                 295                 300

Glu Leu Ser Asn Leu Ser Gln Glu Asp Cys Trp Leu Leu Phe Met Gln
305                 310                 315                 320

Cys Ala Phe Gly His Gln Glu Glu Met Asn Leu Asn Leu Val Ala Ile
                325                 330                 335

Gly Lys Val Ile Val Lys Lys Cys Gly Gly Val Pro Leu Ala Ala Lys
                340                 345                 350

Thr Leu Gly Gly Ile Leu Arg Phe Lys Arg Glu Glu Arg Gln Trp Glu
            355                 360                 365

His Val Arg Asp Ser Glu Ile Trp Asn Leu Pro Gln Asp Glu Ser Ser
370                 375                 380

Ile Leu Pro Ala Leu Arg Leu Ser Tyr His His Leu Pro Leu Asp Leu
385                 390                 395                 400

Arg Gln Cys Phe Ser Tyr Cys Ala Val Phe Pro Lys Asp Thr Lys Met
                405                 410                 415

Glu Lys Glu Asn Leu Ile Ser Leu Trp Met Ala His Gly Phe Leu Leu
                420                 425                 430

Ser Lys Gly Asn Leu Glu Leu Glu Asp Val Gly Asn Glu Val Trp Asn
            435                 440                 445

Glu Leu Tyr Leu Arg Ser Phe Phe Gln Glu Ile Glu Val Gln Tyr Asp
            450                 455                 460

Arg Thr Tyr Phe Lys Met His Asp Leu Ile His Asp Leu Ala Thr Ser
465                 470                 475                 480

Leu Phe Ser Ala Ser Thr Ser Ser Ser Asn Ile Arg Glu Ile Asn Val
```

```
                485                 490                 495
Glu Gly Tyr Leu His Met Met Ser Ile Gly Phe Ala Lys Val Val Ser
            500                 505                 510

Ser Tyr Ser Pro Pro His Leu Gln Lys Phe Val Ser Leu Arg Val Leu
            515                 520                 525

Asn Leu Ser Ser Met Gly Leu Lys Gln Leu Pro Ser Ser Ile Gly Asp
            530                 535                 540

Leu Val His Leu Arg Tyr Leu Asn Leu Ser Leu Asn Asn Met Arg Thr
545                 550                 555                 560

Leu Pro Lys Gln Leu Cys Lys Leu Gln Asn Leu Gln Thr Leu Asn Val
                565                 570                 575

Glu Tyr Cys Trp Ser Leu Cys Cys Phe Pro Lys Glu Thr Ser Lys Leu
            580                 585                 590

Gly Ser Leu Arg Asn Leu Leu Asp Gly Cys Asp Gly Leu Asp Ser
            595                 600                 605

Met Pro Pro Arg Ile Gly Ser Leu Thr Cys Leu Lys Thr Leu Ser Leu
            610                 615                 620

Phe Val Ile Gly Glu Arg Lys Asp Ser Leu Leu Gly Glu Leu Arg Asn
625                 630                 635                 640

Leu Asn Leu Tyr Gly Ser Ile Glu Ile Thr His Leu Glu Arg Val Lys
                645                 650                 655

Asn Asp Arg Asp Ala Lys Glu Ala Asn Leu Ser Ala Lys Glu Asn Leu
            660                 665                 670

His Ser Leu Ser Met Arg Trp Glu Gly Pro His Arg Tyr Glu Ser Glu
            675                 680                 685

Glu Val Glu Val Leu Glu Ser Leu Lys Pro His Ser Asn Val Thr Cys
690                 695                 700

Leu Thr Ile Thr Gly Phe Arg Gly Ile Arg Leu Pro Glu Trp Met Asn
705                 710                 715                 720

His Ser Val Leu Lys Asn Val Val Ser Ile Ala Ile Arg Gly Cys Glu
                725                 730                 735

Asn Cys Ser Cys Leu Pro Pro Phe Gly Asp Leu Pro Cys Leu Glu Ser
            740                 745                 750

Leu Glu Leu Arg Ser Gly Ser Ala Glu Val Glu Tyr Val Glu Asp Ser
            755                 760                 765

Gly Phe Pro Thr Arg Arg Phe Pro Ser Met Arg Lys Leu Thr Ile
            770                 775                 780

Glu Asn Phe Asp Asn Leu Lys Gly Leu Leu Lys Glu Ala Gly Glu Glu
785                 790                 795                 800

Gln Phe Pro Val Leu Glu Glu Leu Thr Ile Arg Cys Cys Pro Val Phe
                805                 810                 815

Val Ile Pro Thr Leu Ser Ser Val Lys Lys Leu Val Val His Gly Asn
            820                 825                 830

Lys Ser Asp Ala Ile Val Leu Arg Ser Ile Tyr Asn Leu Arg Ala Leu
            835                 840                 845

Thr Ser Leu Asn Ile Ser His Asn Phe Thr Ala Thr Ser Leu Pro Glu
850                 855                 860

Glu Met Phe Lys Ser Leu Ala Asn Leu Lys Tyr Leu Glu Ile Ala Phe
865                 870                 875                 880

Ile Ser Asn Leu Lys Glu Leu Pro Asn Ser Leu Ala Ser Leu Asn Ala
                885                 890                 895

Leu Lys His Leu Phe Ile Asn Cys Cys Phe Ala Leu Glu Ser Leu Pro
            900                 905                 910
```

-continued

```
Glu Glu Ala Val Lys Gly Leu Thr Ser Leu Thr Gln Leu Ser Ile Thr
        915                 920                 925

Tyr Cys Lys Arg Leu Lys Cys Leu Pro Glu Gly Leu Gln Gln Leu Thr
        930                 935                 940

Asn Leu Ser Val Arg Tyr Cys Pro Thr Leu Ala Lys Arg Cys Glu Lys
945                 950                 955                 960

Gly Ile Gly Gln Asp Trp Tyr Lys Ile Ala His Ile Pro His Leu Leu
                965                 970                 975

Ile Thr Asp
```